United States Patent
Kataoka et al.

(10) Patent No.: US 9,523,912 B2
(45) Date of Patent: Dec. 20, 2016

(54) PATTERN FORMING METHOD, ACTINIC RAY-SENSITIVE OR RADIATION-SENSITIVE RESIN COMPOSITION, RESIST FILM, MANUFACTURING METHOD OF ELECTRONIC DEVICE, ELECTRONIC DEVICE AND COMPOUND

(71) Applicant: FUJIFILM CORPORATION, Tokyo (JP)

(72) Inventors: Shohei Kataoka, Shizuoka (JP); Akinori Shibuya, Shizuoka (JP); Toshiaki Fukuhara, Shizuoka (JP); Hajime Furutani, Shizuoka (JP); Michihiro Shirakawa, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/840,654

(22) Filed: Aug. 31, 2015

(65) Prior Publication Data

US 2016/0070167 A1   Mar. 10, 2016

Related U.S. Application Data

(63) Continuation of application No. PCT/JP2014/055524, filed on Feb. 26, 2014.

(60) Provisional application No. 61/771,245, filed on Mar. 1, 2013.

(30) Foreign Application Priority Data

Mar. 1, 2013   (JP) ................................. 2013-041153

(51) Int. Cl.
| | | |
|---|---|---|
| *G03F 7/004* | (2006.01) | |
| *G03F 7/038* | (2006.01) | |
| *C07C 233/04* | (2006.01) | |
| *C07C 311/06* | (2006.01) | |
| *C07C 235/88* | (2006.01) | |
| *C07C 311/03* | (2006.01) | |
| *C08F 220/26* | (2006.01) | |
| *H01L 21/027* | (2006.01) | |
| *C07D 327/06* | (2006.01) | |
| *C07D 333/46* | (2006.01) | |
| *C07D 333/76* | (2006.01) | |
| *C07C 311/51* | (2006.01) | |
| *C07C 311/53* | (2006.01) | |

(Continued)

(52) U.S. Cl.
CPC ............... *G03F 7/038* (2013.01); *C07C 25/18* (2013.01); *C07C 233/04* (2013.01); *C07C 235/88* (2013.01); *C07C 311/03* (2013.01); *C07C 311/06* (2013.01); *C07C 311/51* (2013.01); *C07C 311/53* (2013.01); *C07C 381/12* (2013.01); *C07D 327/06* (2013.01); *C07D 333/46* (2013.01); *C07D 333/76* (2013.01); *C07D 411/06* (2013.01); *C08F 220/26* (2013.01); *G03F 7/0392* (2013.01); *G03F 7/0397* (2013.01); *G03F 7/20* (2013.01); *G03F 7/325* (2013.01); *H01L 21/0275* (2013.01); *C07C 2101/14* (2013.01); *C07C 2103/74* (2013.01)

(58) Field of Classification Search
CPC ........ G03F 7/004; G03F 7/325; G03F 7/322; G03F 7/326; G03F 7/329; G03F 7/331; G03F 7/0397; G03F 220/26; G03F 220/28; C07C 311/00; C07C 311/03; C07C 311/06; C07C 233/01; C07C 233/02; C07C 233/04; C07C 235/88; H01L 21/0274; H01L 21/0275; C08F 220/26; C08F 220/28
USPC ............ 430/270.1, 913, 322, 325, 329, 326, 430/330, 331; 526/268, 269, 281, 319; 560/149
See application file for complete search history.

(56) References Cited

U.S. PATENT DOCUMENTS

| | | |
|---|---|---|
| 5,502,251 A | 3/1996 | Pohmer et al. |
| 6,187,504 B1 | 2/2001 | Suwa et al. |

(Continued)

FOREIGN PATENT DOCUMENTS

| | | |
|---|---|---|
| JP | 6-116229 A | 4/1994 |
| JP | 3632410 B2 | 3/2005 |

(Continued)

OTHER PUBLICATIONS

Int. Search Report dated May 27, 2014 issued in Int. Application No. PCT/JP2014/055524 (PCT/ISA/210).
Written Opinion dated May 27, 2014 issued in Int. Application No. PCT/JP2014/055524 (PCT/ISA/237).
Communication issued Jan. 26, 2016, issued by the Japanese Patent Office in counterpart Japanese Patent Application No. 2014-030830.
Office Action dated Aug. 22, 2016 issued by Korean Intellectual Property Office in counterpart Korean Application No. 10-2015-7023676.

*Primary Examiner* — Amanda C Walke
(74) *Attorney, Agent, or Firm* — Sughrue Mion, PLLC

(57) ABSTRACT

There is provided a pattern forming method comprising (i) a step of forming a film containing an actinic ray-sensitive or radiation-sensitive resin composition containing (A) a compound represented by the specific formula, (B) a compound different from the compound (A) and capable of generating an acid upon irradiation with an actinic ray or radiation, and (P) a resin that does not react with the acid generated from the compound (A) and is capable of decreasing the solubility for an organic solvent-containing developer by the action of the acid generated from the compound (B), (ii) a step of exposing the film, and (iii) a step of developing the exposed film by using an organic solvent-containing developer to form a negative pattern; the actinic ray-sensitive or radiation-sensitive resin composition above; a resist film using the composition.

14 Claims, No Drawings

(51) Int. Cl.
*C07D 411/06* (2006.01)
*C07C 381/12* (2006.01)
*C07C 25/18* (2006.01)
*G03F 7/20* (2006.01)
*G03F 7/32* (2006.01)
*G03F 7/039* (2006.01)

(56) References Cited

U.S. PATENT DOCUMENTS

| | | | |
|---|---|---|---|
| 2001/0014427 A1 | 8/2001 | Suwa et al. | |
| 2009/0035692 A1 | 2/2009 | Tarutani et al. | |
| 2011/0171569 A1* | 7/2011 | Nishimae | C07D 339/08 430/7 |
| 2011/0269072 A1 | 11/2011 | Shibuya | |
| 2012/0149916 A1* | 6/2012 | Utsumi | C07C 311/09 549/49 |
| 2012/0156617 A1 | 6/2012 | Kataoka et al. | |
| 2012/0214101 A1* | 8/2012 | Shimizu | G03F 7/0045 430/285.1 |
| 2012/0282548 A1* | 11/2012 | Enomoto | G03F 7/0045 430/284.1 |
| 2013/0017377 A1 | 1/2013 | Kataoka et al. | |

FOREIGN PATENT DOCUMENTS

| | | |
|---|---|---|
| JP | 2008-281975 A | 11/2008 |
| JP | 2009-53688 A | 3/2009 |
| JP | 2009-191055 A | 8/2009 |
| JP | 2009-274963 A | 11/2009 |
| JP | 2010-139996 A | 6/2010 |
| JP | 2010-164958 A | 7/2010 |
| JP | 2011-100105 A | 5/2011 |
| JP | 2011-203644 A | 10/2011 |
| JP | 2011-248332 A | 12/2011 |
| JP | 5001192 B2 | 8/2012 |

* cited by examiner

PATTERN FORMING METHOD, ACTINIC RAY-SENSITIVE OR RADIATION-SENSITIVE RESIN COMPOSITION, RESIST FILM, MANUFACTURING METHOD OF ELECTRONIC DEVICE, ELECTRONIC DEVICE AND COMPOUND

CROSS REFERENCE TO RELATED APPLICATION

This is a continuation of International Application No. PCT/JP2014/055524 filed on Feb. 26, 2014, and claims priority from Japanese Patent Application No. 2013-041153 filed on Mar. 1, 2013, U.S. Provisional Application No. 61/771,245 filed on Mar. 1, 2013, the entire disclosures of which are incorporated therein by reference.

TECHNICAL FIELD

The present invention relates to a pattern forming method, an actinic ray-sensitive or radiation-sensitive resin composition, a resist film, a manufacturing method of an electronic device, an electronic device, and a compound. More specifically, the present invention relates to a pattern forming method suitable for lithography in the process of producing a semiconductor such as IC or the production of a liquid crystal device or a circuit board such as thermal head and further in other photo-fabrication processes, an actinic ray-sensitive or radiation-sensitive resin composition used therein, a resist film, and a compound. The present invention also relates to a manufacturing method of an electronic device, including the pattern forming method above, and an electronic device manufactured by the method.

BACKGROUND ART

Since the advent of a resist for KrF excimer laser (248 nm), a pattern forming method utilizing chemical amplification is used so as to compensate for sensitivity reduction due to light absorption. For example, in the positive chemical amplification method, first, a photoacid generator contained in the exposed area decomposes upon irradiation with light to generate an acid and in the course of baking or the like after exposure (PEB: Post Exposure Bake), an alkali-insoluble group contained in the photosensitive composition is changed into an alkali-soluble group by the catalytic action of the acid generated. Thereafter, development is performed using, for example, an alkali solution, whereby the exposed area is removed and a desired pattern is obtained (see, for example, Japanese Patent No. 3632410, JP-A-2011-100105 (the term "JP-A" as used herein means an "unexamined published Japanese patent application"), JP-A-2009-274963 and Japanese Patent No. 5001192).

As for the alkali developer used in the method above, various developers have been proposed. For example, as the alkali developer, an aqueous alkali developer of 2.38 mass % TMAH (aqueous tetramethylammonium hydroxide solution) is being used for general purposes.

Miniaturization of a semiconductor device has lead to a progress in shortening the wavelength of the exposure light source and increasing the numerical aperture (higher NA) of a projection lens, and an exposure machine using an ArF excimer laser having a wavelength of 193 nm as the light source has been so far developed. As a technique to more increase the resolution, a method of filling the space between the projection lens and the sample with a high refractive-index liquid (hereinafter, sometimes referred to as "immersion liquid") (that is, an immersion method) has been proposed. Furthermore, EUV lithography of performing exposure to ultraviolet light with a shorter wavelength (13.5 nm) has also been proposed.

In recent years, a pattern forming method using an organic solvent-containing developer is also being developed (see, for example, JP-A-2008-281975, JP-A-2010-139996, JP-A-2010-164958 and JP-A-2011-203644).

SUMMARY OF INVENTION

However, in recent years, the need for micronization is abruptly increasing and, for example, in the case of forming particularly an ultrafine pattern (among others, a trench pattern having a trench width of 50 nm or less or a hole pattern having a hole size of 50 nm or less), more improvement is demanded. Specifically, it is demanded to develop a resist composition ensuring that in forming an ultrafine pattern, variation in the line width (hereinafter, sometimes referred to as line width roughness or LWR) is small, the defocus (hereinafter, sometimes referred to as DOF) is high, and the exposure latitude (hereinafter, sometimes referred to as EL) is excellent.

The present invention has been made by taking into account the above-described problems, and an object of the present invention is to provide a pattern forming method, an actinic ray-sensitive or radiation-sensitive resin composition, a resist film and a compound, ensuring that in forming an ultrafine pattern (among others, a trench pattern having a trench width of 50 nm or less or a hole pattern having a hole size of 50 nm or less), the roughness performance such as line width roughness and the defocus performance are high and the resolution and the exposure latitude are excellent, as well as a manufacturing method of an electronic device, using the method, composition, film or compound, and an electronic device.

The present invention includes the following configurations, and the above-described object of the present invention can be attained by these configurations.

[1] A pattern forming method comprising:
 (i) a step of forming a film containing an actinic ray-sensitive or radiation-sensitive resin composition containing (A) a compound represented by the following formula (I-1), (B) a compound different from the compound (A) and capable of generating an acid upon irradiation with an actinic ray or radiation, and (P) a resin that does not react with the acid generated from the compound (A) and is capable of decreasing the solubility for an organic solvent-containing developer by the action of the acid generated from the compound (B),
 (ii) a step of exposing the film, and
 (iii) a step of developing the exposed film by using an organic solvent-containing developer to form a negative pattern:

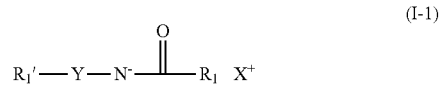
(I-1)

wherein
 each of $R_1$ and $R_1'$ independently represents a monovalent organic group,
 Y represents —$SO_2$— or —CO—, and
 $X^+$ represents a counter cation.
[2] The pattern forming method as described in [1], wherein the compound (A) is represented by the following formula (I-2a) or (I-2b):

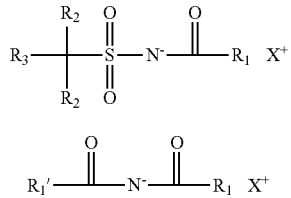

wherein
each $R_2$ independently represents a hydrogen atom, an alkyl group, a cycloalkyl group or an alkoxy group,
$R_3$ represents a hydrogen atom or a monovalent organic group,
two or more members out of two $R_2$ and $R_3$ may combine with each other to form a ring, and
$R_1$, $R_1'$ and $X^+$ have the same meanings as $R_1$, $R_1'$ and $X^+$ in formula (I-1).
[3] The pattern forming method as described in [2],
wherein the compound (A) is represented by the following formula (I-3a) or (I-3b):

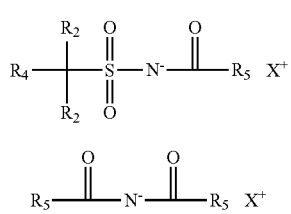

wherein
each of $R_4$ and $R_5$ independently represents a fluorine atom, a hydroxyl group, an alkyl group or a cycloalkyl group,
$CH_2$ contained in the alkyl group or cycloalkyl group represented by $R_4$ and $R_5$ may be replaced by —O—, —C(O)—, —S(O)$_n$—, —S(O)$_2$—NR$_6$—, —C(O)—NR$_6$—, —OC(O)—NR$_6$— or a combination thereof,
$R_6$ represents a hydrogen atom or a monovalent organic group, n represents an integer of 0 to 2,
two or more members out of two $R_2$ and $R_4$ may combine with each other to form a ring, and
$R_2$ and $X^+$ have the same meanings as $R_2$ and $X^+$ in formula (I-2a).
[4] The pattern forming method as described in any one of [1] to [3],
wherein the resin (P) contains a repeating unit represented by the following formula (II):

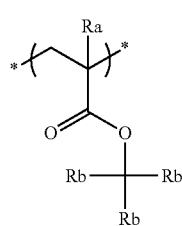

wherein
Ra represents a hydrogen atom or an alkyl group,
each Rb independently represents an alkyl group or a cycloalkyl group, and two Rb may combine with each other to form a ring.
[5] An actinic ray-sensitive or radiation-sensitive resin composition containing:
(A) a compound represented by formula (I-1),
(B) a compound different from the compound (A) and capable of generating an acid upon irradiation with an actinic ray or radiation, and
(P) a resin that does not react with the acid generated from the compound (A) and is capable of decomposing by the action of the acid generated from the compound (B) to produce a polar group:

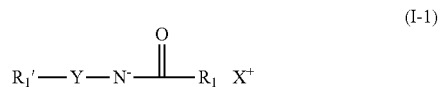

wherein
each of $R_1$ and $R_1'$ independently represents a monovalent organic group, Y represents —SO$_2$— or —CO—, and $X^+$ represents a counter cation.
[6] The actinic ray-sensitive or radiation-sensitive resin composition as described in [5],
wherein the compound (A) is represented by the following formula (I-2a) or (I-2b):

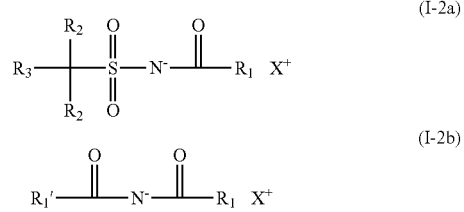

wherein
each $R_2$ independently represents a hydrogen atom, an alkyl group, a cycloalkyl group or an alkoxy group,
$R_3$ represents a hydrogen atom or a monovalent organic group,
two or more members out of two $R_2$ and $R_3$ may combine with each other to form a ring, and
$R_1$, $R_1'$ and $X^+$ have the same meanings as $R_1$, $R_1'$ and $X^+$ in formula (I-1).
[7] The actinic ray-sensitive or radiation-sensitive resin composition as described in [6],
wherein the compound (A) is represented by the following formula (I-3a) or (I-3b):

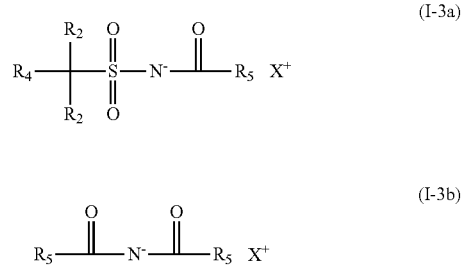

wherein each of $R_4$ and $R_5$ independently represents a fluorine atom, a hydroxyl group, an alkyl group or a cycloalkyl group, $CH_2$ contained in the alkyl group or cycloalkyl group represented by $R_4$ and $R_5$ may be replaced by —O—, —C(O)—, —S(O)$_n$—, —S(O)$_2$—NR$_6$—, —C(O)—NR$_6$—, —OC(O)—NR$_6$— or a combination thereof, $R_6$ represents a hydrogen atom or a monovalent organic group, n represents an integer of 0 to 2, and $R_2$ and $X^+$ have the same meanings as $R_2$ and $X^+$ in formula (I-2a).

[8] The actinic ray-sensitive or radiation-sensitive resin composition as described in any one of [5] to [7], wherein the resin (P) contains a repeating unit represented by the following formula (II):

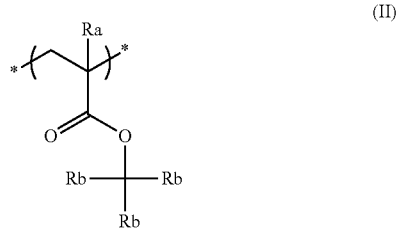

wherein

Ra represents a hydrogen atom or an alkyl group, each Rb independently represents an alkyl group or a cycloalkyl group, and two Rb may combine with each other to form a ring.

[9] A resist film formed of the actinic ray-sensitive or radiation-sensitive resin composition described in any one of [5] to [8].

[10] A method for manufacturing an electronic device, comprising the pattern forming method described in any one of [1] to [4].

[11] An electronic device manufactured by the manufacturing method of an electronic device described in [10].

[12] A compound represented by the following formula (I-3a):

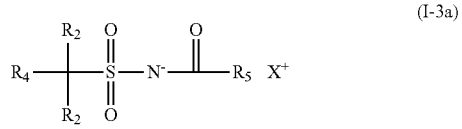

wherein each $R_2$ independently represents a hydrogen atom, an alkyl group, a cycloalkyl group or an alkoxy group, each of $R_4$ and $R_5$ independently represents a fluorine atom, a hydroxyl group, an alkyl group or a cycloalkyl group, $CH_2$ contained in the alkyl group or cycloalkyl group represented by $R_4$ and $R_5$ may be replaced by —O—, —C(O)—, —S(O)$_2$—NR$_6$—, —C(O)—NR$_6$—, —OC(O)—NR$_6$— or a combination thereof, $R_6$ represents a hydrogen atom or a monovalent organic group, n represents an integer of 0 to 2, and $X^+$ represents a counter cation.

According to the present invention, a pattern forming method, an actinic ray-sensitive or radiation-sensitive resin composition, a resist film and a compound, ensuring that in forming an ultrafine pattern (among others, a trench pattern having a trench width of 50 nm or less or a hole pattern having a hole size of 50 nm or less), the roughness performance such as line width roughness and the defocus performance are high and the resolution and the exposure latitude are excellent, as well as a manufacturing method of an electronic device, using the method, composition, film or compound, and an electronic device, can be provided.

DESCRIPTION OF EMBODIMENTS

The present invention is described in detail below.

In the description of the present invention, when a group or an atomic group is denoted without specifying whether substituted or unsubstituted, the group encompasses both a group having no substituent and a group having a substituent. For example, "an alkyl group" referred to without specifying whether substituted or unsubstituted encompasses not only an alkyl group having no substituent (unsubstituted alkyl group) but also an alkyl group having a substituent (substituted alkyl group).

In the present invention, the "actinic ray" or "radiation" means, for example, a bright line spectrum of mercury lamp, a far ultraviolet ray typified by excimer laser, an extreme-ultraviolet ray (EUV light), an X-ray or a particle ray such as an electron beam and ion beam. Also, in the present invention, the "light" means an actinic ray or radiation.

Furthermore, in the description of the present invention, unless otherwise indicated, the "exposure" encompasses not only exposure to a mercury lamp, a far ultraviolet ray typified by excimer laser, an X-ray, an extreme ultraviolet ray (EUV light) or the like but also lithography with a particle beam such as electron beam and ion beam.

The pattern forming method of the present invention includes:

(i) a step of forming a film containing an actinic ray-sensitive or radiation-sensitive resin composition containing (A) a compound represented by the following formula (I-1), (B) a compound different from the compound (A) and capable of generating an acid upon irradiation with an actinic ray or radiation, and (P) a resin that does not react with the acid generated from the compound (A) and is capable of decreasing the solubility for an organic solvent-containing developer by the action of the acid generated from the compound (B), (ii) a step of exposing the film, and (iii) a step of developing the exposed film by using an organic solvent-containing developer to form a negative pattern:

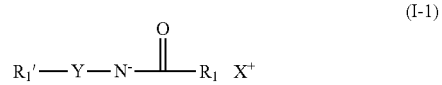

wherein each of $R_1$ and $R_1'$ independently represents a monovalent organic group, Y represents —SO$_2$— or —CO—, and $X^+$ represents a counter cation.

The present invention also relates to an actinic ray-sensitive or radiation-sensitive resin composition containing the compound represented by formula (I-1).

The reason why the pattern forming method of the present invention and the actinic ray-sensitive or radiation-sensitive resin composition of the present invention ensure that in forming an ultrafine pattern (for example, a trench pattern having a trench width of 50 nm or less or a hole pattern having a hole size of 50 nm or less), all of the roughness performance such as line width roughness, the defocus performance and the exposure latitude are excellent, is not clearly known but is presumed as follows.

First, the compound (A) before being decomposed by an actinic ray or radiation can be neutralized by exchanging the salt with the acid generated from the acid generator (B) and acts as a base. The compound (A) has a property of becoming impossible to act as a base when decomposed by an actinic ray or radiation and, that is, a property as a photobase eliminator. Thanks to this compound, the contrast of the effective amount of an acid after neutralization between the exposed area and the unexposed area and in turn, the contrast of the reaction of the resin (P) between the exposed area and the unexposed area may be enhanced, as a result, the dissolution contrast for the developer between the exposed area and the unexposed area may be increased, leading to improvement of the roughness performance and the exposure latitude. Also, the reason why the defocus performance is improved is not elucidated, but it is known that when a pattern is formed using an organic solvent-containing developer, the defocus performance in forming a pattern with a trench or contact hole profile is enhanced.

Incidentally, according to the positive image forming method using an alkali developer, formation of the above-described ultrafine pattern tends to be difficult. This is because in the case of forming a trench pattern or a hole pattern by a positive image forming method, the exposed area works out to the region in which a trench pattern or a hole pattern is to be formed, but it is likely to be optically more difficult to expose and resolve an ultrafine region. However, as described above, use of the compound (A) contributes to enhancing the reaction contrast of the resin (P) between the exposed area and the unexposed area and can enhance the performance also in the positive image forming method. Accordingly, the present invention is not intended to exclude a pattern forming method where a resist film formed of the actinic ray-sensitive or radiation-sensitive resin composition according to the present invention is developed using an alkali developer to form a positive pattern.

The actinic ray-sensitive or radiation-sensitive resin composition usable in the present invention (hereinafter, sometimes referred to as "composition of the present invention" or "resist composition of the present invention") is described below.

The present invention also relates to the actinic ray-sensitive or radiation-sensitive resin composition described below.

The actinic ray-sensitive or radiation-sensitive resin composition according to the present invention is preferably used for negative development (development where the solubility for developer is decreased upon exposure, as a result, the exposed area remains as a pattern and the unexposed area is removed) particularly in the case of an ultrafine pattern (for example, a trench pattern having a trench width of 50 nm or less or a hole pattern having a hole size of 50 nm or less) in the resist film. That is, the actinic ray-sensitive or radiation-sensitive resin composition according to the present invention can be an actinic ray-sensitive or radiation-sensitive resin composition for organic solvent development, which is used for development using an organic solvent-containing developer. The term "for organic solvent development" as used herein means usage where the composition is subjected to at least a step of performing development by using an organic solvent-containing developer.

The actinic ray-sensitive or radiation-sensitive resin composition of the present invention is typically a resist composition and may be either a negative resist composition or a positive resist composition but is preferably a negative resist composition (that is, a resist composition for organic solvent development), because particularly high effects can be obtained. Also, the composition according to the present invention is typically a chemical amplification resist composition.

The actinic ray-sensitive or radiation-sensitive resin composition according to the present invention contains [1] (A) a compound represented by the following formula (I-1), [2] (B) a compound different from the compound (A) and capable of generating an acid upon irradiation with an actinic ray or radiation, and [3] (P) a resin that does not react with the acid generated from the compound (A) and is capable of decreasing the solubility for an organic solvent-containing developer by the action of the acid generated from the compound (B).

Further components which may be contained in the composition according to the present invention includes [4] a hydrophobic resin, [5-1] a basic compound, [5-2] a low molecular compound containing a nitrogen atom and having a group capable of leaving by the action of an acid, [6] a solvent, [7] a surfactant, and the like. The composition of the present invention can be used for pattern formation, for example, according to the method described later as "Pattern Forming Method".

These components are described in sequence below.

[1] (A) Compound Represented by Formula (I-1)

The actinic ray-sensitive or radiation-sensitive resin composition used in the pattern forming method of the present invention contains a compound represented by the following formula (I-1) (hereinafter, sometimes referred to as "compound (A)"). Here, the compound (A) can generate an acid upon irradiation with an actinic ray or radiation, but the acid generated from the compound (A) is lower in the acid strength than an acid generated from the compound (B) upon irradiation with an actinic ray or radiation and does not interact with the resin (P).

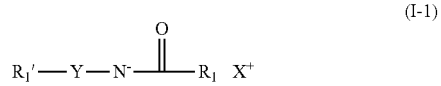

(I-1)

In formula (I-1), each of $R_1$ and $R_1'$ independently represents a monovalent organic group, Y represents —$SO_2$— or —CO—, and $X^+$ represents a counter cation.

The monovalent organic group of $R_1$ and $R_1'$ is preferably a monovalent organic group having a carbon number of 1 to 30, and examples thereof include an alkyl group, a cycloalkyl group, an aryl group, an aralkyl group, and an alkenyl group.

The alkyl group in $R_1$ and $R_1'$ may be linear or branched and may have a substituent. The alkyl group in $R_1$ and $R_1'$ is preferably an alkyl group having a carbon number of 1 to 20 and may contain an oxygen atom, a sulfur atom or a nitrogen atom in the alkyl chain. The alkyl group in $R_1$ and $R_1'$ includes a methyl group, an ethyl group, an n-propyl group, an n-butyl group and the like.

The cycloalkyl group in $R_1$ and $R_1'$ may have a substituent and is preferably a cycloalkyl group having a carbon number of 3 to 20, and the cycloalkyl group may contain an oxygen atom in the ring. The cycloalkyl group in $R_1$ and includes a cyclohexyl group, a cycloheptyl group, a cyclooctyl group, a cyclodecyl group, a cyclododecyl group and the like.

The aryl group in $R_1$ and $R_1'$ may have a substituent and is preferably an aryl group having a carbon number of 6 to 14. The aryl group in $R_1$ and $R_1'$ includes a phenyl group, a naphthyl group and the like.

The aralkyl group in $R_1$ and $R_1'$ may have a substituent and is preferably an aralkyl group having a carbon number of 7 to 20. The aralkyl group in $R_1$ and $R_1'$ includes a benzyl group, a phenethyl group, a naphthylmethyl group, a naphthylethyl group, a naphthylbutyl group and the like.

The alkenyl group in $R_1$ and $R_1'$ may have a substituent and includes, for example, a group having a double bond at an arbitrary position of the alkyl group recited as $R_1$ and $R_1^{1"}$.

Examples of the substituent which may be substituted on the alkyl group, cycloalkyl group, aryl group, aralkyl group and alkenyl group of $R_1$ and $R_1'$ include a halogen atom (e.g., fluorine atom), a hydroxyl group, a nitro group, a cyano group, a carboxy group, a carbonyl group, a cycloalkyl group (preferably having a carbon number of 3 to 10), an aryl group (preferably having a carbon number of 6 to 14), an alkoxy group (preferably having a carbon number of 1 to 10), an acyl group (preferably having a carbon number of 2 to 20), an acyloxy group (preferably having a carbon number of 2 to 10), an alkoxycarbonyl group (preferably having a carbon number of 2 to 20), an aminoacyl group (preferably having a carbon number of 2 to 10), an amino group, a pyrrolidino group, a piperidino group, a morpholino group, a silicon atom-containing group, and a group formed by combining two or more thereof. The cyclic structure in the aryl group, cycloalkyl group and the like may further have an alkyl group (preferably having a carbon number of 1 to 10) as a substituent. The aminoacyl group may further have an alkyl group (preferably having a carbon number of 1 to 10) as a substituent.

Also, $CH_2$ contained in the alkyl group, cycloalkyl group or aralkyl group of $R_1$ and $R_1'$ may be replaced by —O—, —C(O)—, —S(O)$_n$—, —S(O)$_2$—NR$_6$—, —C(O)—NR$_6$—, —OC(O)—NR$_6$— or a combination thereof. $R_6$ represents a hydrogen atom or a monovalent organic group, and n represents an integer of 0 to 2.

Specific examples and preferred examples of the organic group as $R_6$ are the same as specific examples and preferred examples of the monovalent organic group of $R_1$ and $R_1'$.

The counter cation represented by $X^+$ is preferably an onium cation, more preferably a sulfonium cation or an iodonium cation.

Preferred sulfonium cations and iodonium cations include sulfonium cations and iodonium cations in the compounds represented by formulae (ZI) and (ZII) (including formulae (ZI-3), (ZI-4) and the like recited as preferred examples of formula (ZI)) in the later-described compound capable of generating an acid upon irradiation with an actinic ray or radiation (acid generator). Specific examples also include sulfonium cations and iodonium cations in specific examples illustrated later of the acid generator (B).

The compound (A) is preferably a compound represented by the following formula (I-2a) or (I-2b):

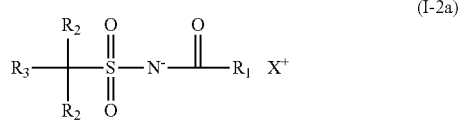

(I-2a)

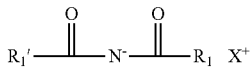

(I-2b)

In formulae (I-2a) and (I-2b), each $R_2$ independently represents a hydrogen atom, an alkyl group, a cycloalkyl group or an alkoxy group, $R_3$ represents a hydrogen atom or a monovalent organic group, two or more members out of two $R_2$ and $R_3$ may combine with each other to form a ring, and $R_1$, $R_1'$ and $X^+$ have the same meanings as $R_1$, $R_1'$ and $X^+$ in formula (I-1).

The alkyl group of $R_2$ may be linear or branched and may have a substituent. The alkyl group of $R_2$ is preferably an alkyl group having a carbon number of 1 to 20 and may contain an oxygen atom, a sulfur atom or a nitrogen atom in the alkyl chain. The alkyl group in $R_1$ and $R_1'$ includes a linear alkyl group such as methyl group, ethyl group, n-propyl group, n-butyl group, n-pentyl group, n-hexyl group, n-octyl group, n-dodecyl group, n-tetradecyl group and n-octadecyl group, and a branched alkyl group such as isopropyl group, isobutyl group, tert-butyl group, neopentyl group and 2-ethylhexyl group.

The cycloalkyl group of $R_2$ may have a substituent and is preferably a cycloalkyl group having a carbon number of 3 to 20. The cycloalkyl group may contain an oxygen atom in the ring. The cycloalkyl group in $R_1$ and $R_1'$ includes a cyclohexyl group, a cycloheptyl group, a cyclooctyl group, a cyclodecyl group, a cyclododecyl group and the like.

The alkoxy group of $R_2$ may have a substituent and is preferably an alkoxy group having a carbon number of 1 to 20, and examples thereof include a methoxy group, an ethoxy group, a propoxy group, a butoxy group, and a pentoxy group.

Specific examples of the substituent which may be substituted on the alkyl group, cycloalkyl group and alkoxy group of $R_2$ are the same as those recited as specific examples of the substituent which may be substituted on the alkyl group, cycloalkyl group, aryl group, aralkyl group and alkenyl group of $R_1$ and $R_1'$.

$R_2$ is preferably a hydrogen atom, an unsubstituted alkyl group, an unsubstituted cycloalkyl group or an unsubstituted alkoxy group, more preferably a hydrogen atom or an unsubstituted alkyl group.

Specific examples and preferred examples of the monovalent organic group as $R_3$ are the same as those recited for the monovalent organic group of $R_1$ and $R_1'$ in formula (I-1).

The ring which may be formed by combining two or more members out of two $R_2$ and $R_3$ with each other may be monocyclic or polycyclic and may have a substituent. Such a ring includes a monocyclic cycloalkane ring having a carbon number of 3 to 10 and a polycyclic cycloalkane ring having a carbon number of 4 to 20. Specific examples of the substituent which the ring may have are the same as those recited as specific examples of the substituent which the alkyl group, cycloalkyl group, aryl group, aralkyl group and alkenyl group of $R_1$ and $R_1'$ may have.

Also, specific examples and preferred examples of $R_1$, $R_1'$ and $X^+$ are the same as those recited as specific examples and preferred examples of $R_1$, $R_1'$ and $X^+$ in formula (I-1).

The compound (A) is preferably a compound represented by the following formula (I-3a) or (I-3b):

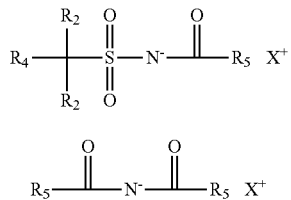

In formulae (I-3a) and (I-3b), each of $R_4$ and $R_5$ independently represents a fluorine atom, a hydroxyl group, an alkyl group or a cycloalkyl group, $CH_2$ contained in the alkyl group or cycloalkyl group represented by $R_4$ and $R_5$ may be replaced by —O—, —C(O)—, —S(O)$_n$—, —S(O)$_2$—NR$_6$—, —C(O)—NR$_6$—, —OC(O)—NR$_6$— or a combination thereof, $R_6$ represents a hydrogen atom or a monovalent organic group, n represents an integer of 0 to 2, two or more members out of two $R_2$ and $R_4$ may combine with each other to form a ring, and $R_2$ and $X^+$ have the same meanings as $R_2$ and $X^+$ in formula (I-2a).

In formulae (I-3a) and (I-3b), the alkyl group as $R_4$ and $R_5$ may be linear or branched and may have a substituent. The alkyl group as $R_4$ and $R_5$ is preferably an alkyl group having a carbon number of 1 to 10, and a part of the alkyl chain may be replaced by —O—, —C(O)—, —S(O)$_n$—, —S(O)$_2$—NR$_6$—, —C(O)—NR$_6$—, —OC(O)—NR$_6$— or a combination thereof.

The alkyl group in $R_4$ and $R_5$ includes a linear alkyl group such as methyl group, ethyl group, n-propyl group, n-butyl group, n-pentyl group, n-hexyl group, n-octyl group, n-dodecyl group, n-tetradecyl group and n-octadecyl group, and a branched alkyl group such as isopropyl group, isobutyl group, tert-butyl group, neopentyl group and 2-ethylhexyl group.

The cycloalkyl group as $R_4$ and $R_5$ may have a substituent and is preferably a cycloalkyl group having a carbon number of 3 to 20. The cycloalkyl group may contain an oxygen atom or a sulfur atom in the ring. Specifically, the cycloalkyl group includes a cyclopropyl group, a cyclopentyl group, a cyclohexyl group, a norbornyl group, an adamantyl group and the like.

The ring which may be formed by combining two or more members out of two $R_2$ and $R_4$ with each other may be monocyclic or polycyclic and may have a substituent. Such a ring includes a monocyclic cycloalkane ring having a carbon number of 3 to 10 and a polycyclic cycloalkane ring having a carbon number of 4 to 20.

Specific examples of the substituent which the alkyl group and cycloalkyl group of $R_4$ and $R_5$ may have and the substituent which the ring that may be formed by combining two or more members out of two $R_2$ and $R_4$ with each other may have are the same as those recited as specific examples of the substituent which the alkyl group, cycloalkyl group, aryl group, aralkyl group and alkenyl group of $R_1$ and $R_1'$ may have.

Specific examples and preferred examples of $R_2$ and $X^+$ are the same as those recited as specific examples and preferred examples of $R_2$ and $X^+$ in formula (I-2a).

The content of the compound (A) is preferably from 0.1 to 10 mass %, more preferably from 0.3 to 8 mass %, still more preferably from 0.5 to 5 mass %, based on the total solid content (excluding the solvent) of the actinic ray-sensitive or radiation-sensitive resin composition. (In this specification, mass ratio is equal to weight ratio.)

Specific examples of the compound (A) represented by formula (I-1) are illustrated below, but the present invention is not limited thereto.

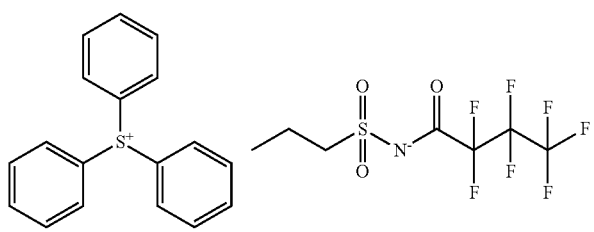

(A-1)

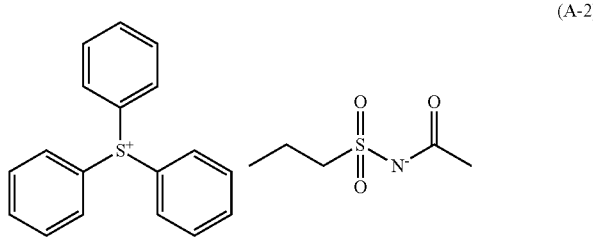

(A-2) (A-3)

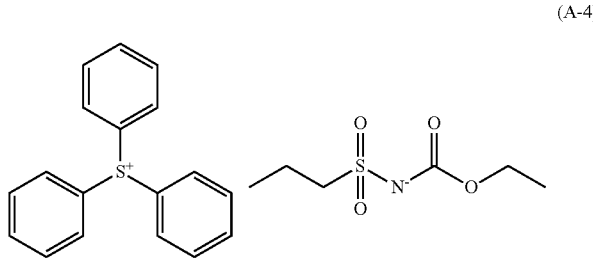

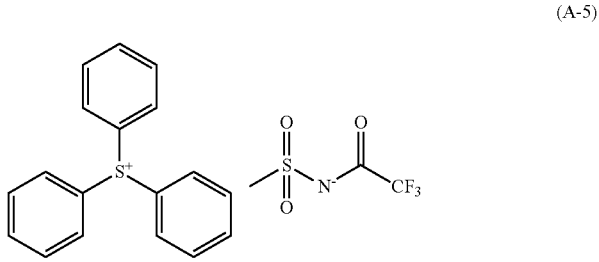

(A-4) (A-5)

-continued
(A-6)
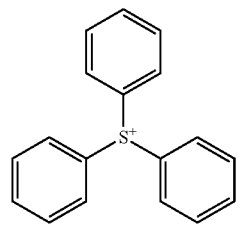 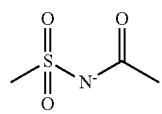
(A-7)
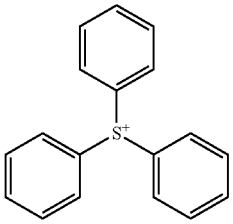 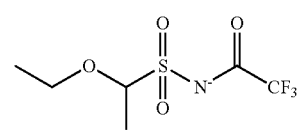
(A-8)
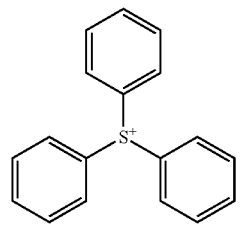 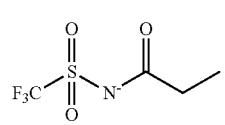
(A-9)
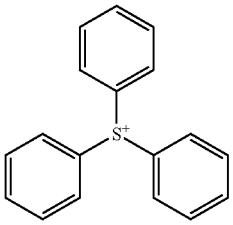 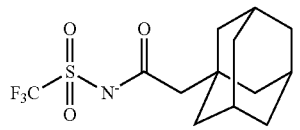
(A-10)
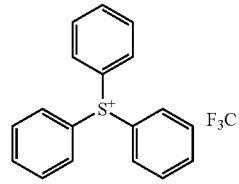 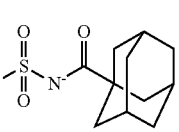
(A-11)
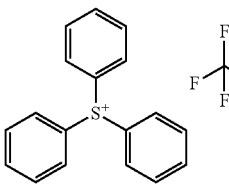 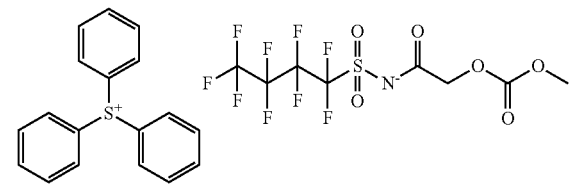
(A-12)
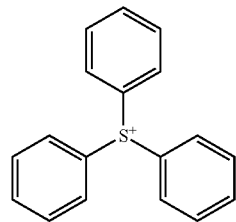 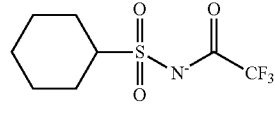
(A-13)
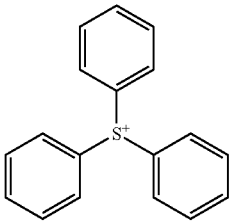 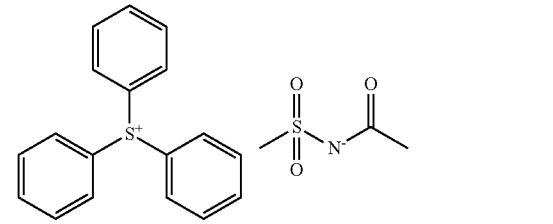
(A-14)
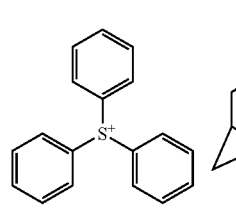 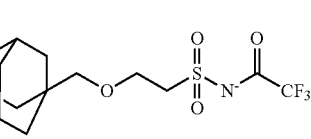
(A-15)
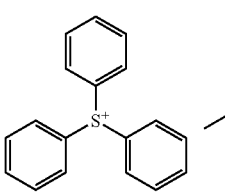 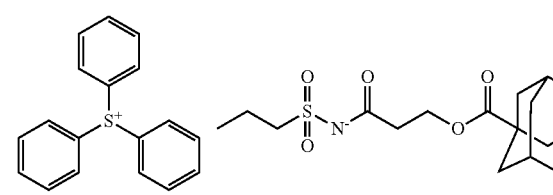
(A-16)
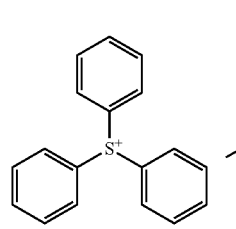 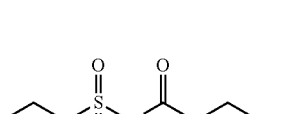
(A-17)
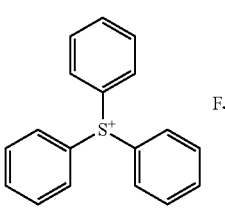 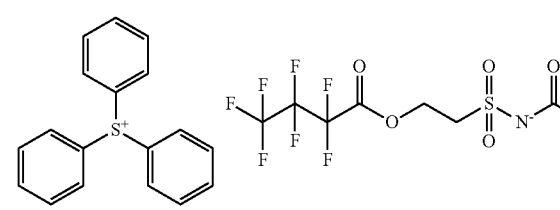
(A-18)
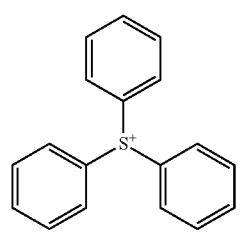 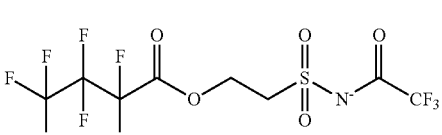

-continued
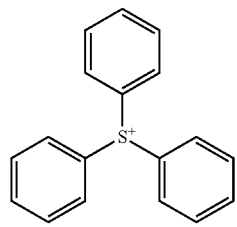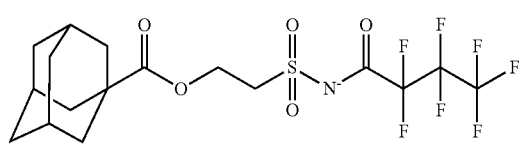
(A-19)
(A-20)
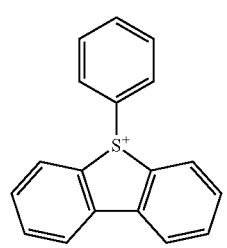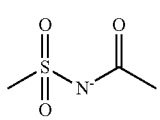
(A-21)
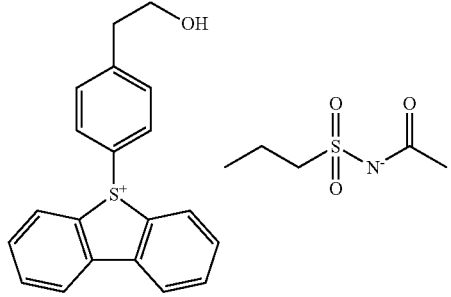
(A-22)
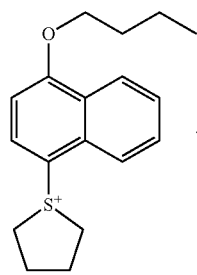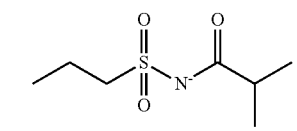
(A-23)
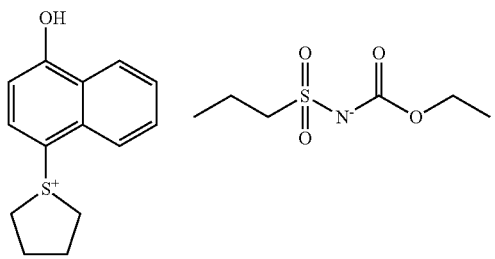
(A-24)
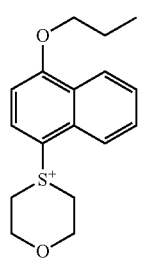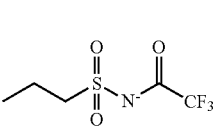
(A-25)
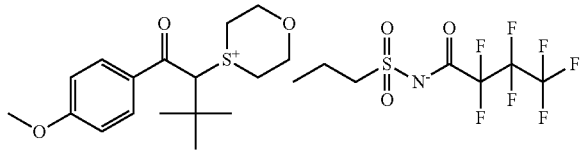
(A-26)
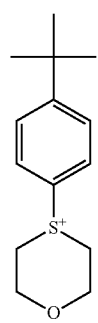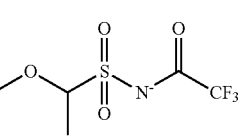
(A-27)
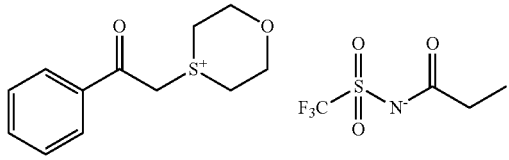

-continued
(A-28)
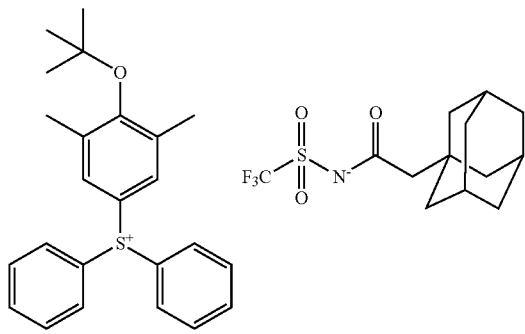
(A-29)
(A-30)
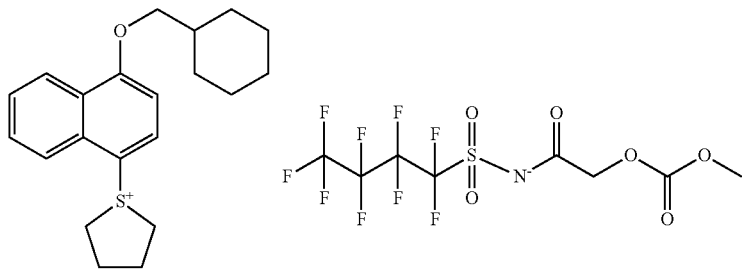
(A-31)
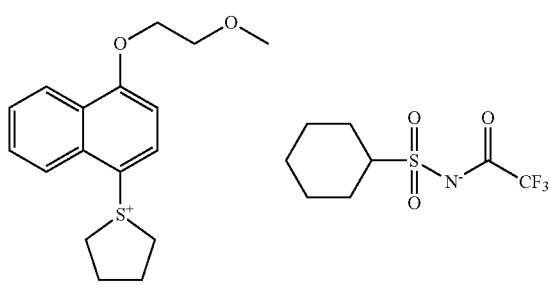
(A-32)
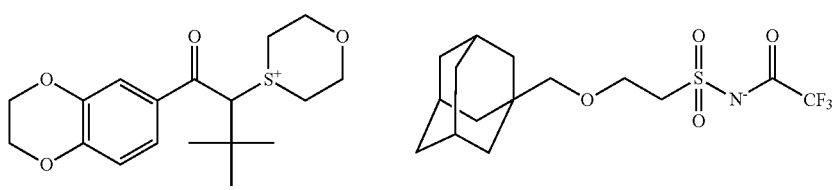
(A-33)
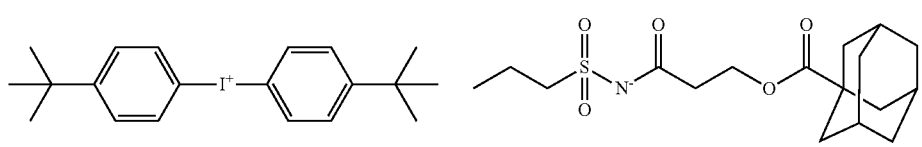
(A-34)
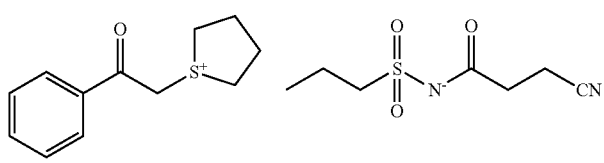
(A-35)
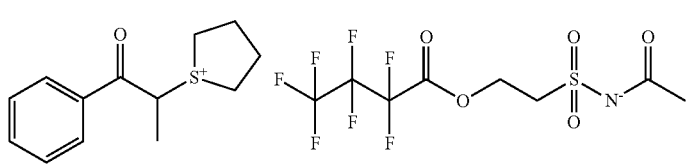

-continued
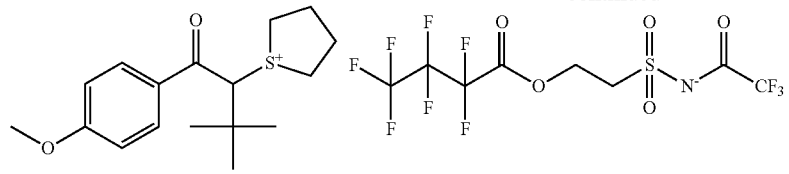
(A-36)
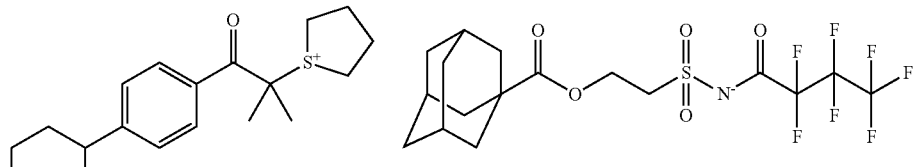
(A-37)
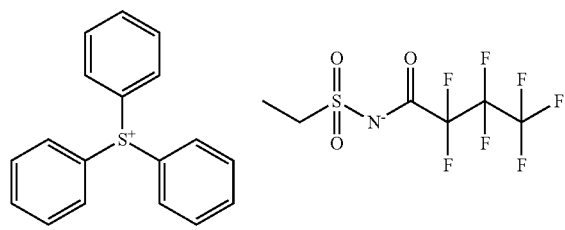
(A-38)
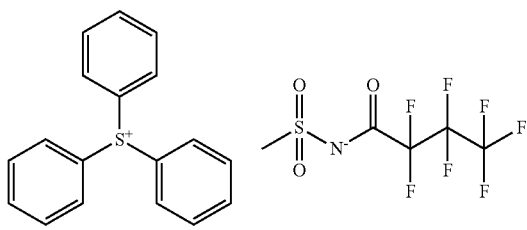
(A-39)
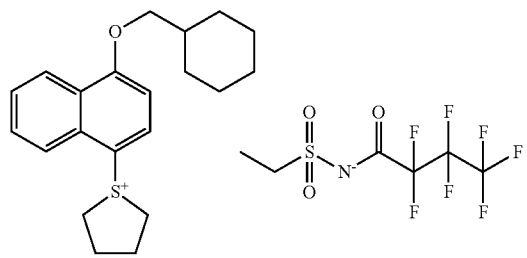
(A-40)
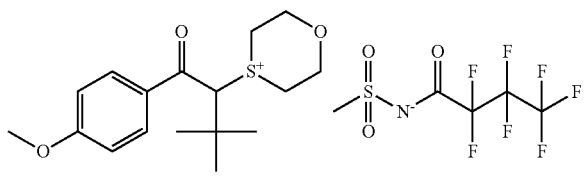
(A-41)
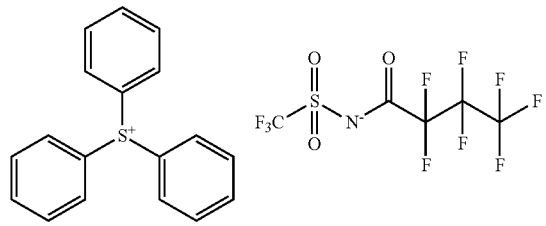
(A-42)
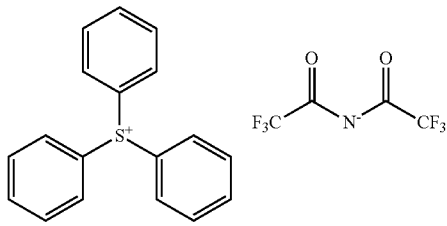
(A-43)
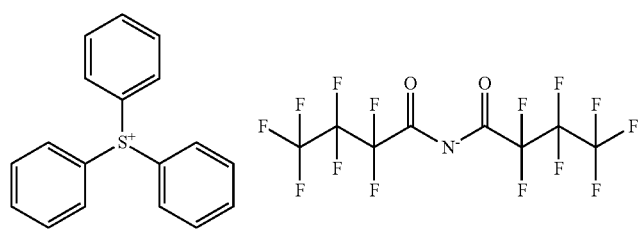
(A-44)
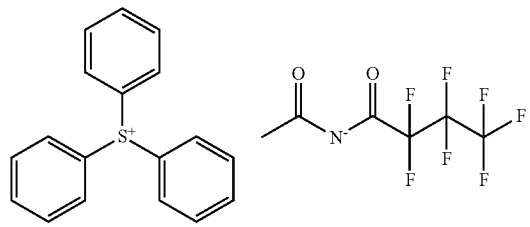
(A-45)
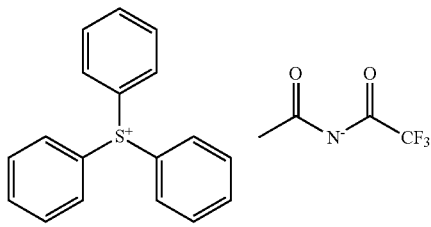
(A-46)

-continued
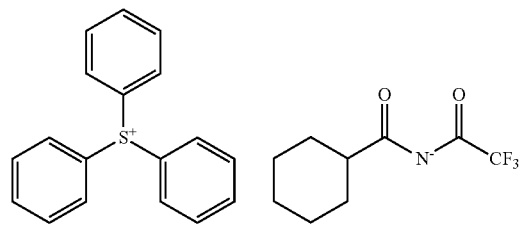
(A-47)
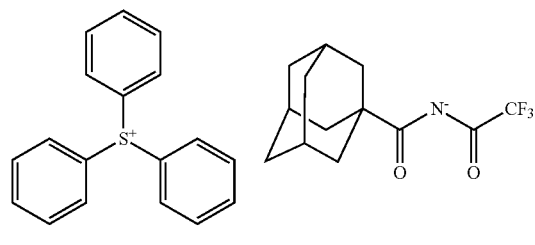
(A-48)
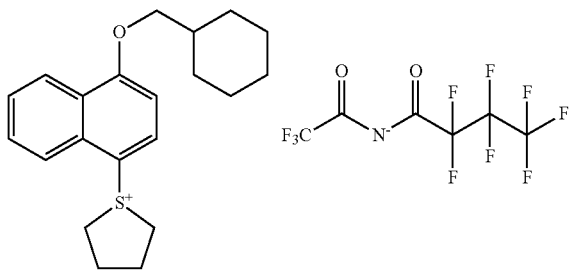
(A-49)
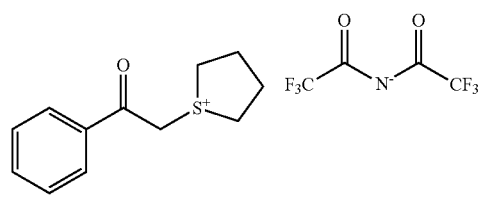
(A-50)
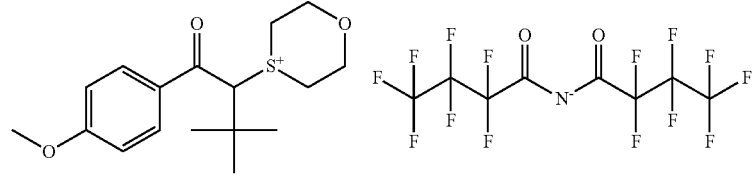
(A-51)
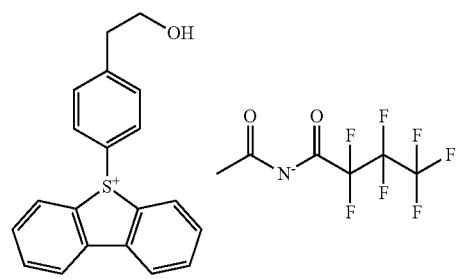
(A-52)
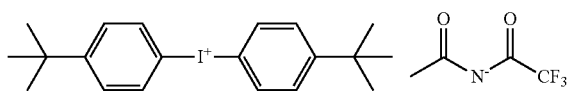
(A-53)
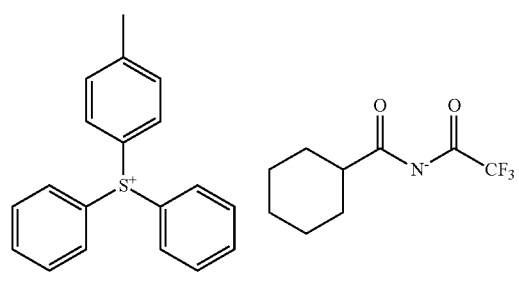
(A-54)
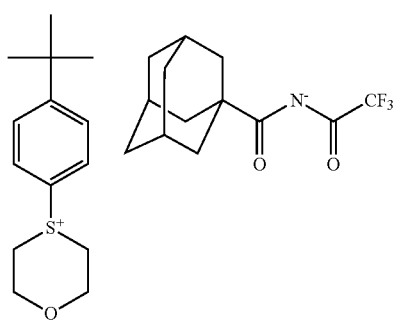
(A-55)

The anion of the compound (A) can be synthesized by various synthesis methods and, as an example, a general synthesis method when Y in formula (I-1) is —SO$_2$— is illustrated below (also when Y is —CO—, the synthesis can be performed in accordance with the following synthesis method).

X represents a halogen atom.

Each of R$_1$ and R$_1$' independently represents a monovalent organic group.

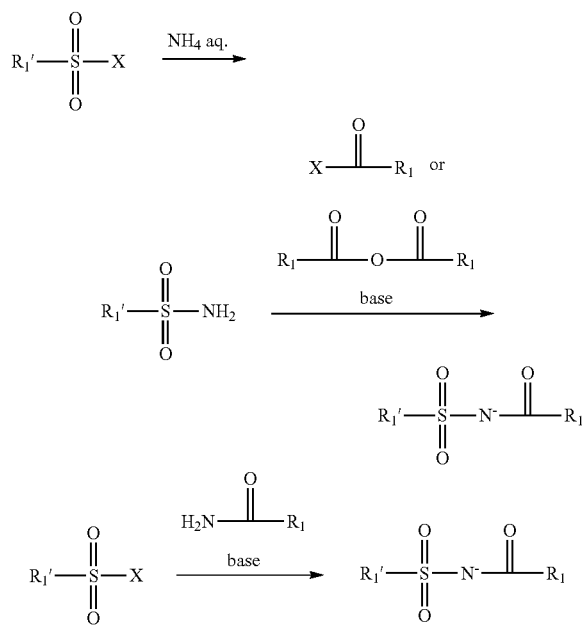

[2] (B) Compound Different from the Compound (A) and Capable of Generating an Acid Upon Irradiation with an Actinic Ray or Radiation The composition of the present invention contains (B) a compound different from the compound (A) and capable of generating an acid upon irradiation with an actinic ray or radiation (hereinafter, sometimes referred to as "acid generator").

The acid generator is not particularly limited as long as it is a known compound, but the acid generator is preferably a compound represented by the following formula (ZI), (ZII) or (ZIII):

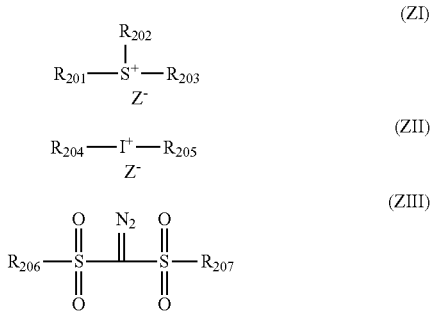

In formula (ZI), each of R$_{201}$, R$_{202}$ and R$_{203}$ independently represents an organic group.

The carbon number of the organic group as R$_{201}$, R$_{202}$ and R$_{203}$ is generally from 1 to 30, preferably from 1 to 20.

Two members out of R$_{201}$ to R$_{203}$ may combine to form a ring structure, and the ring may contain an oxygen atom, a sulfur atom, an ester bond, an amide bond or a carbonyl group. The group formed by combining two members out of R$_{201}$ to R$_{203}$ includes an alkylene group (such as butylene group and pentylene group).

The compound may be a compound having a plurality of structures represented by formula (ZI). For example, the compound may be a compound having a structure where at least one of R$_{201}$ to R$_{203}$ in a compound represented by formula (ZI) is bonded to at least one of R$_{201}$ to R$_{203}$ in another compound represented by formula (ZI) through a single bond or a linking group.

Z$^-$ represents a non-nucleophilic anion (an anion having an extremely low ability of causing a nucleophilic reaction).

Z$^-$ includes, for example, a sulfonate anion, a carboxylate anion, a sulfonylimide anion, a bis(alkylsulfonyl)imide anion, and a tris(alkylsulfonyl)methide anion.

The aliphatic moiety in the aliphatic sulfonate anion and aliphatic carboxylate anion may be an alkyl group or a cycloalkyl group and is preferably a linear or branched alkyl group having a carbon number of 1 to 30 or a cycloalkyl group having a carbon number of 3 to 30.

The aromatic group in the aromatic sulfonate anion and aromatic carboxylate anion is preferably an aryl group having a carbon number of 6 to 14.

The above-described alkyl group, cycloalkyl group and aryl group may have a substituent. Specific examples of the substituent include a nitro group, a halogen atom such as fluorine atom, a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), an alkylthio group (preferably having a carbon number of 1 to 15), an alkylsulfonyl group (preferably having a carbon number of 1 to 15), an alkyliminosulfonyl group (preferably having a carbon number of 2 to 15), an aryloxysulfonyl group (preferably having a carbon number of 6 to 20), an alkylaryloxysulfonyl group (preferably having a carbon number of 7 to 20), a cycloalkylaryloxysulfonyl group (preferably having a carbon number of 10 to 20), an alkyloxyalkyloxy group (preferably having a carbon number of 5 to 20), and a cycloalkylalkyloxyalkyloxy group (preferably having a carbon number of 8 to 20). The aryl group and ring structure in each group may further have an alkyl group (preferably having a carbon number of 1 to 15) as a substituent.

The aralkyl group in the aralkylcarboxylate anion is preferably an aralkyl group having a carbon number of 7 to 12.

Examples of the sulfonylimide anion include saccharin anion.

The alkyl group in the bis(alkylsulfonyl)imide anion and tris(alkylsulfonyl)methide anion is preferably an alkyl group having a carbon number of 1 to 5. The substituent on such an alkyl group includes a halogen atom, a halogen atom-substituted alkyl group, an alkoxy group, an alkylthio group, an alkyloxysulfonyl group, an aryloxysulfonyl group, a cycloalkylaryloxysulfonyl group and the like and is preferably a fluorine atom or a fluorine atom-substituted alkyl group.

Other examples of $Z^-$ include fluorinated phosphorus (e.g., $PF_6^-$), fluorinated boron (e.g., $BF_4^-$), and fluorinated antimony (e.g., $SbF_6^-$).

$Z^-$ is preferably an aliphatic sulfonate anion substituted with a fluorine atom at least on the α-position of sulfonic acid, an aromatic sulfonate anion substituted with a fluorine atom or a fluorine atom-containing group, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a perfluoroaliphatic sulfonate anion (preferably having a carbon number of 4 to 8) or a benzenesulfonate anion having a fluorine atom.

In view of acid strength, the pKa of the acid generated is preferably −1 or less so as to enhance the sensitivity.

The organic group of $R_{201}$, $R_{202}$ and $R_{203}$ includes an aryl group (preferably having a carbon number of 6 to 15), a linear or branched alkyl group (preferably having a carbon number of 1 to 10), a cycloalkyl group (preferably having a carbon number of 3 to 15), and the like.

At least one of $R_{201}$, $R_{202}$ and $R_{203}$ is preferably an aryl group, and it is more preferred that all of those three members are an aryl group. The aryl group may be a heteroaryl group such as indole residue and pyrrole residue, other than a phenyl group, a naphthyl group or the like.

The aryl group, alkyl group and cycloalkyl group as $R_{201}$, $R_{202}$ and $R_{203}$ may further have a substituent. Examples of the substituent include, but are not limited to, a nitro group, a halogen atom such as fluorine atom, a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), and an alkoxycarbonyloxy group (preferably having a carbon number of 2 to 7).

Also, two members selected from $R_{201}$, $R_{202}$ and $R_{203}$ may combine through a single bond or a linking group. Examples of the linking group include, but are not limited to, an alkylene group (preferably having a carbon number of 1 to 3), —O—, —S—, —CO— and —$SO_2$—.

Preferred structures where at least one of $R_{201}$, $R_{202}$ and $R_{203}$ is not an aryl group include cation structures such as compounds illustrated in paragraphs 0046 and 0047 of JP-A-2004-233661 and paragraphs 0040 to 0046 of JP-A-2003-35948, compounds illustrated as formulae (I-1) to (I-70) in U.S. Patent Application Publication No. 2003/0224288A1, and compounds illustrated as formulae (IA-1) to (IA-54) and formulae (IB-1) to (IB-24) in U.S. Patent Application Publication No. 2003/0077540A1.

More preferred examples of the compound represented by formula (ZI) include a compound represented by formula (ZI-3) or (ZI-4) described below. First, the cation represented by formula (ZI-3) is described.

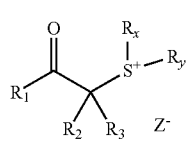

(ZI-3)

In formula (ZI-3), $R_1$ represents an alkyl group, a cycloalkyl group, an alkoxy group, a cycloalkoxy group, an aryl group or an alkenyl group, each of $R_2$ and $R_3$ independently represents a hydrogen atom, an alkyl group, a cycloalkyl group or an aryl group, and $R_2$ and $R_3$ may combine with each other to form a ring, $R_1$ and $R_2$ may combine with each other to form a ring, each of $R_x$ and $R_y$ independently represents an alkyl group, a cycloalkyl group, an alkenyl group, an aryl group, a 2-oxoalkyl group, a 2-oxocycloalkyl group, an alkoxycarbonylalkyl group or an alkoxycarbonylcycloalkyl group, $R_x$ and $R_y$ may combine with each other to form a ring structure, and this ring structure may contain an oxygen atom, a nitrogen atom, a sulfur atom, a ketone group, an ether bond, an ester bond or an amide bond, and $Z^-$ represents a non-nucleophilic anion.

The alkyl group as $R_1$ is preferably a linear or branched alkyl group having a carbon number of 1 to 20 and may contain an oxygen atom, a sulfur atom or a nitrogen atom in the alkyl chain. The alkyl group specifically includes a linear alkyl group such as methyl group, ethyl group, n-propyl group, n-butyl group, n-pentyl group, n-hexyl group, n-octyl group, n-dodecyl group, n-tetradecyl group and n-octadecyl group, and a branched alkyl group such as isopropyl group, isobutyl group, tert-butyl group, neopentyl group and 2-ethylhexyl group. The alkyl group of $R_1$ may have a substituent, and the alkyl group having a substituent includes a cyanomethyl group, a 2,2,2-trifluoroethyl group, a methoxycarbonylmethyl group, an ethoxycarbonylmethyl group and the like.

The cycloalkyl group as $R_1$ is preferably a cycloalkyl group having a carbon number of 3 to 20 and may contain an oxygen atom or a sulfur atom in the ring. Specifically, the cycloalkyl group includes a cyclopropyl group, a cyclopentyl group, a cyclohexyl group, a norbornyl group, an adamantyl group and the like. The cycloalkyl group of $R_1$ may have a substituent, and examples of the substituent include an alkyl group and an alkoxy group.

The alkoxy group as $R_1$ is preferably an alkoxy group having a carbon number of 1 to 20 and specifically includes a methoxy group, an ethoxy group, an isopropyloxy group, a tert-butyloxy group, a tert-amyloxy group, and an n-butyloxy group. The alkoxy group of $R_1$ may have a substituent, and examples of the substituent include an alkyl group and a cycloalkyl group.

The cycloalkoxy group as $R_1$ is preferably a cycloalkoxy group having a carbon number of 3 to 20 and includes a cyclohexyloxy group, a norbornyloxy group, an adamantyloxy group and the like. The cycloalkoxy group of $R_1$ may have a substituent, and examples of the substituent include an alkyl group and a cycloalkyl group.

The aryl group as $R_1$ is preferably an aryl group having a carbon number of 6 to 14 and includes, for example, a phenyl group, a naphthyl group, and a biphenyl group. The aryl group of $R_1$ may have a substituent, and preferred substituents include an alkyl group, a cycloalkyl group, an alkoxy group, a cycloalkoxy group, an aryloxy group, an alkylthio group, and an arylthio group. In the case where the substituent is an alkyl group, a cycloalkyl group, an alkoxy group or a cycloalkoxy group, examples of these groups are the same as those of the above-described alkyl group, cycloalkyl group, alkoxy group and cycloalkoxy group of $R_1$.

The alkenyl group as $R_1$ includes a vinyl group and an allyl group.

Each of $R_2$ and $R_3$ represents a hydrogen atom, an alkyl group, a cycloalkyl group or an aryl group, and $R_2$ and $R_3$ may combine with each other to form a ring. However, at least one of $R_2$ and $R_3$ represents an alkyl group, a cycloalkyl group or an aryl group. Specific examples and preferred examples of the alkyl group, cycloalkyl group and aryl group of $R_2$ and $R_3$ are the same as specific examples and preferred examples recited above for $R_1$. In the case where $R_2$ and $R_3$ combine with each other to form a ring, the total number of carbon atoms contributing to the formation of a ring, contained in $R_2$ and $R_3$, is preferably from 4 to 7, more preferably 4 or 5.

$R_1$ and $R_2$ may combine with each other to form a ring. In the case where $R_1$ and $R_2$ combine with each other to form a ring, it is preferred that $R_1$ is an aryl group (preferably a phenyl or naphthyl group which may have a substituent) and $R_2$ is an alkylene group having a carbon number of 1 to 4 (preferably a methylene group or an ethylene group), and preferred substituents are the same as those recited above for the substituent which may be substituted on an aryl group as $R_1$. In another preferred embodiment when $R_1$ and $R_2$ combine with each other to form a ring, $R_1$ is a vinyl group and $R_2$ is an alkylene group having a carbon number of 1 to 4.

The alkyl group represented by $R_x$ and $R_y$ is preferably an alkyl group having a carbon number of 1 to 15, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

The cycloalkyl group represented by $R_x$ and $R_y$ is preferably a cycloalkyl group having a carbon number of 3 to 20, and examples thereof include a cyclopropyl group, a cyclopentyl group, a cyclohexyl group, a norbornyl group and an adamantyl group.

The alkenyl group represented by $R_x$ and $R_y$ is preferably an alkenyl group having a carbon number of 2 to 30, and examples thereof include a vinyl group, an allyl group and a styryl group.

The aryl group represented by $R_x$ and $R_y$ is preferably, for example, an aryl group having a carbon number of 6 to 20 and specifically thereof includes a phenyl group, a naphthyl group, an azulenyl group, an acenaphthylenyl group, a phenanthrenyl group, a phenalenyl group, a phenanthracenyl group, a fluorenyl group, an anthracenyl group, a pyrenyl group, a benzopyrenyl group and the like. A phenyl group and a naphthyl group are preferred, and a phenyl group is more preferred.

The alkyl group moiety in the 2-oxoalkyl group and alkoxycarbonylalkyl group represented by $R_x$ and $R_y$ includes, for example, those recited above for $R_x$ and $R_y$.

The cycloalkyl group moiety in the 2-oxocycloalkyl group and alkoxycarbonylcycloalkyl group represented by $R_x$ and $R_y$ includes, for example, those recited above for $R_x$ and $R_y$.

$Z^-$ includes, for example, those recited above as $Z^-$ in formula (ZI).

The compound represented by formula (ZI-3) is preferably a compound represented by the following formula (ZI-3a) or (ZI-3b):

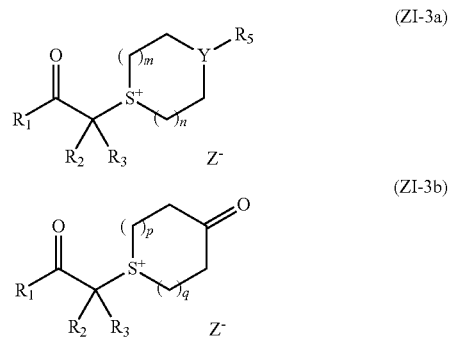

In formulae (ZI-3a) and (ZI-3b), $R_1$, $R_2$ and $R_3$ are as defined above in formula (ZI-3).

Y represents an oxygen atom, a sulfur atom or a nitrogen atom and is preferably an oxygen atom or a nitrogen atom. Each of m, n, p and q represents an integer and is preferably from 0 to 3, more preferably 1 or 2, still more preferably 1. The alkylene group connecting $S^+$ and Y may have a substituent, and preferred substituents include an alkyl group.

$R_5$ represents a monovalent organic group when Y is a nitrogen atom, and is not present when Y is an oxygen atom or a sulfur atom. $R_5$ is preferably a group containing an electron-withdrawing group, more preferably a group represented by any one of the following formulae (ZI-3a-1) to (ZI-3a-4):

In formulae (ZI-3a-1) to (ZI-3a-3), R represents a hydrogen atom, an alkyl group, a cycloalkyl group or an aryl group and is preferably an alkyl group. Specific examples and preferred examples of the alkyl group, cycloalkyl group and aryl group of R are the same as specific examples and preferred examples recited above for $R_1$ in formula (ZI-3).

In (ZI-3a-1) to (ZI-3a-4), * represents a bond connected to the nitrogen atom as Y in the compound represented by formula (ZI-3a).

When Y is a nitrogen atom, $R_5$ is preferably a group represented by $-SO_2-R_4$. $R_4$ represents an alkyl group, a cycloalkyl group or an aryl group and is preferably an alkyl group. Specific examples and preferred examples of the alkyl group, cycloalkyl group and aryl group of $R_4$ are the same as specific examples and preferred examples recited above for $R_1$.

Z⁻ includes, for example, those recited above as Z⁻ in formula (ZI).

The compound represented by formula (ZI-3) is more preferably a compound represented by the following formula (ZI-3a') or (ZI-3b'):

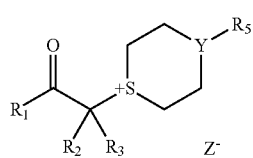
(ZI-3a')

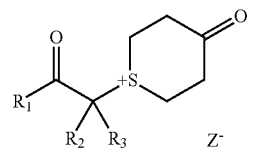
(ZI-3b')

In formulae (ZI-3a') and (ZI-3b'), $R_1$, $R_2$, $R_3$, Y and $R_5$ are as defined in formulae (ZI-3a) and (ZI-3b).

Z⁻ includes, for example, those recited above as Z⁻ in formula (ZI).

Specific examples of the cation moiety in the compound represented by formula (ZI-3) are illustrated below.

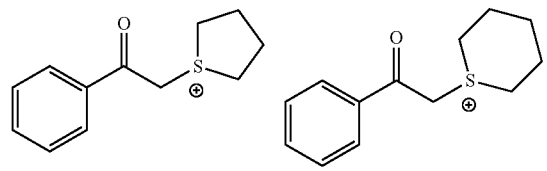

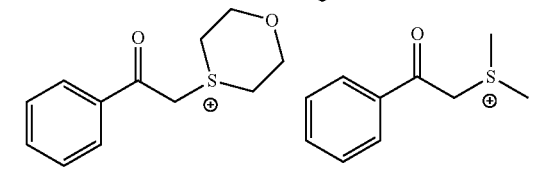

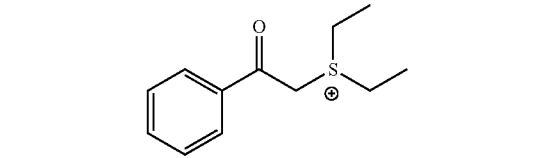

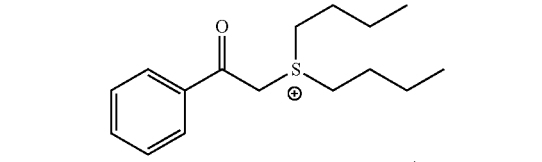

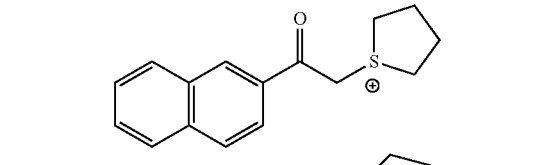

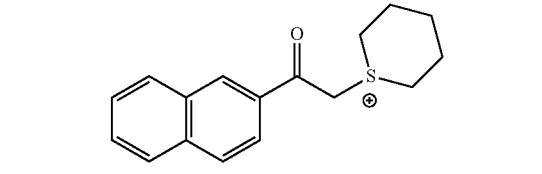

-continued

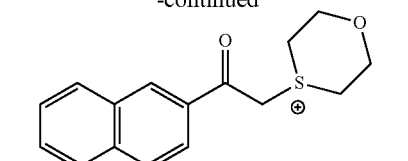

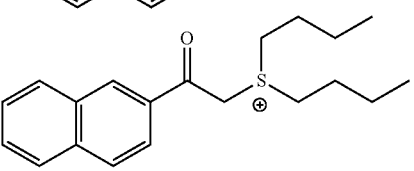

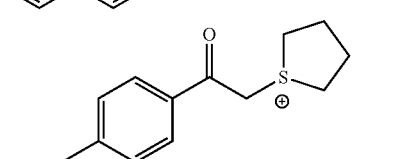

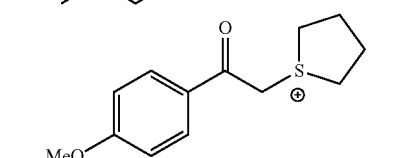

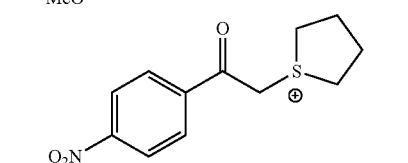

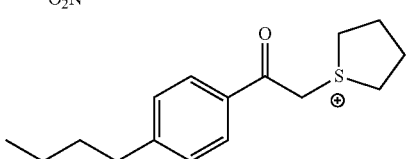

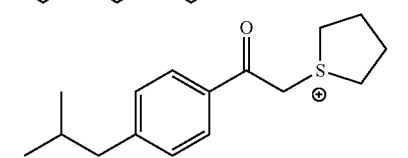

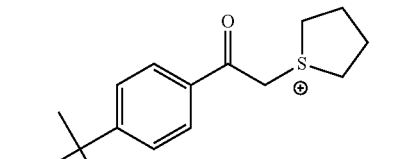


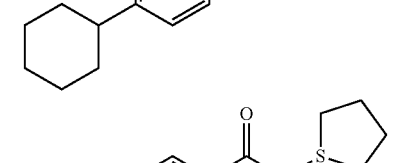

31
-continued
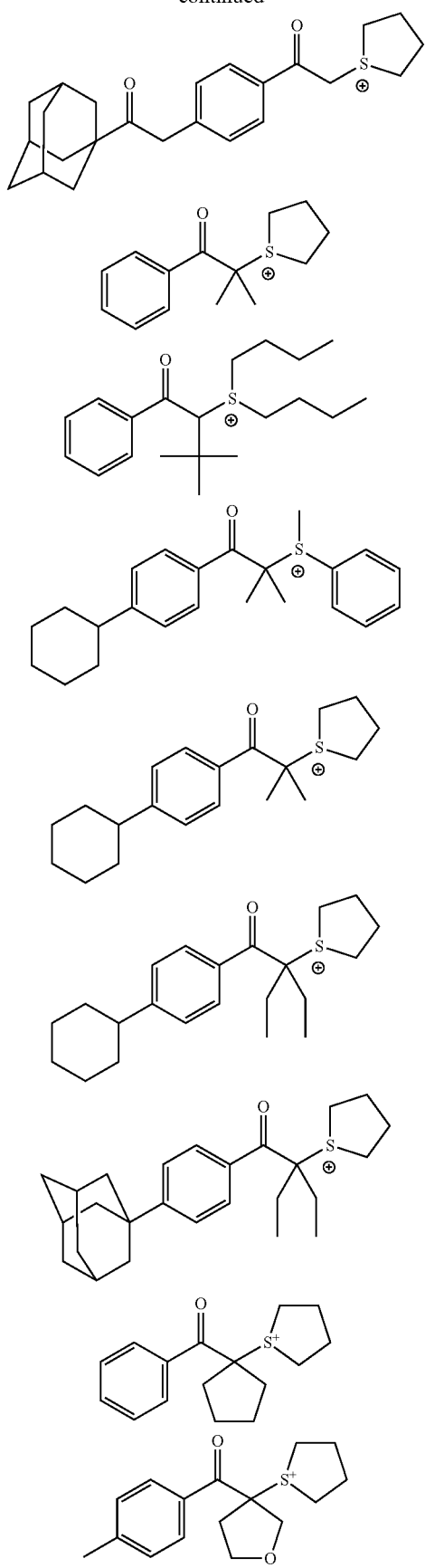
32
-continued
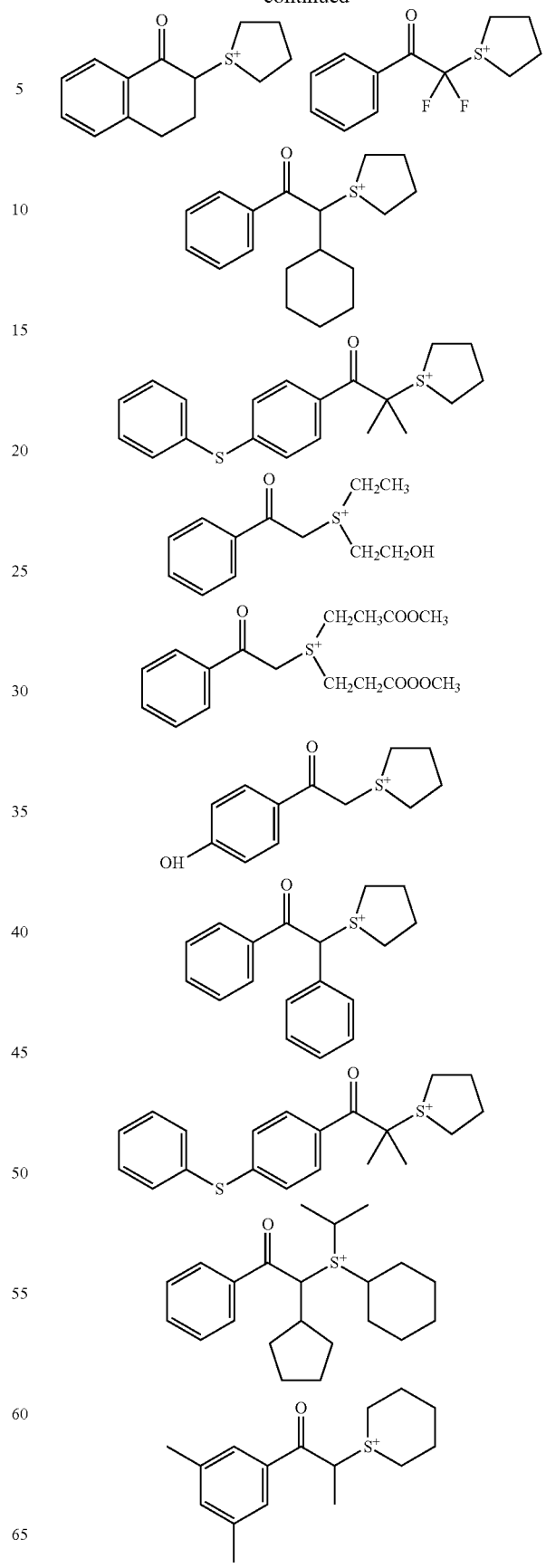

-continued

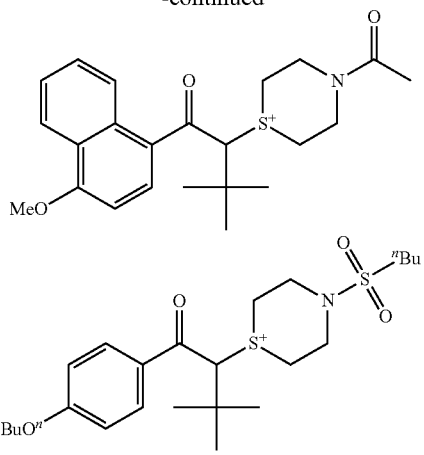

The compound represented by formula (ZI-4) is described below.

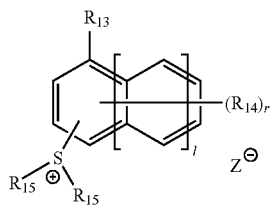

(ZI-4)

In formula (ZI-4), $R_{13}$ represents a hydrogen atom, a fluorine atom, a hydroxyl group, an alkyl group, a cycloalkyl group, an alkoxy group, an alkoxycarbonyl group or a group having a cycloalkyl group. These groups may have a substituent.

$R_{14}$ represents, when a plurality of $R_{14}$ are present, each independently represents, a hydroxyl group, an alkyl group, a cycloalkyl group, an alkoxy group, an alkoxycarbonyl group, an alkylcarbonyl group, an alkylsulfonyl group, a cycloalkylsulfonyl group or a group having a cycloalkyl group. These groups may have a substituent.

Each $R_{15}$ independently represents an alkyl group, a cycloalkyl group or a naphthyl group. Two $R_{15}$ may combine with each other to form a ring, and the ring may contain, as an atom constituting the ring, a heteroatom such as oxygen atom, sulfur atom and nitrogen atom. The groups above may have a substituent.

l represents an integer of 0 to 2.

r represents an integer of 0 to 8.

$Z^-$ represents a non-nucleophilic anion and includes the same nucleophilic anions as $Z^-$ in formula (ZI).

In formula (ZI-4), the alkyl group of $R_{13}$, $R_{14}$ and $R_{15}$ is linear or branched and is preferably an alkyl group having a carbon number of 1 to 10.

The cycloalkyl group of $R_{13}$, $R_{14}$ and $R_{15}$ includes a monocyclic or polycyclic cycloalkyl group.

The alkoxy group of $R_{13}$ and $R_{14}$ is linear or branched and is preferably an alkoxy group having a carbon number of 1 to 10.

The alkoxycarbonyl group of $R_{13}$ and $R_{14}$ is linear or branched and is preferably an alkoxycarbonyl group having a carbon number of 2 to 11.

The group having a cycloalkyl group of $R_{13}$ and $R_{14}$ includes a group having a monocyclic or polycyclic cycloalkyl group. These groups may further have a substituent.

Specific examples of the alkyl group in the alkylcarbonyl group of $R_{14}$ are the same as those recited above for the alkyl group of $R_{13}$ to $R_{15}$.

The alkylsulfonyl or cycloalkylsulfonyl group of $R_{14}$ is linear, branched or cyclic and is preferably an alkylsulfonyl or cycloalkylsulfonyl group having a carbon number of 1 to 10.

The substituent which each of the groups above may have includes a halogen atom (e.g., fluorine atom), a hydroxyl group, a carboxyl group, a cyano group, a nitro group, an alkoxy group, an alkoxyalkyl group, an alkoxycarbonyl group, an alkoxycarbonyloxy group and the like.

The ring structure which may be formed by combining two $R_{15}$ with each other includes a 5- or 6-membered ring formed by two $R_{15}$ together with the sulfur atom in formula (ZI-4), preferably a 5-membered ring (that is, a tetrahydrothiophene ring or a 2,5-dihydrothiophene ring), and may be fused with an aryl group or a cycloalkyl group. The divalent $R_{15}$ may have a substituent, and the substituent includes, for example, a hydroxyl group, a carboxyl group, a cyano group, a nitro group, an alkyl group, a cycloalkyl group, an alkoxy group, an alkoxyalkyl group, an alkoxycarbonyl group, and an alkoxycarbonyloxy group. As for the substituent on the ring structure, a plurality of substituents may be present, and these substituents may combine with each other to form a ring.

In formula (ZI-4), $R_{15}$ is preferably, for example, a methyl group, an ethyl group, a naphthyl group, or a divalent group capable of forming a tetrahydrothiophene ring structure together with the sulfur atom when two $R_{15}$ are combined with each other, more preferably a divalent group capable of forming a tetrahydrothiophene ring structure together with the sulfur atom when two $R_{15}$ are combined with each other.

The substituent which $R_{13}$ and $R_{14}$ may have is preferably a hydroxyl group, an alkoxy group, an alkoxycarbonyl group, or a halogen atom (particularly fluorine atom).

l is preferably 0 or 1, more preferably 1.

r is preferably from 0 to 2.

Specific examples of the cation structure in the cation represented by formula (ZI-3) or (ZI-4) include cation structures in the chemical structures illustrated in paragraphs 0046, 0047, 0072 to 0077 and 0107 to 0110 of JP-A-2011-53360 and cation structures in the chemical structures illustrated in paragraphs 0135 to 0137, 0151 and 0196 to 0199 of JP-A-2011-53430, in addition to the above-described cation structures such as compounds illustrated in JP-A-2004-233661, JP-A-2003-35948 and U.S. Patent Application Publication Nos. 2003/0224288A1 and 2003/0077540A1.

In formulae (ZII) and (ZIII), each of $R_{204}$ to $R_{207}$ independently represents an aryl group, an alkyl group or a cycloalkyl group.

The aryl group, alkyl group and cycloalkyl group of $R_{204}$ to $R_{207}$ are the same as the aryl group, alkyl group and cycloalkyl group of $R_{201}$ to $R_{203}$ in the compound (ZI).

The aryl group, alkyl group and cycloalkyl group of $R_{204}$ to $R_{207}$ may have a substituent. This substituent also includes those which the aryl group, alkyl group and cycloalkyl group of $R_{201}$ to $R_{203}$ in the compound (ZI) may have.

$Z^-$ includes, for example, those recited above as $Z^-$ in formula (ZI).

Other than the compound represented by formula (ZI-3) or (ZI-4), a compound represented by the following formula (I') is also preferred as the acid generator. By virtue of using the compound represented by the following formula (I'), the transparency to exposure light is enhanced and LWR and DOF are improved.

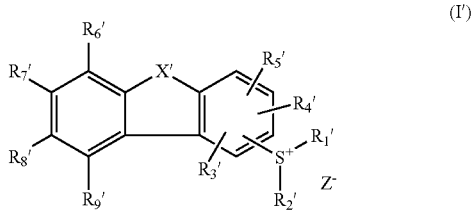

In formula (I'), X' represents an oxygen atom, a sulfur atom or —N(Rx)-.

Each of $R_1'$ and $R_2'$ independently represents an alkyl group, a cycloalkyl group or an aryl group.

Each of $R_3'$ to $R_9'$ independently represents a hydrogen atom, an alkyl group, a cycloalkyl group, an alkoxy group, an alkoxycarbonyl group, an acyl group, an alkylcarbonyloxy group, an aryl group, an aryloxy group, an aryloxycarbonyl group or an arylcarbonyloxy group.

Rx represents a hydrogen atom, an alkyl group, a cycloalkyl group, an acyl group, an alkenyl group, an alkoxycarbonyl group, an aryl group, an arylcarbonyl group or an aryloxycarbonyl group.

$R_1'$ and $R_2'$ may combine with each other to form a ring. Also, any two or more members out of $R_6'$ to $R_9'$, a pair of $R_3'$ and $R_9'$, a pair of $R_4'$ and $R_5'$, a pair of $R_5'$ and Rx, or a pair of $R_6'$ and Rx may combine with each other to form a ring.

X' is preferably a sulfur atom or —N(Rx)- from the standpoint of keeping the absorbancy (for example, absorbance at a wavelength of 193 nm) low.

$Z^-$ includes, for example, those recited above as Z in formula (ZI).

The alkyl group as $R_1'$ to $R_9'$ and Rx may have a substituent and is preferably a linear or branched alkyl group having a carbon number of 1 to 20, and the alkyl group may contain an oxygen atom, a sulfur atom or a nitrogen atom in the alkyl chain. The alkyl group specifically includes a linear alkyl group such as methyl group, ethyl group, n-propyl group, n-butyl group, n-pentyl group, n-hexyl group, n-octyl group, n-dodecyl group, n-tetradecyl group and n-octadecyl group, and a branched alkyl group such as isopropyl group, isobutyl group, tert-butyl group, neopentyl group and 2-ethylhexyl group.

Incidentally, the alkyl group having a substituent of Rx includes a cyanomethyl group, a 2,2,2-trifluoroethyl group, a methoxycarbonylmethyl group, an ethoxycarbonylmethyl group and the like.

The alkyl group having a substituent of $R_1'$ and $R_2'$ includes a methoxyethyl group and the like.

Other examples include a group formed by substituting a cycloalkyl group on a linear or branched alkyl group (for example, an adamantylmethyl group, an adamantylethyl group, a cyclohexylethyl group and a camphor residue).

The cycloalkyl group as $R_1'$ to $R_9'$ and Rx may have a substituent and is preferably a cycloalkyl group having a carbon number of 3 to 20, and the cycloalkyl group may contain an oxygen atom in the ring and specifically includes a cyclopropyl group, a cyclopentyl group, a cyclohexyl group, a norbornyl group, an adamantyl group and the like.

The acyl group as $R_3'$ to $R_9'$ and Rx may have a substituent and is preferably an acyl group having a carbon number of 1 to 10. The acyl group specifically includes an acetyl group, a propionyl group, an isobutyryl group and the like.

The alkenyl group as Rx is preferably an alkenyl group having a carbon number of 2 to 8 and includes, for example, a vinyl group, an allyl group, and a butenyl group.

The alkoxy group as $R_3'$ to $R_9'$ may have a substituent and is preferably an alkoxy group having a carbon number of 1 to 20. The alkoxy group specifically includes a methoxy group, an ethoxy group, an isopropyloxy group, a cyclohexyloxy group and the like.

The alkoxycarbonyl group as $R_3'$ to $R_9'$ may have a substituent and is preferably an alkoxycarbonyl group having a carbon number of 2 to 20. The alkoxycarbonyl group specifically includes a methoxycarbonyl group, an ethoxycarbonyl group, an isopropyloxycarbonyl group, a cyclohexyloxycarbonyl group and the like.

The alkylcarbonyloxy group as $R_3'$ to $R_9'$ may have a substituent and is preferably an alkylcarbonyloxy group having a carbon number of 2 to 20. The alkylcarbonyloxy group specifically includes a methylcarbonyloxy group, an ethylcarbonyloxy group, an isopropylcarbonyloxy group, a cyclohexylcarbonyloxy group and the like.

The aryl group as $R_1'$ to $R_9'$ and Rx may have a substituent and is preferably an aryl group having a carbon number of 6 to 14, and the aryl group includes, for example, a phenyl group and a naphthyl group.

The aryloxy group as $R_3'$ to $R_9'$ may have a substituent and is preferably an aryloxy group having a carbon number of 6 to 14, and aryloxy group includes, for example, a phenyloxy group and a naphthyloxy group.

The aryloxycarbonyl group as $R_3'$ to $R_9'$ and Rx may have a substituent and is preferably an aryloxycarbonyl group having a carbon number of 7 to 15, and the aryloxycarbonyl group includes, for example, a phenyloxycarbonyl group and a naphthyloxycarbonyl group.

The arylcarbonyloxy group as $R_3'$ to $R_9'$ may have a substituent and is preferably an arylcarbonyloxy group having a carbon number of 7 to 15, and the arylcarbonyloxy group includes, for example, a phenylcarbonyloxy group and a naphthylcarbonyloxy group.

The arylcarbonyl group as Rx may have a substituent and is preferably an arylcarbonyl group having a carbon number of 7 to 15, and the arylcarbonyl group includes, for example, a phenylcarbonyl group and a naphthylcarbonyl group.

The substituent which each of the alkyl group as $R_3'$ to $R_9'$, the cycloalkyl group as $R_1'$ to $R_9'$ and Rx, the acyl group as $R_3'$ to $R_9'$ and Rx, the alkoxy group as $R_3'$ to $R_9'$, the alkoxycarbonyl group as $R_3'$ to $R_9'$, the alkylcarbonyloxy group as $R_3'$ to $R_9'$, the aryl group as $R_1'$ to $R_9'$ and Rx, the aryloxy group as $R_3'$ to $R_9'$, the aryloxycarbonyl group as $R_3'$ to $R_9'$ and Rx, the arylcarbonyloxy group as $R_3'$ to $R_9'$, and the arylcarbonyl group as Rx may further have includes an alkyl group (may be linear, branched of cyclic, preferably having a carbon number of 1 to 12), an aryl group (preferably having a carbon number of 6 to 14), a nitro group, a halogen atom such as fluorine atom, a carboxyl group, a hydroxyl group, an amino group, a cyano group, an alkoxy group (preferably having a carbon number of 1 to 15), a cycloalkyl group (preferably having a carbon number of 3 to 15), an acyl group (preferably having a carbon number of 2 to 12), and the like.

The ring structure which may be formed by combining $R_1'$ and $R_2'$ with each other includes a 5- or 6-membered ring formed by divalent $R_1'$ and $R_2'$ (for example, an ethylene group, a propylene group or a 1,2-cyclohexylene group) together with the sulfur atom in formula (I'), preferably a 5-membered ring (that is, a tetrahydrothiophene ring). However, in view of decomposition efficiency for generation of an acid anion, $R_1'$ and $R_2'$ are preferably not combined with each other to form a ring.

The ring structure which may be formed by combining any two or more members out of $R_6'$ to $R_9'$, a pair of $R_3'$ and $R_9'$, a pair of $R_4'$ and $R_5'$, a pair of $R_5'$ and Rx, or a pair of $R_6'$ and Rx with each other is preferably a 5- or 6-membered ring, more preferably a 6-membered ring.

Each of $R_1'$ and $R_2'$ is preferably an alkyl group or an aryl group, among others.

Particularly preferred examples of $R_3'$ to $R_9'$ include an alkyl group which may have a substituent, and a hydrogen atom, but in the case of using the composition for an ArF resist, a hydrogen atom is more preferred in view of absorption intensity at 193 nm.

Rx is preferably an alkyl group or an acyl group, among others.

Formulae (2) and (2') which are preferred structures of the non-nucleophilic anion $Z^-$ are described below.

First, the sulfonate anion represented by formula (2) is described.

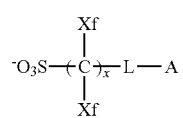

(2)

In formula (2), each Xf independently represents a fluorine atom or an alkyl group substituted with at least one fluorine atom, L represents a single bond or a divalent linking group and in the case where a plurality of L are present, each may be the same as or different from every other member, A represents an organic group having a cyclic structure, and x represents an integer of 1 to 20.

The anion of formula (2) is described in more detail.

Xf represents a fluorine atom or an alkyl group substituted with at least one fluorine atom, and the alkyl group in the fluorine atom-substituted alkyl group is preferably an alkyl group having a carbon number of 1 to 10, more preferably an alkyl group having a carbon number of 1 to 4. Also, the fluorine atom-substituted alkyl group of Xf is preferably a perfluoroalkyl group.

Xf is preferably a fluorine atom or a perfluoroalkyl group having a carbon number of 1 to 4 and specifically, is preferably a fluorine atom, $CF_3$, $CHF_2$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$, more preferably a fluorine atom, $CF_3$, $CHF_2$ or $C_2F_5$, and it is still more preferred that both Xf are a fluorine atom.

L represents a single bond or a divalent linking group, and the divalent linking group includes —COO—, —OCO—, —CO—, —O—, —S—, —SO—, —SO$_2$—, —N(Ri)- (wherein Ri represents a hydrogen atom or an alkyl group), an alkylene group (preferably having a carbon number of 1 to 6), a cycloalkylene group (preferably having a carbon number of 3 to 10), an alkenylene group (preferably having a carbon number of 2 to 6), a divalent linking group formed by combining a plurality of these members, and the like and is preferably —COO—, —OCO—, —CO—, —SO$_2$—, —CON(Ri)-, —SO$_2$N(Ri)-, —CON(Ri)-alkylene group,-, —N(Ri)CO-alkylene group-, —COO— alkylene group- or —OCO-alkylene group-, more preferably —COO—, —OCO—, —SO$_2$—, —CON(Ri)- or —SO$_2$N(Ri)-. In the case where a plurality of L are present, each may be the same as or different from every other member.

Specific examples and preferred examples of the alkyl group of Ri are the same as specific examples and preferred examples recited above for the alkyl group of $R_1'$ to $R_9'$.

The cyclic organic group of A is not particularly limited as long as it has a cyclic structure, and examples thereof include an alicyclic group and a heterocyclic group (including not only those having aromaticity but also those not having aromaticity, for example, including structures such as tetrahydropyran ring, lactone ring, sultone ring and cyclic ketone).

The alicyclic group may be monocyclic or polycyclic and is preferably a monocyclic cycloalkyl group such as cyclopentyl group, cyclohexyl group and cyclooctyl group, or a polycyclic cycloalkyl group such as norbornyl group, a norbornenyl group, a tricyclodecanyl group (for example, a tricyclo[5.2.1.0(2,6)]decanyl group), tetracyclodecanyl group, tetracyclododecanyl group and adamantyl group. In addition, a nitrogen atom-containing alicyclic group such as piperidine group, a decahydroquinoline group and decahydroisoquinoline group is also preferred. Above all, an alicyclic group having a bulky structure with a carbon number of 7 or more, such as norbornyl group, tricyclodecanyl group, tetracyclodecanyl group, tetracyclododecanyl group, adamantyl group, decahydroquinoline group and decahydroisoquinoline group, is preferred from the standpoint of suppressing in-film diffusion in the PEB (post-exposure baking) step and improving the exposure latitude.

The aryl group includes a benzene ring, a naphthalene ring, a phenanthrene ring, and an anthracene ring. Among these, naphthalene with low absorbance is preferred in view of absorbance for light at 193 nm.

The heterocyclic group includes a furan ring, a thiophene ring, a benzofuran ring, a benzothiophene ring, a dibenzofuran ring, a dibenzothiophene ring, and a pyridine ring. Among these, a furan ring, a thiophene ring and a pyridine ring are preferred.

The above-described cyclic organic group may have a substituent, and the substituent includes an alkyl group (may be linear, branched or cyclic; preferably having a carbon number of 1 to 12), an aryl group (preferably having a carbon number of 6 to 14), a hydroxy group, an alkoxy group, an ester group, an amido group, a urethane group, a ureido group, a thioether group, a sulfonamido group, a sulfonic acid ester group and the like.

Incidentally, the carbon constituting the cyclic organic group (the carbon contributing to ring formation) may be carbonyl carbon.

x is preferably from 1 to 8, more preferably from 1 to 4, still more preferably from 1 to 3, and most preferably 1.

The disulfonylimide acid anion represented by formula (2') is described below.

(2')

In formula (2'),

Xf is as defined in formula (2), and preferred examples are also the same. In formula (2'), two Xf may combine with each other to form a ring structure.

The disulfonylimide acid anion of $Z^-$ is preferably a bis(alkylsulfonyl)imide anion.

The alkyl group in the bis(alkylsulfonyl)imide anion is preferably an alkyl group having a carbon number of 1 to 5.

Two alkyl groups in the bis(alkylsulfonyl)imide anion may combine with each other to make an alkylene group (preferably having a carbon number of 2 to 4) and thereby form a ring together with the imide group and two sulfonyl groups. The ring structure which may be formed by the bis(alkylsulfonyl)imide anion is preferably a 5- to 7-membered ring, more preferably a 6-membered ring.

The substituent which may be substituted on the above-described alkyl group and the alkylene group formed by combining two alkyl groups with each other includes a halogen atom, a halogen atom-substituted alkyl group, an alkoxy group, an alkylthio group, an alkyloxysulfonyl group, an aryloxysulfonyl group, a cycloalkylaryloxysulfonyl group and the like and is preferably a fluorine atom or a fluorine atom-substituted alkyl group.

As $Z^-$, a sulfonate anion represented by the following formula (B-1) is also preferred:

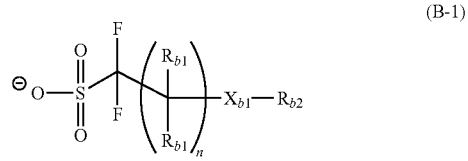

(B-1)

In formula (B-1), each $R_{b1}$ independently represents a hydrogen atom, a fluorine atom or a trifluoromethyl group ($CF_3$).

n represents an integer of 0 to 4.

n is preferably an integer of 0 to 3, more preferably 0 or 1.

$X_{b1}$ represents a single bond, an alkylene group, an ether bond, an ester bond (—OCO— or —COO—), a sulfonic acid ester bond (—OSO$_2$— or —SO$_3$—), or a combination thereof.

$X_{b1}$ is preferably an ester bond (—OCO— or —COO—) or a sulfonic acid ester bond (—OSO$_2$— or —SO$_3$—), more preferably an ester bond (—OCO— or —COO—).

$R_{b2}$ represents an organic group having a carbon number of 6 or more.

The organic group having a carbon number of 6 or more of $R_{b2}$ is preferably a bulky group, and examples thereof include an alkyl group, an alicyclic group, an aryl group, and a heterocyclic group, each having a carbon number of 6 or more.

The alkyl group having a carbon number of 6 or more of $R_{b2}$ may be linear or branched and is preferably a linear or branched alkyl group having a carbon number of 6 to 20, and examples thereof include a linear or branched hexyl group, a linear or branched heptyl group, and a linear or branched octyl group. In view of bulkiness, a branched alkyl group is preferred.

The alicyclic group having a carbon number of 6 or more of $R_{b2}$ may be monocyclic or polycyclic. The monocyclic alicyclic group includes, for example, a monocyclic cycloalkyl group such as cyclohexyl group and cyclooctyl group. The polycyclic alicyclic group includes, for example, a polycyclic cycloalkyl group such as norbornyl group, tricyclodecanyl group, tetracyclodecanyl group, tetracyclododecanyl group and adamantyl group. Above all, an alicyclic group having a bulky structure with a carbon number of 7 or more, such as norbornyl group, tricyclodecanyl group, tetracyclodecanyl group, tetracyclododecanyl group and adamantyl group, is preferred from the standpoint of suppressing in-film diffusion in the PEB (post-exposure baking) step and improving MEEF (Mask Error Enhancement Factor).

The aryl group having a carbon number of 6 or more of $R_{b2}$ may be monocyclic or polycyclic. This aryl group includes, for example, a phenyl group, a naphthyl group, a phenanthryl group, and an anthryl group. Among these, a naphthyl group having a relatively low absorbance at 193 nm is preferred.

The heterocyclic group having a carbon number of 6 or more of $R_{b2}$ may be monocyclic or polycyclic, but a polycyclic heterocyclic group can more suppress diffusion of an acid. Also, the heterocyclic group may have aromaticity or may not have aromaticity. The heterocyclic ring having aromaticity includes, for example, a benzofuran ring, a benzothiophene ring, a dibenzofuran ring, and a dibenzothiophene ring. The heterocyclic ring not having aromaticity includes, for example, a tetrahydropyran ring, a lactone ring, a sultone ring, and a decahydroisoquinoline ring.

The substituent having a carbon number of 6 or more of $R_{b2}$ may further have a substituent. This further substituent includes, for example, an alkyl group (may be linear or branched; preferably having a carbon number of 1 to 12), a cycloalkyl group (may be monocyclic, polycyclic or spirocyclic; preferably having a carbon number of 3 to 20), an aryl group (preferably having a carbon number of 6 to 14), a hydroxy group, an alkoxy group, an ester group, an amido group, a urethane group, a ureido group, a thioether group, a sulfonamido group, and a sulfonic acid ester group. Incidentally, the carbon constituting the above-described alicyclic group, aryl group or heterocyclic group (the carbon contributing to ring formation) may be carbonyl carbon.

Specific examples of the sulfonate anion structure represented by formula (B-1) are illustrated below, but the present invention is not limited thereto.

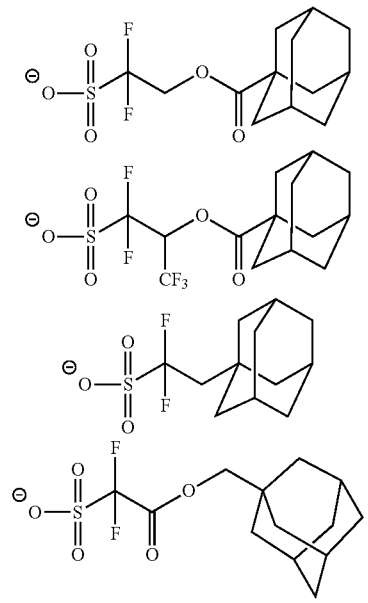

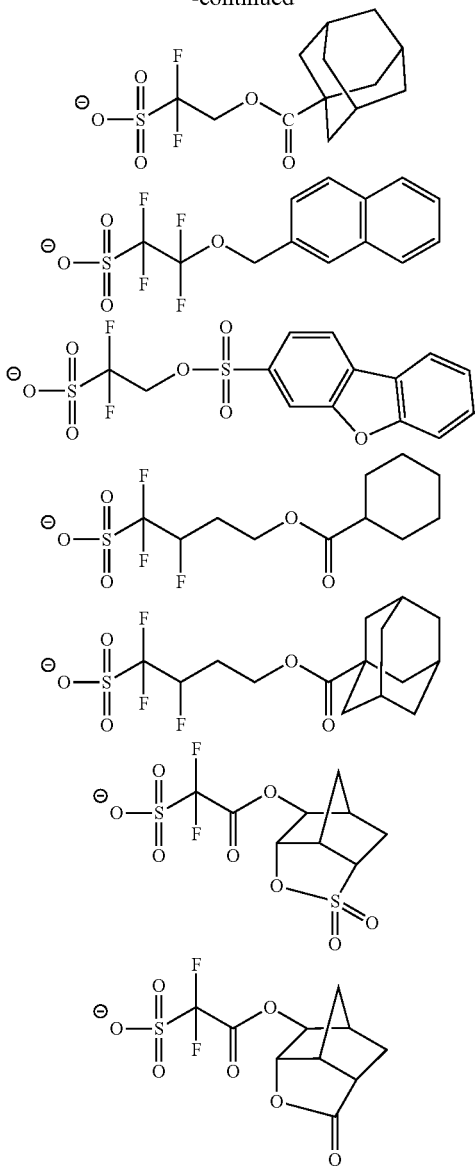

As Z⁻, a sulfonate anion represented by the following formula (A-I) is also preferred:

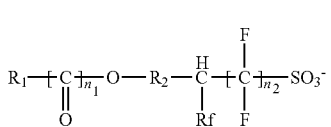

(A-I)

In formula (A-I), $R_1$ is an alkyl group, a monovalent alicyclic hydrocarbon group, an aryl group or a heteroaryl group, $R_2$ is a divalent linking group, Rf is a fluorine atom or an alkyl group substituted with at least one fluorine atom, and each of $n_1$ and $n_2$ is independently 0 or 1.

The alkyl group represented by $R_1$ is preferably an alkyl group having a carbon number of 1 to 20, more preferably an alkyl group having a carbon number of 1 to 10, still more preferably an alkyl group having a carbon number of 1 to 5, yet still more preferably an alkyl group having a carbon number of 1 to 4.

The alkyl group above may have a substituent (preferably fluorine atom), and the alkyl group having a substituent is preferably an alkyl group having a carbon number of 1 to 5 and being substituted with at least one fluorine atom, more preferably a perfluoroalkyl group having a carbon number of 1 to 5.

The alkyl group represented by $R_1$ is preferably a methyl group, an ethyl group or a trifluoromethyl group, more preferably a methyl group or an ethyl group.

The monovalent alicyclic hydrocarbon group represented by $R_1$ preferably has a carbon number of 5 or more. Also, the carbon number of the monovalent alicyclic hydrocarbon group is preferably 20 or less, more preferably 15 or less. The monovalent alicyclic hydrocarbon group may be a monocyclic alicyclic hydrocarbon group or a polycyclic alicyclic hydrocarbon group. A part of —CH₂— of the alicyclic hydrocarbon group may be substituted for by —O— or —C(=O)—.

The monocyclic alicyclic hydrocarbon group is preferably an alicyclic hydrocarbon group having a carbon number of 5 to 12, and examples thereof include a cyclopentyl group, a cyclohexyl group, a cycloheptyl group, a cyclooctyl group, a cyclododecanyl group, a cyclopentenyl group, a cyclohexenyl group, a cyclooctadienyl group, and a piperidine ring group, with a cyclopentyl group, a cyclohexyl group and a cyclooctyl group being preferred.

The polycyclic alicyclic hydrocarbon group is preferably an alicyclic hydrocarbon group having a carbon number of 10 to 20.

The aryl group represented by $R_1$ preferably has a carbon number of 6 or more. Also, the carbon number of the aryl group is preferably 20 or less, more preferably 15 or less.

The heteroaryl group represented by $R_1$ preferably has a carbon number of 2 or more. Also, the carbon number of the heteroaryl group is preferably 20 or less, more preferably 15 or less.

These aryl group and heteroaryl group may be a monocyclic aryl group and a monocyclic heteroaryl group, or a polycyclic aryl group and a polycyclic heteroaryl group.

The monocyclic aryl group includes a phenyl group and the like.

The polycyclic aryl group includes a naphthyl group, an anthracenyl group and the like.

The monocyclic heteroaryl group includes a pyridyl group, a thienyl group, a furanyl group and the like.

The polycyclic heteroaryl group includes a quinolyl group, an isoquinolyl group and the like.

The monovalent alicyclic hydrocarbon group, aryl group and heteroaryl group as $R_1$ may further have a substituent, and this further substituent includes a hydroxyl group, a halogen atom (e.g., fluorine atom, chlorine atom, bromine atom, iodine atom), a nitro group, a cyano group, an amido group, a sulfonamido group, an alkyl group, an alkoxy group, an alkoxycarbonyl group, an acyl group such as formyl group, acetyl group and benzoyl group, an acyloxy group such as acetoxy group and butyryloxy group, and a carboxy group.

Among others, $R_1$ is preferably a cyclohexyl group or an adamantyl group.

The divalent linking group represented by $R_2$ is not particularly limited but includes —COO—, —OCO—, —CO—, —O—, —S—, —SO—, —SO₂—, an alkylene group (preferably an alkylene group having a carbon number of 1 to 30), a cycloalkylene group (preferably a cycloalkylene group having a carbon number of 3 to 30), an alkenylene group (preferably an alkenylene group having a carbon number of 2 to 30), an arylene group (preferably an arylene group having a carbon number of 6 to 30), a heteroarylene group (preferably a heteroarylene group having a carbon number of 2 to 30), and a group formed by combining two or more thereof. These alkylene group, cycloalkylene group, alkenylene group, arylene group and heteroarylene group may further have a substituent, and specific examples of the substituent are the same as those recited above for the substituent which the monovalent alicyclic hydrocarbon group, aryl group and heteroaryl group of $R_1$ may further have.

The divalent linking group represented by $R_2$ is preferably an alkylene group, a cycloalkylene group, an alkenylene group, an arylene group or a heteroarylene group, more preferably an alkylene group, still more preferably an alkylene group having a carbon number of 1 to 10, yet still more preferably an alkylene group having a carbon number of 1 to 5.

Rf is a fluorine atom or an alkyl group substituted with at least one fluorine atom. The carbon number of this alkyl group is preferably from 1 to 30, more preferably from 1 to 10, still more preferably from 1 to 4. Also, the alkyl group substituted with at least one fluorine atom is preferably a perfluoroalkyl group.

Rf is preferably a fluorine atom or a perfluoroalkyl group having a carbon number of 1 to 4. More specifically, Rf is more preferably a fluorine atom or $CF_3$.

$n_1$ is preferably 1.

$n_2$ is preferably 1.

Specific preferred examples of the sulfonate anion represented by formula (A-I) are illustrated below, but the present invention is not limited thereto.

[Sulfonate Anion Represented by Formula (A-I)]

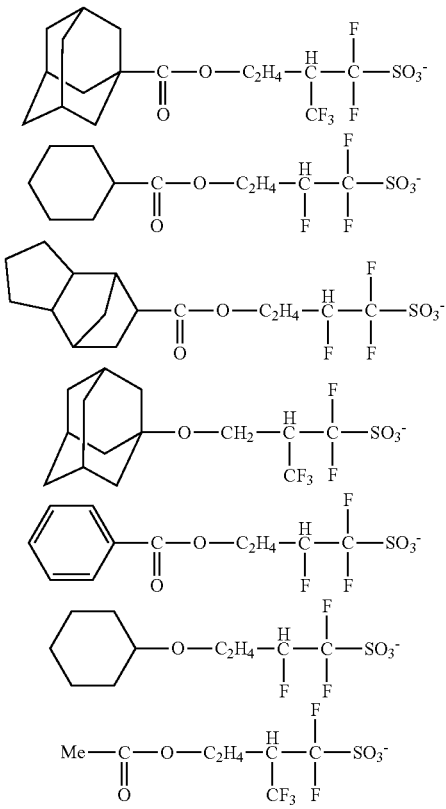

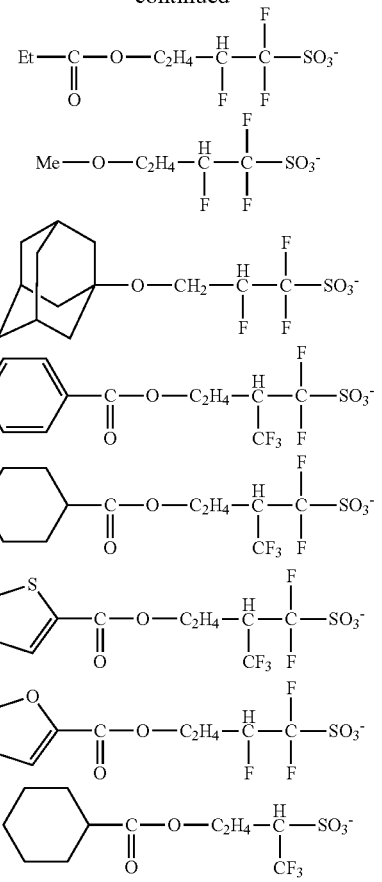

Furthermore, the acid generator also includes a compound represented by the following formula (ZV):

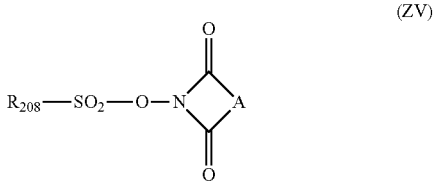

In formula (ZV), $R_{208}$ represents an alkyl group, a cycloalkyl group or an aryl group, and A represents an alkylene group, an alkenylene group or an arylene group.

Specific examples of the aryl group of $R_{208}$ are the same as specific examples of the aryl group of $R_{201}$ to $R_{203}$ in formula (ZI).

Specific examples of the alkyl group and cycloalkyl group of $R_{208}$ are the same as specific examples of the alkyl group and cycloalkyl group of $R_{201}$ to $R_{203}$ in formula (ZI).

The alkylene group of A includes an alkylene group having a carbon number of 1 to 12 (for example, a methylene group, an ethylene group, a propylene group, an isopropylene group, a butylene group and an isobutylene group); the alkenylene group of A includes an alkenylene group having a carbon number of 2 to 12 (for example, a vinylene group, a propenylene group and a butenylene group); and the arylene group of A includes an arylene group having a carbon number of 6 to 10 (for example, a phenylene group, a tolylene group and a naphthylene group).

As for the compound (B), the fluorine content ratio represented by (total mass of all fluorine atoms contained in the compound)/(total mass of all atoms contained in the compound) is preferably 0.30 or less, more preferably 0.25 or less, still more preferably 0.20 or less, yet still more preferably 0.15 or less, and most preferably 0.10 or less.

Among acid generators, particularly preferred examples are illustrated below.

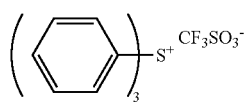
(z1)

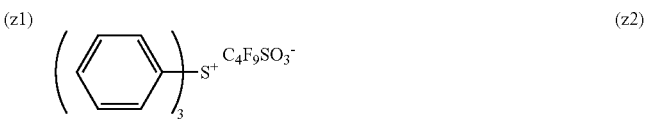
(z2)

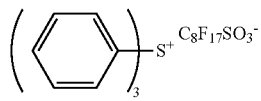
(z3)

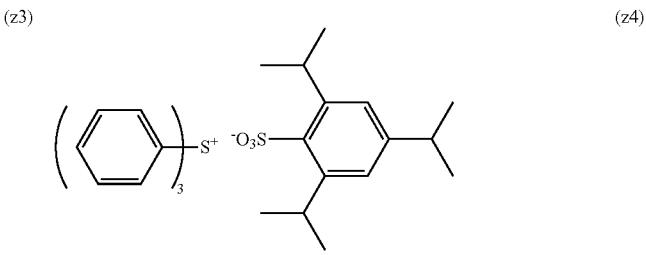
(z4)

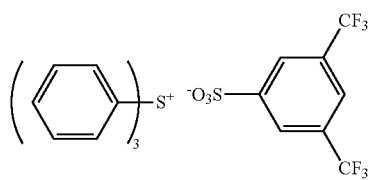
(z5)

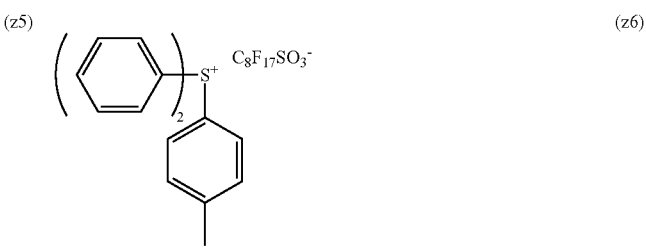
(z6)

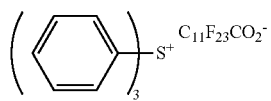
(z7)

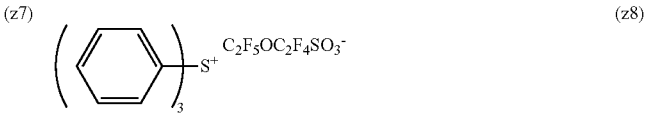
(z8)

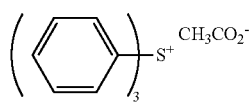
(z9)

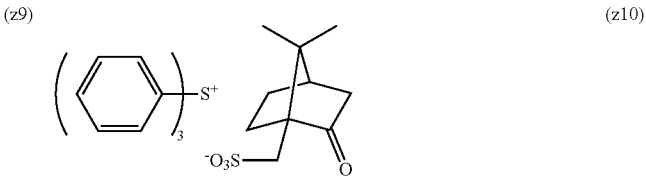
(z10)

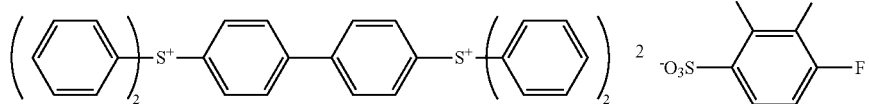
(z11)

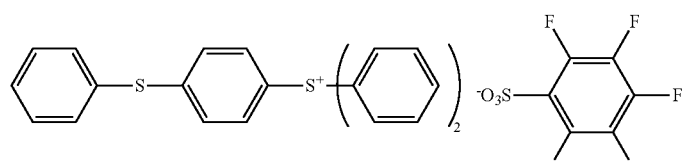
(z12)

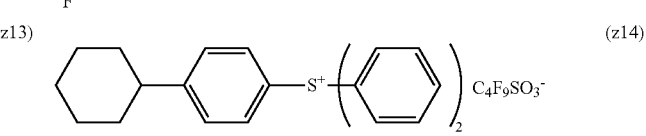
(z13)

(z14)

-continued
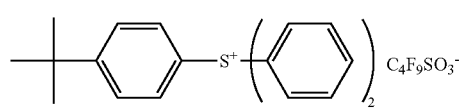 (z15)
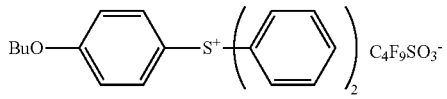 (z16)
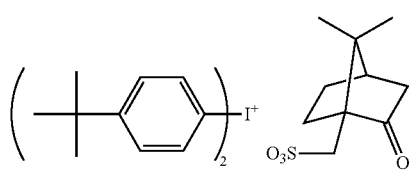 (z17)
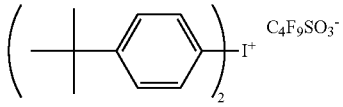 (z18)
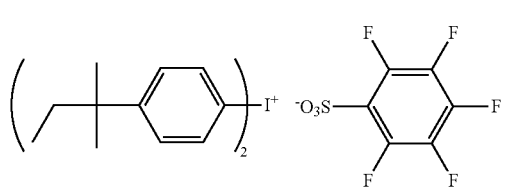 (z19)
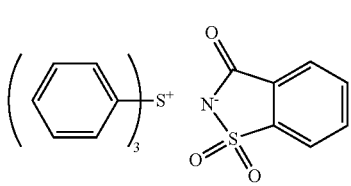 (z20)
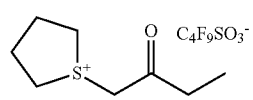 (z21)
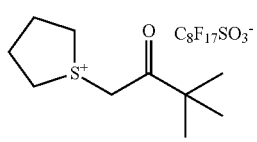 (z22)
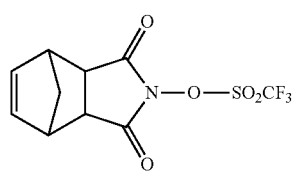 (z23)
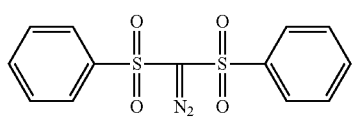 (z24)
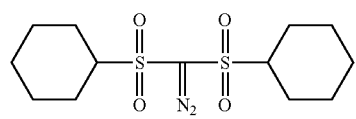 (z25)
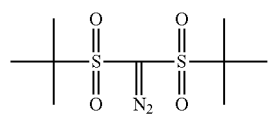 (z26)
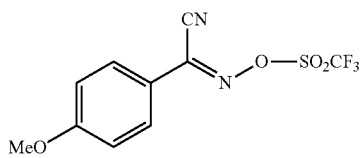 (z27)
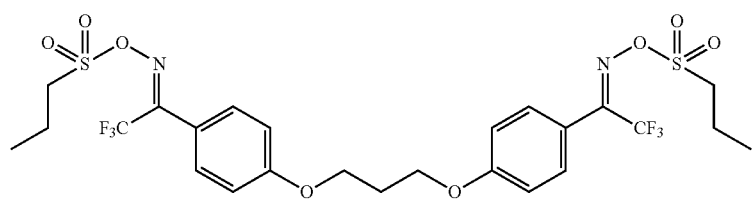 (z28)
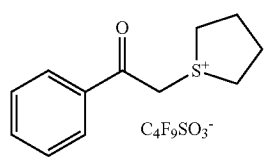 (z29)
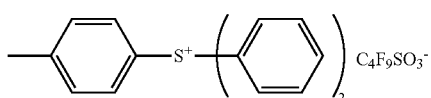 (z30)

-continued
(z31) 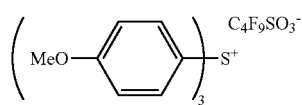
(z32) 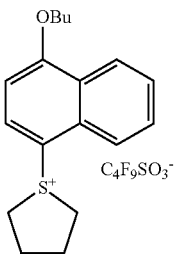
(z33) 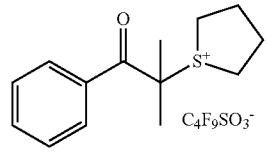
(z34) 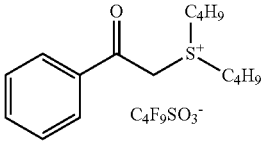
(z35) 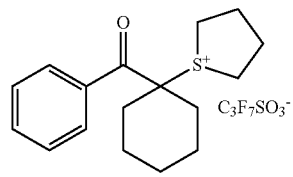
(z36) 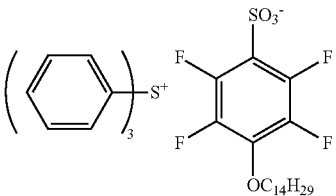
(z37) 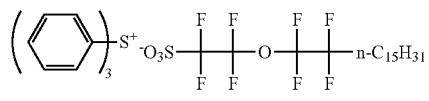
(z38) 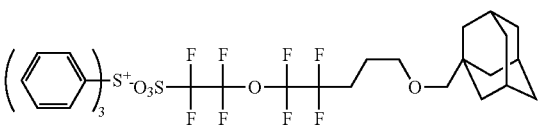
(z39) 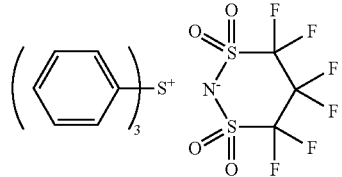
(z40) 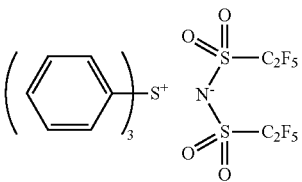
(z41) 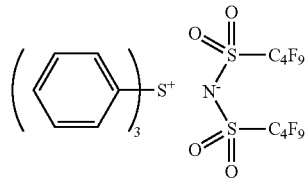
(z42) 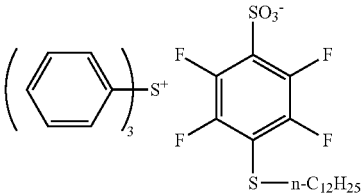
(z43) 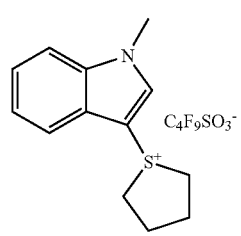
(z44) 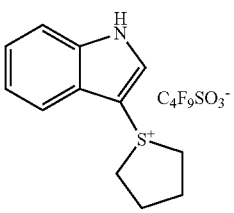
(z45) 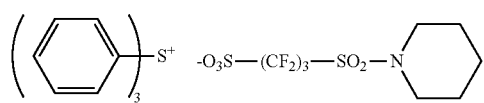
(z46) 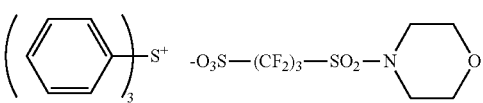

-continued
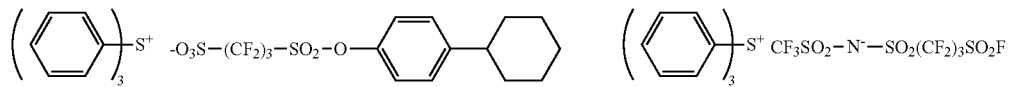
(z47)
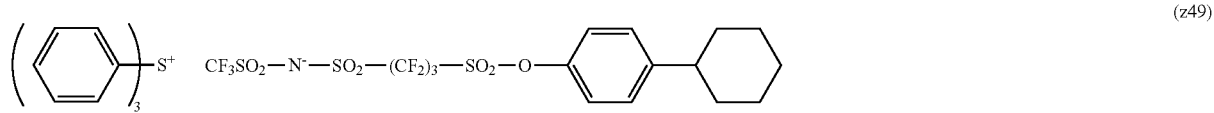
(z48)
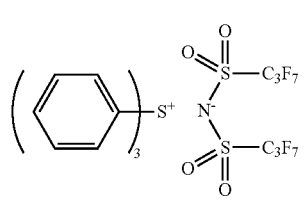
(z50)
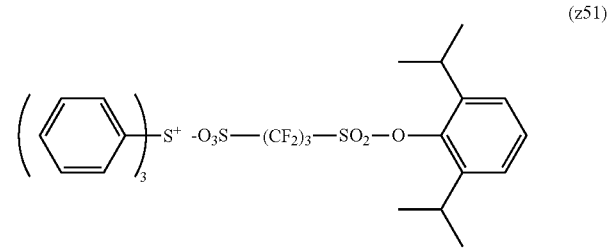
(z49)
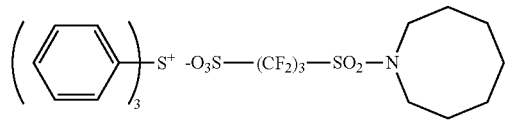
(z52)
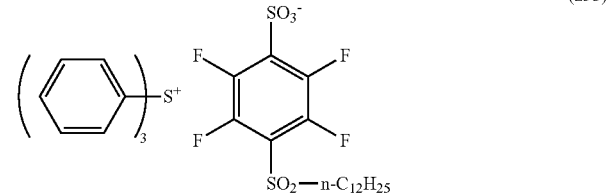
(z51)
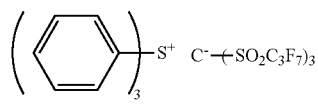
(z54)
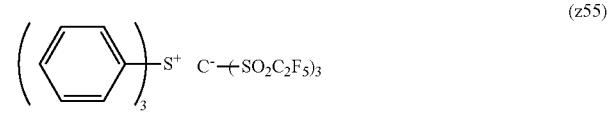
(z53)
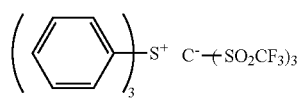
(z56)
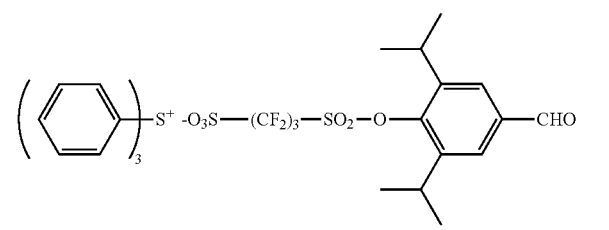
(z55)
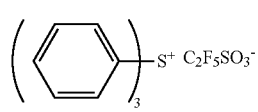
(z58)
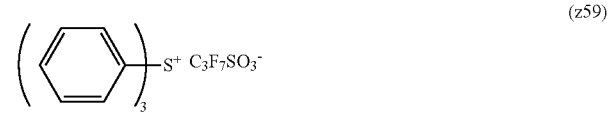
(z57)
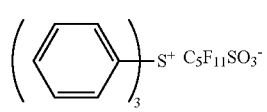
(z60)
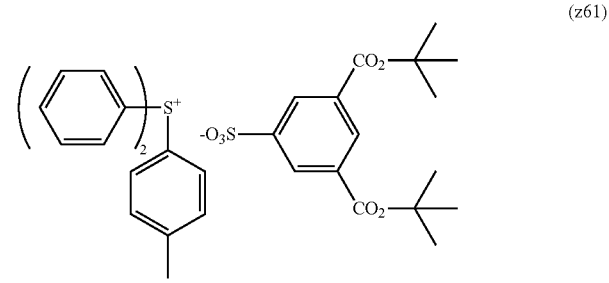
(z59)
(z61)

-continued
(z62)
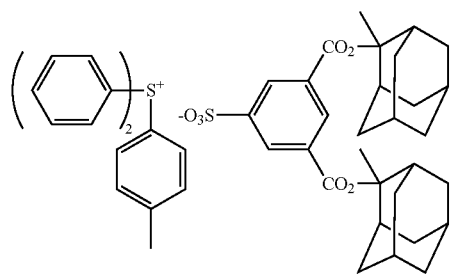
(z63)
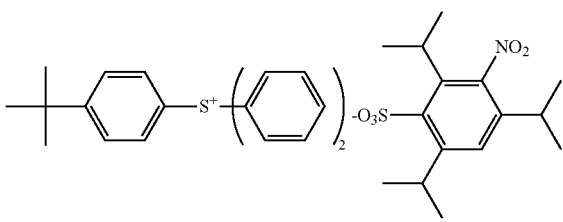
(z64)
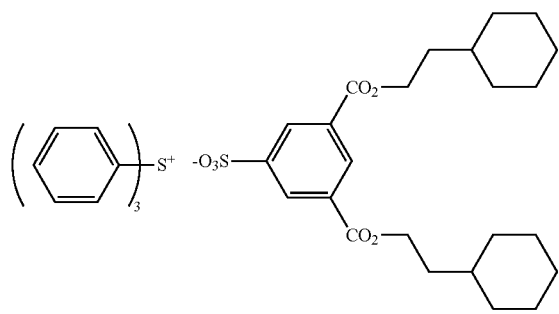
(z65)
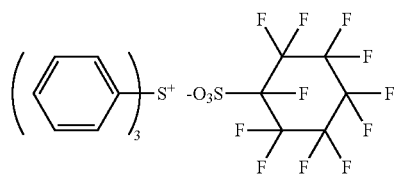
(z66)
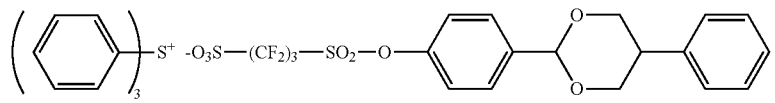
(z67)
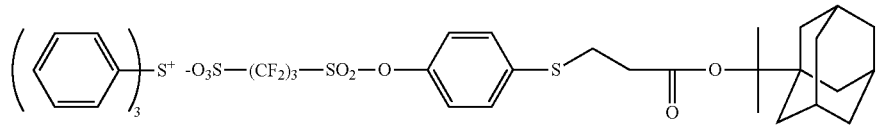
(z68)
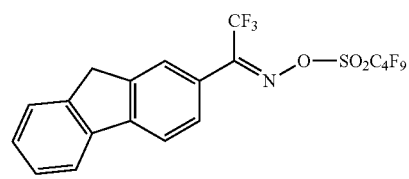
(z69)
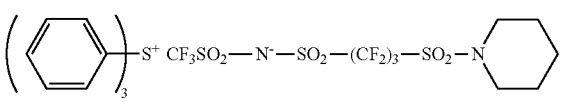
(z70)
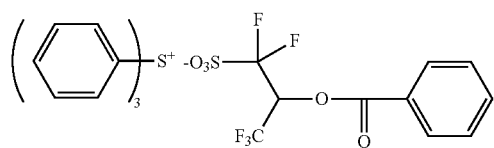
(z71)
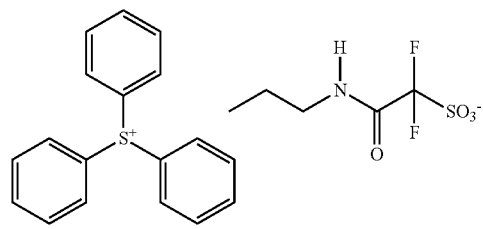
(z72)
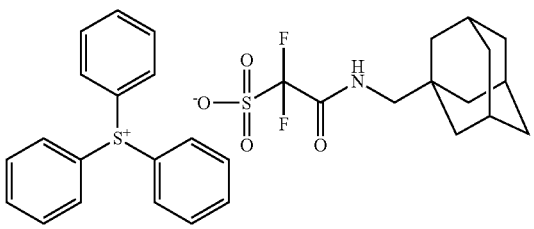

-continued
(z73)
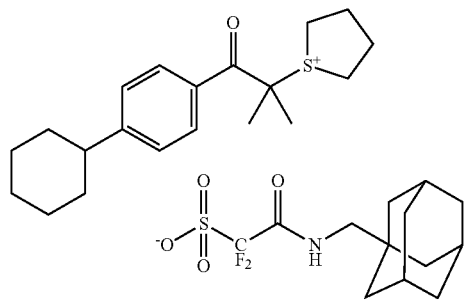
(z74)
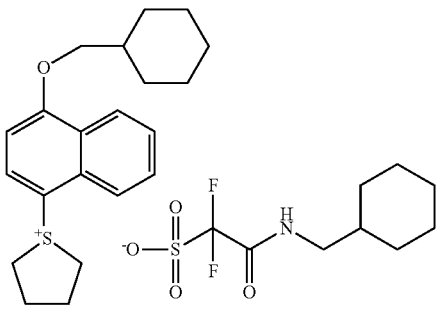
(z75)
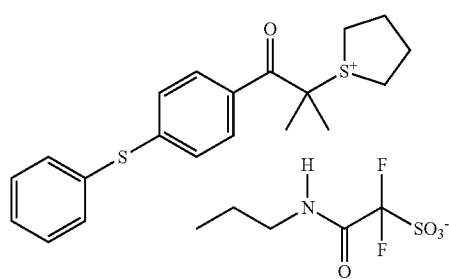
(z76)
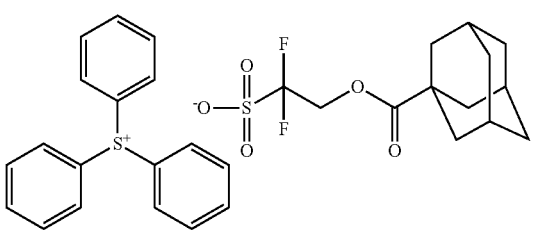
(z77)
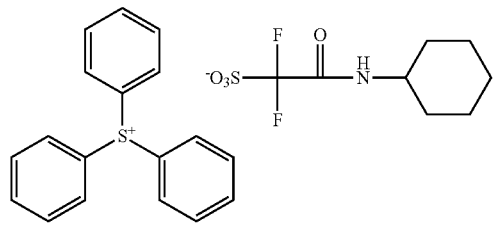
(z78)
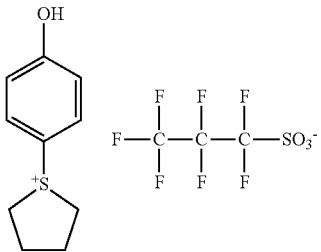
(z79)
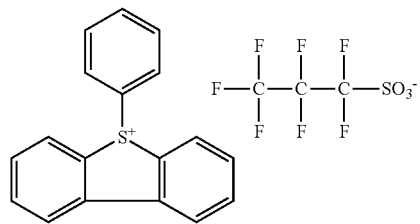
(z80)
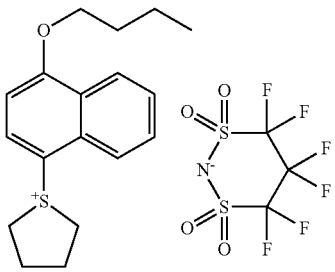
(z81)
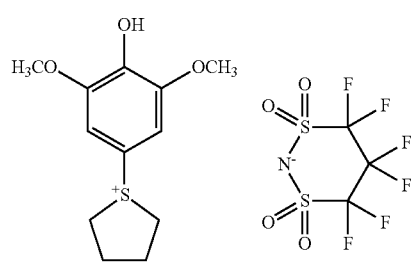
(z82)
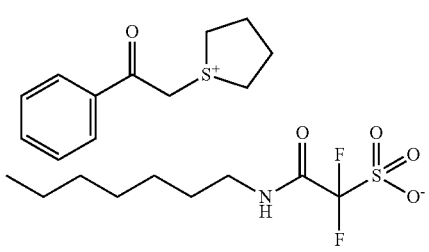

-continued
(z83) 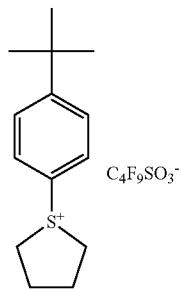
(z84) 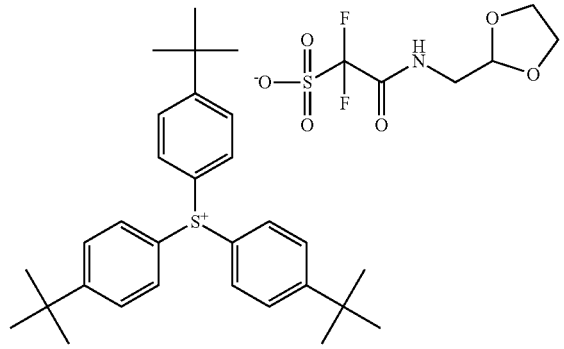
(z85) 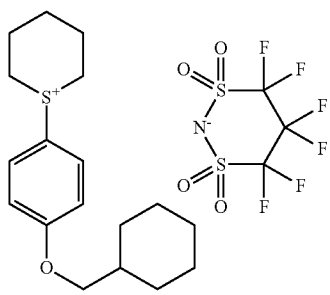
(z86) 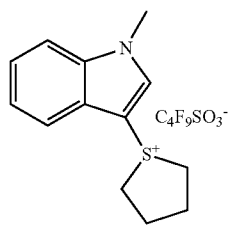
(z87) 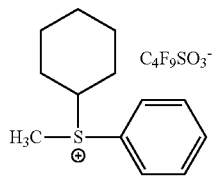
(z88) 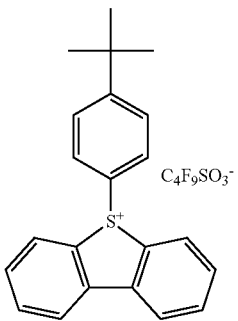
(z89) 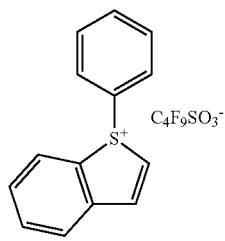
(z90) 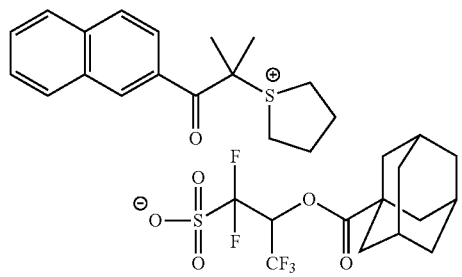
(z91) 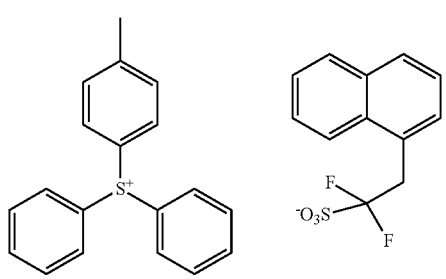

-continued
(z92) 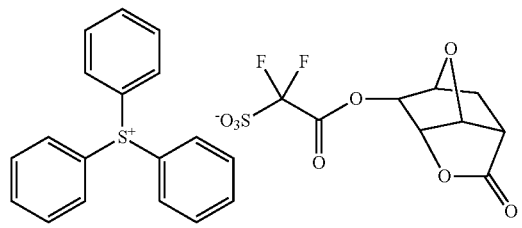
(z93) 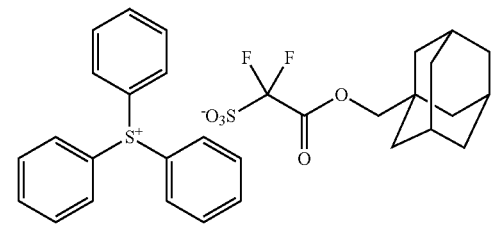
(z94) 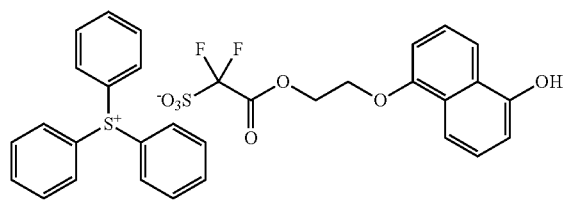
(z95) 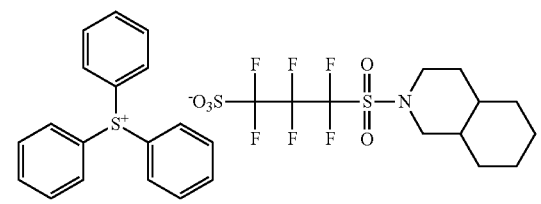
(z96) 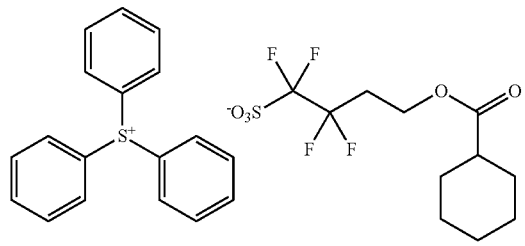
(z97) 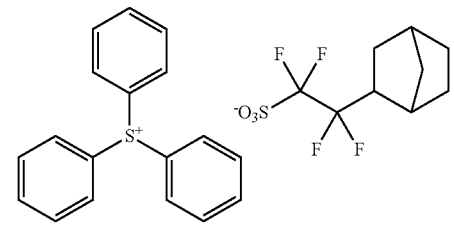
(z98) 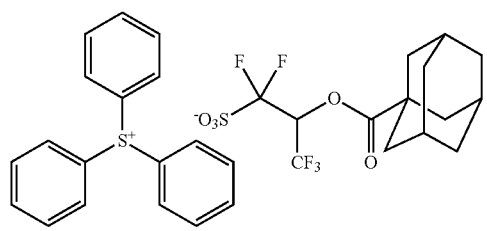
(z99) 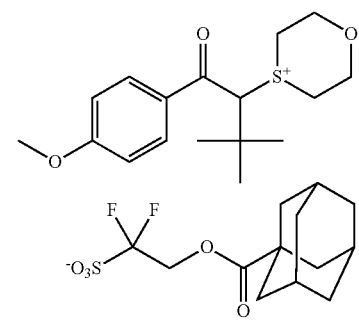
(Z-100) 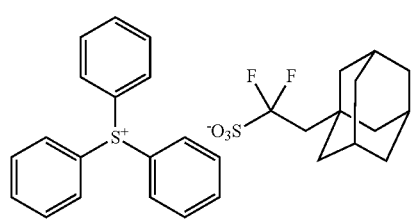
(Z-101) 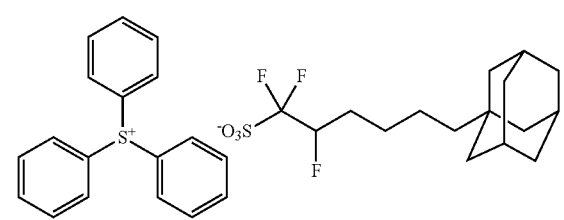
(Z-102) 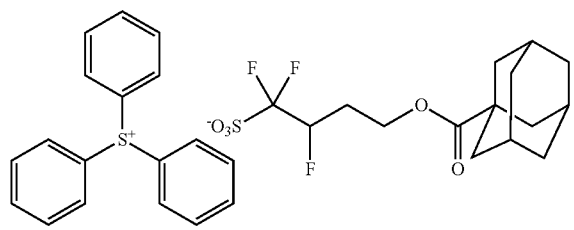
(Z-103) 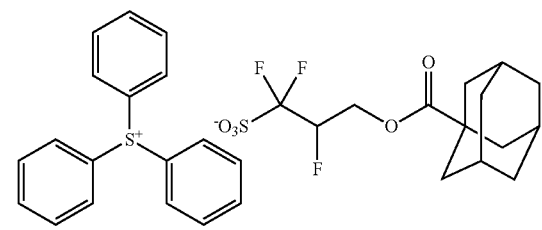

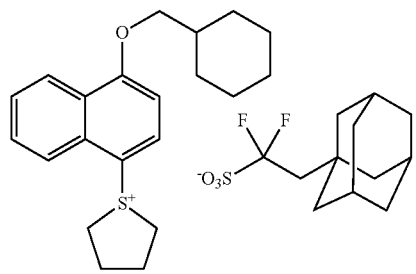

(Z-104)

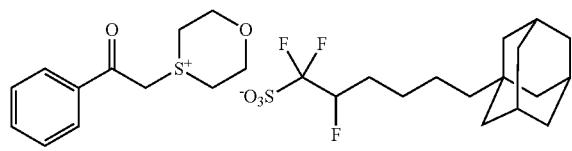

(Z-105)

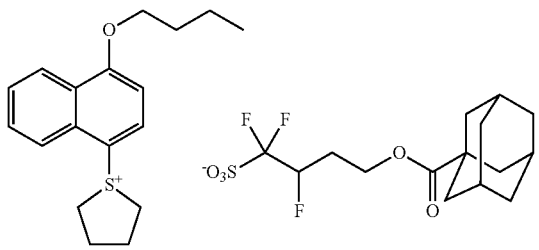

(Z-106)

As for the acid generator, one kind may be used alone, or two or more kinds may be used in combination.

The content of the acid generator in the composition is preferably from 0.1 to 30 mass %, more preferably from 3 to 25 mass %, still more preferably from 5 to 20 mass %, based on the total solid content of the composition.

[3] (P) Resin that does not react with the acid generated from the compound (A) and is capable of decomposing by the action of the acid generated from the compound (B) to produce a polar group The composition of the present invention contains (P) a resin that does not react with the acid generated from the compound (A) and is capable of decreasing the solubility for an organic solvent-containing developer by the action of the acid generated from the compound (B).

The resin (P) is, for example, a resin having a group capable of decomposing by the action of the acid generated from the compound (B) to produce a polar group (hereinafter, sometimes referred to as "acid-decomposable group"), on either one or both of the main chain and the side chain of the resin (hereinafter, sometimes referred to as "acid-decomposable resin" or "resin (P)").

Here, the resin (P) is a resin capable of increasing the polarity by the action of the acid generated from the compound (B) to decrease the solubility for an organic solvent-containing developer. Also, the resin (P) is at the same time a resin capable of increasing the polarity by the action of the acid generated from the compound (B) to increase the solubility for an alkali developer.

As described above, the resin (P) is a resin that does not react with the acid generated from the compound (A).

The "the resin (P) does not react with the acid generated from the compound (A)" indicates that the acid generated from the compound (A) upon irradiation with an actinic ray or radiation causes no decomposition of the acid-decomposable group in the resin (P) and no decrease in the solubility for an organic solvent-containing developer. Specifically, when the following evaluation is performed and the film thickness after baking is finally less than 30 nm, this comes under "the resin (P) does not react with the acid generated from the compound (A)".

<Evaluation Method of Acid Decomposability>

10 g of the resin (P) and 2.0 g of the compound (A) are dissolved in a solvent (propylene glycol monomethyl ether acetate (PGMEA)) to obtain a resist solution having a solid content concentration of 3.5 mass %, and the obtained solution is filtered through a polyethylene filter having a pore size of 0.03 µm to prepare a resist composition. An organic antireflection film, ARC29SR (produced by Nissan Chemical Industries, Ltd.), is coated on a silicon wafer and baked at 205° C. for 60 seconds to form an antireflection film having a thickness of 100 nm, and the resist composition is coated thereon and baked (PB: Prebake) at 100° C. over 60 seconds to form a resist film having a thickness of 100 nm. The entire surface of the obtained wafer is exposed at an exposure dose of 60 mJ/cm$^2$ by using an ArF excimer laser scanner (PAS5500/1100, manufactured by ASML) and subsequently, the wafer is heated at 100° C. for 60 seconds (PEB: Post Exposure Bake). Thereafter, the resist film is put into contact with an organic developer (butyl acetate) by puddling the organic developer (butyl acetate) for 30 seconds, then rinsed by puddling a rising solution (4-methyl-2-pentanol) for 30 seconds while spinning off the developer, and after rotating the wafer at a rotational speed of 4,000 rpm for 30 seconds, baked at 90° C. for 60 seconds. Subsequently, the film thickness after baking is measured.

The acid-decomposable group preferably has a structure where a polar group is protected by a group capable of leaving by the action of an acid.

The polar group is not particularly limited as long as it is a group capable of being sparingly solubilized or insolubilized in an organic solvent-containing developer, but examples thereof include an acidic group (a group capable of dissociating in an aqueous 2.38 mass % tetramethylammonium hydroxide solution which has been conventionally used as the developer for a resist) such as phenolic hydroxyl group, carboxyl group, fluorinated alcohol group (preferably a hexafluoroisopropanol group), sulfonic acid group, sulfonamide group, sulfonylimide group, (alkylsulfonyl)(alkylcarbonyl)methyl ene group, (alkylsulfonyl)(alkylcarbonyl) imide group, bis(alkylcarbonyl)methylene group, bis(alkylcarbonyl)imide group, bis(alkylsulfonyl)methylene group, bis(alkylsulfonyl)imide group, tris(alkylcarbonyl)methylene group and tris(alkylsulfonyl)methylene group, and an alcoholic hydroxyl group.

Incidentally, the alcoholic hydroxyl group is a hydroxyl group bonded to a hydrocarbon group and indicates a hydroxyl group except for a hydroxyl group directly bonded on an aromatic ring (phenolic hydroxyl group), and the hydroxyl group excludes an aliphatic alcohol substituted with an electron-withdrawing group such as fluorine atom on the α-position (for example, a fluorinated alcohol group (e.g., hexafluoroisopropanol group)). The alcoholic hydroxyl group is preferably a hydroxyl group having a pKa of 12 to 20.

Preferred polar groups include a carboxyl group, a fluorinated alcohol group (preferably a hexafluoroisopropanol group), and a sulfonic acid group.

The group preferred as the acid-decomposable group is a group where a hydrogen atom of the group above is substituted for by a group capable of leaving by the action of an acid.

The group capable of leaving by the action of an acid includes, for example, —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, each of $R_{36}$ to $R_{39}$ independently represents an alkyl group, a cycloalkyl group, an aryl group, an aralkyl group or an alkenyl group. $R_{36}$ and $R_{37}$ may combine with each other to form a ring.

Each of $R_{01}$ and $R_{02}$ independently represents a hydrogen atom, an alkyl group, a cycloalkyl group, an aryl group, an aralkyl group or an alkenyl group.

The alkyl group of $R_{36}$ to $R_{39}$, $R_{01}$ and $R_{02}$ is preferably an alkyl group having a carbon number of 1 to 8, and examples thereof include a methyl group, an ethyl group, a propyl group, an n-butyl group, a sec-butyl group, a hexyl group, and an octyl group.

The cycloalkyl group of $R_{36}$ to $R_{39}$, $R_{01}$ and $R_{02}$ may be monocyclic or polycyclic and is preferably a cycloalkyl group having a carbon number of 3 to 20.

The aryl group of $R_{36}$ to $R_{39}$, $R_{01}$ and $R_{02}$ is preferably an aryl group having a carbon number of 6 to 10, and examples thereof include a phenyl group, a naphthyl group, and an anthryl group.

The aralkyl group of $R_{36}$ to $R_{39}$, $R_{01}$ and $R_{02}$ is preferably an aralkyl group having a carbon number of 7 to 12, and examples thereof include a benzyl group, a phenethyl group, and a naphthylmethyl group.

The alkenyl group of $R_{36}$ to $R_{39}$, $R_{01}$ and $R_{02}$ is preferably an alkenyl group having a carbon number of 2 to 8, and examples thereof include a vinyl group, an allyl group, a butenyl group, and a cyclohexenyl group.

The ring formed by combining $R_{36}$ and $R_{37}$ is preferably a cycloalkyl group (monocyclic or polycyclic). The cycloalkyl group is preferably a monocyclic cycloalkyl group such as cyclopentyl group and cyclohexyl group, or a polycyclic cycloalkyl group such as norbornyl group, tetracyclododecanyl group, tetracyclododecanyl group and adamantyl group, more preferably a monocyclic cycloalkyl group having a carbon number of 5 to 6, still more preferably a monocyclic cycloalkyl group having a carbon number of 5.

The acid-decomposable group is preferably a cumyl ester group, an enol ester group, an acetal ester group, a tertiary alkyl ester group or the like, more preferably a tertiary alkyl ester group.

The resin (P) preferably contains a repeating unit having an acid-decomposable group.

Also, the resin (P) preferably contains, as the repeating unit having an acid-decomposable group, (AI) a repeating unit capable of decomposing by the action of an acid to produce a carboxyl group (hereinafter, sometimes referred to as "repeating unit (AI)"), more preferably a repeating unit represented by the following formula (aI). The repeating unit represented by formula (aI) generates a carboxyl group as a polar group by the action of an acid, and a high hydrogen bonding interaction is exhibited among a plurality of carboxyl groups, so that the glass transition temperature (Tg) of the resin (P) can be more enhanced. In turn, even when a film is deposited in the periphery of a resist pattern by CVD method (particularly, high-temperature CVD method), high rectangularity in the cross-sectional profile of the resist pattern is less likely to be impaired by heat during film growth, as a result, an increase in the process cost can be more suppressed.

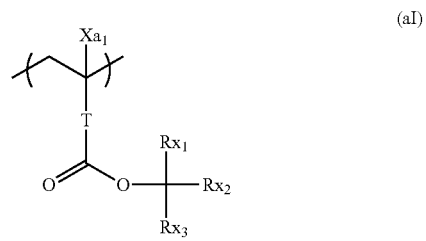

(aI)

In formula (aI), $Xa_1$ represents a hydrogen atom, an alkyl group, a cyano group or a halogen atom, T represents a single bond or a divalent linking group, each of $Rx_1$ to $Rx_3$ independently represents an alkyl group or a cycloalkyl group, and two members out of $Rx_1$ to $Rx_3$ may combine to form a ring structure.

The divalent linking group of T includes an alkylene group, a —COO-Rt- group, a —O-Rt- group, a phenylene group, and the like. In the formulae, Rt represents an alkylene group or a cycloalkylene group.

T is preferably a single bond or a —COO-Rt- group. Rt is preferably an alkylene group having a carbon number of 1 to 5, more preferably a —$CH_2$— group, —$(CH_2)_2$— group or a —$(CH_2)_3$— group. T is more preferably a single bond.

The alkyl group of $Xa_1$ may have a substituent, and the substituent includes, for example, a hydroxyl group and a halogen atom (preferably fluorine atom).

The alkyl group of $Xa_1$ is preferably an alkyl group having a carbon number of 1 to 4 and includes a methyl group, an ethyl group, a propyl group, a hydroxymethyl group, a trifluoromethyl group and the like but is preferably a methyl group.

$Xa_1$ is preferably a hydrogen atom or a methyl group.

The alkyl group of $Rx_1$, $Rx_2$ and $Rx_3$ may be linear or branched and is preferably an alkyl group having a carbon number of 1 to 4, such as methyl group, ethyl group, n-propyl group, isopropyl group, n-butyl group, isobutyl group and tert-butyl group.

The cycloalkyl group of $Rx_1$, $Rx_2$ and $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

The ring structure formed by combining two members out of $Rx_1$, $Rx_2$ and $Rx_3$ is preferably a monocyclic cycloalkane ring such as cyclopentyl ring and cyclohexyl ring, or a polycyclic cycloalkane ring such as norbornane ring, tetracyclodecane ring, tetracyclododecane ring and adamantane ring, more preferably a monocyclic cycloalkane ring having a carbon number of 5 or 6.

Each of $Rx_1$, $Rx_2$ and $Rx_3$ is independently preferably an alkyl group, more preferably a linear or branched alkyl group having a carbon number of 1 to 4.

Each of the groups above may have a substituent, and the substituent includes, for example, an alkyl group (having a carbon number of 1 to 4), a cycloalkyl group (having a carbon number of 3 to 8), a halogen atom, an alkoxy group (having a carbon number of 1 to 4), a carboxyl group, and an alkoxycarbonyl group (having a carbon number of 2 to 6). The carbon number is preferably 8 or less. Above all, from the standpoint of more enhancing the dissolution contrast for an organic solvent-containing developer between before and after acid decomposition, the substituent is preferably a group not containing a heteroatom such as oxygen atom, nitrogen atom and sulfur atom (for example, preferably not an alkyl group substituted with a hydroxyl group), more preferably a group composed of only a hydrogen atom and a carbon atom, still more preferably a linear or branched alkyl group or a cycloalkyl group.

The resin (P) is more preferably a resin containing, as the repeating unit having an acid-decomposable group, a repeating unit represented by formula (II):

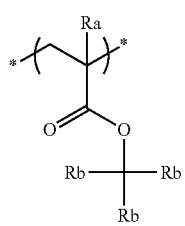

(II)

In formula (II),

Ra represents a hydrogen atom or an alkyl group, and each Rb independently represents an alkyl group or a cycloalkyl group, and two Rb may combine with each other to form a ring.

Specific examples and preferred examples of the alkyl group of Ra include those recited above for the alkyl group of $Xa_1$ in formula (aI).

Specific examples and preferred examples of the alkyl group of Rb include those recited above for the alkyl group of $Rx_1$ to $Rx_3$ in formula (aI).

Specific examples and preferred examples of the cycloalkyl group of Rb include those recited above for the cycloalkyl group of $Rx_1$ to $Rx_3$ in formula (aI). Specific examples of the ring which may be formed by combining two Rb with each other are the same as those recited for the ring structure that is formed by combining two members out of $Rx_1$, $Rx_2$ and $Rx_3$ in formula (aI).

Specific examples of the repeating unit represented by formula (aI) or (II) are illustrated below, but the present invention is not limited to these specific examples.

In specific examples, Rx represents a hydrogen atom, $CH_3$, $CF_3$ or $CH_2OH$. Each of Rxa and Rxb represents an alkyl group having a carbon number 1 to 4. $Xa_1$ represents a hydrogen atom, $CH_3$, $CF_3$ or $CH_2OH$. Z represents a substituent and when a plurality of Z are present, each may be the same as or different from every other member. p represents 0 or a positive integer. Specific examples and preferred examples of Z are the same as specific examples and preferred examples of the substituent which each of the groups such as $Rx_1$ to $Rx_3$ may have.

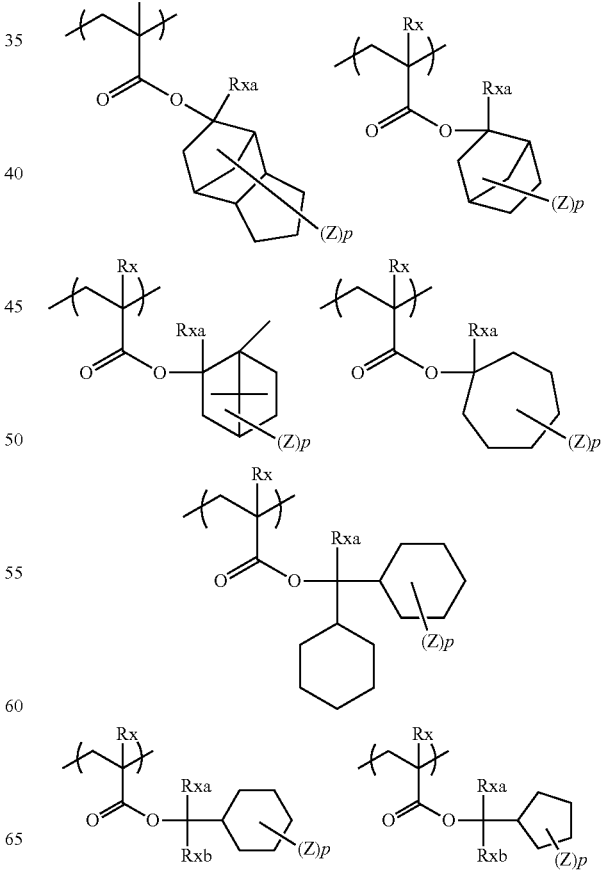

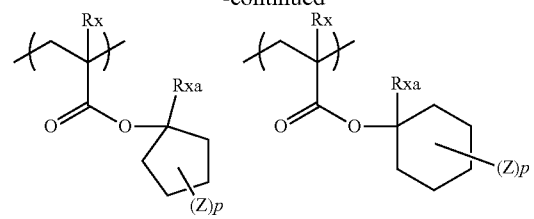
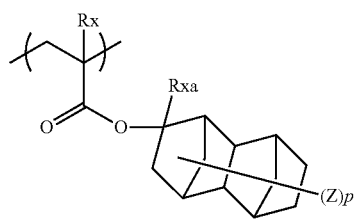
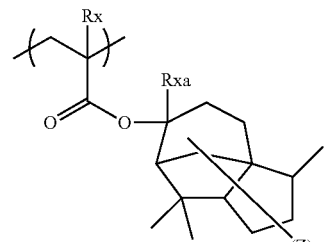
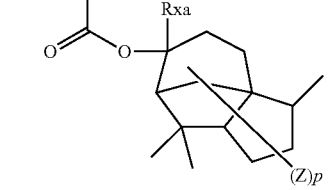
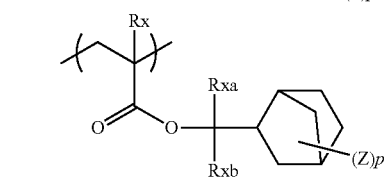
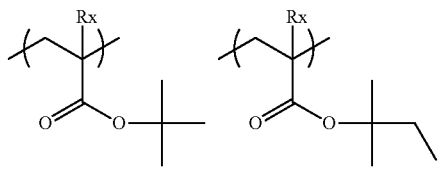
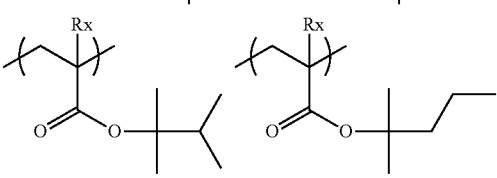
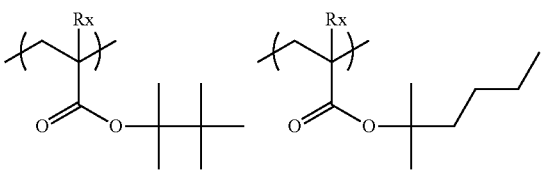
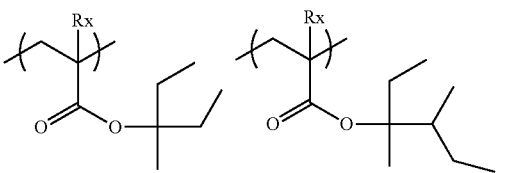
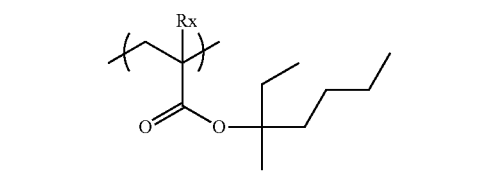
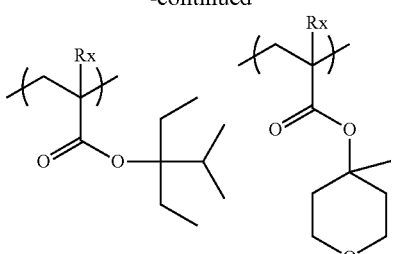
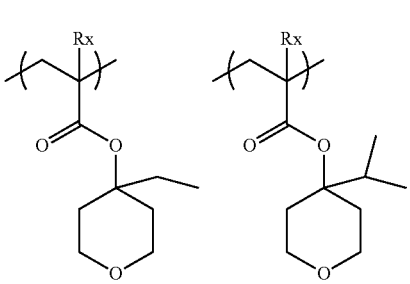
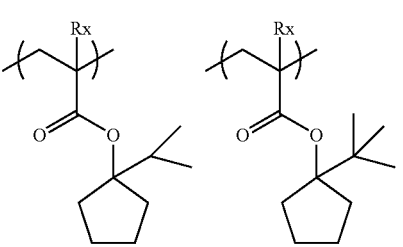
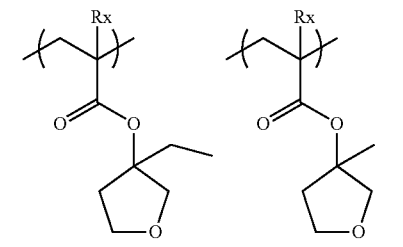
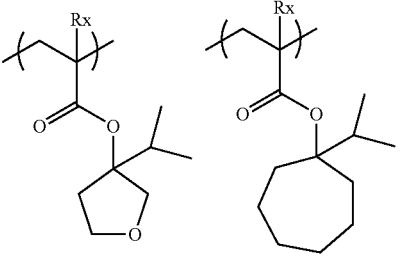
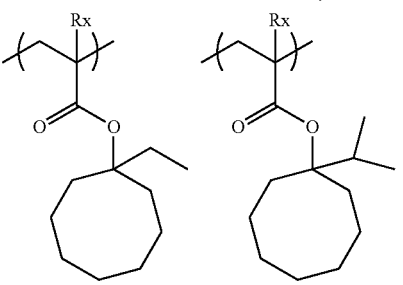

71
-continued
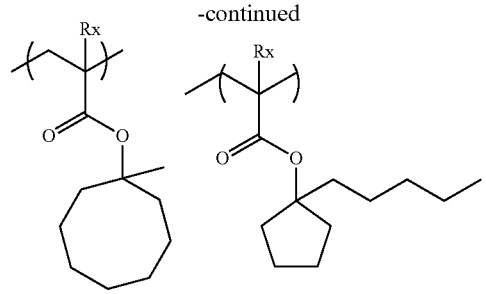
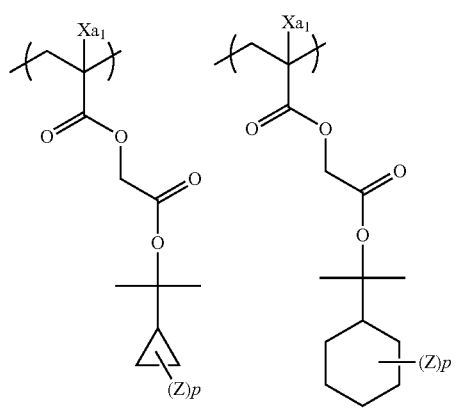
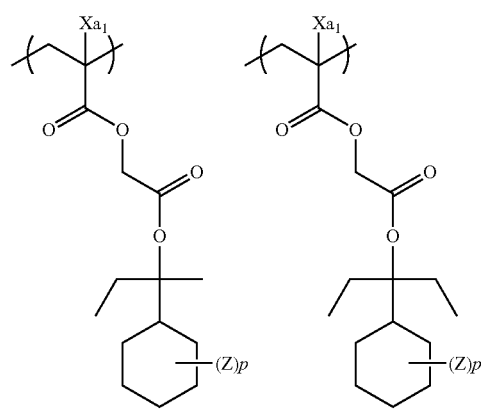
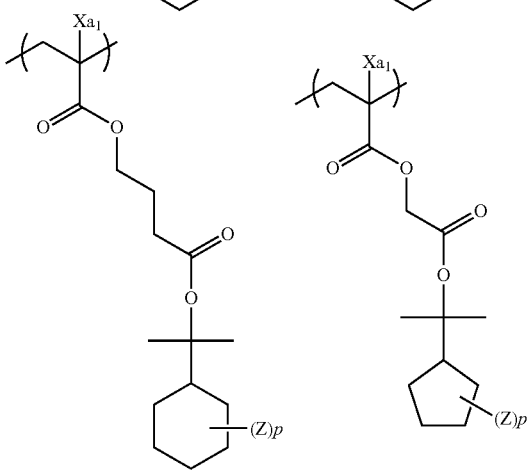
72
-continued
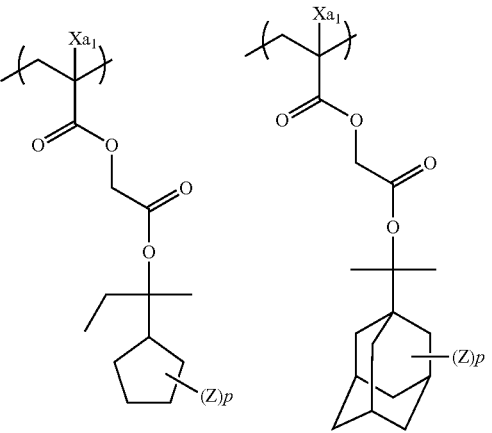
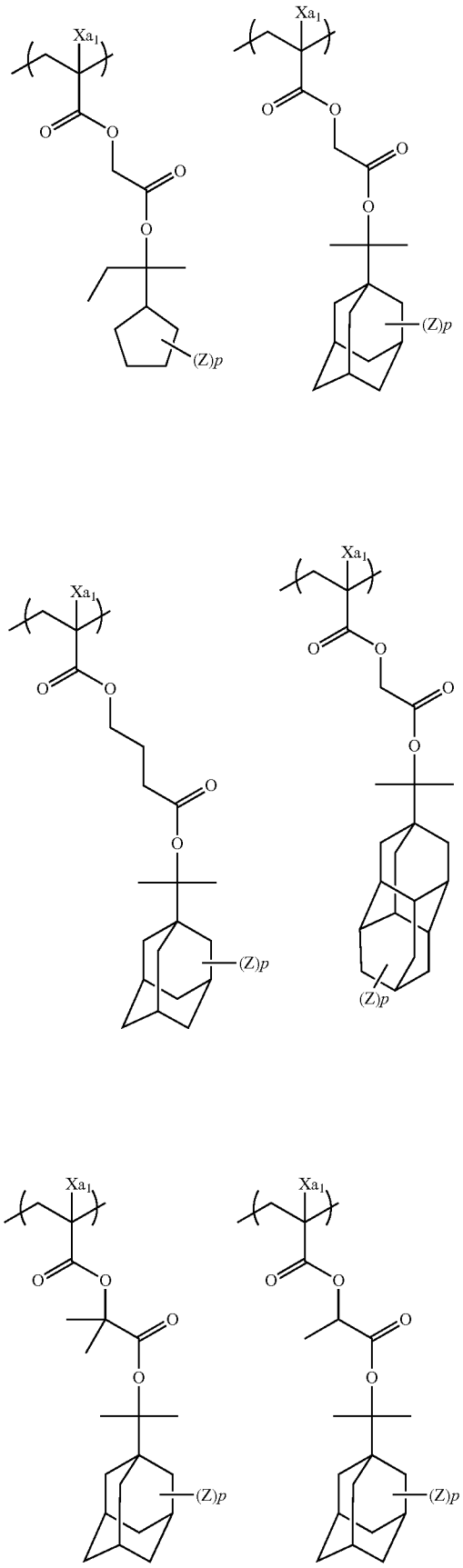

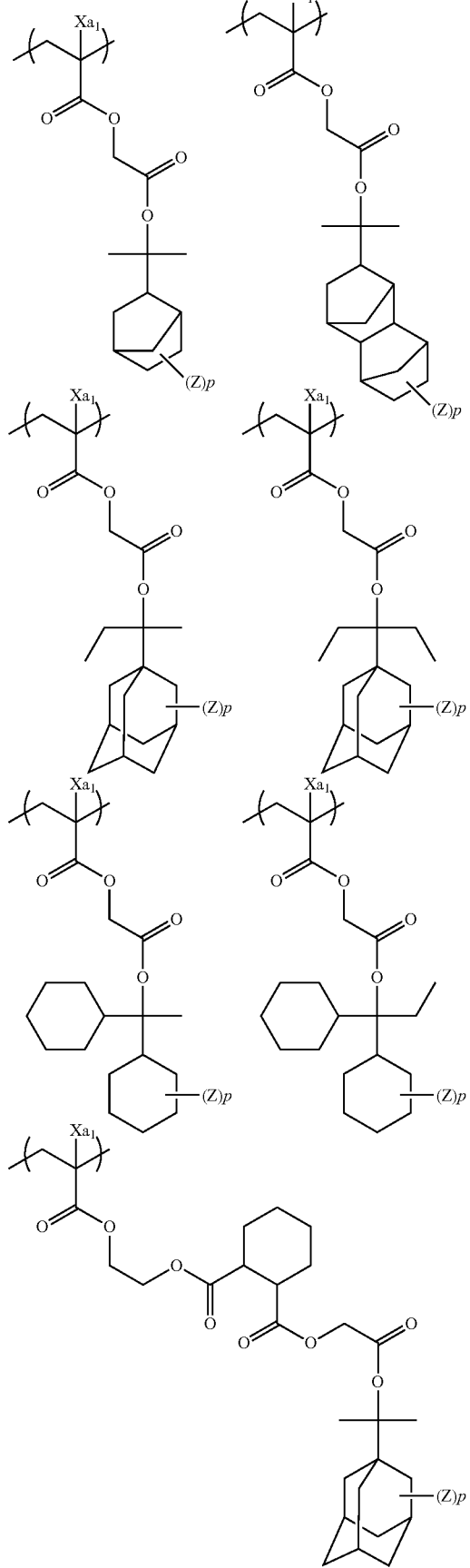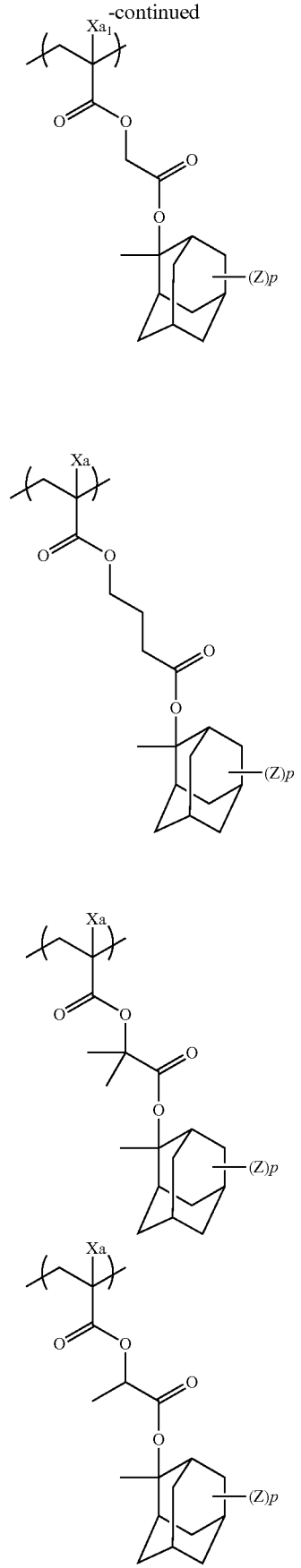

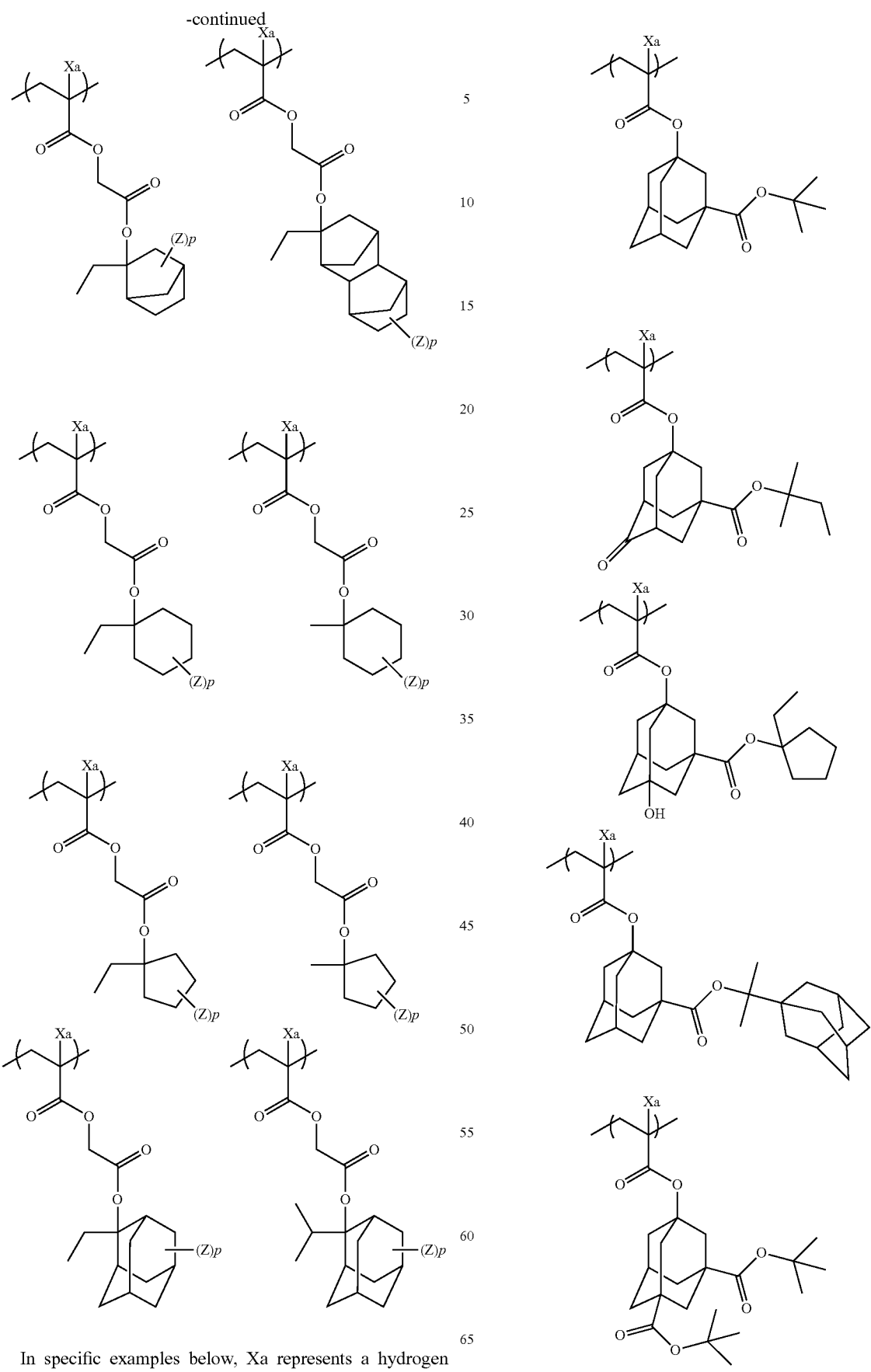
In specific examples below, Xa represents a hydrogen atom, an alkyl group, a cyano group or a halogen atom.

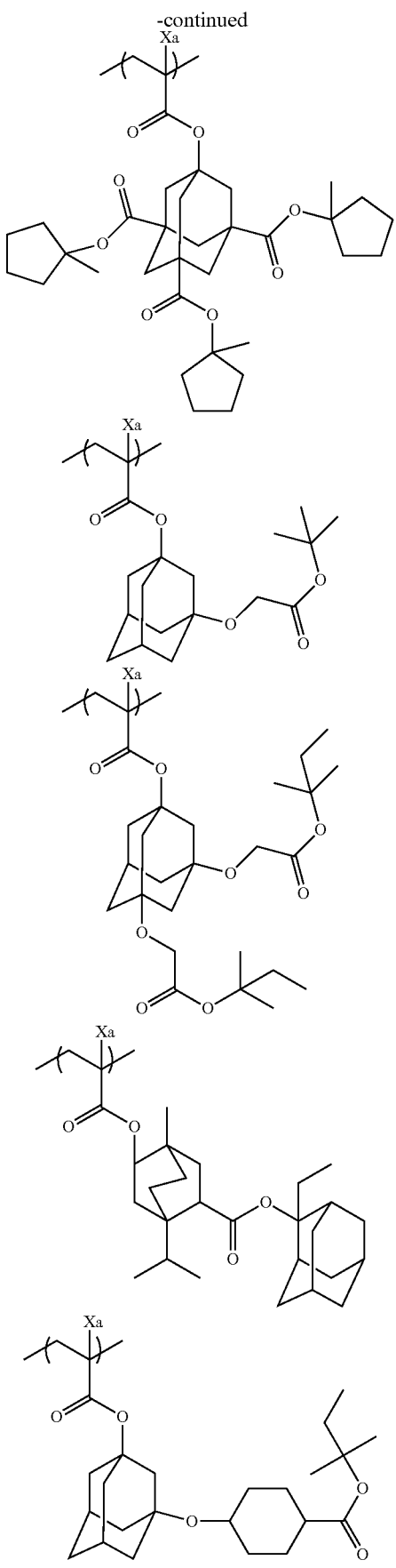
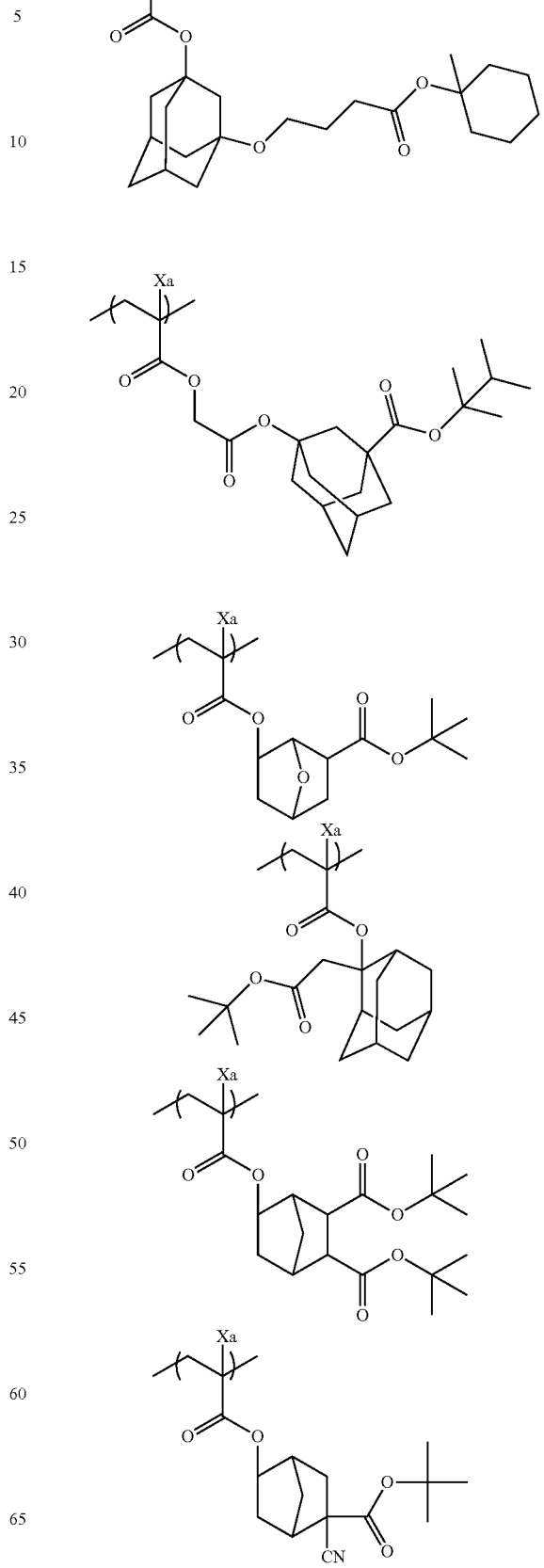

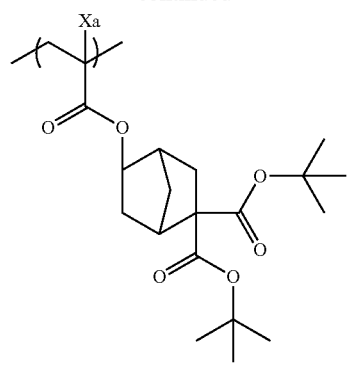
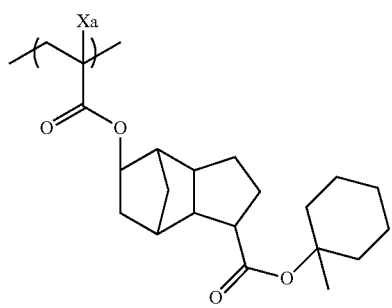
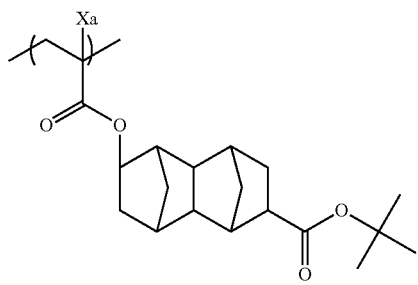
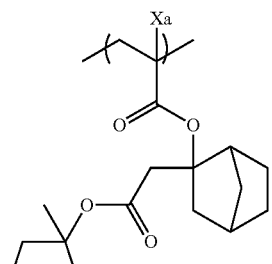
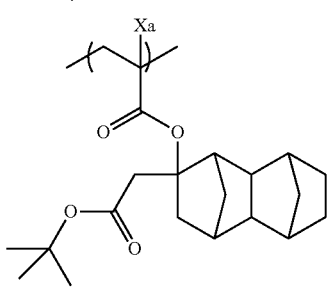
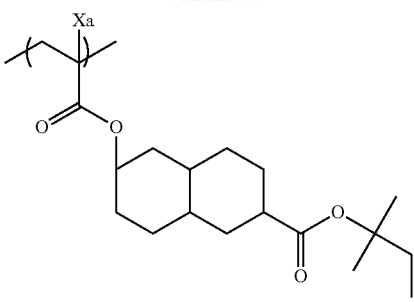
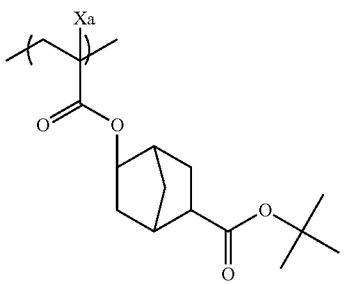
Also, the resin (P) may contain, as the repeating unit having an acid-decomposable group, a repeating unit capable of decomposing by the action of an acid to produce an alcoholic hydroxyl group, which is illustrated below.
In specific examples below, $Xa_1$ represents a hydrogen atom, $CH_3$, $CF_3$ or $CH_2OH$.
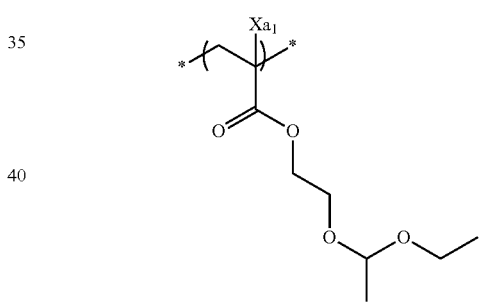
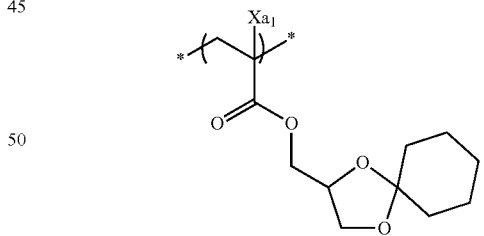
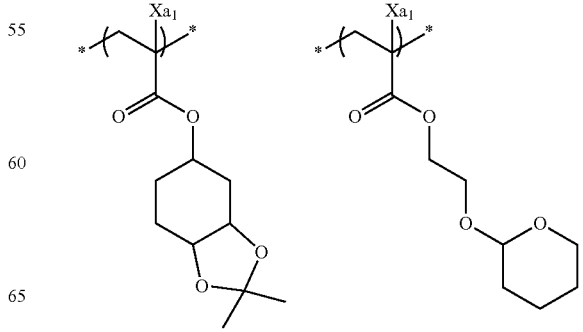

81 82
-continued -continued
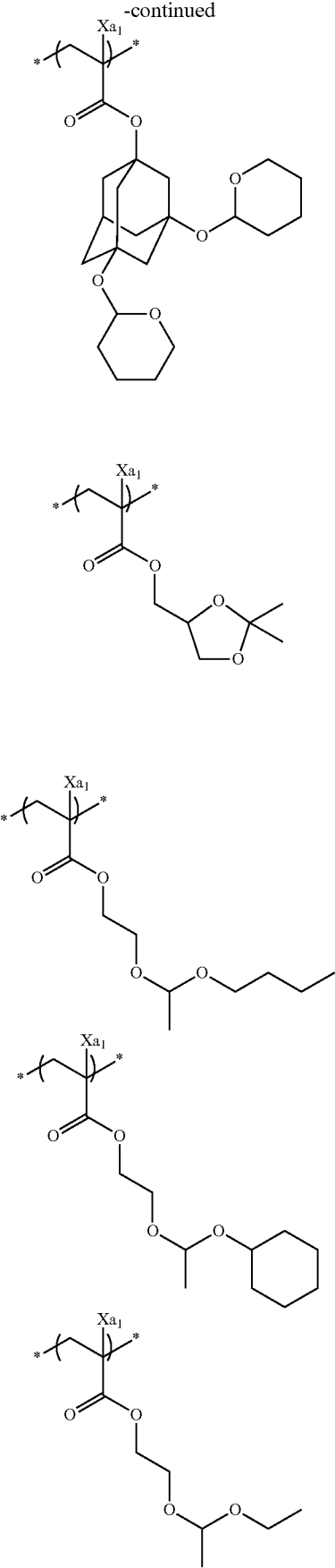
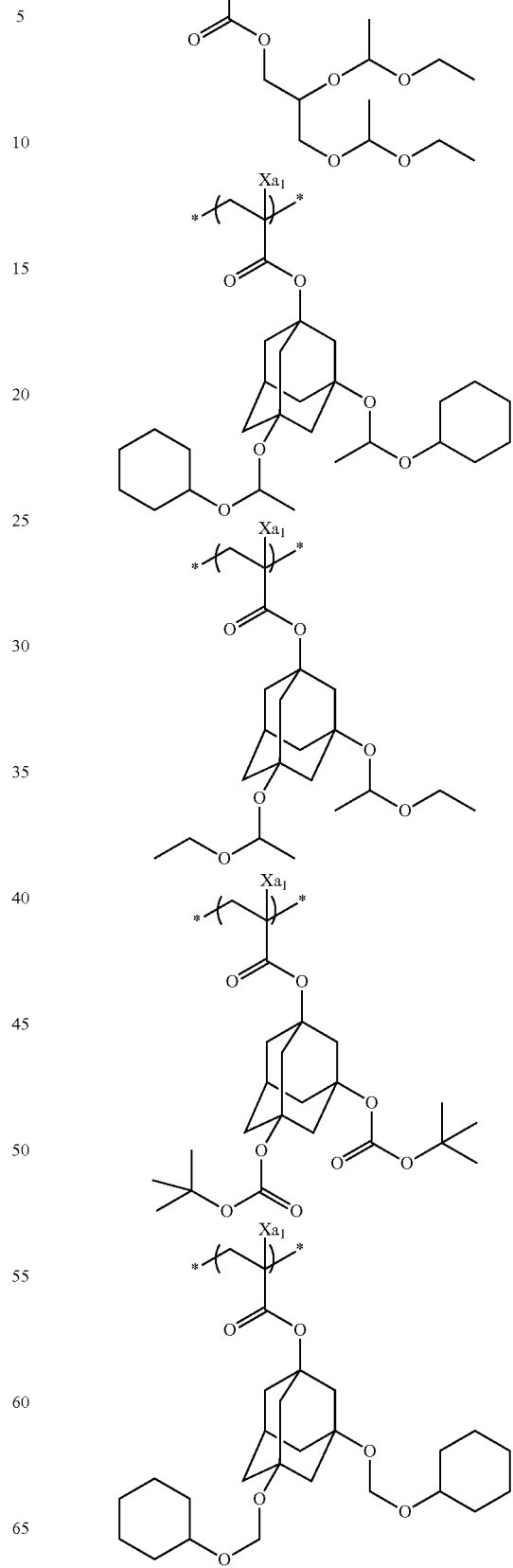

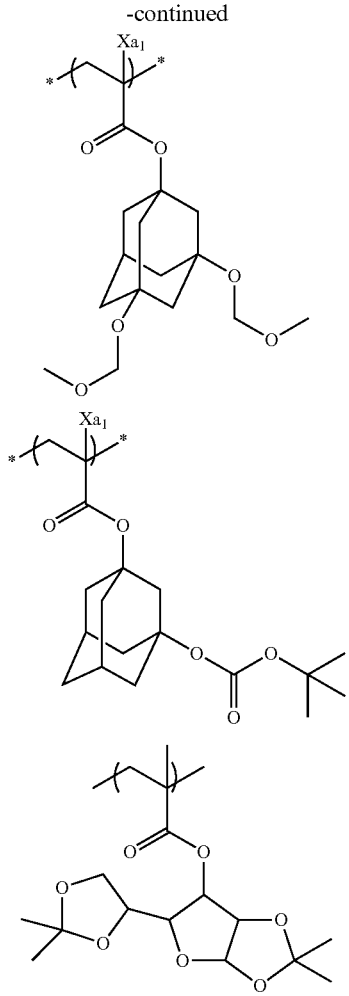

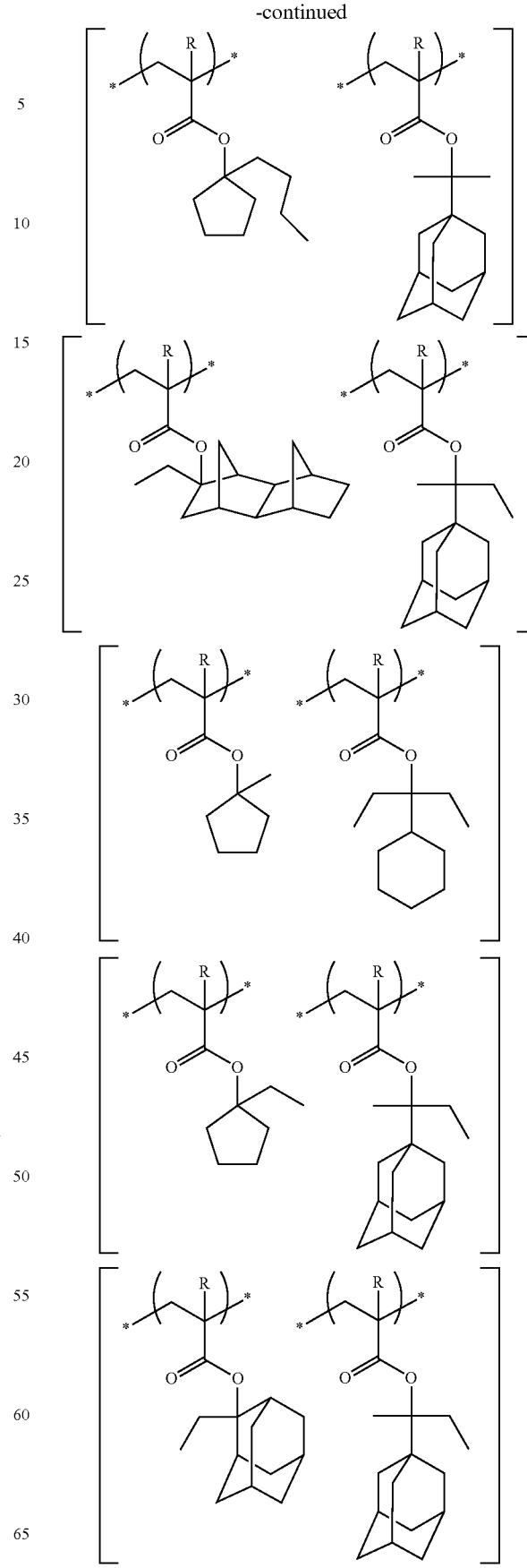

As for the repeating unit having an acid-decomposable group, one kind may be used, or two or more kinds may be used in combination.

In the case where the resin (P) contains two or more acid-decomposable group-containing repeating units, preferred combinations of two or more acid-decomposable group-containing repeating units are illustrated below, but the present invention is not limited thereto. In addition, in the following formulae, each of R independently represents a hydrogen atom or a methyl group.

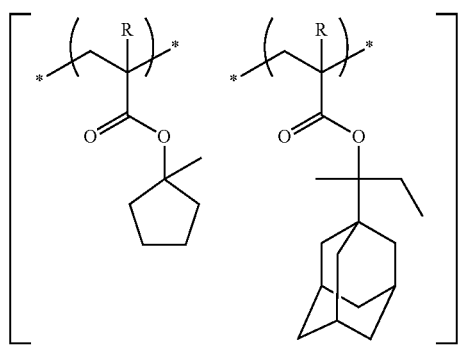

85
-continued
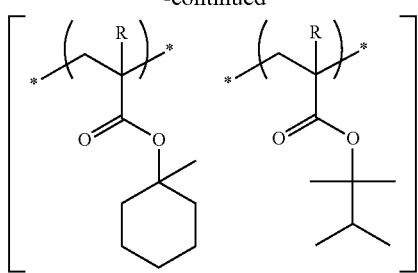
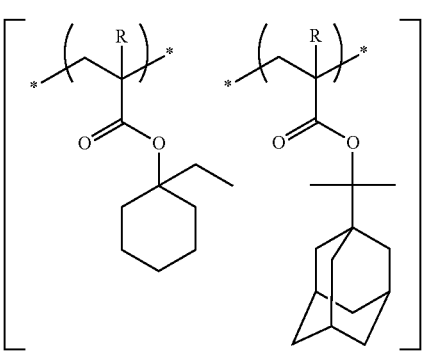
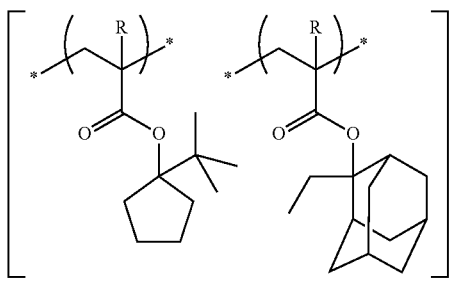
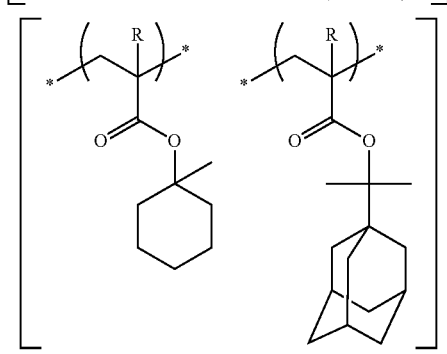
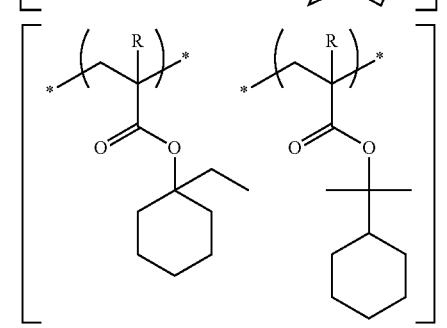
86
-continued
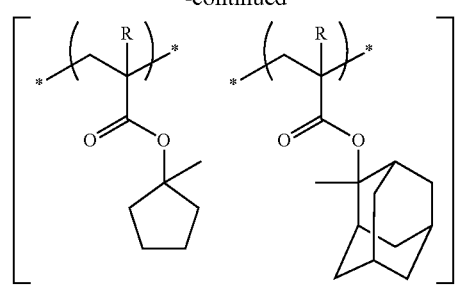
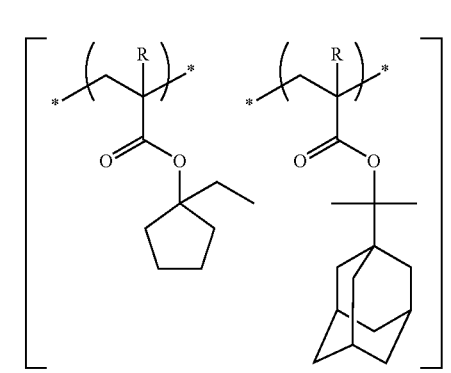
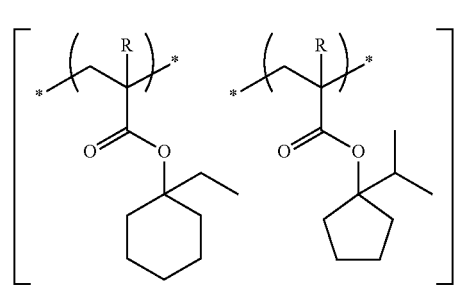
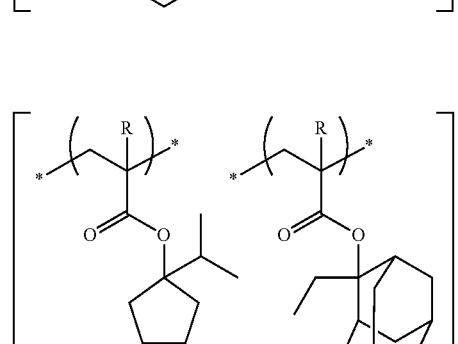
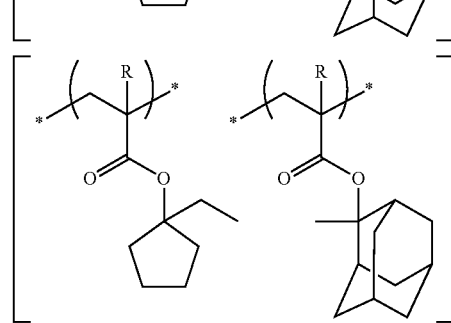

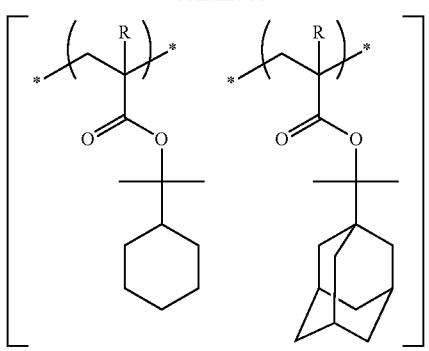

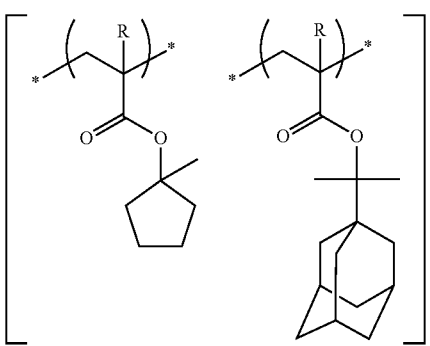

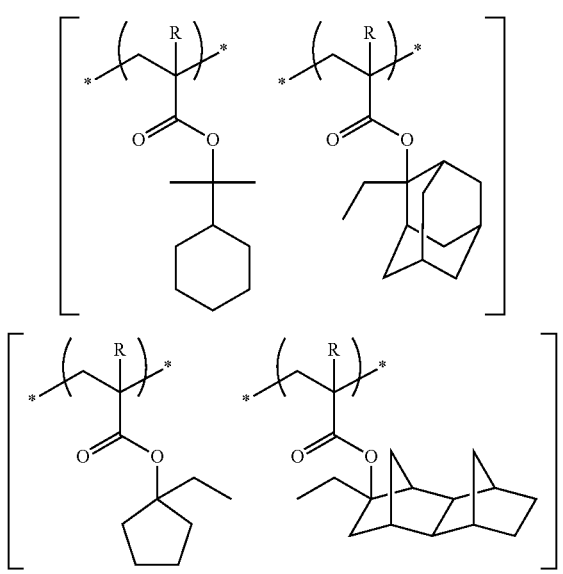

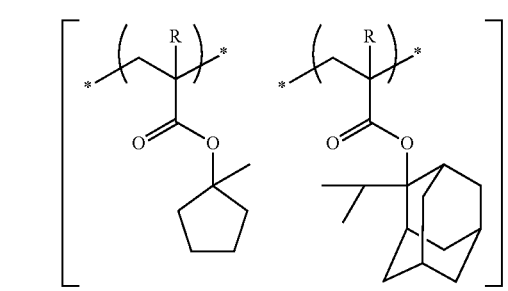

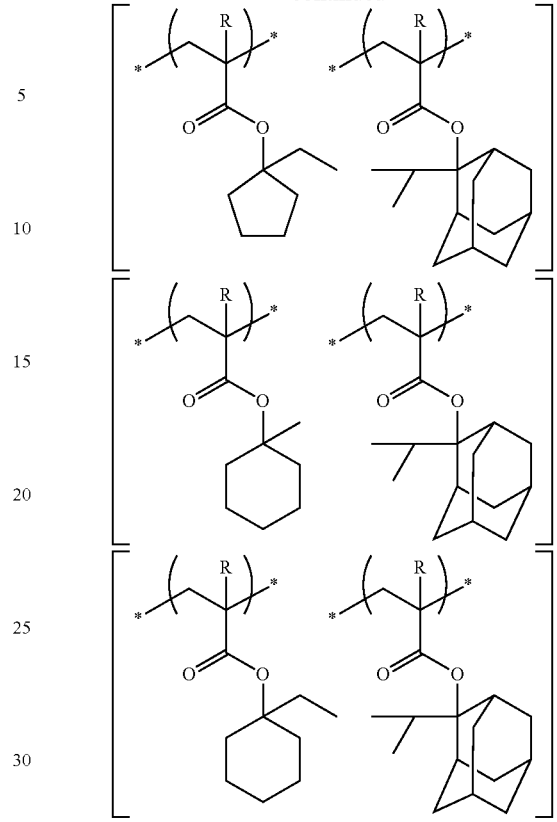

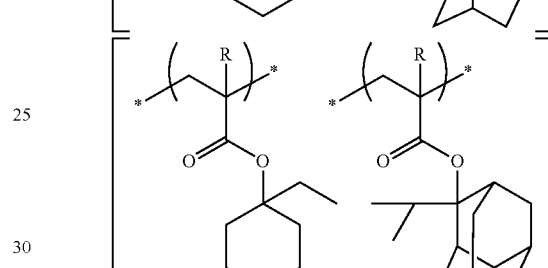

The content of the acid-decomposable group-containing repeating unit contained in the resin (P) (in the case where a plurality of acid-decomposable group-containing repeating units are present, the total thereof) is preferably 15 mol % or more, more preferably 20 mol % or more, still more preferably 25 mol % or more, yet still more preferably 40 mol % or more, based on all repeating units in the resin (P). Above all, it is preferred that the resin (P) contains the repeating unit (AI) and the content of the repeating unit (AI) is 50 mol % or more based on all repeating units in the resin (P).

When the content of the acid-decomposable group-containing repeating unit is 50 mol % or more based on all repeating units in the resin (P), the glass transition temperature (Tg) of the resin (P) can be made high without fail and in turn, the effect capable of suppressing an increase in the production cost can be obtained more reliably.

Also, the content of the acid-decomposable group-containing repeating unit is preferably 80 mol % or less, more preferably 70 mol % or less, still more preferably 65 mol % or less, based on all repeating units in the resin (P).

The resin (P) may contain a repeating unit having a lactone structure or a sultone structure.

As the lactone structure or sultone structure, any structure may be used as long as it has a lactone structure or a sultone structure, but the structure is preferably a 5- to 7-membered ring lactone structure or a 5- to 7-membered ring sultone structure, more preferably a 5- to 7-membered ring lactone structure to which another ring structure is fused in the form of forming a bicyclo or spiro structure, or a 5- to 7-membered ring sultone structure to which another ring structure is fused in the form of forming a bicyclo or Spiro structure.

The resin more preferably contains a repeating unit having a lactone structure represented by any one of the following formulae (LC1-1) to (LC1-21) or a sultone structure represented by any one of the following formulae (SL1-1) to (SL1-3). The lactone structure or sultone structure may be bonded directly to the main chain. Preferred lactone structures are (LC1-1), (LC1-4), (LC1-5), (LC1-6), (LC1-13), (LC1-14) and (LC1-17), with the lactone structure of (LC1-4) being more preferred. By using such a specific lactone structure, LER and development defect are improved.

LC1-1
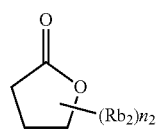

LC1-2
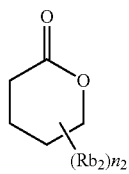

LC1-3
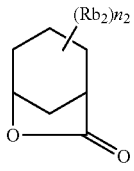

LC1-4
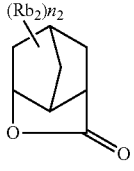

LC1-5
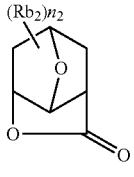

LC1-6
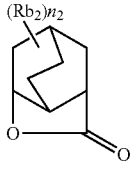

LC1-7
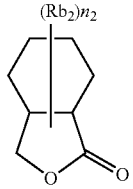

LC1-8
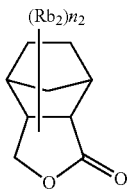

LC1-9
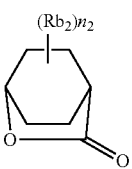

LC1-10
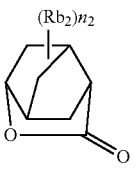

LC1-11
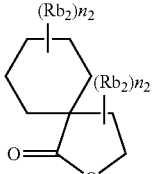

LC1-12
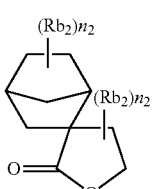

LC1-13
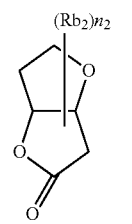

LC1-14
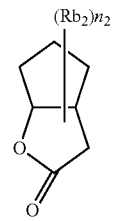

LC1-15
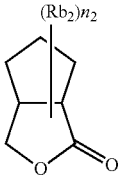

LC1-16
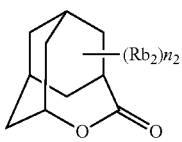

LC1-17
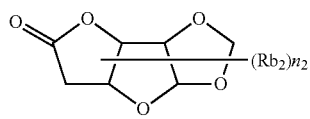

LC1-18
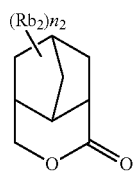

LC1-19
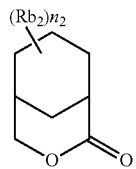

LC1-20
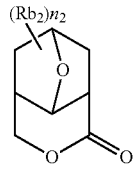

LC1-21
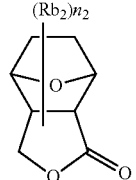

SL1-1
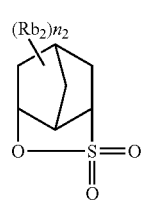

SL1-2
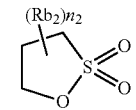

SL1-3
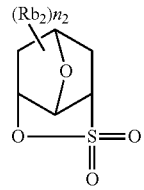

The lactone structure moiety or sultone structure moiety may or may not have a substituent ($Rb_2$). Preferred substituents ($Rb_2$) include an alkyl group having a carbon number of 1 to 8, a cycloalkyl group having a carbon number of 4 to 7, an alkoxy group having a carbon number of 1 to 8, an alkoxycarbonyl group having a carbon number of 2 to 8, a carboxyl group, a halogen atom, a hydroxyl group, a cyano group, an acid-decomposable group, and the like. Among these, an alkyl group having a carbon number of 1 to 4, a cyano group and an acid-decomposable group are more preferred. $n_2$ represents an integer of 0 to 4. When $n_2$ is an integer of 2 or more, each substituent ($Rb_2$) may be the same as or different from every other substituent ($Rb_2$), and also, the plurality of substituents ($Rb_2$) may combine with each other to form a ring.

The repeating unit having a lactone or sultone structure usually has an optical isomer, and any optical isomer may be used. One optical isomer may be used alone, or a plurality of optical isomers may be mixed and used. In the case of mainly using one optical isomer, the optical purity (ee) thereof is preferably 90% or more, more preferably 95% or more.

The repeating unit having a lactone or sultone structure is preferably a repeating unit represented by the following formula (III):

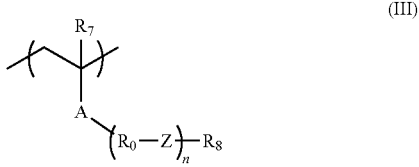

In formula (III),

A represents an ester bond (a group represented by —COO—) or an amide bond (a group represented by —CONH—), $R_0$ represents, when a plurality of $R_0$ are present, each independently represents, an alkylene group, a cycloalkylene group or a combination thereof, Z represents, when a plurality of Z are present, each independently represents, a single bond, an ether bond, an ester bond, an amide bond, a urethane bond
(a group represented by

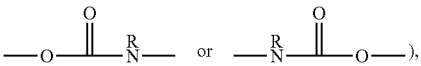

or a urea bond
(a group represented by

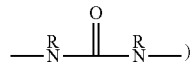

wherein each R independently represents a hydrogen atom, an alkyl group, a cycloalkyl group or an aryl group, $R_8$ represents a monovalent organic group having a lactone structure or a sultone structure, n is the repetition number of the structure represented by —$R_0$—Z— and represents an integer of 0 to 5, preferably 0 or 1, more preferably 0, and when n is 0, —$R_0$—Z— is not present and a single bond is formed, and $R_7$ represents a hydrogen atom, a halogen atom or an alkyl group.

The alkylene group and cycloalkylene group of $R_0$ may have a substituent.

Z is preferably an ether bond or an ester bond, more preferably an ester bond.

The alkyl group of $R_7$ is preferably an alkyl group having a carbon number of 1 to 4, more preferably a methyl group or an ethyl group, still more preferably a methyl group.

The alkyl group in the alkylene group and cycloalkylene group of $R_0$ and in $R_7$ may be substituted, and the substituent includes, for example, a halogen atom such as fluorine atom, chlorine atom and bromine atom, a mercapto group, a hydroxyl group, an alkoxy group such as methoxy group, ethoxy group, isopropoxy group, tert-butoxy group and benzyloxy group, and an acyloxy group such as acetyloxy group and propionyloxy group.

$R_7$ is preferably a hydrogen atom, a methyl group, a trifluoromethyl group or a hydroxymethyl group.

The chain alkylene group in $R_0$ is preferably a chain alkylene group having a carbon number of 1 to 10, more preferably having a carbon number of 1 to 5, and examples thereof include a methylene group, an ethylene group and a propylene group. The cycloalkylene group is preferably a cycloalkylene group having a carbon number of 3 to 20, and examples thereof include a cyclohexylene group, a cyclopentylene group, a norbornylene group and an adamantylene group. For bringing out the effects of the present invention, a chain alkylene group is more preferred, and a methylene group is still more preferred.

The monovalent organic group having a lactone or sultone structure represented by $R_8$ is not limited as long as it has a lactone or sultone structure. Specific examples thereof include those having a lactone or sultone structure represented by any one of formulae (LC1-1) to (LC1-21) and (SL1-1) to (SL1-3), and among these, the structure represented by (LC1-4) is preferred. In (LC1-1) to (LC1-21), $n_2$ is preferably 2 or less.

$R_8$ is preferably a monovalent organic group having an unsubstituted lactone or sultone structure, or a monovalent organic group having a lactone or sultone structure containing a methyl group, a cyano group or an alkoxycarbonyl group as a substituent, more preferably a monovalent organic group having a lactone structure containing a cyano group as a substituent (cyanolactone).

Specific examples of the repeating unit containing a group having a lactone or sultone structure are illustrated below, but the present invention is not limited thereto.

(In the formulae, Rx represents H, $CH_3$, $CH_2OH$ or $CF_3$.)

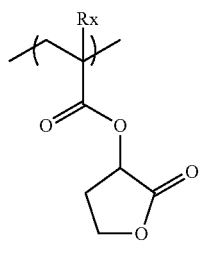
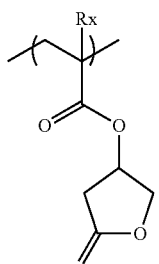
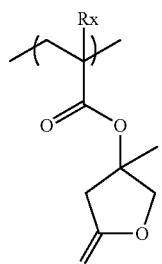

-continued

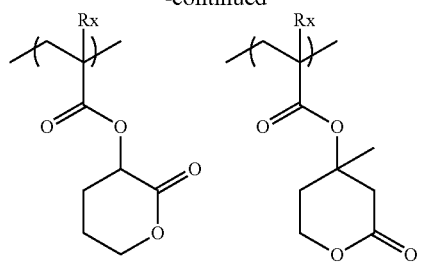

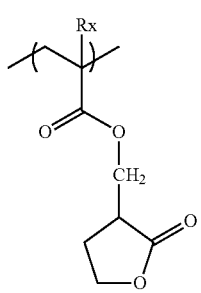 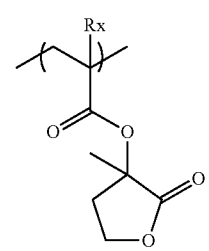

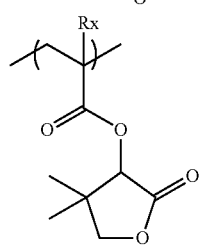 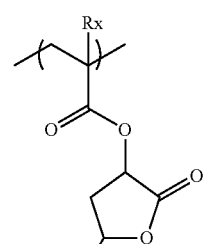

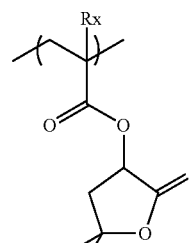 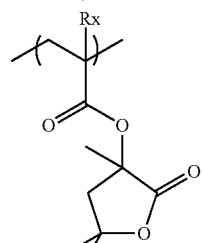

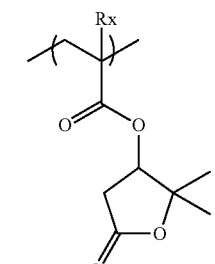 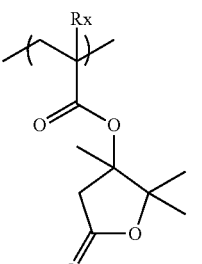

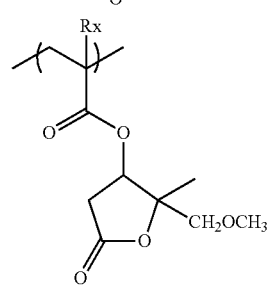

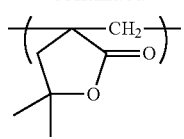
(In the formulae, Rx represents H, CH₃, CH₂OH or CF₃.)
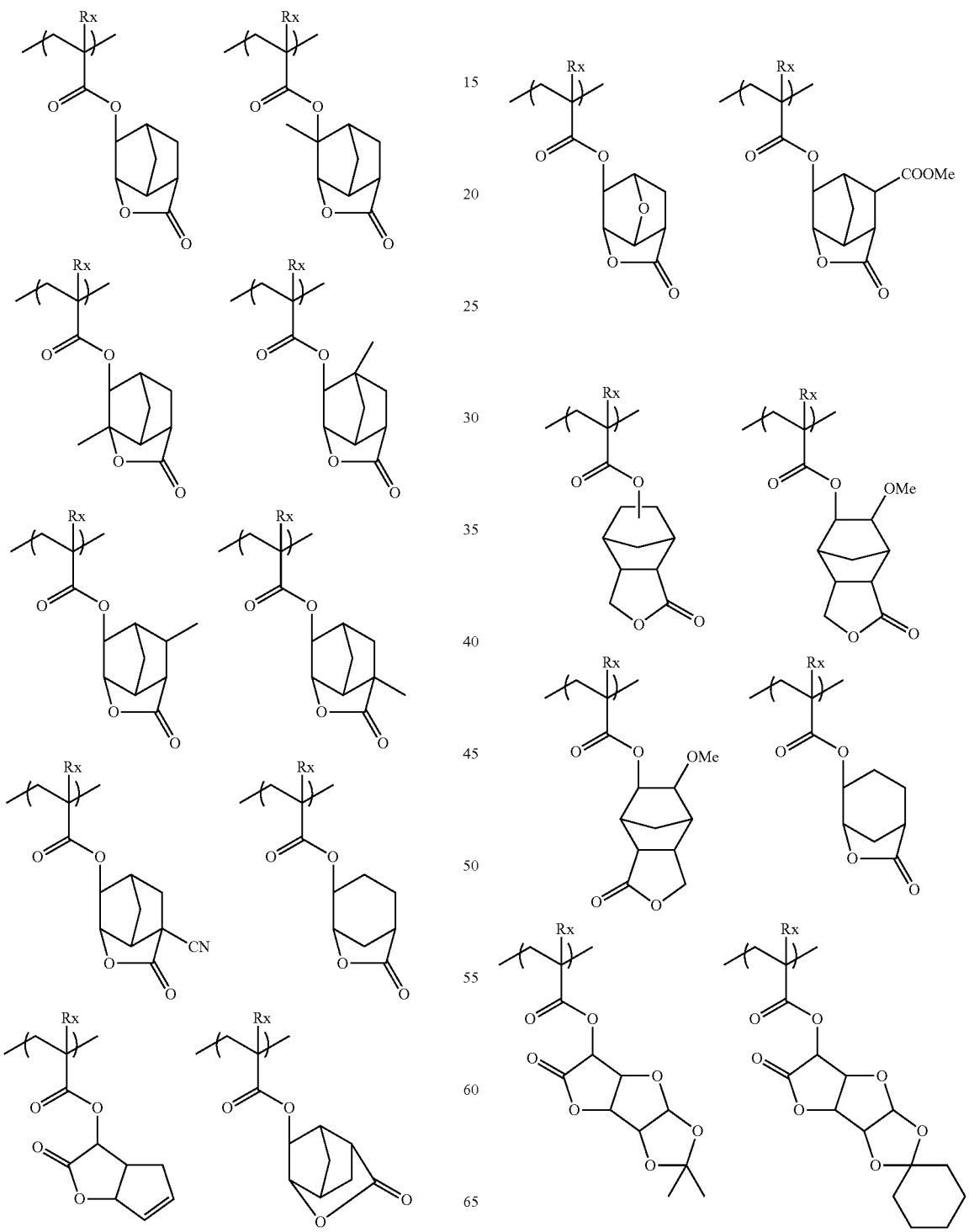

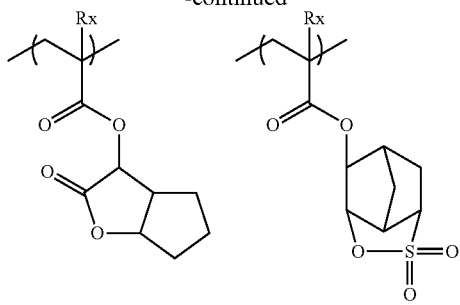
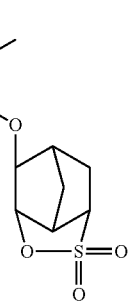
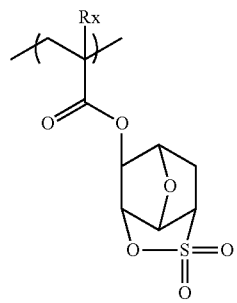
(In the formulae, Rx represents H, CH$_3$, CH$_2$OH or CF$_3$.)
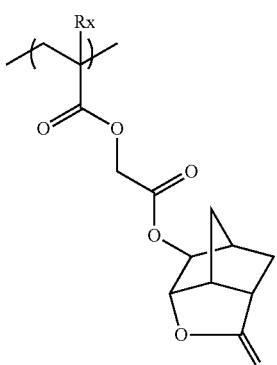
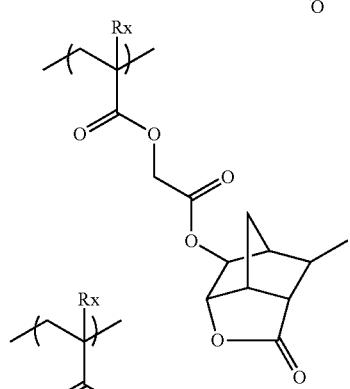
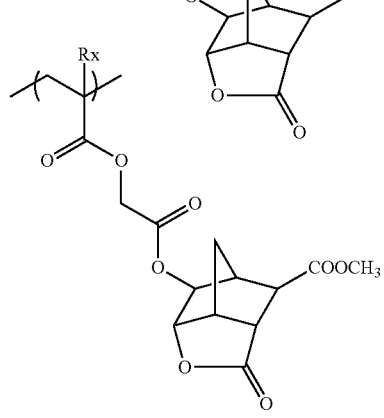
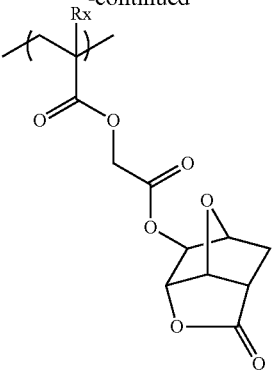
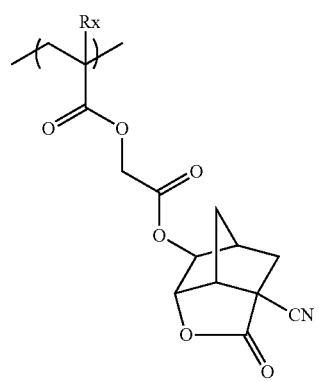
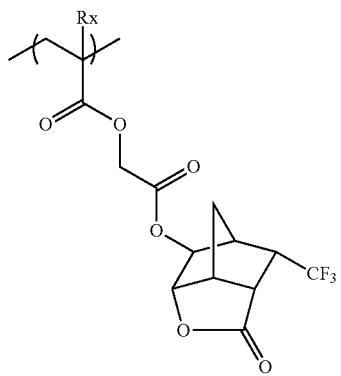
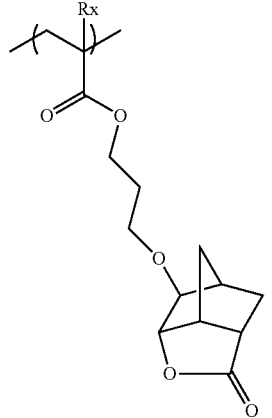

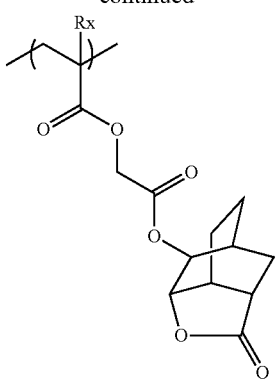
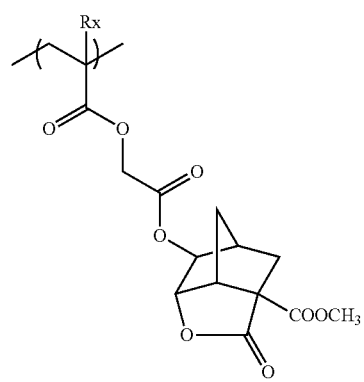
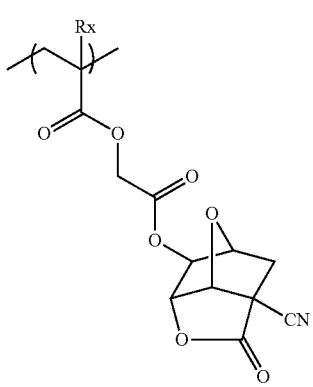
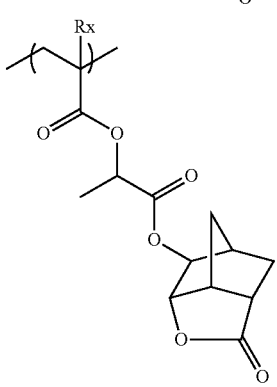
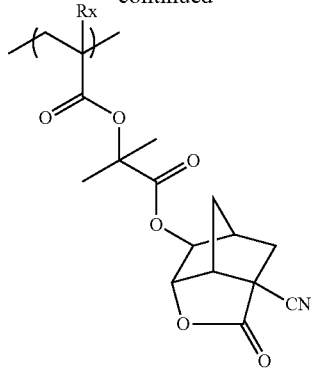
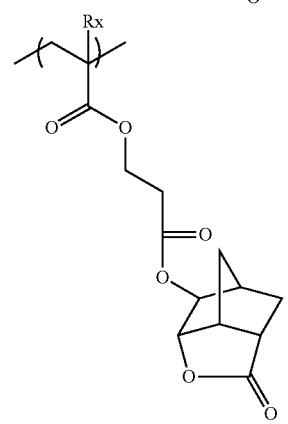
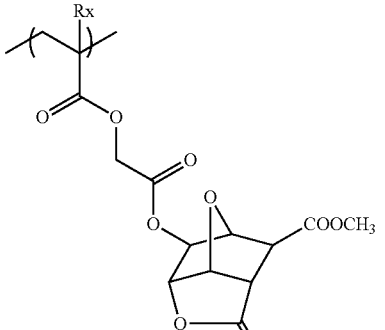
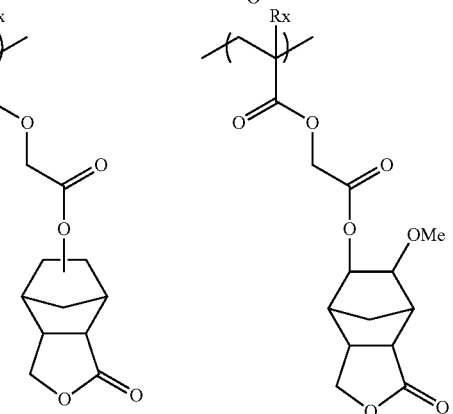
In order to increase the effects of the present invention, two or more kinds of repeating units having a lactone or sultone structure may be used in combination.
In the case where the resin (P) contains a repeating unit having a lactone or sultone structure, the content of the repeating unit having a lactone or sultone structure is preferably from 5 to 60 mol %, more preferably from 5 to 55 mol %, still more preferably from 10 to 50 mol %, based on all repeating units in the resin (P).

Also, the resin (P) may contain a repeating unit having a cyclic carbonic acid ester structure.

The repeating unit having a cyclic carbonic acid ester structure is preferably a repeating unit represented by the following formula (A-1):

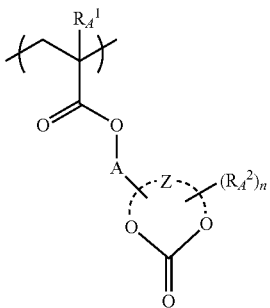

(A-1)

In formula (A-1), $R_A^1$ represents a hydrogen atom or an alkyl group, $R_A^2$ represents, when n is 2 or more, each independently represents, a substituent, A represents a single bond or a divalent linking group, Z represents an atomic group necessary for forming a monocyclic or polycyclic structure together with the group represented by —O—C(=O)—O— in the formula, and n represents an integer of 0 or more.

Formula (A-1) is described in detail below.

The alkyl group represented by $R_A^1$ may have a substituent such as fluorine atom. $R_A^1$ preferably represents a hydrogen atom, a methyl group or a trifluoromethyl group, more preferably represents a methyl group.

The substituent represented by $R_A^2$ is, for example, an alkyl group, a cycloalkyl group, a hydroxyl group, an alkoxy group, an amino group or an alkoxycarbonylamino group and is preferably an alkyl group having a carbon number of 1 to 5, and examples thereof include a linear alkyl group having a carbon number of 1 to 5 and a branched alkyl group having a carbon number of 3 to 5. The alkyl may have a substituent such as hydroxyl group.

n represents the number of substituents and is an integer of 0 or more. n is preferably from 0 to 4, more preferably 0.

The divalent linking group represented by A includes, for example, an alkylene group, a cycloalkylene group, an ester bond, an amide bond, an ether bond, a urethane bond, a urea bond, and a combination thereof. The alkylene group is preferably an alkylene group having a carbon number of 1 to 10, more preferably an alkylene group having a carbon number of 1 to 5.

In one embodiment of the present invention, A is preferably a single bond or an alkylene group.

The monocyclic ring containing —O—C(=O)—O— represented by Z includes, for example, a 5- to 7-membered ring where in the cyclic carbonic acid ester represented by the following formula (a), $n_A$ is from 2 to 4, and is preferably a 5- or 6-membered ring ($n_A$ is 2 or 3), more preferably a 5-membered ring ($n_A$ is 2).

The polycyclic ring containing —O—C(=O)—O— represented by Z includes, for example, a structure where the cyclic carbonic acid ester represented by the following formula (a) forms a condensed ring together with one other ring structure or two or more other ring structures, and a structure where a spiro ring is formed. The "other ring structure" capable of forming a condensed ring or a spiro ring may be an alicyclic hydrocarbon group or an aromatic hydrocarbon group or may be a heterocyclic ring.

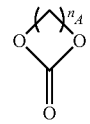

(a)

In the resin (P), one of repeating units represented by formula (A-1) may be contained alone, or two or more thereof may be contained.

In the resin (P), the content percentage of the repeating unit having a cyclic carbonic acid ester structure (preferably the repeating unit represented by formula (A-1)) is preferably from 3 to 80 mol %, more preferably from 3 to 60 mol %, still more preferably from 3 to 30 mol %, and most preferably from 10 to 15 mol %, based on all repeating units constituting the resin (P). With such a content percentage, the developability, low defect rate, low LWR, low PEB temperature dependency, profile and the like of the resist can be improved.

Specific examples of the repeating unit represented by formula (A-1) are illustrated below, but the present invention is not limited thereto.

In specific examples, $R_A^1$ has the same meaning as $R_A^1$ in formula (A-1).

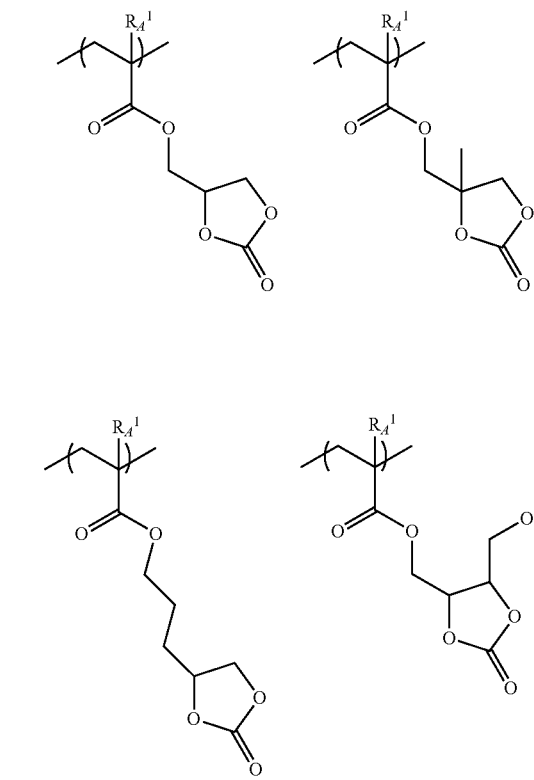

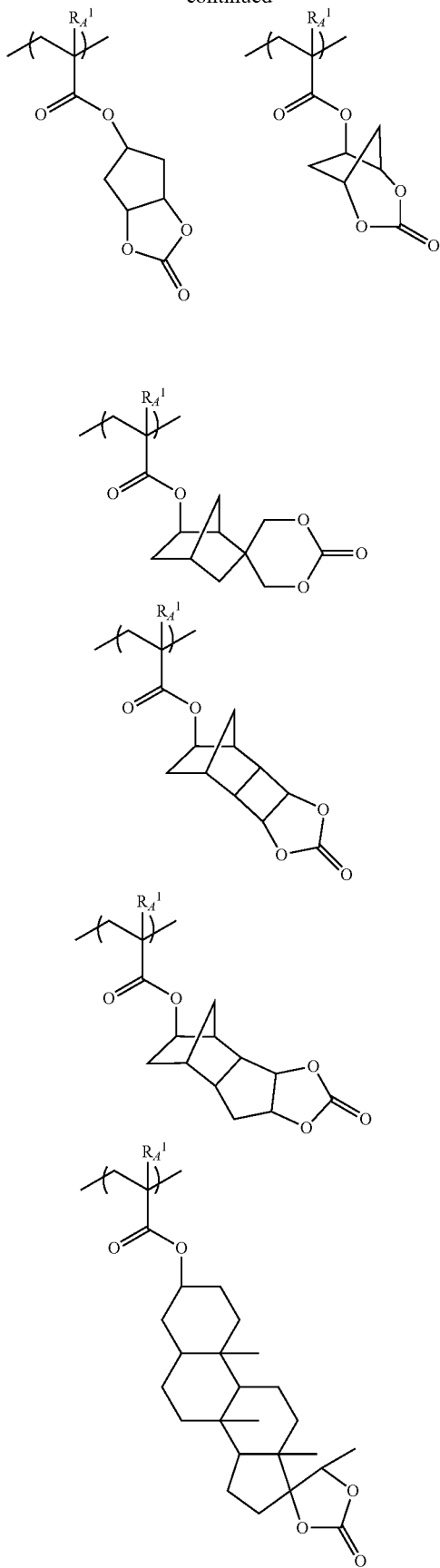
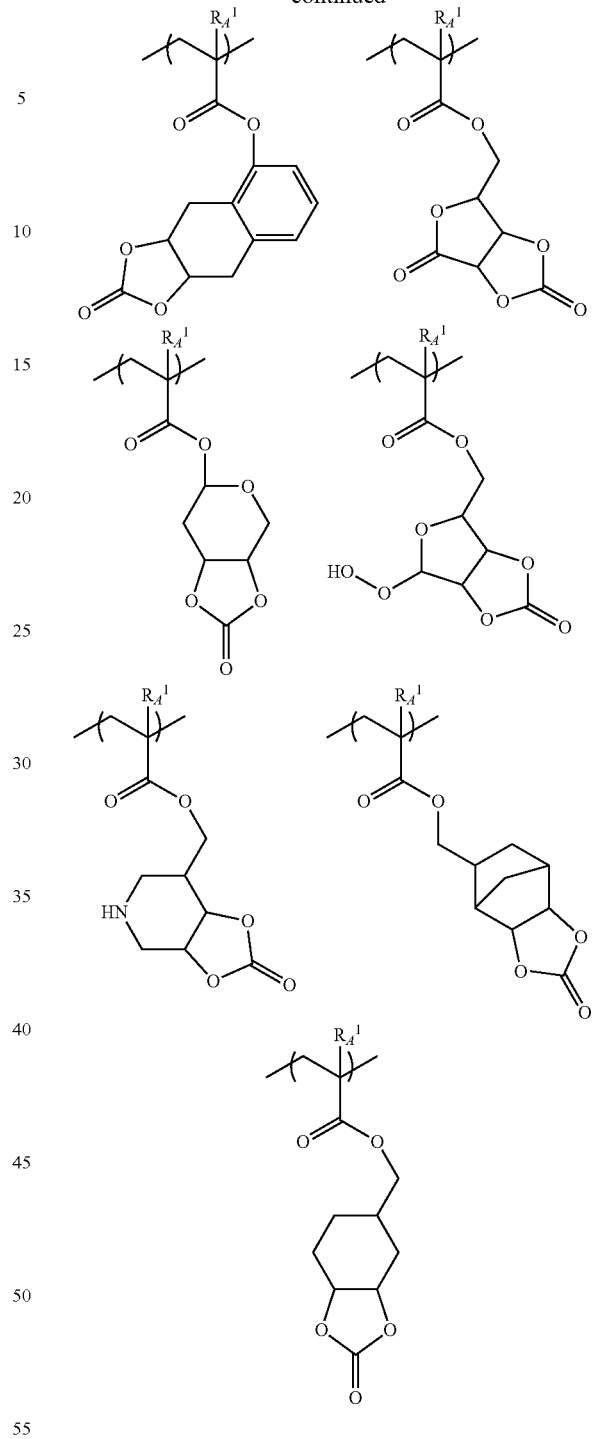

The resin (P) may contain a repeating unit having a hydroxyl group, a cyano group or a carbonyl group. Thanks to this repeating unit, the adherence to substrate and affinity for developer are enhanced. The repeating unit having a hydroxyl group, a cyano group or a carbonyl group is preferably a repeating unit having an alicyclic hydrocarbon structure substituted with a hydroxyl group, a cyano group or a carbonyl group and preferably has no acid-decomposable group.

Also, the repeating unit having an alicyclic hydrocarbon structure substituted with a hydroxyl group, a cyano group or a carbonyl group is preferably different from the repeating unit having an acid-decomposable group (that is, preferably a repeating unit stable to acid).

The alicyclic hydrocarbon structure in the alicyclic hydrocarbon structure substituted with a hydroxyl group, a cyano group or a carbonyl group is preferably an adamantyl group, a diadamantyl group or a norbornane group.

The repeating is more preferably a repeating unit represented by any one of the following formulae (AIIa) to (AIIc):

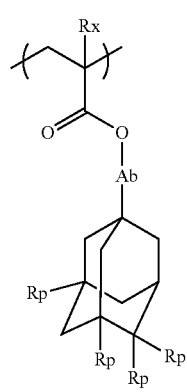
(AIIa)

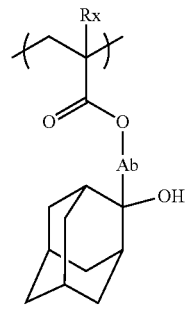
(AIIb)

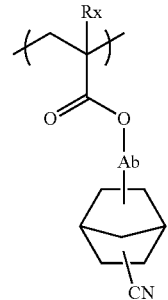
(AIIc)

In the formulae, Rx represents a hydrogen atom, a methyl group, a hydroxymethyl group or a trifluoromethyl group.

Ab represents a single bond or a divalent linking group.

The divalent linking group represented by Ab includes, for example, an alkylene group, a cycloalkylene group, an ester bond, an amide bond, an ether bond, a urethane bond, a urea bond, and a combination thereof. The alkylene group is preferably an alkylene group having a carbon number of 1 to 10, more preferably an alkylene group having a carbon number of 1 to 5, and examples thereof include a methylene group, an ethylene group, and a propylene group.

In one embodiment of the present invention, Ab is preferably a single bond or an alkylene group.

Rp represents a hydrogen atom, a hydroxyl group or a hydroxyalkyl group. Each Rp may be the same as or different from every other Rp, but out of a plurality of Rp, at least one represents a hydroxyl group or a hydroxyalkyl group.

The resin (P) may or may not contain a repeating unit having a hydroxyl group, a cyano group or a carbonyl group, but in the case where the resin (P) contains a repeating unit having a hydroxyl group, a cyano group or a carbonyl group, the content of the repeating unit having a hydroxyl group, a cyano group or a carbonyl group is preferably from 1 to 40 mol %, more preferably from 3 to 30 mol %, still more preferably from 5 to 25 mol %, based on all repeating units in the resin (P).

Specific examples of the repeating unit having a hydroxyl group, a cyano group or a carbonyl group are illustrated below, but the present invention is not limited thereto.

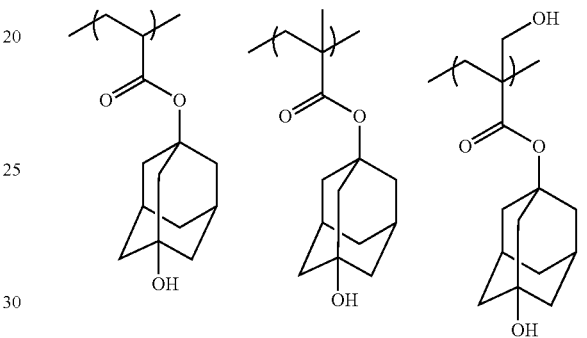

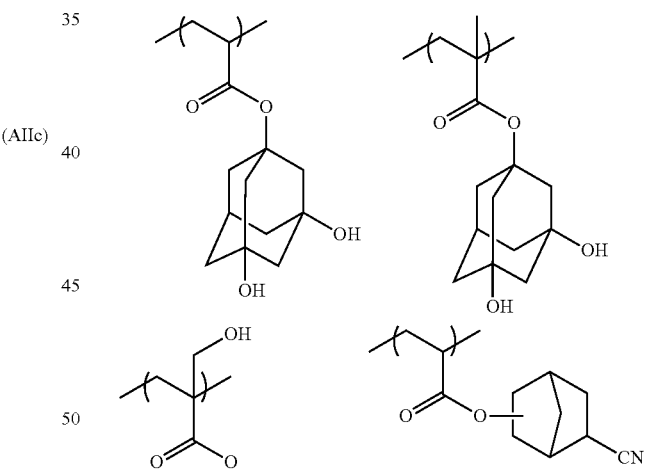

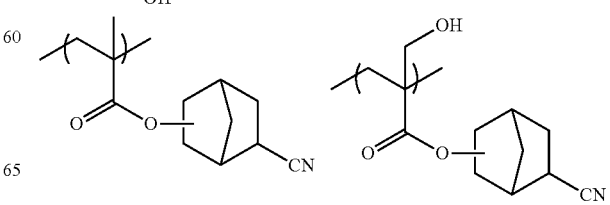

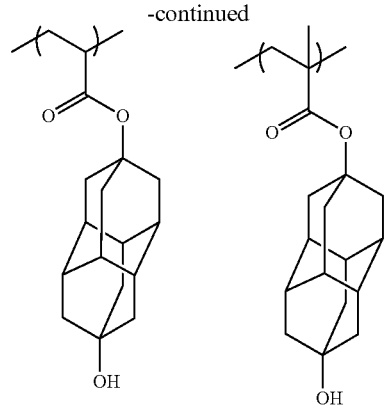

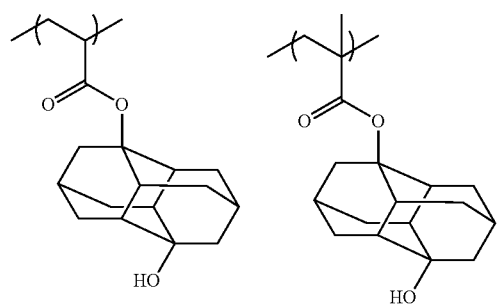

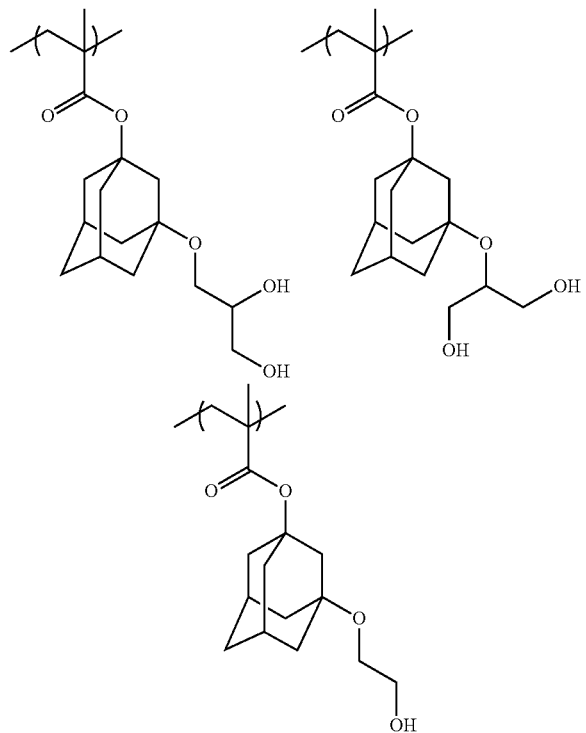

The repeating unit is still more preferably a repeating unit represented by the following formula (AIIIa) or (AIIIb):

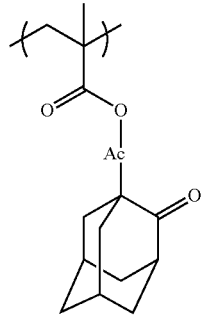

(AIIIa)

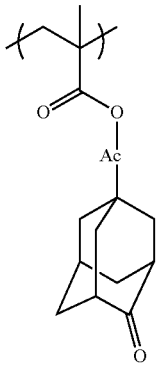

(AIIIb)

In formulae (AIIIa) and (AIIIb), Ac represents a single bond or a divalent linking group, and the preferred range thereof is the same as that of Ab in the repeating unit represented by any one of formulae (AIIa) to (AIIc).

Specific examples of the repeating unit represented by formula (AIIIa) or (AIIIb) are illustrated below, but the present invention is not limited thereto.

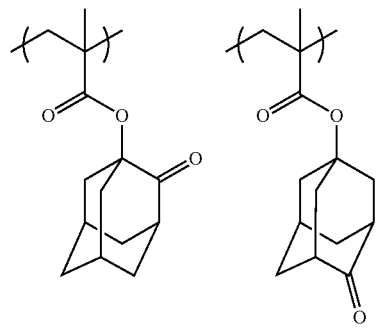

In addition, for example, monomers and corresponding repeating units described in paragraph [0011] et seq. of International Publication No. 2011/122336 may also be appropriately used.

The resin (P) may contain a repeating unit having an acid group. The acid group includes a carboxyl group, a sulfonamide group, a sulfonylimide group, a bissulfonylimide group, a naphthol structure, and an aliphatic alcohol group substituted with an electron-withdrawing group on the α-position (for example, a hexafluoroisopropanol group), and it is more preferred to contain a repeating unit having a carboxyl group. By virtue of containing a repeating unit having an acid group, the resolution increases in the usage of forming contact holes. As for the repeating unit having an acid group, all of a repeating unit where an acid group is directly bonded to the main chain of the resin, such as repeating unit by an acrylic acid or a methacrylic acid, a repeating unit where an acid group is bonded to the main chain of the resin through a linking group, and a repeating unit where an acid group is introduced into the polymer chain terminal by using an acid group-containing polymerization initiator or chain transfer agent at the polymerization, are preferred. The linking group may have a monocyclic or polycyclic cyclohydrocarbon structure. In particular, a repeating unit formed by an acrylic acid or a methacrylic acid is preferred.

The resin (P) may or may not contain a repeating unit having an acid group, but in the case of containing a repeating unit having an acid group, the content thereof is preferably 25 mol % or less, more preferably 20 mol % or less, based on all repeating units in the resin (P). In the case where the resin (P) contains a repeating unit having an acid group, the content of the acid group-containing repeating unit in the resin (P) is usually 1 mol % or more.

Specific examples of the repeating unit having an acid group are illustrated below, but the present invention is not limited thereto.

In specific examples, Rx represents H, CH$_3$, CH$_2$OH or CF$_3$.

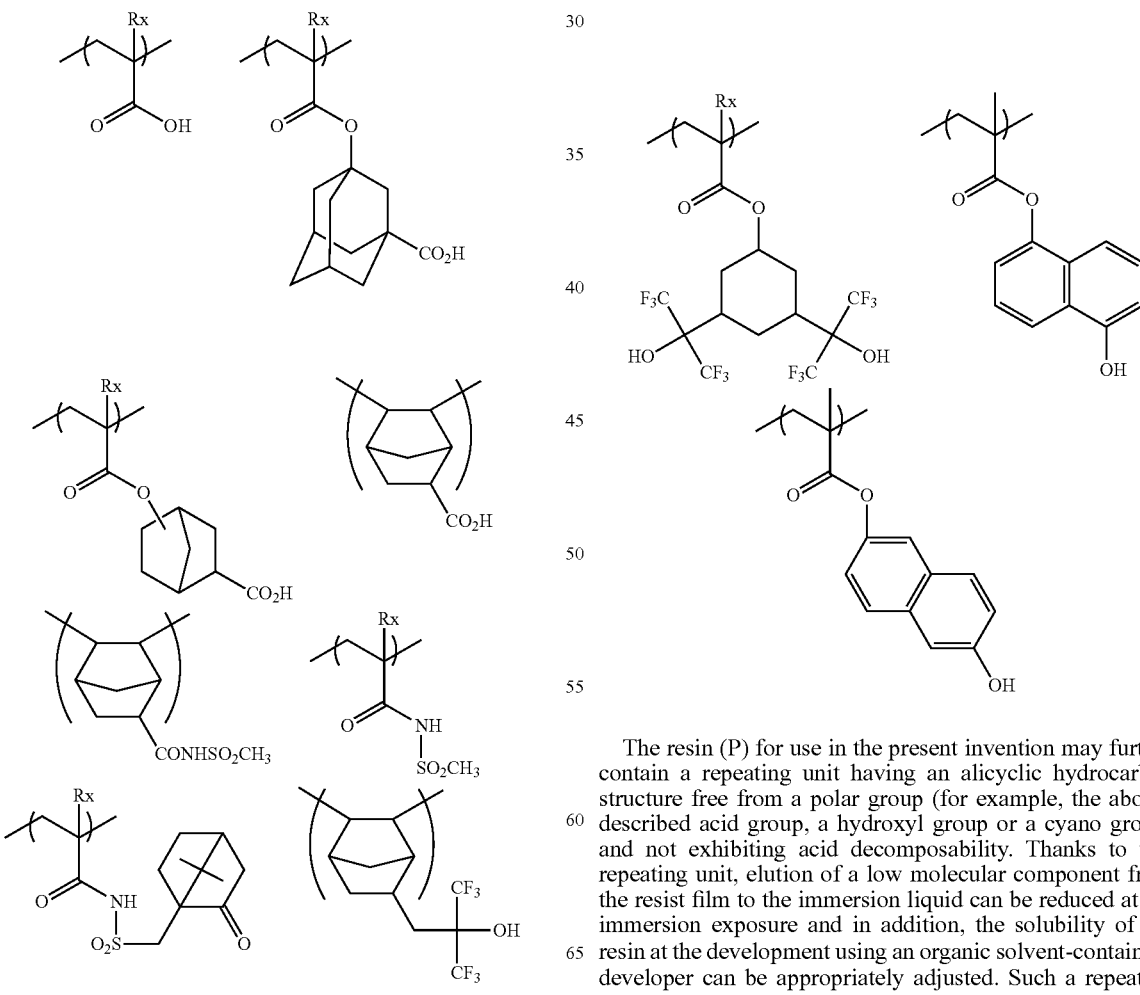

The resin (P) for use in the present invention may further contain a repeating unit having an alicyclic hydrocarbon structure free from a polar group (for example, the above-described acid group, a hydroxyl group or a cyano group) and not exhibiting acid decomposability. Thanks to this repeating unit, elution of a low molecular component from the resist film to the immersion liquid can be reduced at the immersion exposure and in addition, the solubility of the resin at the development using an organic solvent-containing developer can be appropriately adjusted. Such a repeating unit includes a repeating unit represented by formula (IV):

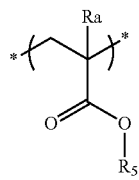

(IV)

In formula (IV), $R_5$ represents a hydrocarbon group having at least one cyclic structure and containing no polar group.

Ra represents a hydrogen atom, an alkyl group or a —$CH_2$—O—$Ra_2$ group, wherein $Ra_2$ represents a hydrogen atom, an alkyl group or an acyl group. Ra is preferably a hydrogen atom, a methyl group, a hydroxymethyl group or a trifluoromethyl group, more preferably a hydrogen atom or a methyl group.

The cyclic structure contained in $R_5$ includes a monocyclic hydrocarbon group and a polycyclic hydrocarbon group. The monocyclic hydrocarbon group includes a cycloalkyl group having a carbon number of 3 to 12, and a cycloalkenyl group having a carbon number of 3 to 12. The monocyclic hydrocarbon group is preferably a monocyclic hydrocarbon group having a carbon number of 3 to 7, more preferably a cyclopentyl group or a cyclohexyl group.

The polycyclic hydrocarbon group includes a ring-assembly hydrocarbon group and a crosslinked cyclic hydrocarbon group. Examples of the ring-assembly hydrocarbon group include a bicyclic hydrocarbon ring, a tricyclic hydrocarbon ring, and a tetracyclic hydrocarbon ring. The crosslinked cyclic hydrocarbon ring includes a condensed cyclic hydrocarbon ring and a condensed ring formed by fusing a plurality of 5- to 8-membered cycloalkane rings.

Preferred crosslinked cyclic hydrocarbon rings include a norbornyl group, an adamantyl group, a bicyclooctanyl group, a tricyclo[5,2,1,0$^{2,6}$]decanyl group, and the like. More preferred crosslinked cyclic hydrocarbon rings are a norbornyl group and an adamantyl group.

Such an alicyclic hydrocarbon group may have a substituent, and preferred substituents include a halogen atom, an alkyl group, a hydroxyl group with a hydrogen atom being substituted for, an amino group with a hydrogen atom being substituted for, and the like.

The substituent for the hydrogen atom includes, for example, an alkyl group, a cycloalkyl group, an aralkyl group, a substituted methyl group, a substituted ethyl group, an alkoxycarbonyl group, and an aralkyloxycarbonyl group.

The resin (P) may or may not contain a repeating unit having an alicyclic hydrocarbon structure free from a polar group and not exhibiting acid decomposability, but in the case of containing this repeating unit, the content thereof is preferably from 1 to 50 mol %, more preferably from 5 to 50 mol %, further more preferably 5 to 30 mol %, particularly more preferably 5 to 15 mol %, based on all repeating units in the resin (P).

Specific examples of the repeating unit having an alicyclic hydrocarbon structure free from a polar group and not exhibiting acid decomposability are illustrated below, but the present invention is not limited thereto. In the formulae, Ra represents H, $CH_3$, $CH_2OH$ or $CF_3$.

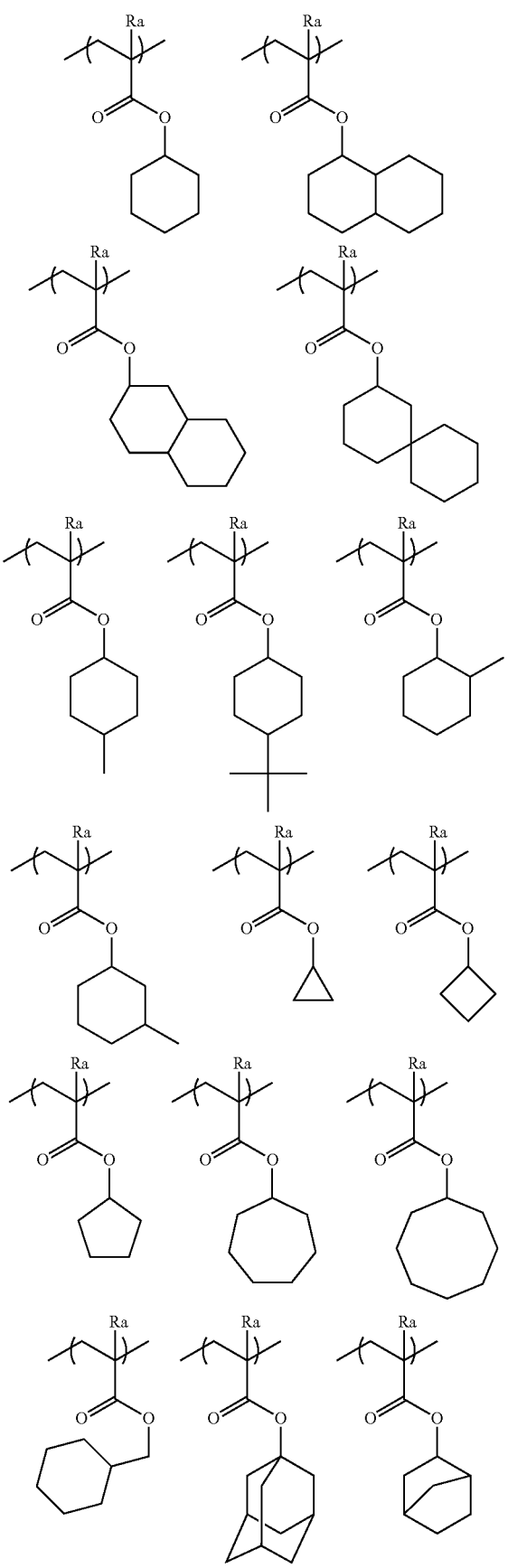

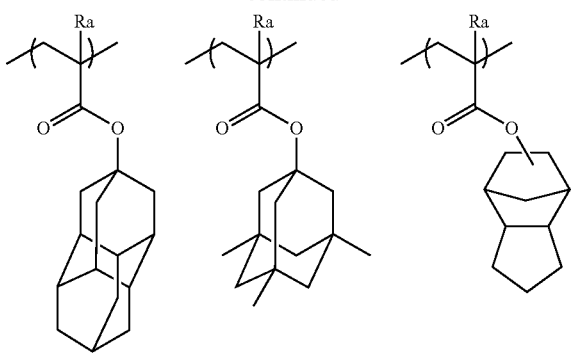
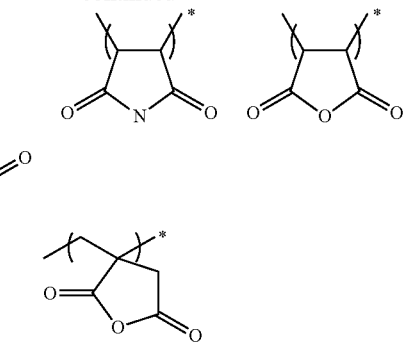

The resin (P) may contain a repeating unit containing a group capable of enhancing the adherence of the resist film to the substrate. Examples of the repeating unit containing a group capable of enhancing the adherence of the resist film to the substrate include repeating units illustrated in paragraphs [0057] to [0131] of International Publication No. 2014/017144.

In the case of irradiating the composition of the present invention with KrF excimer laser light, electron beam, X-ray or high-energy beam at a wavelength of 50 nm or less (e.g., EUV), the resin (P) preferably contains an aromatic ring-containing unit typified by a hydroxystyrene repeating unit. More preferably, the resin (P) is a copolymer of a hydroxystyrene and a hydroxystyrene protected by a group capable of leaving by the action of an acid, or a copolymer of a hydroxystyrene and a tertiary alkyl (meth)acrylate.

Specifically, such a resin includes a resin containing a repeating unit represented by the following formula (A):

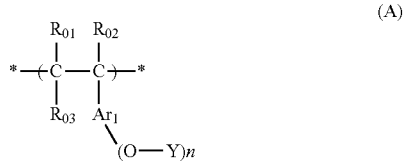

(A)

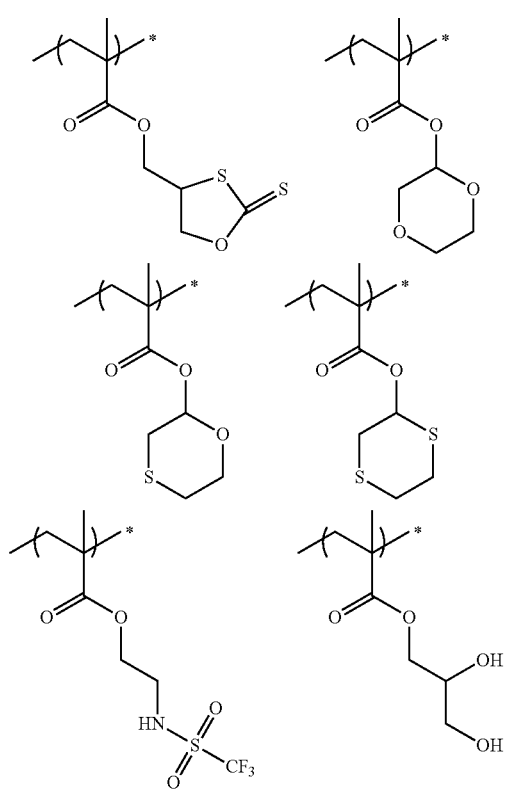

In the formula, each of $R_{01}$, $R_{02}$ and $R_{03}$ independently represents, for example, a hydrogen atom, an alkyl group, a cycloalkyl group, a halogen atom, a cyano group or an alkoxycarbonyl group, and $Ar_1$ represents, for example, an aromatic ring group. Incidentally, $R_{03}$ and $Ar_1$ may be an alkylene group and these two members may combine to form a 5- or 6-membered ring together with the —C—C— chain.

Each of n Ys independently represents a hydrogen atom or a group capable of leaving by the action of an acid, provided that at least one Y represents a group capable of leaving by the action of an acid.

n represents an integer of 1 to 4 and is preferably 1 or 2, more preferably 1.

The alkyl group as $R_{01}$ to $R_{03}$ is, for example, an alkyl group having a carbon number of 20 or less and is preferably a methyl group, an ethyl group, a propyl group, an isopropyl group, an n-butyl group, a sec-butyl group, a hexyl group, a 2-ethylhexyl group, an octyl group or a dodecyl group. The alkyl group is more preferably an alkyl group having a carbon number of 8 or less. These alkyl groups may have a substituent.

As the alkyl group contained in the alkoxycarbonyl group, the same as those for the alkyl group in $R_{01}$ to $R_{03}$ are preferred.

The cycloalkyl group may be a monocyclic cycloalkyl group or a polycyclic cycloalkyl group and is preferably a monocyclic cycloalkyl group having a carbon number of 3 to 8, such as cyclopropyl group, cyclopentyl group and cyclohexyl group. These cycloalkyl groups may have a substituent.

The halogen atom includes a fluorine atom, a chlorine atom, a bromine atom and an iodine atom and is preferably a fluorine atom.

In the case where $R_{03}$ represents an alkylene group, the alkylene group is preferably an alkylene group having a carbon number of 1 to 8, such as methylene group, ethylene group, propylene group, butylene group, hexylene group and octylene group.

The aromatic ring group as $Ar_1$ is preferably an aromatic ring group having a carbon number of 6 to 14, and examples thereof include a benzene group, a toluene group and a naphthalene group. These aromatic ring groups may have a substituent.

The group Y capable of leaving by the action of an acid includes, for example, groups represented by —C($R_{36}$)($R_{37}$)($R_{38}$), —C(=O)—O—C($R_{36}$)($R_{37}$)($R_{38}$), —C($R_{o1}$)($R_{o2}$)(O$R_{39}$), —C($R_{o1}$)($R_{o2}$)—C(=O)—O—C($R_{36}$)($R_{37}$)($R_{38}$) and —CH($R_{36}$)(Ar).

In the formulae, each of $R_{36}$ to $R_{39}$ independently represents an alkyl group, a cycloalkyl group, an aryl group, an aralkyl group or an alkenyl group. $R_{36}$ and $R_{37}$ may combine with each other to form a ring structure.

Each of $R_{o1}$ and $R_{o2}$ independently represents a hydrogen atom, an alkyl group, a cycloalkyl group, an aryl group, an aralkyl group or an alkenyl group.

Ar represents an aryl group.

The alkyl group as $R_{36}$ to $R_{39}$, $R_{o1}$ and $R_{o2}$ is preferably an alkyl group having a carbon number of 1 to 8, and examples thereof include a methyl group, an ethyl group, a propyl group, an n-butyl group, a sec-butyl group, a hexyl group, and an octyl group.

The cycloalkyl group as $R_{36}$ to $R_{39}$, $R_{o1}$ and $R_{o2}$ may be a monocyclic cycloalkyl group or a polycyclic cycloalkyl group. The monocyclic cycloalkyl group is preferably a cycloalkyl group having a carbon number of 3 to 8, and examples thereof include a cyclopropyl group, a cyclobutyl group, a cyclopentyl group, a cyclohexyl group, and a cyclooctyl group. The polycyclic cycloalkyl group is preferably a cycloalkyl group having a carbon number of 6 to 20, and examples thereof include an adamantyl group, a norbornyl group, an isoboronyl group, a camphanyl group, a dicyclopentyl group, an α-pinanyl group, a tricyclodecanyl group, a tetracyclododecyl group, and an androstanyl group. Incidentally, a part of carbon atoms in the cycloalkyl group may be substituted with a heteroatom such as oxygen atom.

The aryl group as $R_{36}$ to $R_{39}$, $R_{o1}$, $R_{o2}$ and Ar is preferably an aryl group having a carbon number of 6 to 10, and examples thereof include a phenyl group, a naphthyl group, and an anthryl group.

The aralkyl group as $R_{36}$ to $R_{39}$, $R_{o1}$ and $R_{o2}$ is preferably an aralkyl group having a carbon number of 7 to 12, and preferred examples thereof include a benzyl group, a phenethyl group, and a naphthylmethyl group.

The alkenyl group as $R_{36}$ to $R_{39}$, $R_{o1}$ and $R_{o2}$ is preferably an alkenyl group having a carbon number of 2 to 8, and examples thereof include a vinyl group, an allyl group, a butenyl group, and a cyclohexenyl group.

The ring which can be formed by combining $R_{36}$ and $R_{37}$ with each other may be monocyclic or polycyclic. The monocyclic ring is preferably a cycloalkane structure having a carbon number of 3 to 8, and examples thereof include a cyclopropane structure, a cyclobutane structure, a cyclopentane structure, a cyclohexane structure, a cycloheptane structure, and a cyclooctane structure. The polycyclic ring is preferably a cycloalkane structure having a carbon number of 6 to 20, and examples thereof include an adamantane structure, a norbornane structure, a dicyclopentane structure, a tricyclodecane structure, and a tetracyclododecane structure. Incidentally, a part of carbon atoms in the ring structure may be substituted with a heteroatom such as oxygen atom.

Each of the groups above may have a substituent, and the substituent includes, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The carbon number of such a substituent is preferably 8 or less.

The group Y capable of leaving by the action of an acid is more preferably a structure represented by the following formula (B):

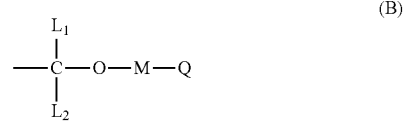

In the formula, each of $L_1$ and $L_2$ independently represents a hydrogen atom, an alkyl group, a cycloalkyl group, an aryl group or an aralkyl group.

M represents a single bond or a divalent linking group.

Q represents an alkyl group, a cycloalkyl group, a cyclic aliphatic group, an aromatic ring group, an amino group, an ammonium group, a mercapto group, a cyano group or an aldehyde group. The cyclic aliphatic group and the aromatic ring group may contain a heteroatom.

At least two members of Q, M and $L_1$ may combine with each other to form a 5- or 6-membered ring.

The alkyl group as $L_1$ and $L_2$ is, for example, an alkyl group having a carbon number of 1 to 8 and specifically, includes a methyl group, an ethyl group, a propyl group, an n-butyl group, a sec-butyl group, a hexyl group, and an octyl group.

The cycloalkyl group as $L_1$ and $L_2$ is, for example, a cycloalkyl group having a carbon number of 3 to 15 and specifically, includes a cyclopentyl group, a cyclohexyl group, a norbornyl group, and an adamantyl group.

The aryl group as $L_1$ and $L_2$ is, for example, an aryl group having a carbon number of 6 to 15 and specifically, includes a phenyl group, a tolyl group, a naphthyl group, and an anthryl group.

The aralkyl group as $L_1$ and $L_2$ is, for example, an aralkyl group having a carbon number of 6 to 20 and specifically, includes a benzyl group and a phenethyl group.

The divalent linking group as M includes, for example, an alkylene group (such as methylene group, ethylene group, propylene group, butylene group, hexylene group and octylene group), a cycloalkylene group (such as cyclopentylene group and cyclohexylene group), an alkenylene group (such as ethenylene group, propenylene group and butenylene group), an arylene group (such as phenylene group, tolylene group and naphthylene group), —S—, —O—, —CO—, —SO$_2$—, —N($R_0$)—, and a combination of two or more thereof. Here, $R_0$ is a hydrogen atom or an alkyl group. The alkyl group as $R_0$ is, for example, an alkyl group having a carbon number of 1 to 8 and specifically, includes a methyl group, an ethyl group, a propyl group, an n-butyl group, a sec-butyl group, a hexyl group, and an octyl group.

The alkyl group and cycloalkyl group as Q are the same as respective groups described above for $L_1$ and $L_2$.

The cyclic aliphatic group and aromatic ring group as Q include, for example, the cycloalkyl group and aryl group described above for $L_1$ and $L_2$. These cycloalkyl group and aryl group are preferably a group having a carbon number of 3 to 15.

The heteroatom-containing cyclic aliphatic group or aromatic ring group as Q includes, for example, a group having a heterocyclic structure such as thiirane, cyclothiolane, thiophene, furan, pyrrole, benzothiophene, benzofuran, benzopyrrole, triazine, imidazole, benzimidazole, triazole, thiadiazole, thiazole and pyrrolidone, but the ring is not limited thereto as long as it is a ring composed of carbon and a heteroatom or a ring composed of only a heteroatom.

The ring structure which may be formed by combining at least two members of Q, M and $L_1$ with each other includes, for example, a 5- or 6-membered ring structure where a propylene group or a butylene group is formed by the members above. Incidentally, this 5- or 6-membered ring structure contains an oxygen atom.

In formula (2), each of the groups represented by $L_1$, $L_2$, M and Q may have a substituent, and the substituent includes, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The carbon number of such a substituent is preferably 8 or less.

The group represented by -(M-Q) is preferably a group having a carbon number of 1 to 20, more preferably a group having a carbon number of 1 to 10, still more preferably a group having a carbon number of 1 to 8.

The resin (P) may further contain a repeating unit represented by the following formula (4). In this case, the resin (P) becomes the same component as the compound (B). In this way, in the actinic ray-sensitive or radiation-sensitive resin composition, the resin (P) and the compound (B) may be different components or the same component.

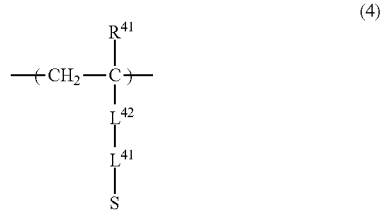

(4)

$R^{41}$ represents a hydrogen atom or a methyl group. $L^{41}$ represents a single bond or a divalent linking group. $L^{42}$ represents a divalent linking group. S represents a structural moiety capable of decomposing upon irradiation with an actinic ray or radiation to generate an acid on the side chain.

$R^{41}$ is a hydrogen atom or a methyl group as described above and is preferably a hydrogen atom.

The divalent linking group of $L^{41}$ and $L^{42}$ includes, for example, an alkylene group, a cycloalkylene group, an arylene group, —O—, —SO$_2$—, —CO—, —N(R)—, —S—, —CS—, and a combination of two or more thereof, and a linking group having a total carbon number of 20 or less is preferred. Here, R represents an aryl group, an alkyl group or a cycloalkyl group.

The alkylene group of $L^{41}$ and $L^{42}$ is preferably an alkylene group having a carbon number of 1 to 12, such as methylene group, ethylene group, propylene group, butylene group, hexylene group, octylene group and dodecanylene group.

The cycloalkylene group of $L^{41}$ and $L^{42}$ is preferably a cycloalkylene group having a carbon number of 5 to 8, such as cyclopentylene group and cyclohexylene group.

The arylene group of $L^{41}$ and $L^{42}$ is preferably an arylene group having a carbon number of 6 to 14, such as phenylene group and naphthylene group.

These alkylene group, cycloalkylene group and arylene group may further have a substituent. The substituent includes, for example, an alkyl group, a cycloalkyl group, an aryl group, an amino group, an amido group, a ureido group, a urethane group, a hydroxy group, a carboxy group, a halogen atom, an alkoxy group, a thioether group, an acyl group, an acyloxy group, an alkoxycarbonyl group, a cyano group, and a nitro group and is preferably a halogen atom (particularly, fluorine atom).

S represents a structural moiety capable of decomposing upon irradiation with an actinic ray or radiation to generate an acid on the side chain. S is preferably a structural moiety capable of decomposing upon irradiation with an actinic ray or radiation to produce an acid anion on the side chain of the resin, and the structural moiety is preferably a structural moiety contained in a photoinitiator for cationic photopolymerization, a photoinitiator for radical photopolymerization, a photodecoloring agent for dyes, a photodiscoloring agent, or a known compound capable of generating an acid by light, which is used in a microresist and the like, more preferably an ionic structural moiety.

S is more preferably an ionic structural moiety containing a sulfonium salt or an iodonium salt. More specifically, S is preferably a group represented by the following formula (PZI) or (PZII):

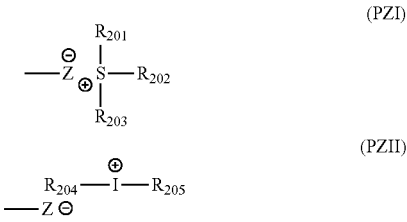

In formula (PZI), each of $R_{201}$ to $R_{203}$ independently represents an organic group.

The carbon number of the organic group as $R_{201}$ to $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene group, pentylene group). When a repeating unit where two members out of $R_{201}$ to $R_{203}$ are combined to form a ring structure is used, it can be advantageously expected to keep the exposure machine from contamination by a decomposition product during exposure.

$Z^-$ represents an acid anion generated resulting from decomposition upon irradiation with an actinic ray or radiation and is preferably a non-nucleophilic anion. The non-nucleophilic anion includes, for example, a sulfonate anion, a carboxylate anion, a sulfonylimide anion, a bis(alkylsulfonyl)imide anion, and a tris(alkylsulfonyl)methyl anion.

The non-nucleophilic anion is an anion having an extremely low ability of causing a nucleophilic reaction, and this anion can suppress the decomposition over time due to an intramolecular nucleophilic reaction. Thanks to this anion, the aging stability of the resin and in turn, the aging stability of the composition are enhanced.

The organic group of $R_{201}$ to $R_{203}$ includes an aryl group, an alkyl group, and a cycloalkyl group, and specific examples and preferred examples of these groups are the same as those recited above for $R_{201}$ to $R_{203}$ in formula (ZI) described in the compound (B).

In formula (PZII), each of $R_{204}$ and $R_{205}$ independently represents an aryl group, an alkyl group or a cycloalkyl group. Specific examples and preferred examples of these aryl, alkyl and cycloalkyl groups are the same as those recited above for $R_{201}$ to $R_{203}$ in formula (ZI) described in the compound (B).

$Z^-$ represents an acid anion generated resulting from decomposition upon irradiation with an actinic ray or radiation and is preferably a non-nucleophilic anion, and examples thereof are the same as those for $Z^-$ in formula (PZI).

The resin (P) for use in the composition of the present invention may contain, in addition to the above-described repeating structural units, various repeating structural units for the purpose of controlling dry etching resistance, suitability for standard developer, adherence to substrate, resist profile and properties generally required of an actinic ray-sensitive or radiation-sensitive resin composition, such as resolution, heat resistance and sensitivity.

Such a repeating structural unit includes repeating structural units corresponding to the monomers described below, but the present invention is not limited thereto.

Thanks to such a repeating structural unit, the performance required of the resin used in the composition of the present invention, particularly
(1) solubility for the coating solvent,
(2) film-forming property (glass transition temperature),
(3) alkali developability,
(4) film loss (selection of hydrophilic, hydrophobic or alkali-soluble group),
(5) adherence of unexposed area to substrate,
(6) dry etching resistance,
and the like, can be subtly controlled.

Such a monomer includes, for example, a compound having one addition-polymerizable unsaturated bond selected from acrylic acid esters, methacrylic acid esters, acrylamides, methacrylamides, allyl compounds, vinyl ethers and vinyl esters.

Other than these compounds, an addition-polymerizable unsaturated compound copolymerizable with the monomers corresponding to the above-described various repeating structural units may be copolymerized.

In the resin (P) for use in the composition of the present invention, the molar ratio of respective repeating structural units contained is appropriately set so as to control dry etching resistance of the actinic ray-sensitive or radiation-sensitive resin composition, suitability for standard developer, adherence to substrate, resist profile and performances generally required of an actinic ray-sensitive or radiation-sensitive resin composition, such as resolution, heat resistance and sensitivity.

In the case where the composition of the present invention is used for ArF exposure, in view of transparency to ArF light, the resin (P) for use in the composition of the present invention preferably has substantially no aromatic ring (specifically, the proportion of an aromatic group-containing repeating unit in the resin is preferably 5 mol % or less, more preferably 3 mol % or less, and ideally 0 mol %, that is, the resin does not have an aromatic group). The resin (P) preferably has a monocyclic or polycyclic alicyclic hydrocarbon structure.

The form of the resin (P) for use in the present invention may be any form of random type, block type, comb type and star type. The resin (P) can be synthesized, for example, by radical, cationic or anionic polymerization of unsaturated monomers corresponding to respective structures. The target resin can also be obtained by polymerizing unsaturated monomers corresponding to precursors of respective structures and then performing a polymer reaction.

In the case where the composition of the present invention contains the later-described resin (D), the resin (P) preferably contains no fluorine atom and no silicon atom in view of compatibility with the resin (D).

The resin (P) for use in the composition of the present invention is preferably a resin where all repeating units are composed of a (meth)acrylate-based repeating unit. In this case, all repeating units may be a methacrylate-based repeating unit, all repeating units may be an acrylate-based repeating unit, or all repeating units may be composed of a methacrylate-based repeating unit and an acrylate-based repeating unit, but the content of the acrylate-based repeating unit is preferably 50 mol % or less based on all repeating units.

The resin (P) for use in the present invention can be synthesized by a conventional method (for example, radical polymerization). The general synthesis method includes, for example, a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. The reaction solvent includes, for example, tetrahydrofuran, 1,4-dioxane, ethers such as diisopropyl ether, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate, propylene glycol monomethyl ether and cyclohexanone. The polymerization is more preferably performed using the same solvent as the solvent used in the photosensitive composition of the present invention. By the use of the same solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred initiators include azobisisobutyronitrile, azobisdimethylvaleronitrile, dimethyl 2,2'-azobis(2-methylpropionate), and the like. The initiator is added additionally or in parts as needed, and after the completion of reaction, the reaction solution is poured in a solvent to collect the desired polymer by powder, solid or other recovery methods. The concentration at the reaction is from 5 to 50 mass %, preferably from 10 to 30 mass %, and the reaction temperature is usually from 10 to 150° C., preferably from 30 to 120° C., more preferably from 60 to 100° C.

After the completion of reaction, the reaction solution is allowed to cool to room temperature and purified. In the purification, there may be applied a normal method, for example, a liquid-liquid extraction method of performing water washing or combining it with an appropriate solvent to remove residual monomers or oligomer components, a purification method in a solution state, such as ultrafiltration of extracting and removing only polymers having a molecular weight not more than a specific value, a reprecipitation method of adding dropwise the resin solution in a poor solvent to solidify the resin in the poor solvent and thereby remove residual monomers and the like, or a purification method in a solid state, such as washing of a resin slurry with a poor solvent after separation of the slurry by filtration.

For example, the resin is precipitated as a solid by contacting the reaction solution with a solvent in which the resin is sparingly soluble or insoluble (poor solvent) and which is in a volumetric amount of 10 times or less, preferably from 10 to 5 times, the reaction solution.

The solvent used at the operation of precipitation or reprecipitation from the polymer solution (precipitation or reprecipitation solvent) may be sufficient if it is a poor solvent for the polymer, and the solvent which can be used may be appropriately selected from, for example, a hydrocarbon, a halogenated hydrocarbon, a nitro compound, an ether, a ketone, an ester, a carbonate, an alcohol, a carboxylic acid, water, and a mixed solvent containing such a solvent, according to the kind of the polymer. Among these solvents, a solvent containing at least an alcohol (particularly, methanol or the like) or water is preferred as the precipitation or reprecipitation solvent.

The amount of the precipitation or reprecipitation solvent used may be appropriately selected by taking into account the efficiency, yield and the like, but in general, the amount used is from 100 to 10,000 parts by mass, preferably from 200 to 2,000 parts by mass, more preferably from 300 to 1,000 parts by mass, per 100 parts by mass of the polymer solution.

The temperature at the precipitation or reprecipitation may be appropriately selected by taking into account the efficiency or operability but is usually on the order of 0 to 50° C., preferably in the vicinity of room temperature (for example, approximately from 20 to 35° C.). The precipitation or reprecipitation operation may be performed using a commonly employed mixing vessel such as stirring tank by a known method such as batch system and continuous system.

The precipitated or reprecipitated polymer is usually subjected to commonly employed solid-liquid separation such as filtration and centrifugation, then dried and used. The filtration is performed using a solvent-resistant filter element preferably under pressure. The drying is performed under atmospheric pressure or reduced pressure (preferably under reduced pressure) at a temperature of approximately from 30 to 100° C., preferably on the order of 30 to 50° C.

Incidentally, after the resin is once precipitated and separated, the resin may be again dissolved in a solvent and then put into contact with a solvent in which the resin is sparingly soluble or insoluble. That is, there may be used a method including, after the completion of radical polymerization reaction, bringing the polymer into contact with a solvent in which the polymer is sparingly soluble or insoluble, to precipitate a resin (step a), separating the resin from the solution (step b), anew dissolving the resin in a solvent to prepare a resin solution A (step c), bringing the resin solution A into contact with a solvent in which the resin is sparingly soluble or insoluble and which is in a volumetric amount of less than 10 times (preferably 5 times or less) the resin solution A, to precipitate a resin solid (step d), and separating the precipitated resin (step e).

Also, in order to keep the resin from aggregation or the like after preparation of the composition, as described, for example, in JP-A-2009-037108, a step of dissolving the synthesized resin in a solvent to make a solution and heating the solution at approximately from 30 to 90° C. for approximately from 30 minutes to 4 hours may be added.

The weight average molecular weight of the resin (P) for use in the present invention is, as described above, 7,000 or more, preferably from 7,000 to 200,000, more preferably from 7,000 to 50,000, still more preferably from 7,000 to 40,000, yet still more preferably from 7,000 to 30,000, in terms of polystyrene by the GPC method. If the weight average molecular weight is less than 7,000, the solubility for an organic developer becomes too high and a precise pattern may not be formed.

The polydispersity (molecular weight distribution) is usually from 1.0 to 3.0, preferably from 1.0 to 2.6, more preferably from 1.0 to 2.0, still more preferably from 1.4 to 2.0. As the molecular weight distribution is smaller, not only the resolution and resist profile are more excellent but also the side wall of the resist pattern is smoother and the roughness is more improved.

In the actinic ray-sensitive or radiation-sensitive resin composition of the present invention, the blending ratio of the resin (P) in the entire composition is preferably from 30 to 99 mass %, more preferably from 60 to 95 mass %, based on the total solid content.

Also, in the present invention, as for the resin (P), one kind may be used or a plurality of kinds may be used in combination.

Specific examples of the resin (P) are illustrated below, but the present invention is not limited thereto.

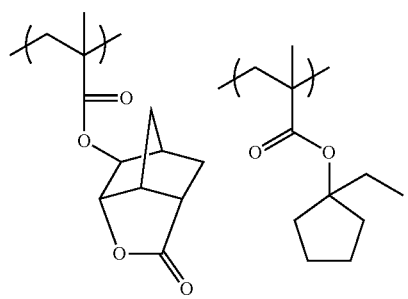

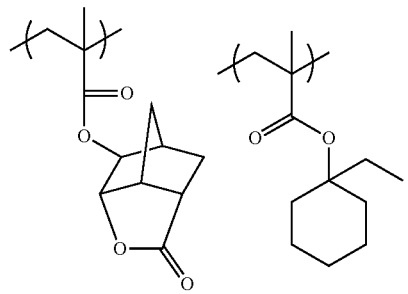

-continued
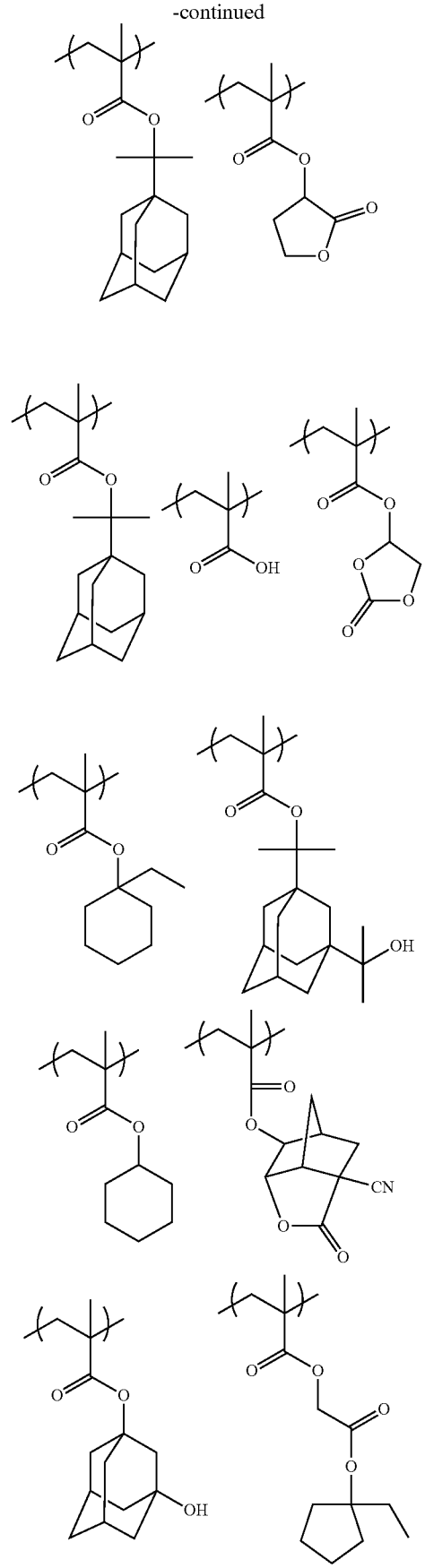
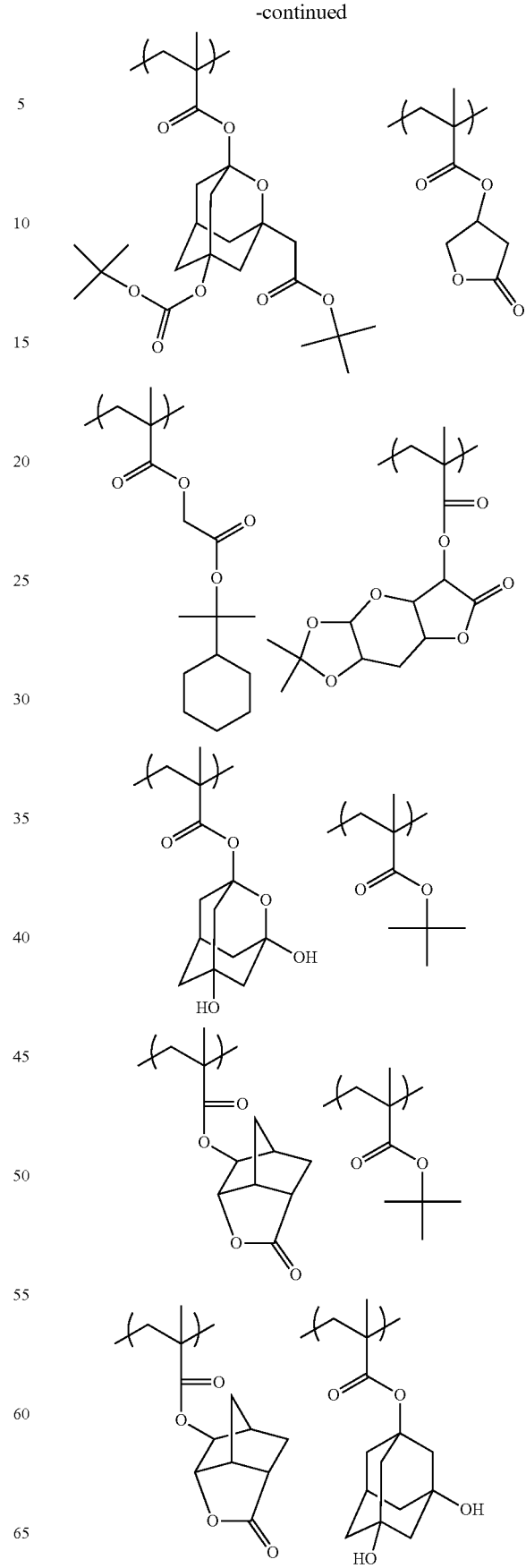

125
-continued
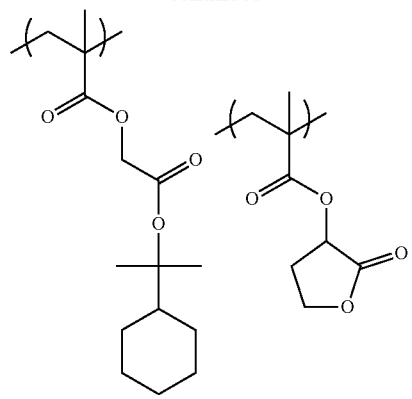
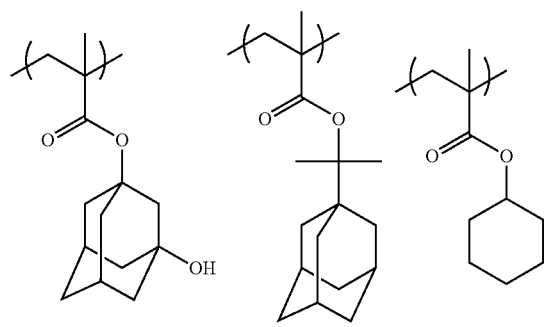
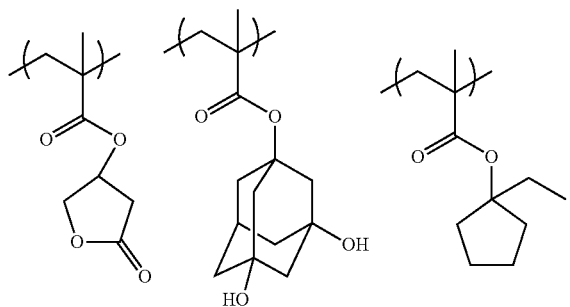
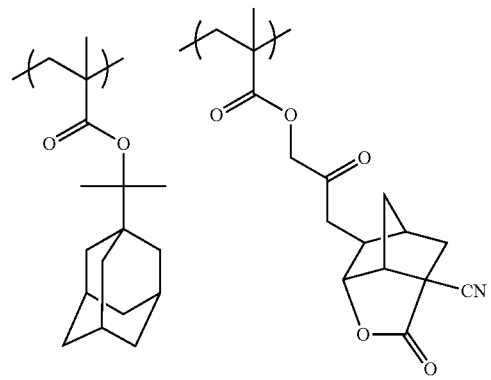
126
-continued
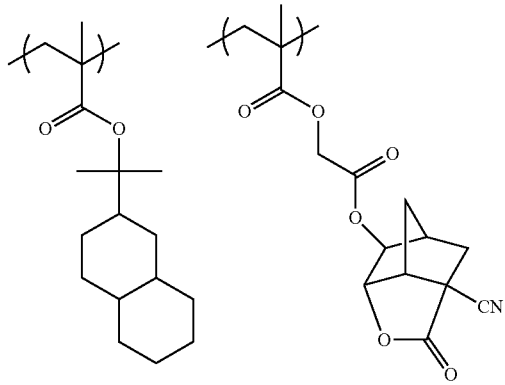
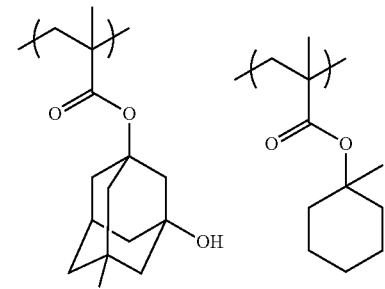
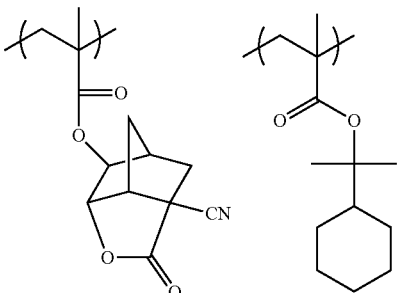
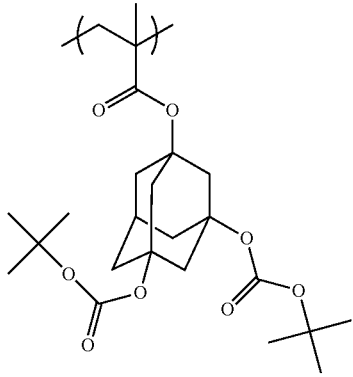
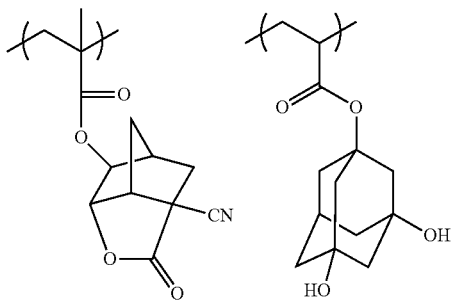

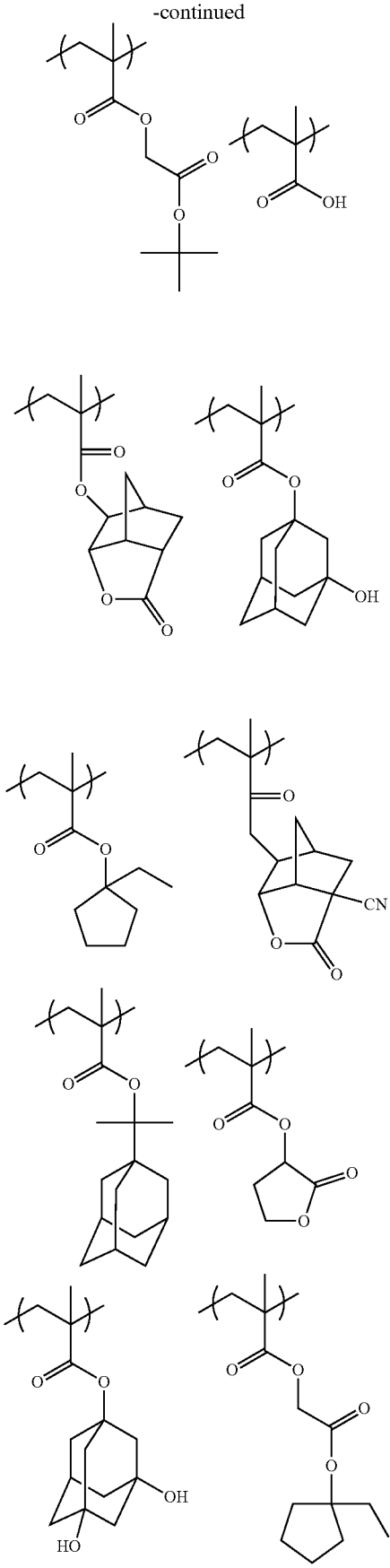
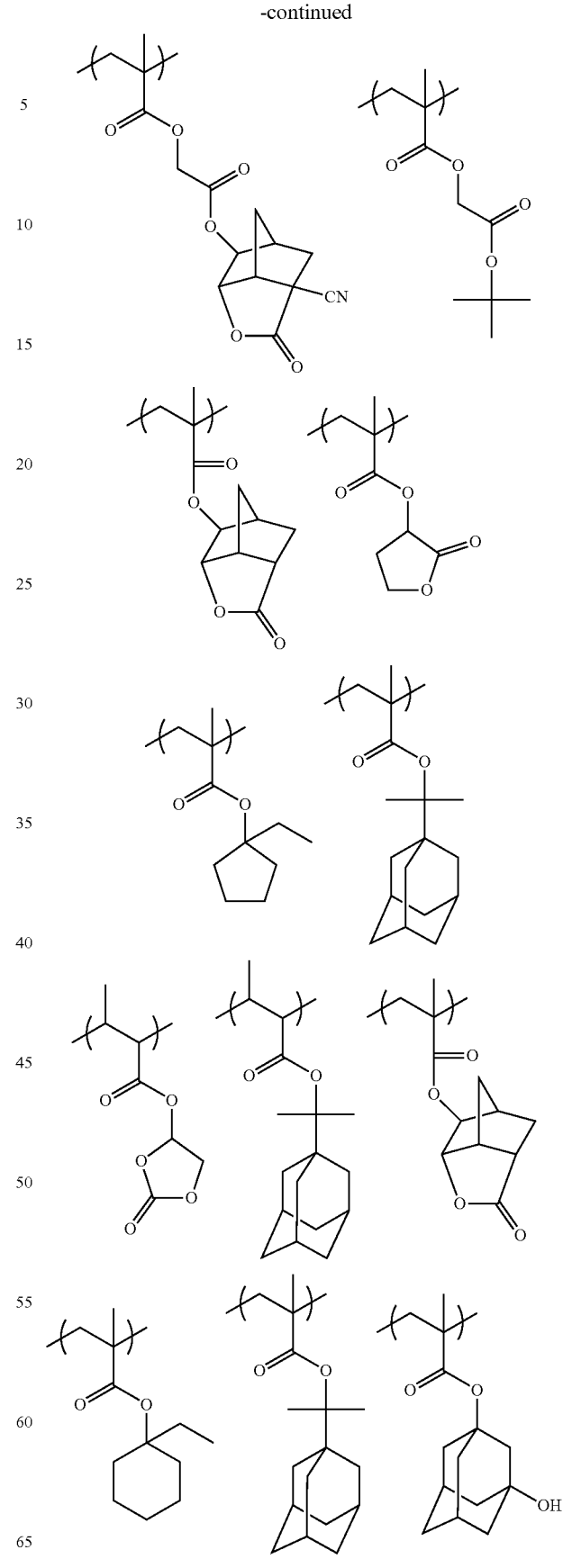

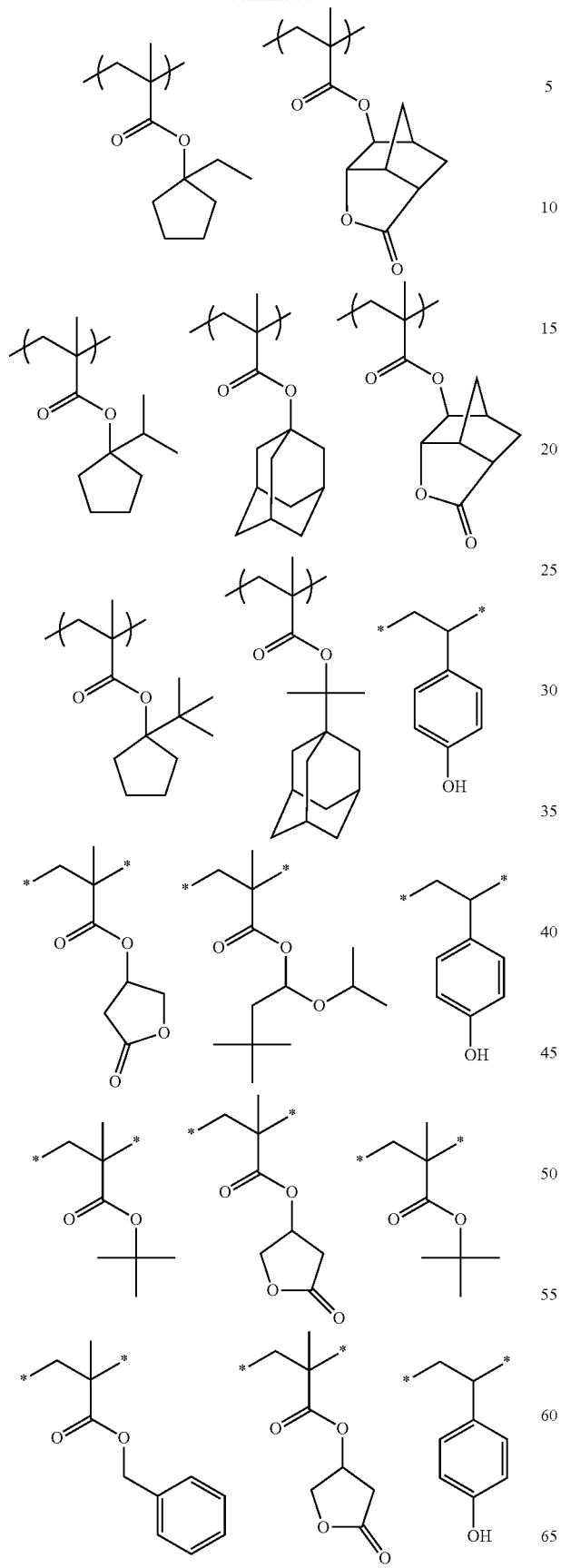
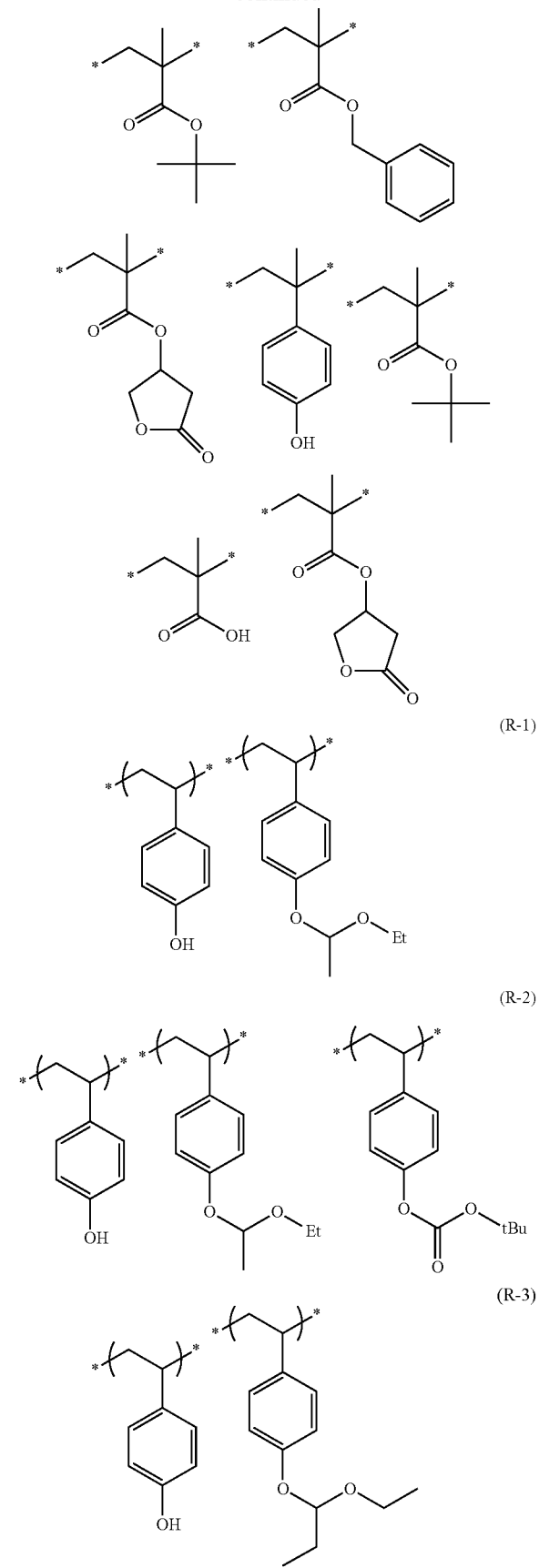

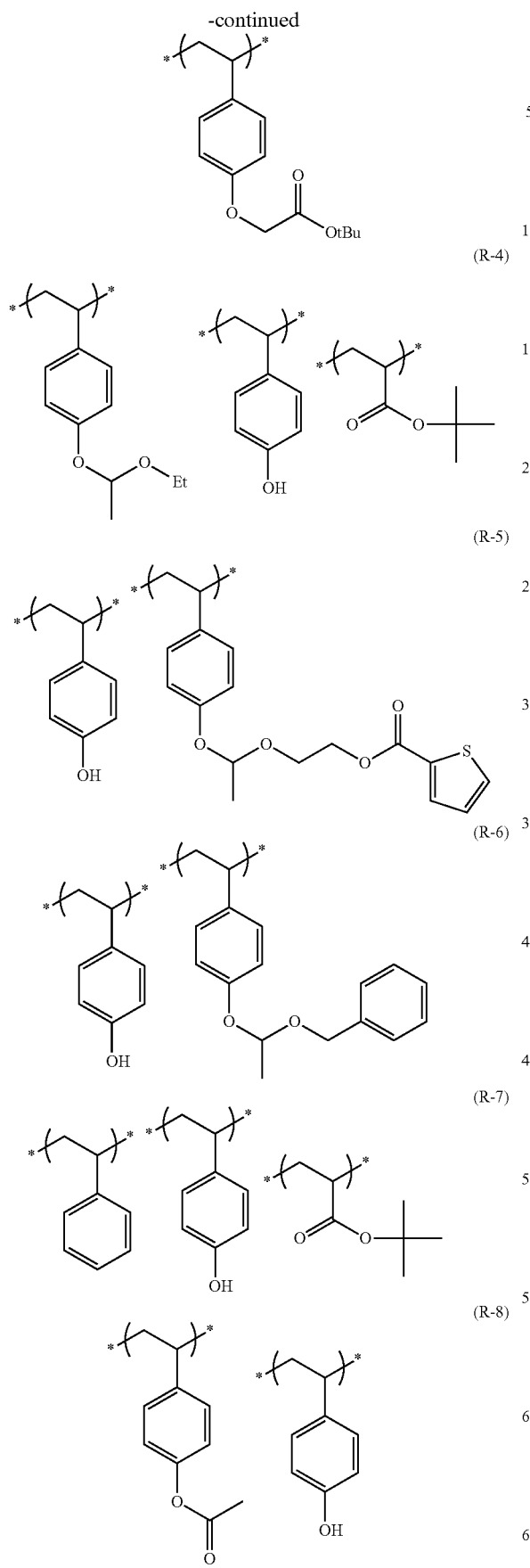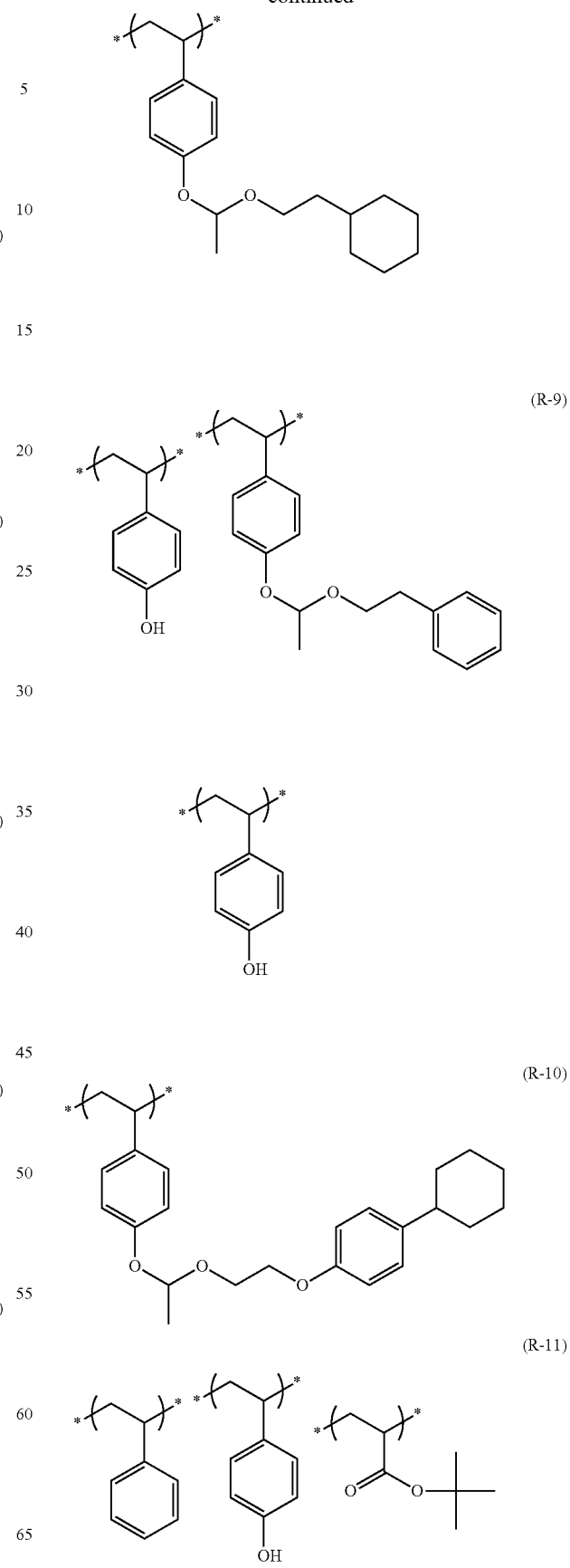

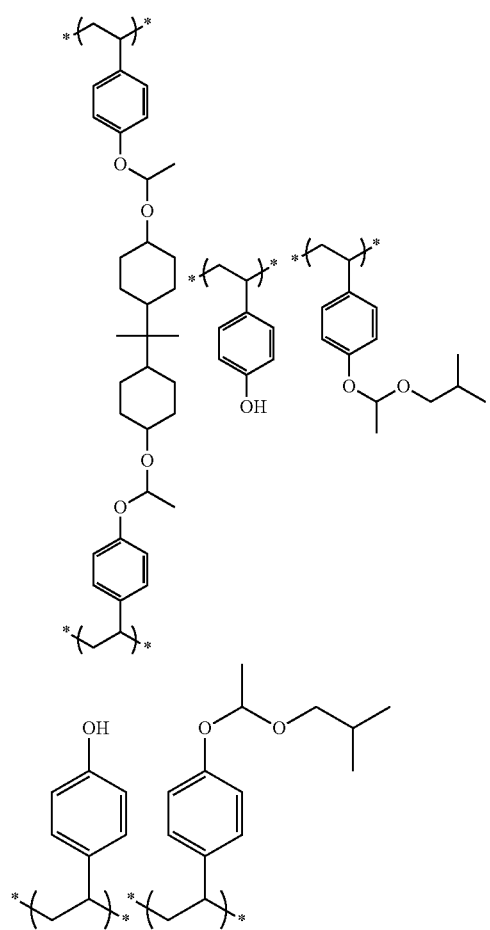
(R-12)
(R-13)
(R-14)
(R-15)
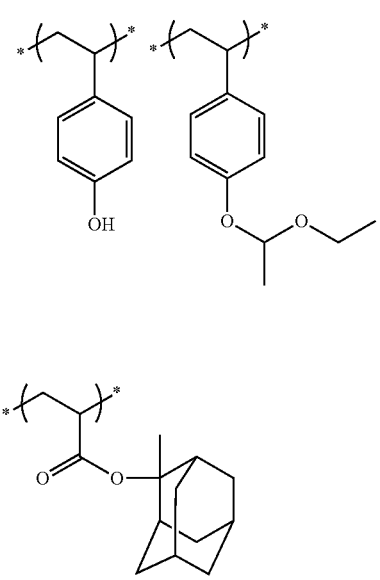
(R-16)
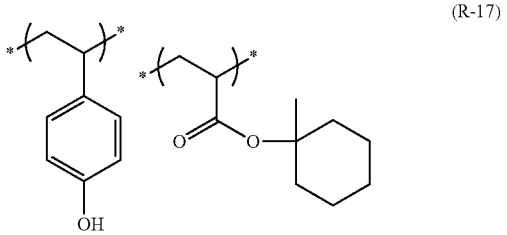
(R-17)
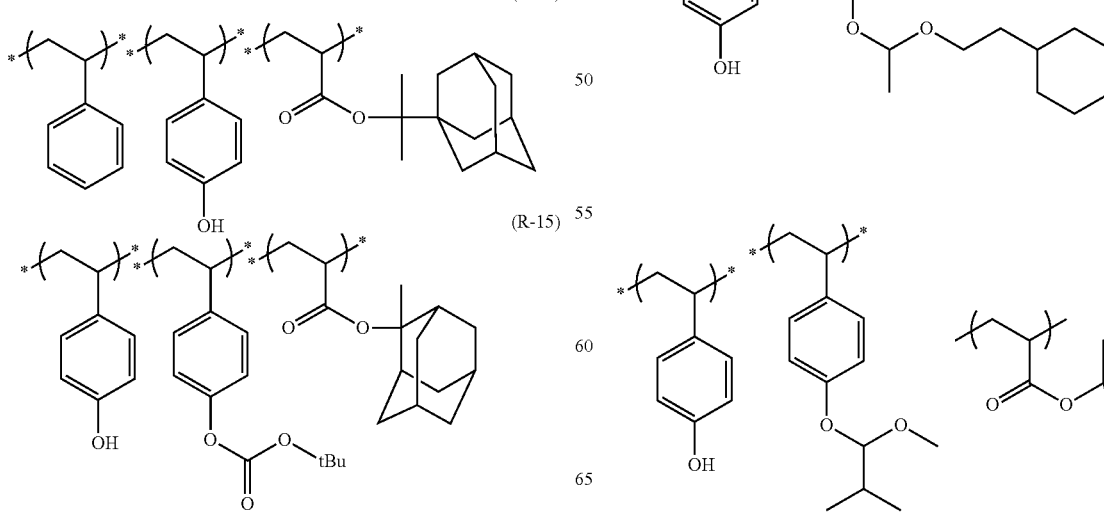
R-18
R-19

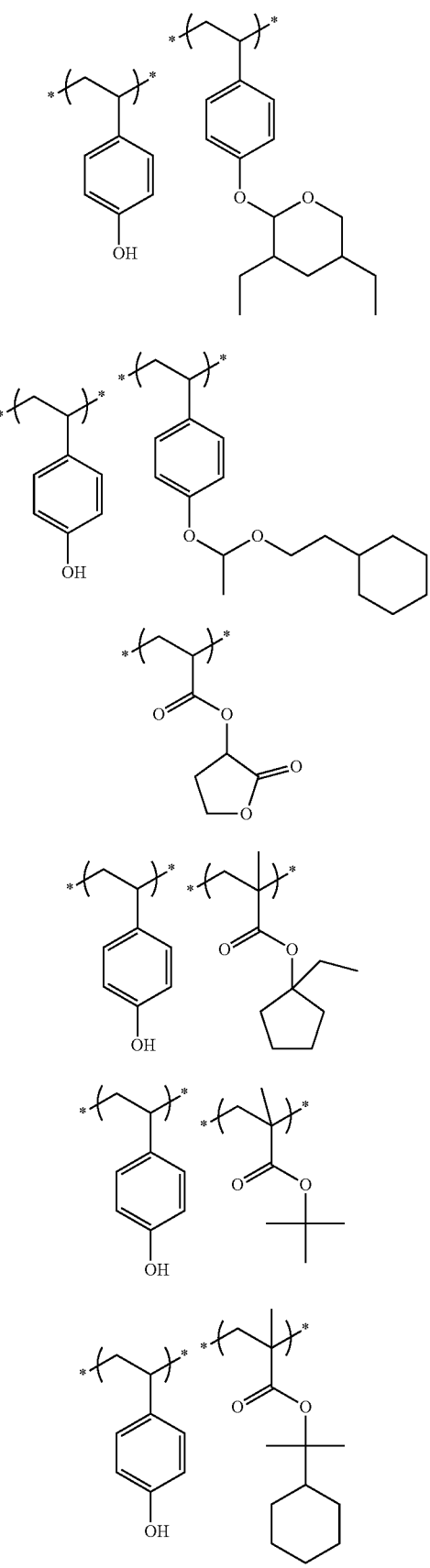
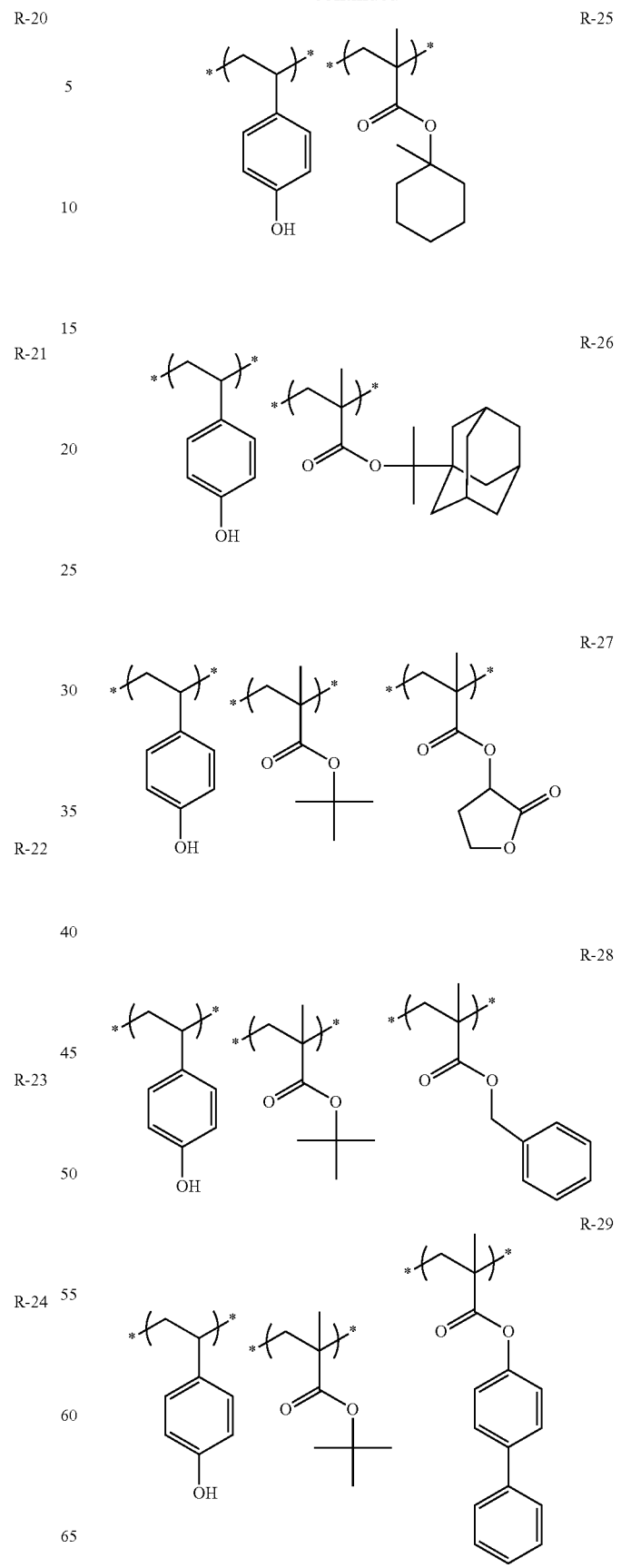

-continued
R-30
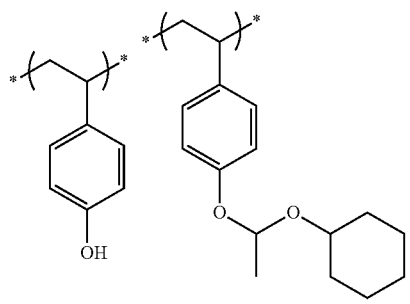
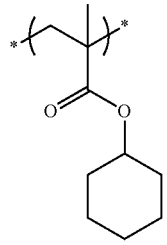
R-33
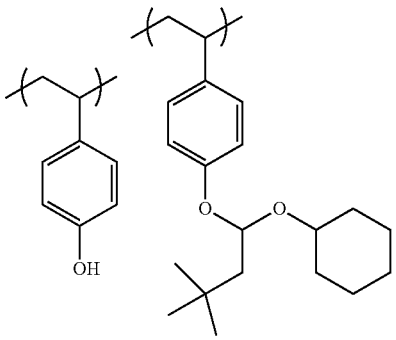
In these specific examples, "tBu" indicates a tert-butyl group.
A compositional ratio of each of the repeating units in the following specific examples is represented by molar ratio.
R-31
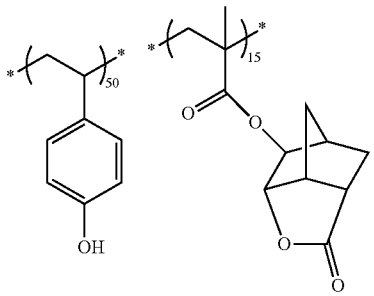
Mw: = 10000
Mw/Mn: = 1.6
R-32
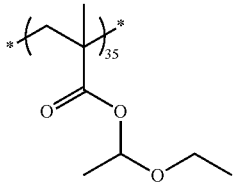
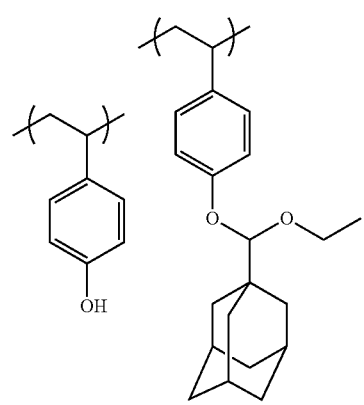
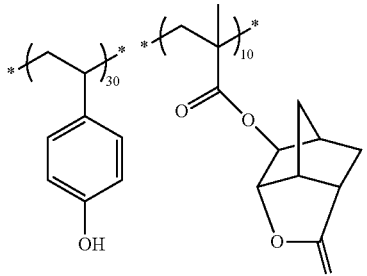
Mw: = 8800
Mw/Mn: = 1.7
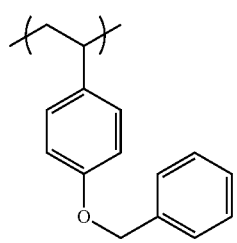
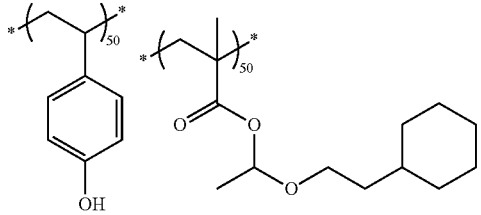
Mw: = 12000
Mw/Mn: = 1.7
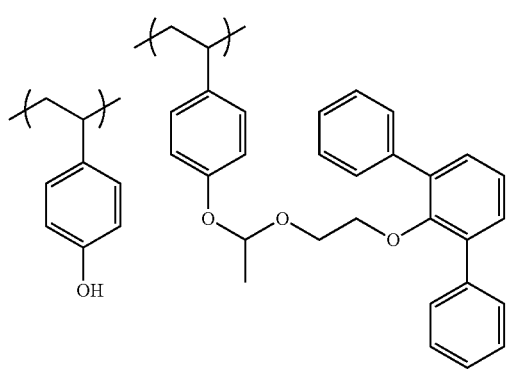

139
-continued
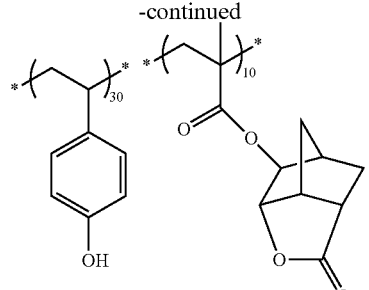
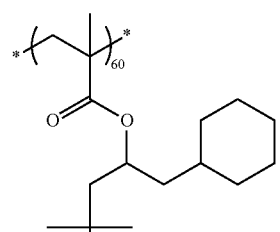
Mw: = 20000
Mw/Mn: = 1.7
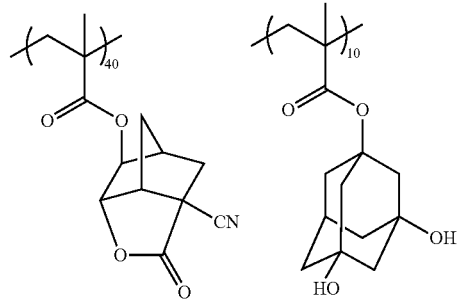
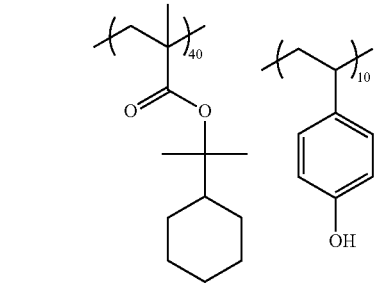
Mw = 10000
Mw/Mn = 1.60
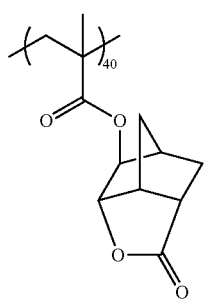
140
-continued
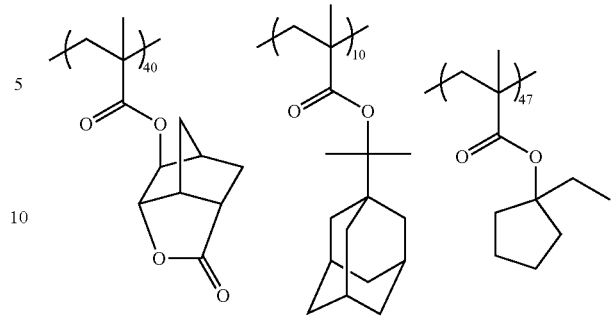
Mw = 11000
Mw/Mn = 1.85
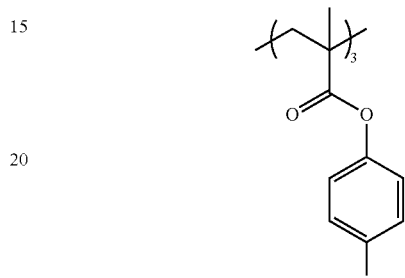
Mw = 7000
Mw/Mn = 1.65
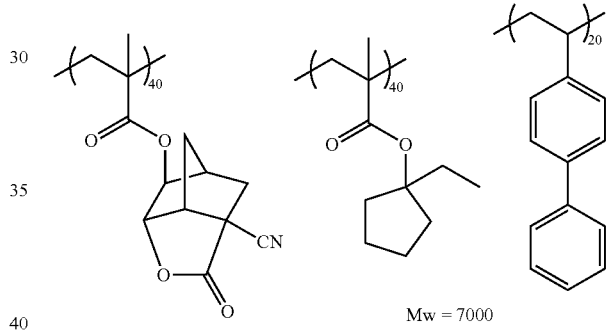
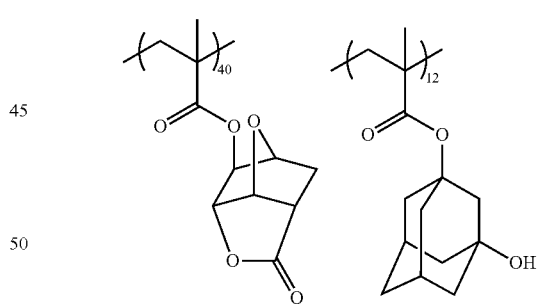
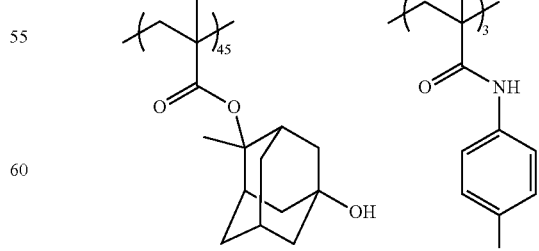
Mw = 8000
Mw/Mn = 1.65
Mw = 7500
Mw/Mn = 1.50

141
-continued
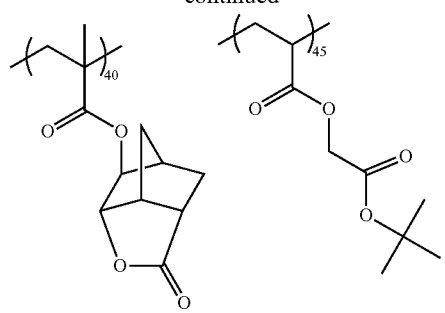
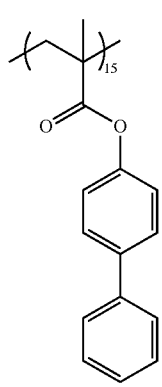
Mw = 19000
Mw/Mn = 1.70
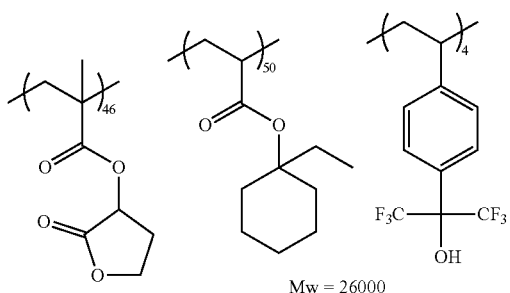
Mw = 26000
Mw/Mn = 1.85
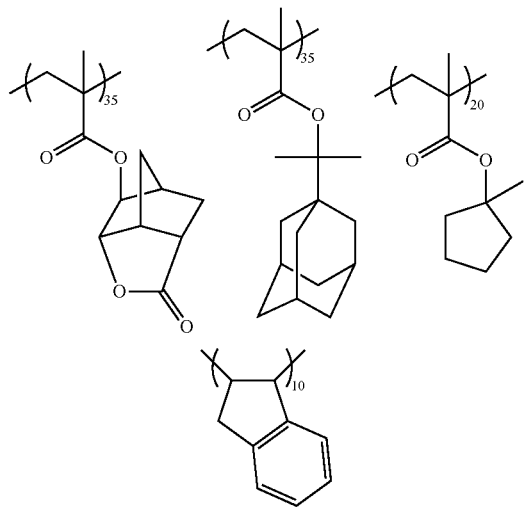
Mw = 21000
Mw/Mn = 1.60
142
-continued
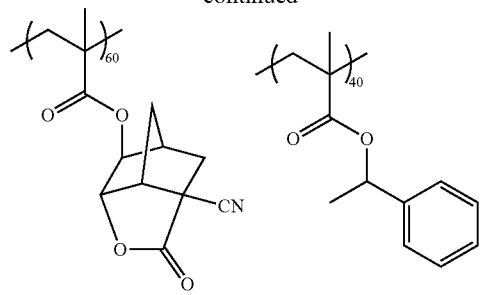
Mw = 6500
Mw/Mn = 1.50
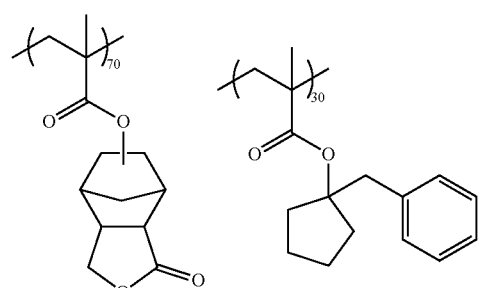
Mw = 8000
Mw/Mn = 1.85
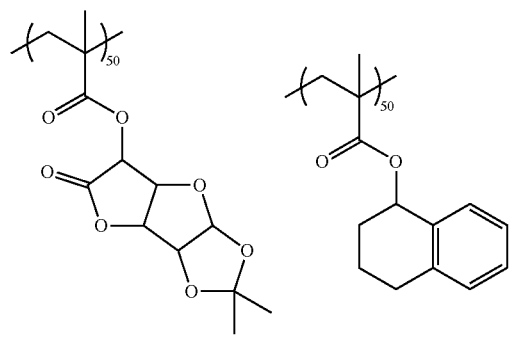
Mw = 28500
Mw/Mn = 1.55
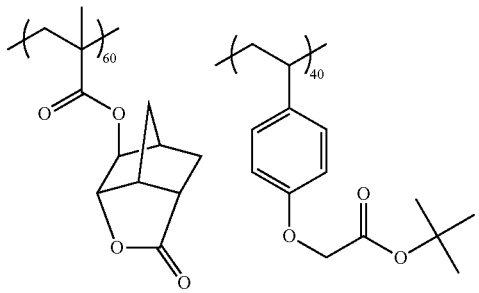
Mw = 7000
Mw/Mn = 1.65

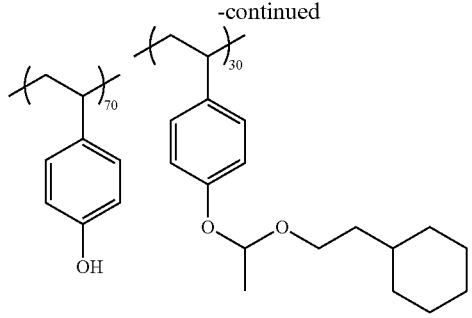
Mw = 15100
Mw/Mn = 1.40
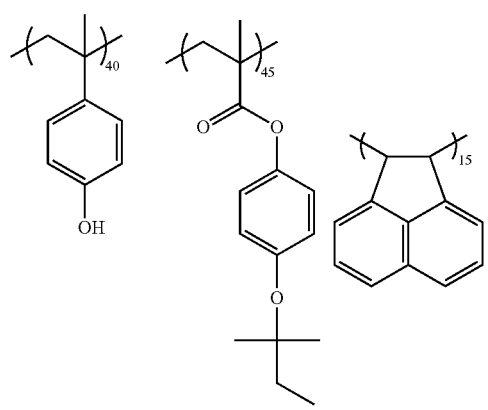
Mw = 8000
Mw/Mn = 1.35
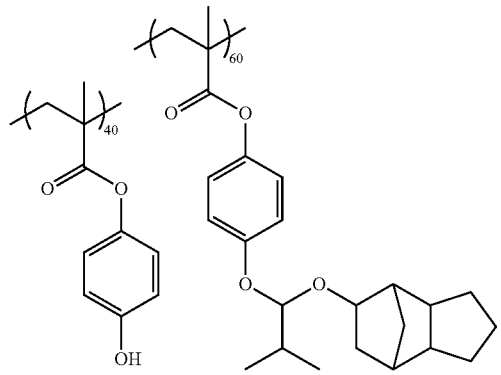
Mw = 9000
Mw/Mn = 1.25
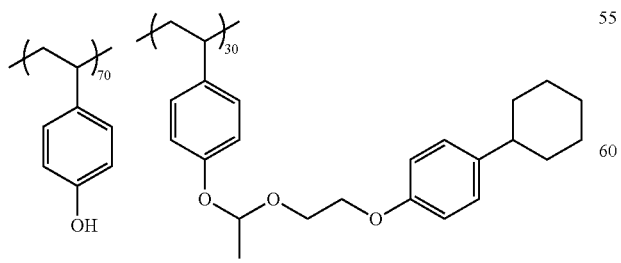
Mw = 4800
Mw/Mn = 1.15
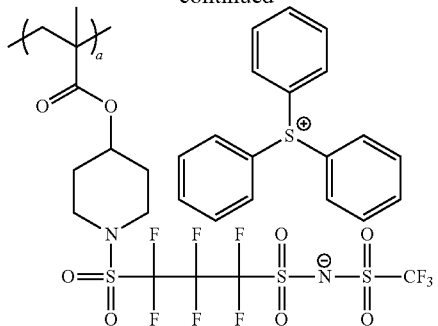
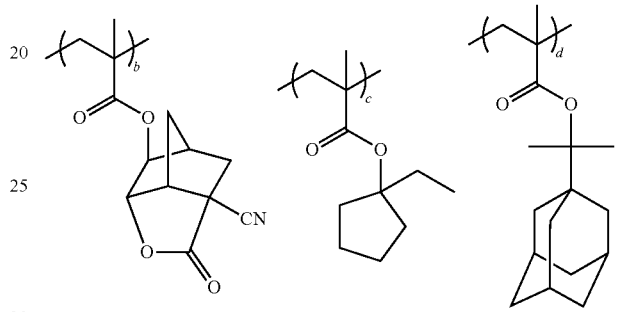
a/b/c/d = 5/43/37/15
Mw = 10500, MW/Mn = 1.77
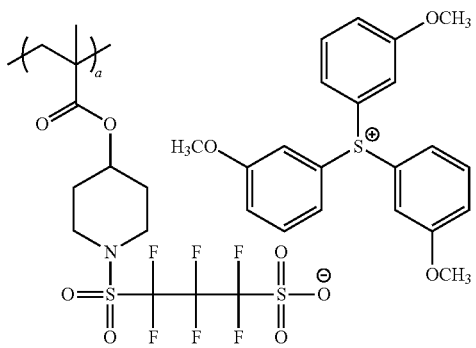
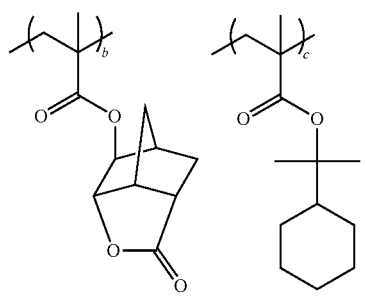
a/b/c = 10/30/60
Mw = 8500, Mw/Mn = 1.78

145
-continued
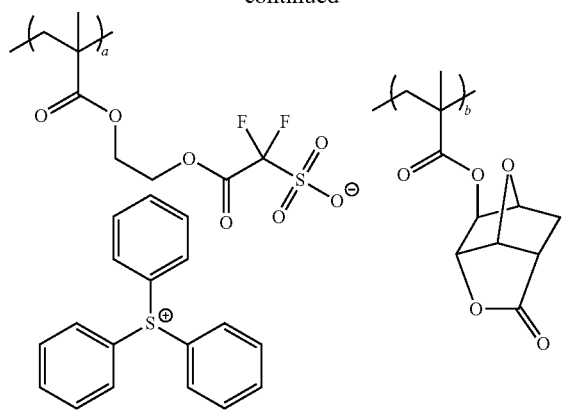
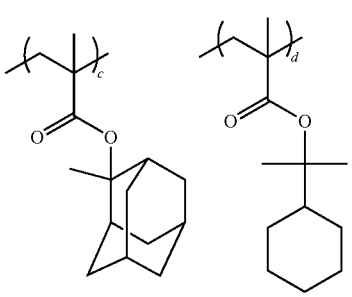
a/b/c/d = 10/40/10/40
Mw = 11500, Mw/Mn = 1.82
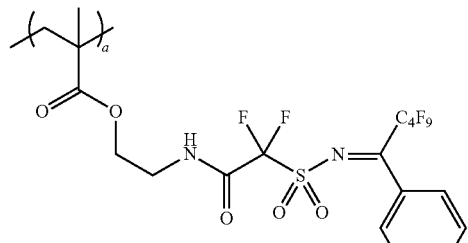
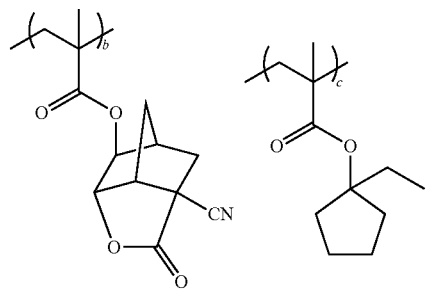
a/b/c = 20/35/45
Mw = 9000, Mw/Mn = 16.8
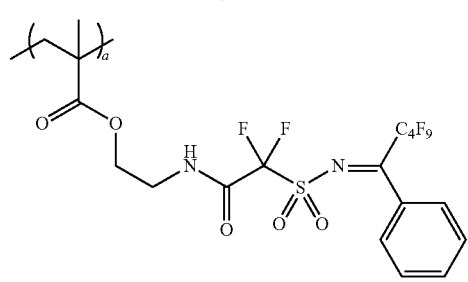
146
-continued
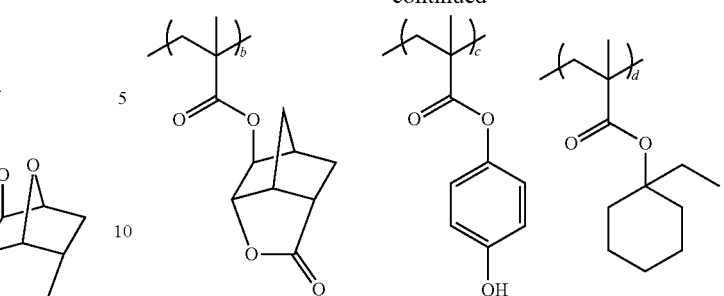
a/b/c/d = 20/15/15/50
Mw = 16000, Mw/Mn = 1.65
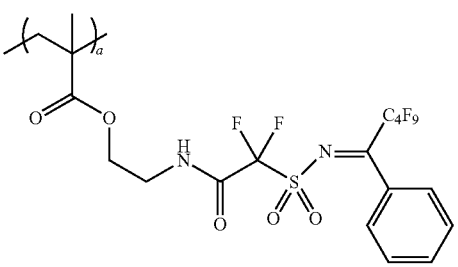
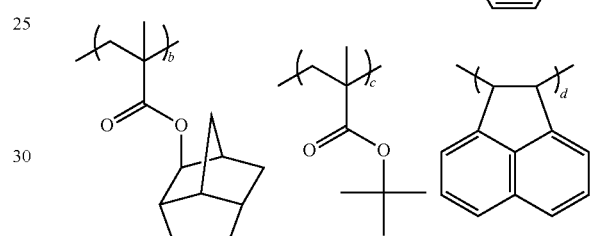
a/b/c/d = 20/20/50/10
Mw = 9500, Mw/Mn = 1.74
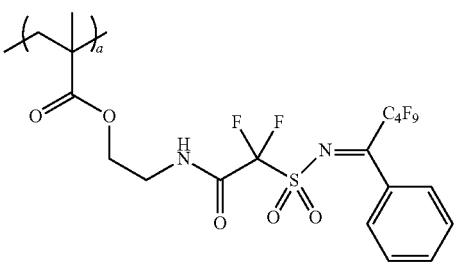
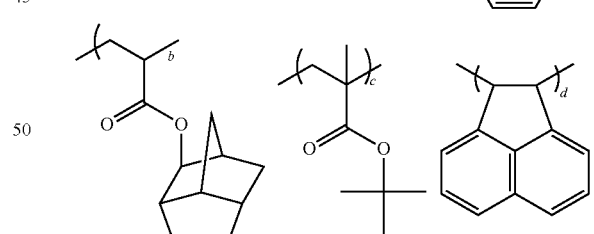
a/b/c/d = 20/20/50/10
Mw = 9500, Mw/Mn = 1.74
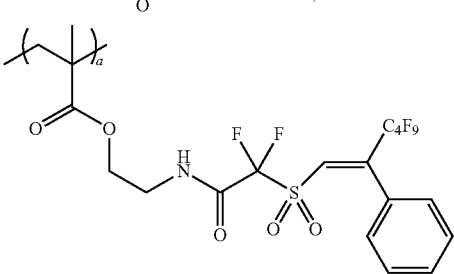

147
-continued
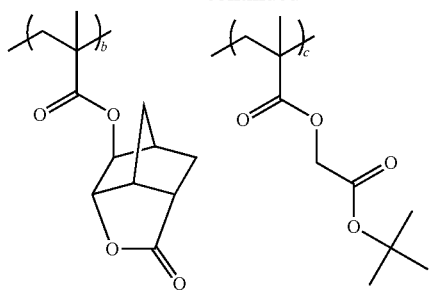
a/b/c/d = 20/35/45
Mw = 7500, Mw/Mn = 1.55
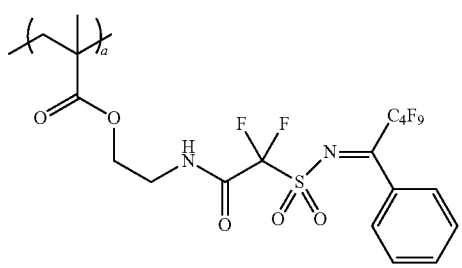
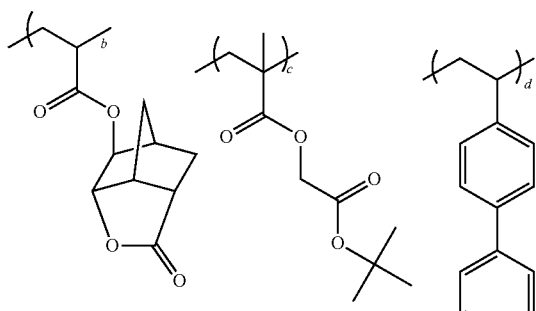
a/b/c/d = 15/30/50/5
Mw = 10000, Mw/Mn = 1.75
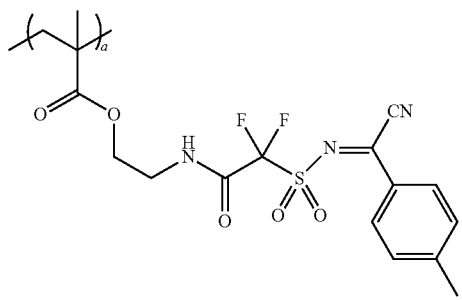
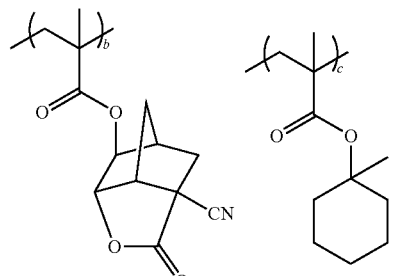
a/b/c = 15/40/45
Mw = 6500, Mw/Mn = 1.72
148
-continued
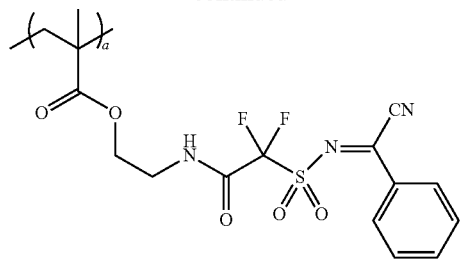
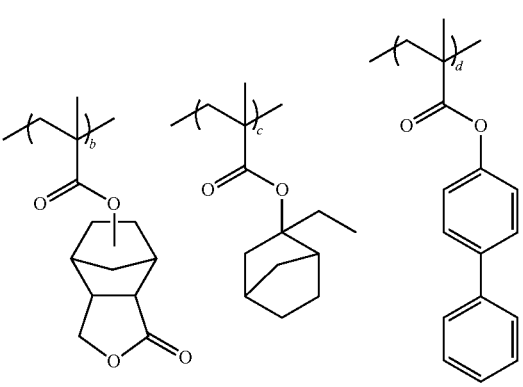
a/b/c/d = 15/25/45/15
Mw = 13000, Mw/Mn = 1.90
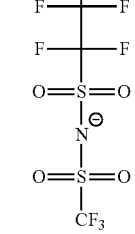
a/b/c = 10/35/55
Mw = 16000
Mw/Mn = 1.80

149
-continued
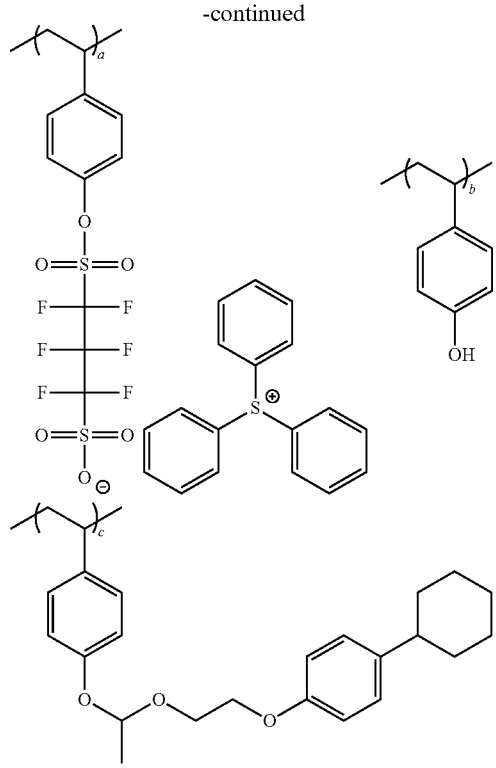
a/b/c = 15/20/65
Mw = 5500, Mw/Mn = 1.15
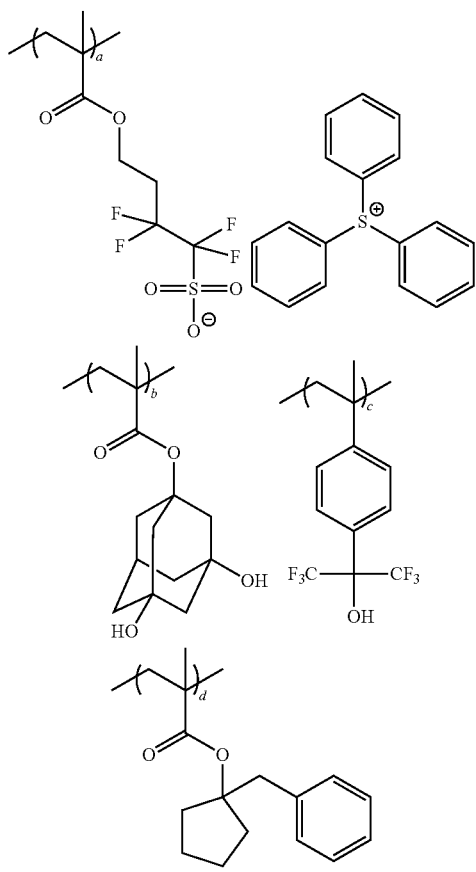
a/b/c/d = 10/30/10/50
Mw = 25000 Mw/Mn = 2.00
150
-continued
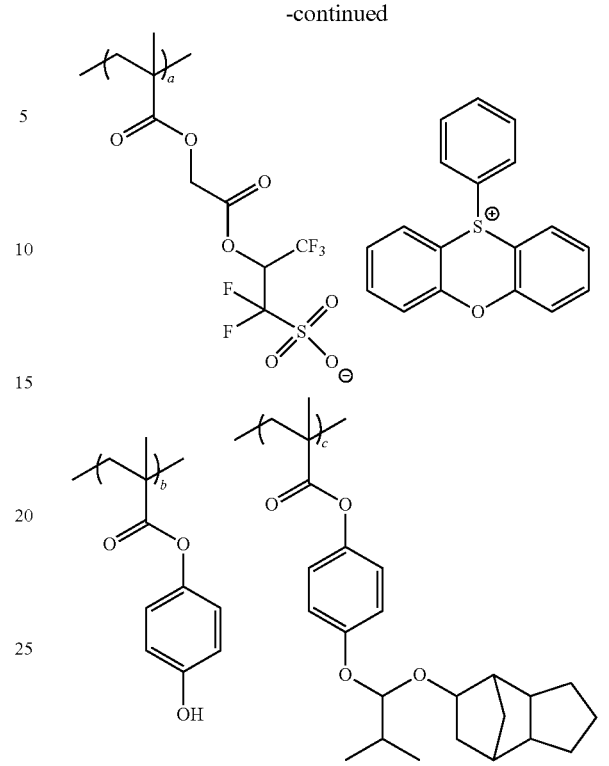
a/b/c/d = 10/25/50/15
Mw = 19000, Mw/Mn = 1.60
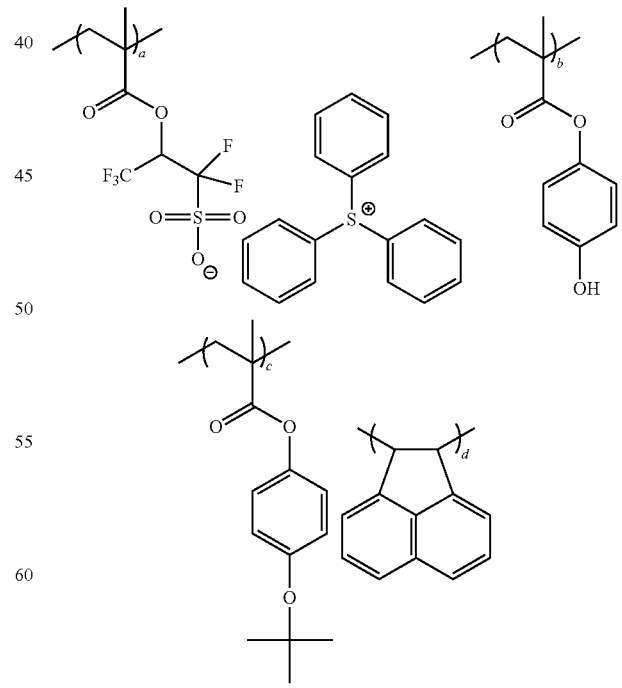
a/b/c/d = 15/15/55/15
Mw = 8500, Mw/Mn = 1.45

-continued

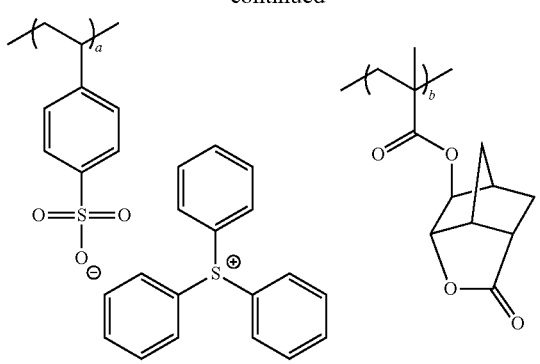

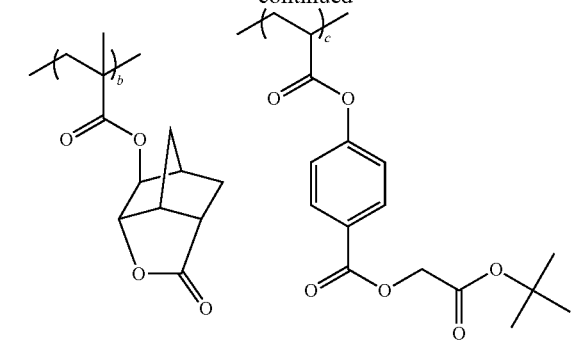

A/B/C = 20/30/50
mW = 8000, Mw/Mn = 1.75

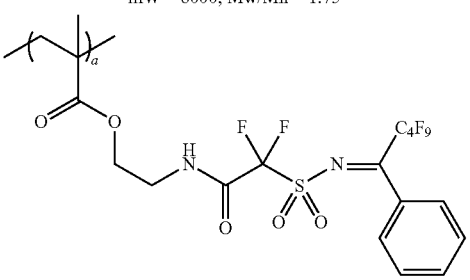

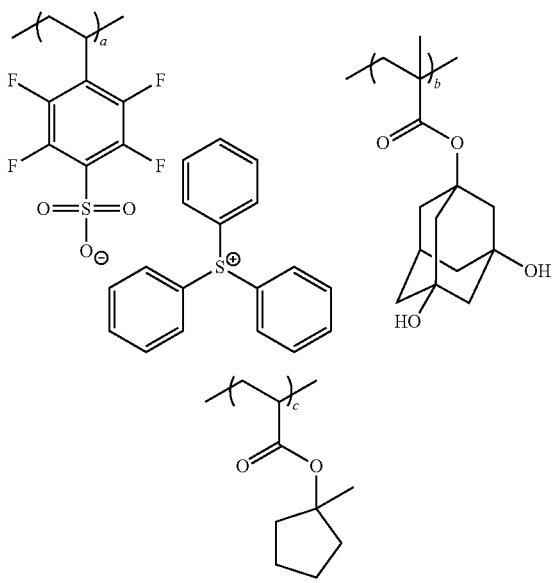

a/b/c = 15/30/55
Mw = 6500, Mw/Mn = 1.40

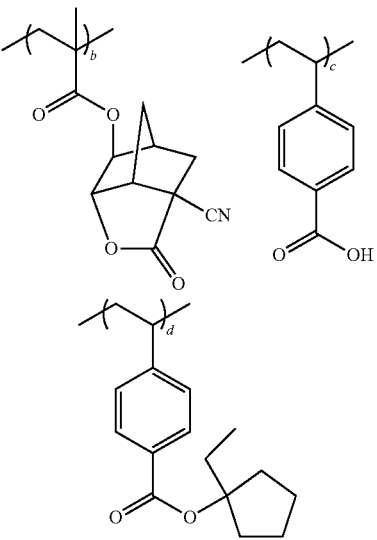

a/b/c/d = 15/25/10/50
Mw = 9000, Mw/Mn = 1.75

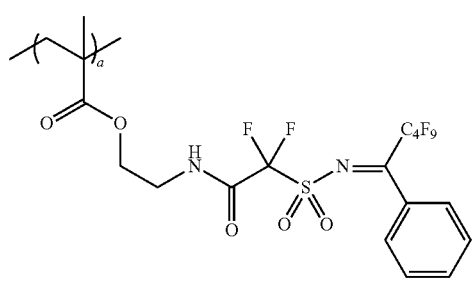

a/b/c = 15/40/45
Mw = 8000, Mw/Mn = 1.50

[4] (D) Hydrophobic Resin

The actinic ray-sensitive or radiation-sensitive resin composition of the present invention may contain a hydrophobic resin (hereinafter, sometimes referred to as "hydrophobic resin (D)" or simply as "resin (D)") particularly when the composition is applied to immersion exposure. Incidentally, the hydrophobic resin (D) is preferably different from the resin (P).

The hydrophobic resin (D) is unevenly distributed to the film surface layer and when the immersion medium is water, the static/dynamic contact angle on the resist film surface for water as well as the followability of immersion liquid can be enhanced.

The hydrophobic resin (D) is preferably designed, as described above, to be unevenly distributed to the interface but unlike a surfactant, need not necessarily have a hydrophilic group in the molecule and may not contribute to uniform mixing of polar/nonpolar substances.

In view of uneven distribution to the film surface layer, the hydrophobic resin (D) preferably contains any one or more of "a fluorine atom", "a silicon atom" and "a $CH_3$ partial structure contained in the side chain moiety of the resin", more preferably two or more thereof.

In the case where the hydrophobic resin (D) contains a fluorine atom and/or a silicon atom, the fluorine atom and/or silicon atom in the hydrophobic resin (D) may be contained in the main chain of the resin or may be contained in the side chain.

In the case where the hydrophobic resin (D) contains a fluorine atom, the resin is preferably a resin containing a fluorine atom-containing alkyl group, a fluorine atom-containing cycloalkyl group or a fluorine atom-containing aryl group, as a fluorine atom-containing partial structure.

The fluorine atom-containing alkyl group (preferably having a carbon number of 1 to 10, more preferably a carbon number of 1 to 4) is a linear or branched alkyl group with at least one hydrogen atom being substituted for by a fluorine atom and may further have a substituent other than fluorine atom.

The fluorine atom-containing cycloalkyl group is a monocyclic or polycyclic cycloalkyl group with at least one hydrogen atom being substituted for by a fluorine atom and may further have a substituent other than fluorine atom.

The fluorine atom-containing aryl group is an aryl group such as phenyl group or naphthyl group with at least one hydrogen atom being substituted for by a fluorine atom and may further have a substituent other than fluorine atom.

As the fluorine atom-containing alkyl group, fluorine atom-containing cycloalkyl group and fluorine atom-containing aryl group, the groups represented by the following formulae (F2) to (F4) are preferred, but the present invention is not limited thereto.

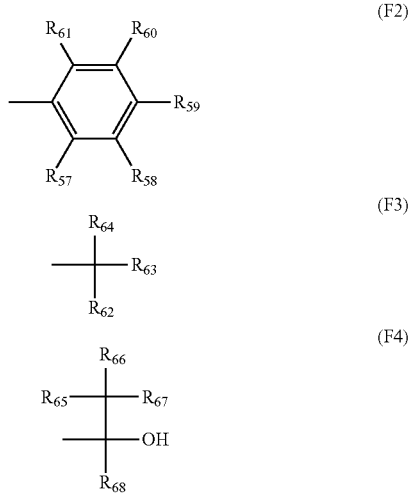

In formulae (F2) to (F4), each of $R_{57}$ to $R_{68}$ independently represents a hydrogen atom, a fluorine atom or an alkyl group (linear or branched), provided that at least one of $R_{57}$ to $R_{61}$, at least one of $R_{62}$ to $R_{64}$, and at least one of $R_{65}$ to $R_{68}$ each independently represents a fluorine atom or an alkyl group (preferably having a carbon number of 1 to 4) with at least one hydrogen atom being substituted for by a fluorine atom.

It is preferred that all of $R_{57}$ to $R_{61}$ and $R_{65}$ to $R_{67}$ are a fluorine atom. Each of $R_{62}$, $R_{63}$ and $R_{68}$ is preferably an alkyl group (preferably having a carbon number of 1 to 4) with at least one hydrogen atom being substituted for by a fluorine atom, more preferably a perfluoroalkyl group having a carbon number of 1 to 4. $R_{62}$ and $R_{63}$ may combine with each other to form a ring.

Specific examples of the group represented by formula (F2) include a p-fluorophenyl group, a pentafluorophenyl group, and a 3,5-di(trifluoromethyl)phenyl group.

Specific examples of the group represented by formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-tert-butyl group, a perfluoroisopentyl group, a perfluorooctyl group, a perfluoro(trimethyl)hexyl group, a 2,2,3,3-tetrafluorocyclobutyl group, and a perfluorocyclohexyl group. Among these, a hexafluoroisopropyl group, a heptafluoroisopropyl group, a hexafluoro(2-methyl) isopropyl group, an octafluoroisobutyl group, a nonafluoro-tert-butyl group and a perfluoroisopentyl group are preferred, and a hexafluoroisopropyl group and a heptafluoroisopropyl group are more preferred.

Specific examples of the group represented by formula (F4) include —C(CF$_3$)$_2$OH, —C(C$_2$F$_5$)$_2$OH, —C(CF$_3$)(CH$_3$)OH, and —CH(CF$_3$)OH, with —C(CF$_3$)$_2$OH being preferred.

The fluorine atom-containing partial structure may be bonded directly to the main chain or may be bonded to the main chain through a group selected from the group consisting of an alkylene group, a phenylene group, an ether bond, a thioether bond, a carbonyl group, an ester bond, an amide bond, a urethane bond and a ureylene bond, or through a group formed by combining two or more of these members.

Specific examples of the repeating unit having a fluorine atom are illustrated below, but the present invention is not limited thereto.

In specific examples, $X_1$ represents a hydrogen atom, —CH$_3$, —F or —CF$_3$. $X_2$ represents —F or —CF$_3$.

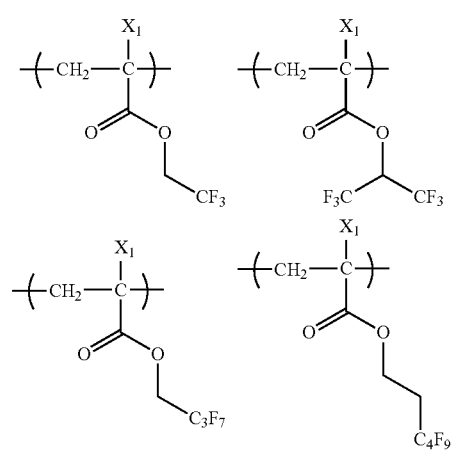

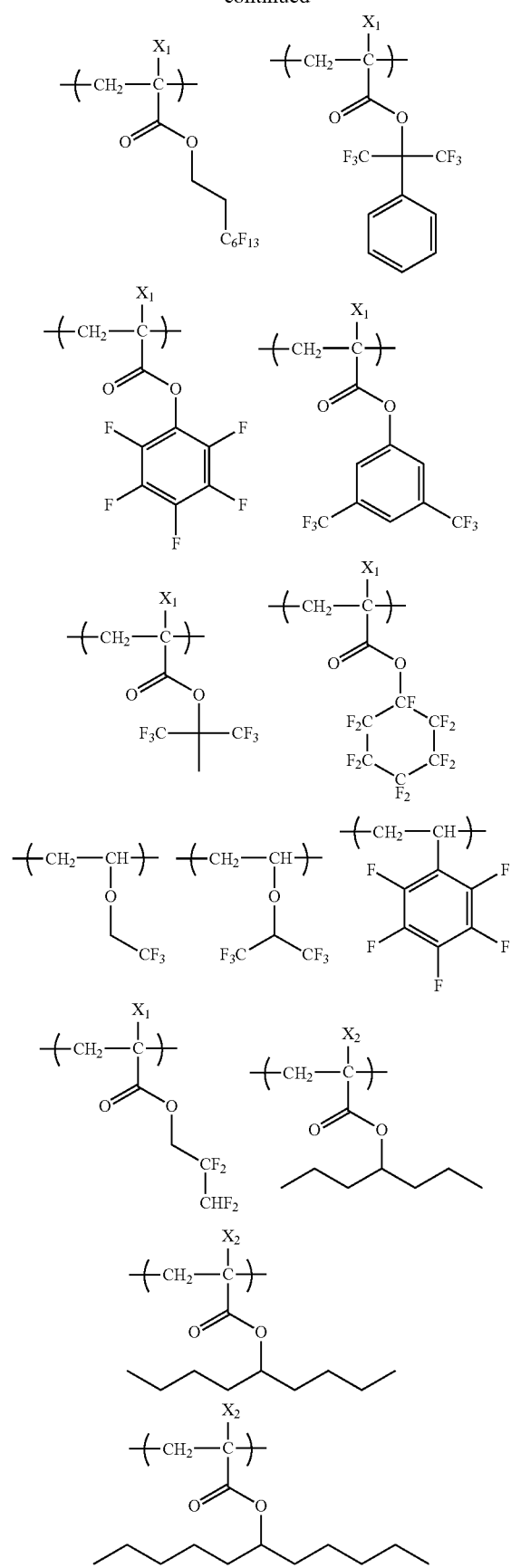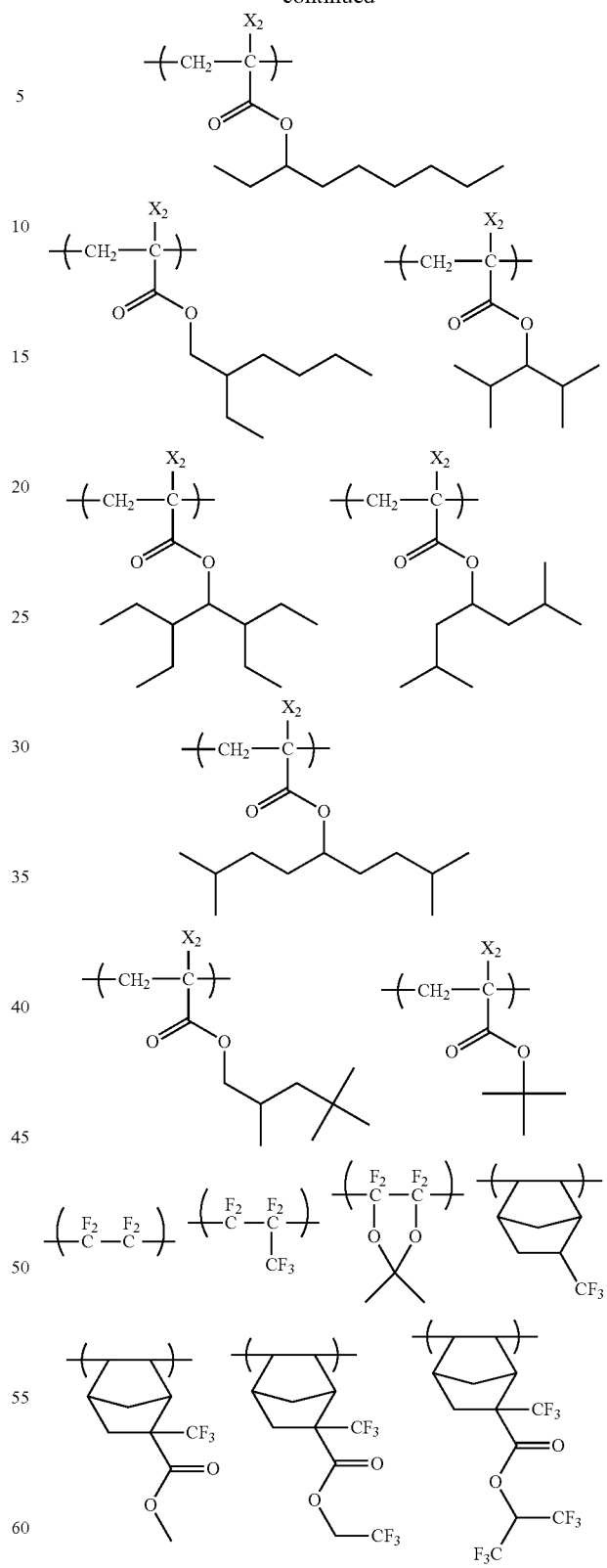
The hydrophobic resin (D) may contain a silicon atom. The resin is preferably a resin having an alkylsilyl structure (preferably a trialkylsilyl group) or a cyclic siloxane structure, as a silicon atom-containing partial structure.

Specifically, the alkylsilyl structure or cyclic siloxane structure includes, for example, the groups represented by the following formulae (CS-1) to (CS-3):

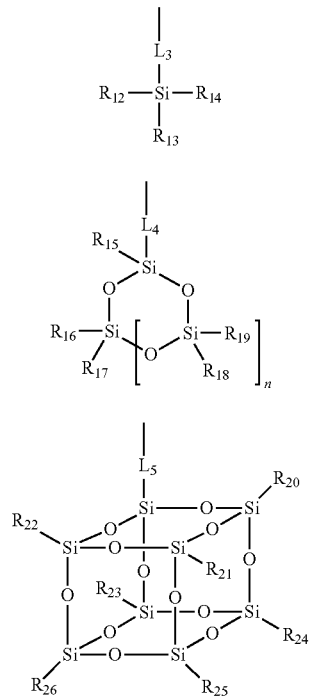

In formulae (CS-1) to (CS-3), each of $R_{12}$ to $R_{26}$ independently represents a linear or branched alkyl group (preferably having a carbon number of 1 to 20) or a cycloalkyl group (preferably having a carbon number of 3 to 20).

Each of $L_3$ to $L_5$ represents a single bond or a divalent linking group. The divalent linking group includes a single member or a combination of two or more members (preferably having a total carbon number of 12 or less), selected from the group consisting of an alkylene group, a phenylene group, an ether bond, a thioether bond, a carbonyl group, an ester bond, an amide bond, a urethane bond and a urea bond.

n represents an integer of 1 to 5. n is preferably an integer of 2 to 4.

Specific examples of the repeating unit having a group represented by formulae (CS-1) to (CS-3) are illustrated below, but the present invention is not limited thereto. In specific examples, $X_1$ represents a hydrogen atom, —$CH_3$, —F or —$CF_3$.

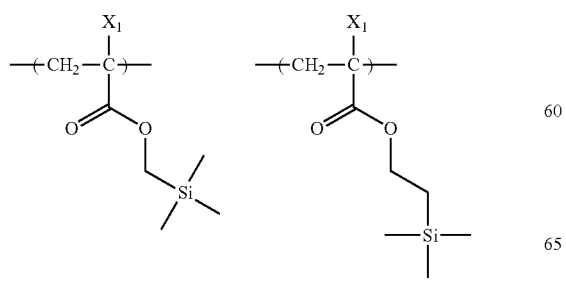

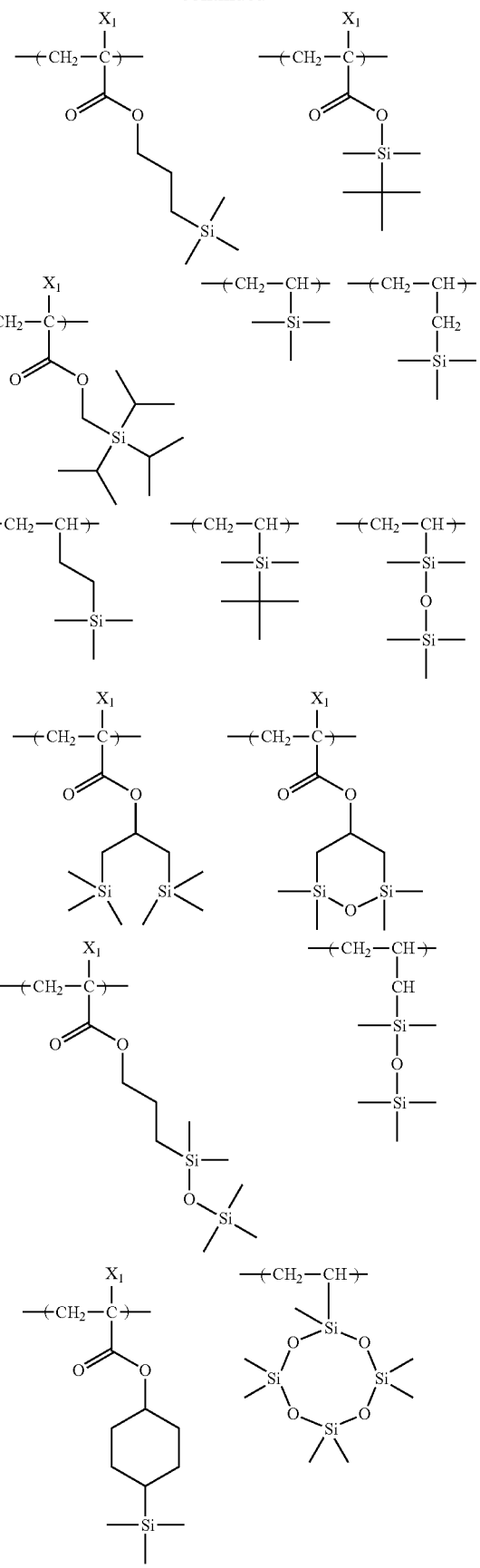

-continued

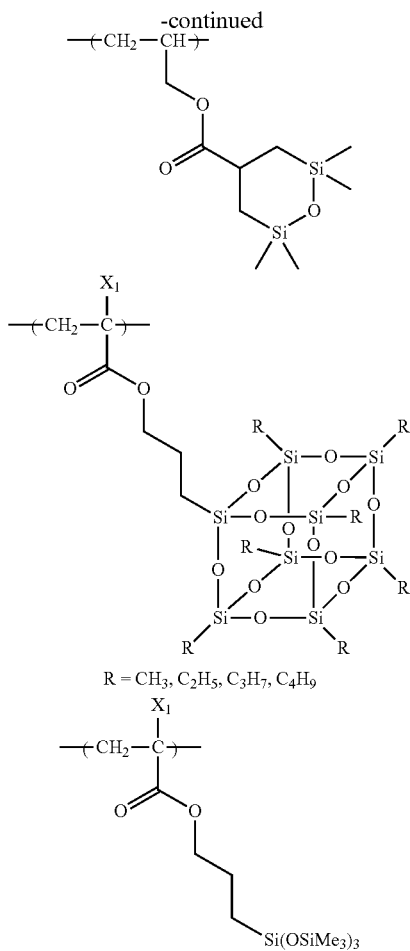

In addition, it is also preferred that, as described above, the hydrophobic resin (D) contains a $CH_3$ partial structure in the side chain moiety.

Here, the $CH_3$ partial structure contained in the side chain moiety of the resin (D) (hereinafter, sometimes simply referred to as "side chain $CH_3$ partial structure") encompasses a $CH_3$ partial structure contained in an ethyl group, a propyl group and the like.

On the other hand, a methyl group bonded directly to the main chain of the resin (D) (for example, an α-methyl group of a repeating unit having a methacrylic acid structure) little contributes to surface localization of the resin (D) due to the effect of the main chain and therefore, is not encompassed by the $CH_3$ partial structure of the present invention.

More specifically, in the case where the resin (D) contains, for example, a repeating unit derived from a monomer containing a polymerizable moiety having a carbon-carbon double bond, such as repeating unit represented by the following formula (M), and where $R_{11}$ to $R_{14}$ are $CH_3$ "itself", this $CH_3$ is not encompassed by the $CH_3$ partial structure contained in the side chain moiety of the present invention.

On the other hand, a $CH_3$ partial structure connected to the C—C main chain through some atom comes under the $CH_3$ partial structure of the present invention. For example, when $R_{11}$ is an ethyl group ($CH_2CH_3$), this is counted as having "one" $CH_3$ partial structure of the present invention.

$$\text{(M)}$$

In formula (M), each of $R_{11}$ to $R_{14}$ independently represents a side chain moiety.

The side chain moiety of $R_{11}$ to $R_{14}$ includes a hydrogen atom, a monovalent organic group and the like.

The monovalent organic group of $R_{11}$ to $R_{14}$ includes an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, an arylaminocarbonyl group, and the like, and these groups may further have a substituent.

The hydrophobic resin (D) is preferably a resin containing a repeating unit having a $CH_3$ partial structure in the side chain moiety, and it is more preferred to contain, as such a repeating unit, (x) at least one repeating unit out of a repeating unit represented by the following formula (II) and a repeating unit represented by the following formula (III).

The repeating unit represented by formula (II) is described in detail below.

$$\text{(II)}$$

In formula (II), $X_{b1}$ represents a hydrogen atom, an alkyl group, a cyano group or a halogen atom, and $R_2$ represents an organic group having one or more $CH_3$ partial structures and being stable to acid. Here, the organic group stable to acid is, more specifically, preferably an organic group not containing the "group capable of decomposing by the action of an acid to produce a polar group" described in the resin (P) above.

The alkyl group of $X_{b1}$ is preferably an alkyl group having a carbon number of 1 to 4 and includes a methyl group, an ethyl group, a propyl group, a hydroxymethyl group, a trifluoromethyl group, and the like but is preferably a methyl group.

$X_{b1}$ is preferably a hydrogen atom or a methyl group.

$R_2$ includes an alkyl group, a cycloalkyl group, an alkenyl group, a cycloalkenyl group, an aryl group, and an aralkyl group, each having one or more $CH_3$ partial structures. These cycloalkyl group, alkenyl group, cycloalkenyl group, aryl group and aralkyl group may further have an alkyl group as a substituent.

$R_2$ is preferably an alkyl group or an alkyl-substituted cycloalkyl group, each having one or more $CH_3$ partial structures.

The organic group having one or more $CH_3$ partial structures and being stable to acid of $R_2$ preferably contains from two to ten, more preferably from two to eight, $CH_3$ partial structures.

The alkyl group having one or more $CH_3$ partial structures of $R_2$ is preferably a branched alkyl group having a carbon number of 3 to 20.

The cycloalkyl group having one or more $CH_3$ partial structures of $R_2$ may be monocyclic or polycyclic and specifically includes a group having a carbon number of 5 or more and containing a monocyclo, bicyclo, tricyclo or tetracyclo structure or the like. The carbon number thereof is preferably from 6 to 30, more preferably from 7 to 25.

The alkenyl group having one or more $CH_3$ partial structures of $R_2$ is preferably a linear or branched alkenyl group having a carbon number of 1 to 20, more preferably a branched alkenyl group.

The aryl group having one or more $CH_3$ partial structures of $R_2$ is preferably an aryl group having a carbon number of 6 to 20 and includes, for example, a phenyl group and a naphthyl group but is preferably a phenyl group.

The aralkyl group having one or more $CH_3$ partial structures of $R_2$ is preferably an aralkyl group having a carbon number of 7 to 12 and includes, for example, a benzyl group, a phenethyl group and a naphthylmethyl group.

Specific preferred examples of the repeating unit represented by formula (II) are illustrated below, but the present invention is not limited thereto.

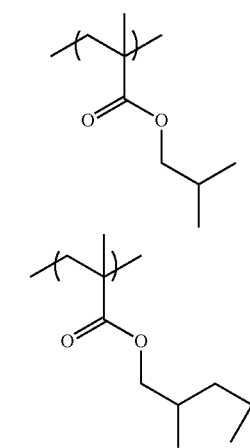
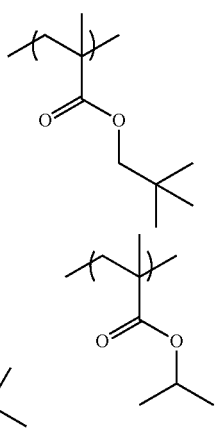
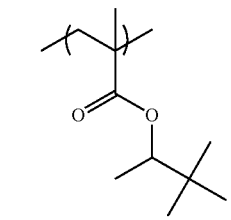
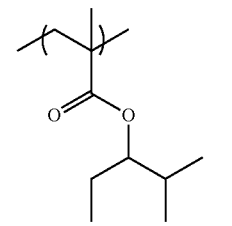
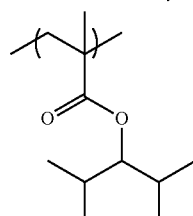
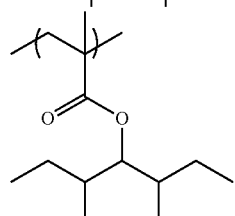
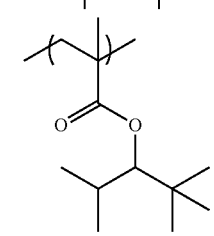
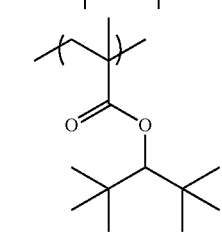

-continued

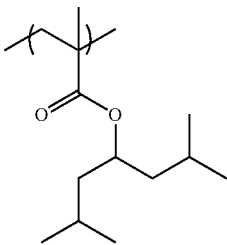
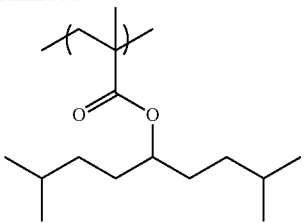
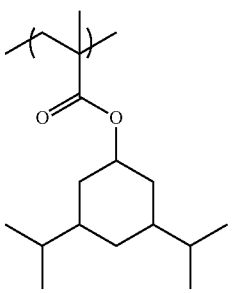
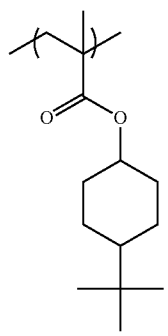
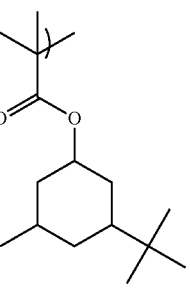
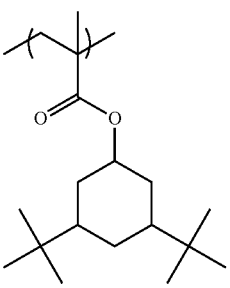
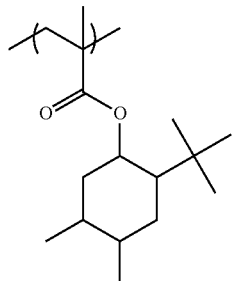
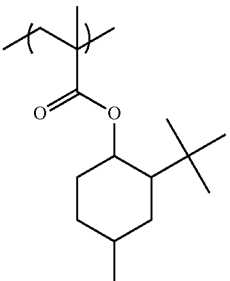
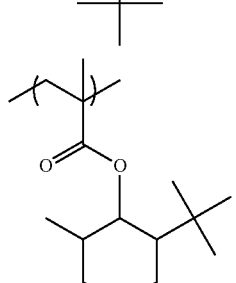
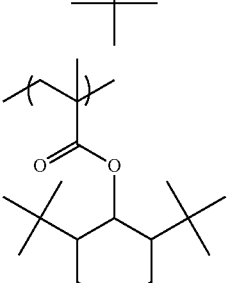

-continued

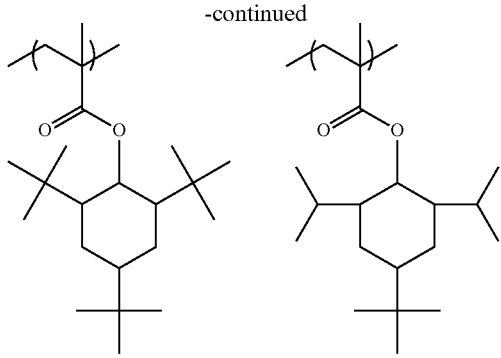

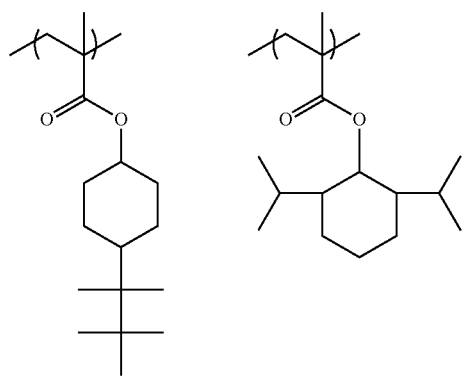

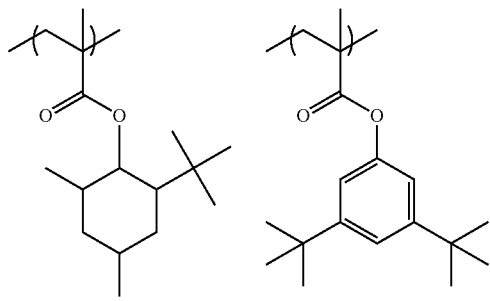

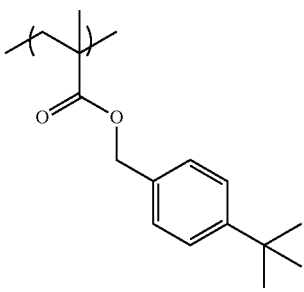

The repeating unit represented by formula (II) is preferably a repeating unit stable to acid (non-acid-decomposable) and specifically, is preferably a repeating unit not having a group capable of decomposing by the action of an acid to produce a polar group.

The repeating unit represented by formula (III) is described in detail below.

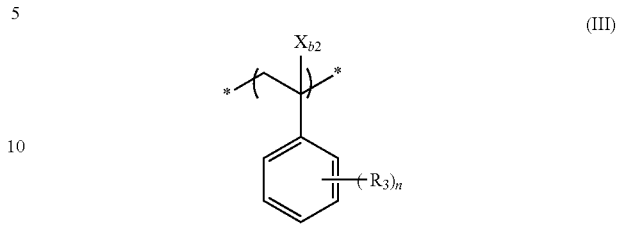

In formula (III), $X_{b2}$ represents a hydrogen atom, an alkyl group, a cyano group or a halogen atom, $R_3$ represents an organic group having one or more $CH_3$ partial structures and being stable to acid, and n represents an integer of 1 to 5.

The alkyl group of $X_{b2}$ is preferably an alkyl group having a carbon number of 1 to 4 and includes a methyl group, an ethyl group, a propyl group, a hydroxymethyl group, a trifluoromethyl group, and the like. A hydrogen atom is preferred.

$X_{b2}$ is preferably a hydrogen atom.

$R_3$ is an organic group stable to acid and therefore, more specifically, is preferably an organic group not containing the "group capable of decomposing by the action of an acid to produce a polar group" described in the resin (P).

$R_3$ includes an alkyl group having one or more $CH_3$ partial structures.

The organic group having one or more $CH_3$ partial structures and being stable to acid of $R_3$ preferably contains from one to ten, more preferably from one to eight, still more preferably from one to four, $CH_3$ partial structures.

The alkyl group having one or more $CH_3$ partial structures of $R_3$ is preferably a branched alkyl group having a carbon number of 3 to 20.

n represents an integer of 1 to 5, preferably an integer of 1 to 3, more preferably 1 or 2.

Specific preferred examples of the repeating unit represented by formula (III) are illustrated below, but the present invention is not limited thereto.

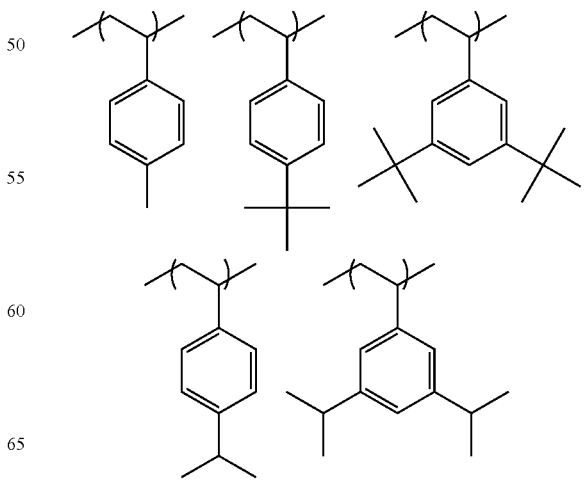

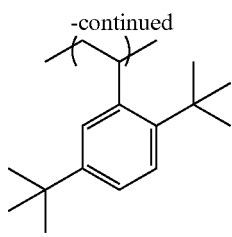

The repeating unit represented by formula (III) is preferably a repeating unit stable to acid (non-acid-decomposable) and specifically, is preferably a repeating unit not having a group capable of decomposing by the action of an acid to produce a polar group.

In the case where the resin (D) contains a $CH_3$ partial structure in the side chain moiety and furthermore, does not have a fluorine atom and a silicon atom, the content of the (x) at least one repeating unit out of a repeating unit represented by formula (II) and a repeating unit represented by formula (III) is preferably 90 mol % or more, more preferably 95 mol % or more, based on all repeating units in the resin (D). The content is usually 100 mol % or less based on all repeating units in the resin (D).

When the resin (D) contains the (x) at least one repeating unit out of a repeating unit represented by formula (II) and a repeating unit represented by formula (III) in a ratio of 90 mol % or more based on all repeating units in the resin (D), the surface free energy of the resin (D) is increased and in turn, the resin (D) is less likely to be unevenly distributed to the surface of the resist film, as a result, the static/dynamic contact angle of the resist film for water can be unfailingly raised and the followability of immersion liquid can be enhanced.

Furthermore, in both of (i) a case of containing a fluorine atom and/or a silicon atom and (ii) a case of containing a $CH_3$ partial structure in the side chain moiety, the hydrophobic resin (D) may contain at least one group selected from the group consisting of the following (x) to (z). Such a group is suitably used particularly when the composition of the present invention is used for an alkali developing process.

(x) An acid group
(y) A lactone structure-containing group, an acid anhydride group, or an acid imide group
(z) A group capable of decomposing by the action of an acid The acid group (x) includes a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, a tris(alkylsulfonyl)methylene group, and the like.

Preferred acid groups include a fluorinated alcohol group (preferably hexafluoroisopropanol), a sulfonimide group, and a bis(alkylcarbonyl)methylene group.

The repeating unit having (x) an acid group includes a repeating unit where the acid group is directly bonded to the main chain of the resin, such as repeating unit formed by an acrylic acid or a methacrylic acid, a repeating unit where the acid group is bonded to the main chain of the resin through a linking group, and the like, and the acid group may also be introduced into the polymer chain terminal by using an acid group-containing polymerization initiator or chain transfer agent at the polymerization. All of these cases are preferred.

The repeating unit having (x) an acid group may have at least either a fluorine atom or a silicon atom.

The content of the repeating unit having (x) an acid group is preferably from 1 to 50 mol %, more preferably from 3 to 35 mol %, still more preferably from 5 to 20 mol %, based on all repeating units in the hydrophobic resin (D).

Specific examples of the repeating unit having (x) an acid group are illustrated below, but the present invention is not limited thereto. In the formulae, Rx represents a hydrogen atom, $CH_3$, $CF_3$ or $CH_2OH$.

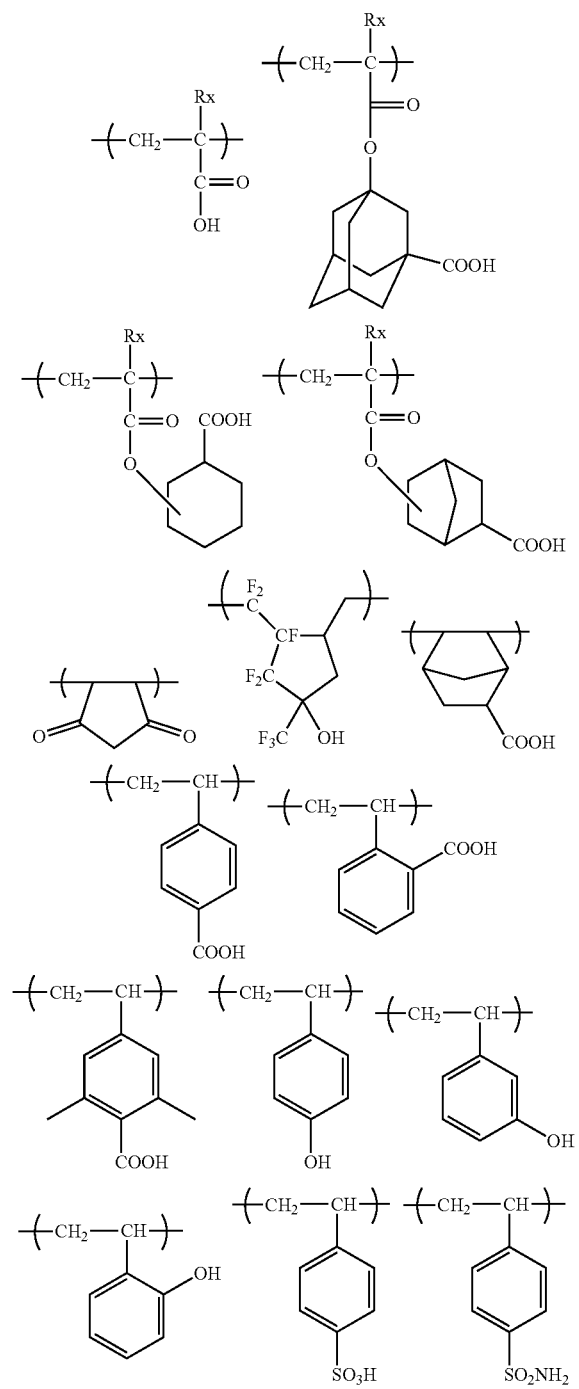

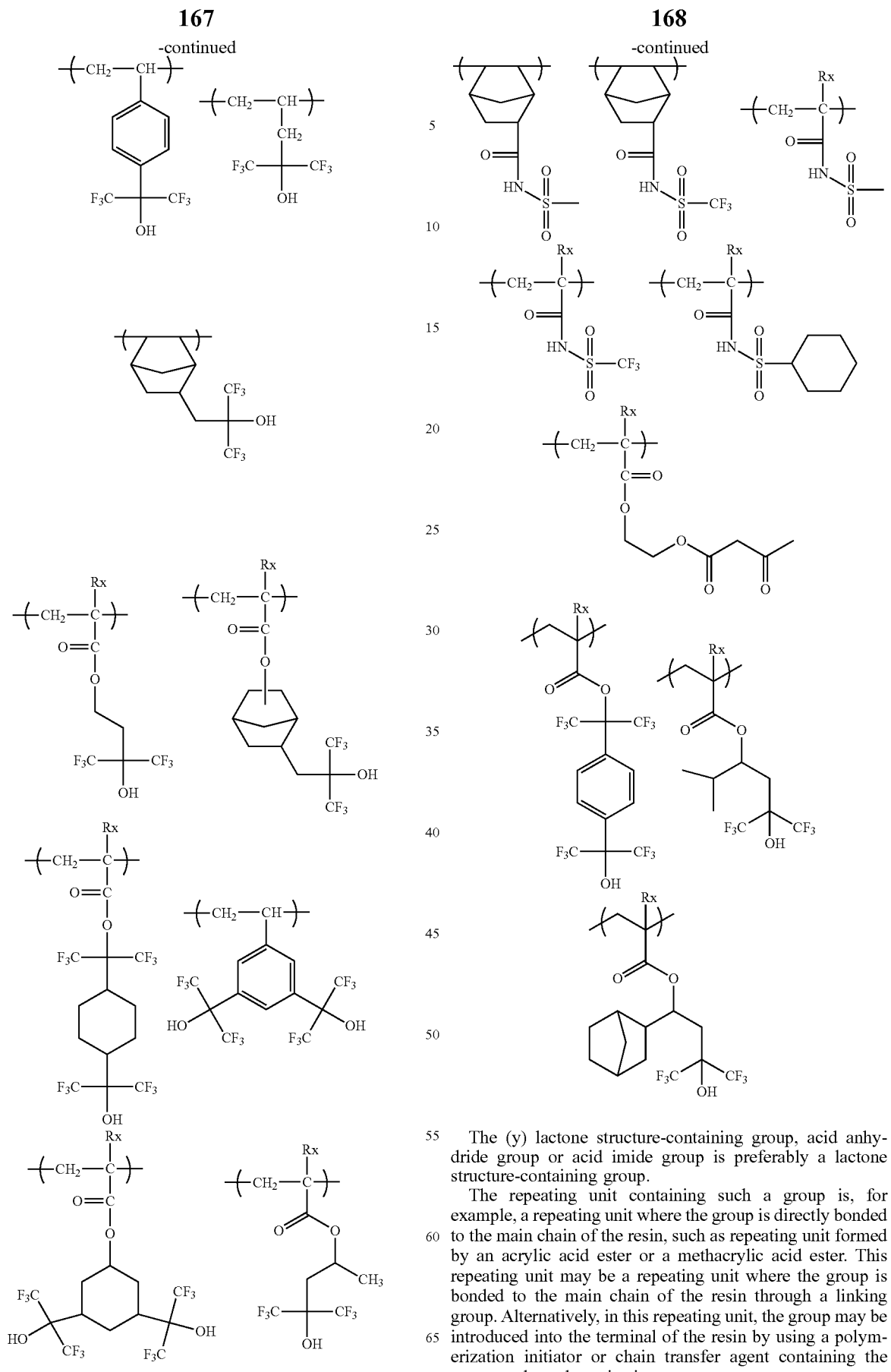

The (y) lactone structure-containing group, acid anhydride group or acid imide group is preferably a lactone structure-containing group.

The repeating unit containing such a group is, for example, a repeating unit where the group is directly bonded to the main chain of the resin, such as repeating unit formed by an acrylic acid ester or a methacrylic acid ester. This repeating unit may be a repeating unit where the group is bonded to the main chain of the resin through a linking group. Alternatively, in this repeating unit, the group may be introduced into the terminal of the resin by using a polymerization initiator or chain transfer agent containing the group at the polymerization.

Examples of the repeating unit having a lactone structure-containing group are the same as those of the repeating unit having a lactone structure described above in the paragraph of the acid-decomposable resin (P). Also, repeating units disclosed in paragraph [0725] of U.S. Patent Application Publication No. 2012/0135348A1 may also be suitably used.

The content of the repeating unit having a lactone structure-containing group, an acid anhydride group or an acid imide group is preferably from 1 to 100 mol %, more preferably from 3 to 98 mol %, still more preferably from 5 to 95 mol %, based on all repeating units in the hydrophobic resin (D).

Examples of the repeating unit having (z) a group capable of decomposing by the action of an acid, contained in the hydrophobic resin (D), are the same as those of the repeating unit having an acid-decomposable group described in the resin (P). The repeating unit having (z) a group capable of decomposing by the action of an acid may contain at least either a fluorine atom or a silicon atom. In the hydrophobic resin (D), the content of the repeating unit having (z) a group capable of decomposing by the action of an acid is preferably from 1 to 80 mol %, more preferably from 10 to 80 mol %, still more preferably from 20 to 60 mol %, based on all repeating units in the resin (D).

The hydrophobic resin (D) may further contain a repeating unit represented by the following formula (III):

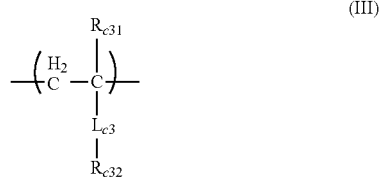

(III)

In formula (III), $R_{c31}$ represents a hydrogen atom, an alkyl group (which may be substituted with a fluorine atom or the like), a cyano group or a —$CH_2$—O—$R_{ace}$ group, wherein $R_{ac2}$ represents a hydrogen atom, an alkyl group or an acyl group. $R_{c31}$ is preferably a hydrogen atom, a methyl group, a hydroxymethyl group or a trifluoromethyl group, more preferably a hydrogen atom or a methyl group.

$R_{c32}$ represents a group having an alkyl group, a cycloalkyl group, an alkenyl group, a cycloalkenyl group or an aryl group. These groups may be substituted with a fluorine atom or a silicon atom-containing group.

$L_{c3}$ represents a single bond or a divalent linking group.

In formula (III), the alkyl group of $R_{c32}$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The aryl group is preferably an aryl group having a carbon number of 6 to 20, more preferably a phenyl group or a naphthyl group, and these groups may have a substituent.

$R_{c32}$ is preferably an unsubstituted alkyl group or an alkyl group substituted with a fluorine atom.

The divalent linking group of $L_{c3}$ is preferably an alkylene group (preferably having a carbon number of 1 to 5), an ether bond, a phenylene group or an ester bond (a group represented by —COO—).

The content of the repeating unit represented by formula (III) is preferably from 1 to 100 mol %, more preferably from 10 to 90 mol %, still more preferably from 30 to 70 mol %, based on all repeating units in the hydrophobic resin.

It is also preferred that the hydrophobic resin (D) further contains a repeating unit represented by the following formula (CII-AB):

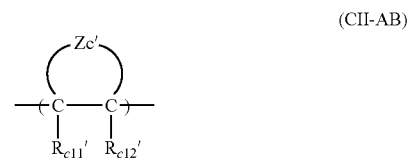

(CII-AB)

In formula (CII-AB), each of $R_{c11}'$ and $R_{c12}'$ independently represents a hydrogen atom, a cyano group, a halogen atom or an alkyl group, and $Z_c'$ represents an atomic group for forming an alicyclic structure containing two carbon atoms (C—C) to which $Z_c'$ is bonded.

The content of the repeating unit represented by formula (CII-AB) is preferably from 1 to 100 mol %, more preferably from 10 to 90 mol %, still more preferably from 30 to 70 mol %, based on all repeating units in the hydrophobic resin.

Specific examples of the repeating units represented by formulae (III) and (CII-AB) are illustrated below, but the present invention is not limited thereto. In the formulae, Ra represents H, $CH_3$, $CH_2OH$, $CF_3$ or CN.

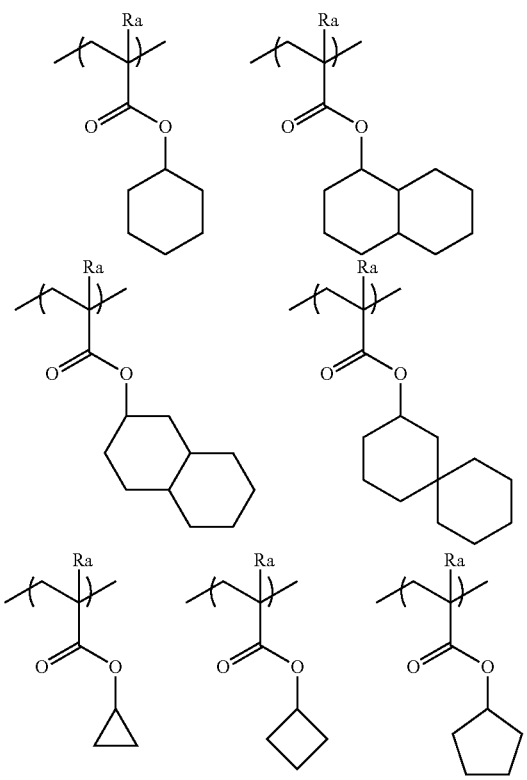

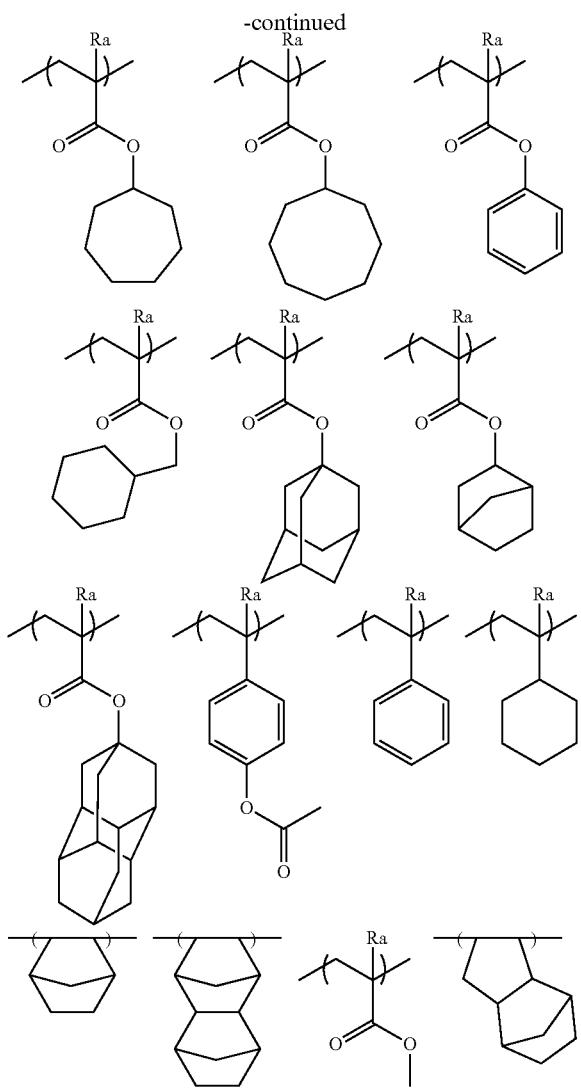

In the case where the hydrophobic resin (D) contains a fluorine atom, the fluorine atom content is preferably from 5 to 80 mass %, more preferably from 10 to 80 mass %, based on the weight average molecular weight of the hydrophobic resin (D). Also, the fluorine atom-containing repeating unit preferably accounts for 10 to 100 mol %, more preferably from 30 to 100 mol %, based on all repeating units contained in the hydrophobic resin (D).

In the case where the hydrophobic resin (D) contains a silicon atom, the silicon atom content is preferably from 2 to 50 mass %, more preferably from 2 to 30 mass %, based on the weight average molecular weight of the hydrophobic resin (D). Also, the silicon atom-containing repeating unit preferably accounts for 10 to 100 mol %, more preferably from 20 to 100 mol %, based on all repeating units contained in the hydrophobic resin (D).

On the other hand, particularly when the resin (D) contains a $CH_3$ partial structure in the side chain moiety, an embodiment where the resin (D) contains substantially no fluorine atom and no silicon atom is also preferred, and in this case, specifically, the content of the repeating unit having a fluorine atom or a silicon atom is, based on all repeating units in the resin (D), preferably 5 mol % or less, more preferably 3 mol % or less, still more preferably 1 mol % or less, and ideally 0 mol %, that is, not containing a fluorine atom and a silicon atom. Also, the resin (D) preferably consists of substantially only a repeating unit composed of only an atom selected from a carbon atom, an oxygen atom, a hydrogen atom, a nitrogen atom and a sulfur atom. More specifically, the repeating unit composed of only an atom selected from a carbon atom, an oxygen atom, a hydrogen atom, a nitrogen atom and a sulfur atom preferably accounts for 95 mol % or more, more preferably 97 mol % or more, still more preferably 99 mol % or more, and ideally 100 mol %, based on all repeating units in the resin (D).

The weight average molecular weight of the hydrophobic resin (D) is preferably from 1,000 to 100,000, more preferably from 1,000 to 50,000, still more preferably from 2,000 to 15,000, in terms of standard polystyrene.

As for the hydrophobic resin (D), one resin may be used, or a plurality of resins may be used in combination.

The content of the hydrophobic resin (D) in the composition is preferably from 0.01 to 10 mass %, more preferably from 0.05 to 8 mass %, still more preferably from 0.1 to 7 mass %, based on the total solid content of the composition of the present invention.

In the hydrophobic resin (D), similarly to the resin (P), it is of course preferred that the content of impurities such as metal is small, but the content of residual monomers or oligomer components is also preferably from 0.01 to 5 mass %, more preferably from 0.01 to 3 mass %, still more preferably from 0.05 to 1 mass %. Within this range, an actinic ray-sensitive or radiation-sensitive resin composition free from in-liquid extraneous substances and a change in sensitivity or the like over time can be obtained. Furthermore, in view of resolution, resist profile, side wall of resist pattern, roughness and the like, the molecular weight distribution (Mw/Mn, sometimes referred to as "polydispersity") is preferably from 1 to 5, more preferably from 1 to 3, still more preferably from 1 to 2.

As the hydrophobic resin (D), various commercially products may be used, or the resin may be synthesized by a conventional method (for example, radical polymerization). For example, the general synthesis method includes a batch polymerization method of dissolving monomer species and an initiator in a solvent and heating the solution, thereby effecting the polymerization, a dropping polymerization method of adding dropwise a solution containing monomer species and an initiator to a heated solvent over 1 to 10 hours, and the like. A dropping polymerization method is preferred.

The reaction solvent, polymerization initiator, reaction conditions (such as temperature and concentration) and method for purification after reaction are the same as those described for the resin (P), but in the synthesis of the hydrophobic resin (D), the concentration at the reaction is preferably from 30 to 50 mass %.

Specific examples of the hydrophobic resin (D) are illustrated below. Also, the molar ratio of repeating units (corresponding to respective repeating units starting from the left), weight average molecular weight and polydispersity of each resin are shown in the Tables later.

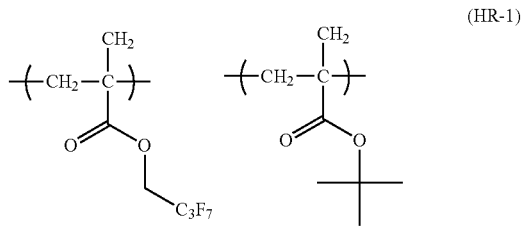

(HR-1)

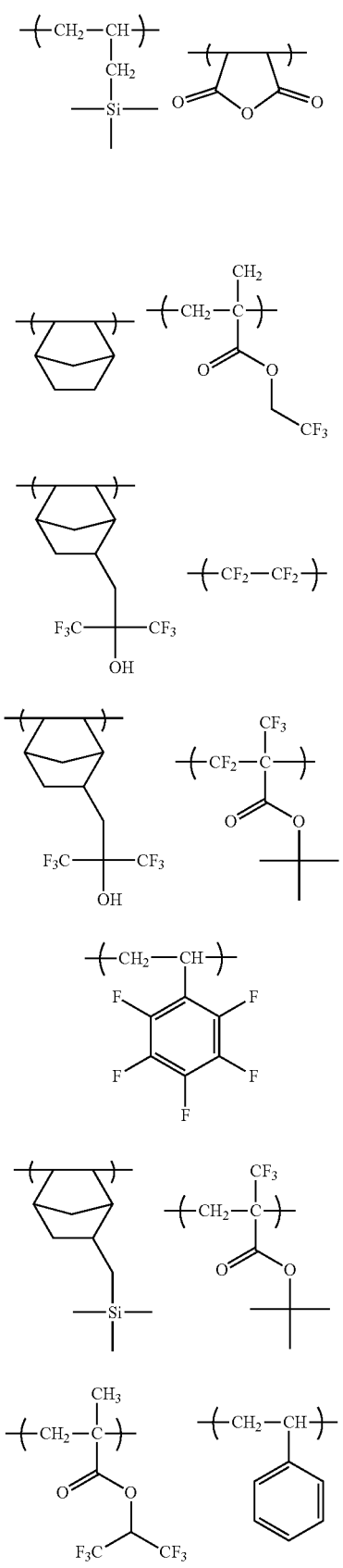
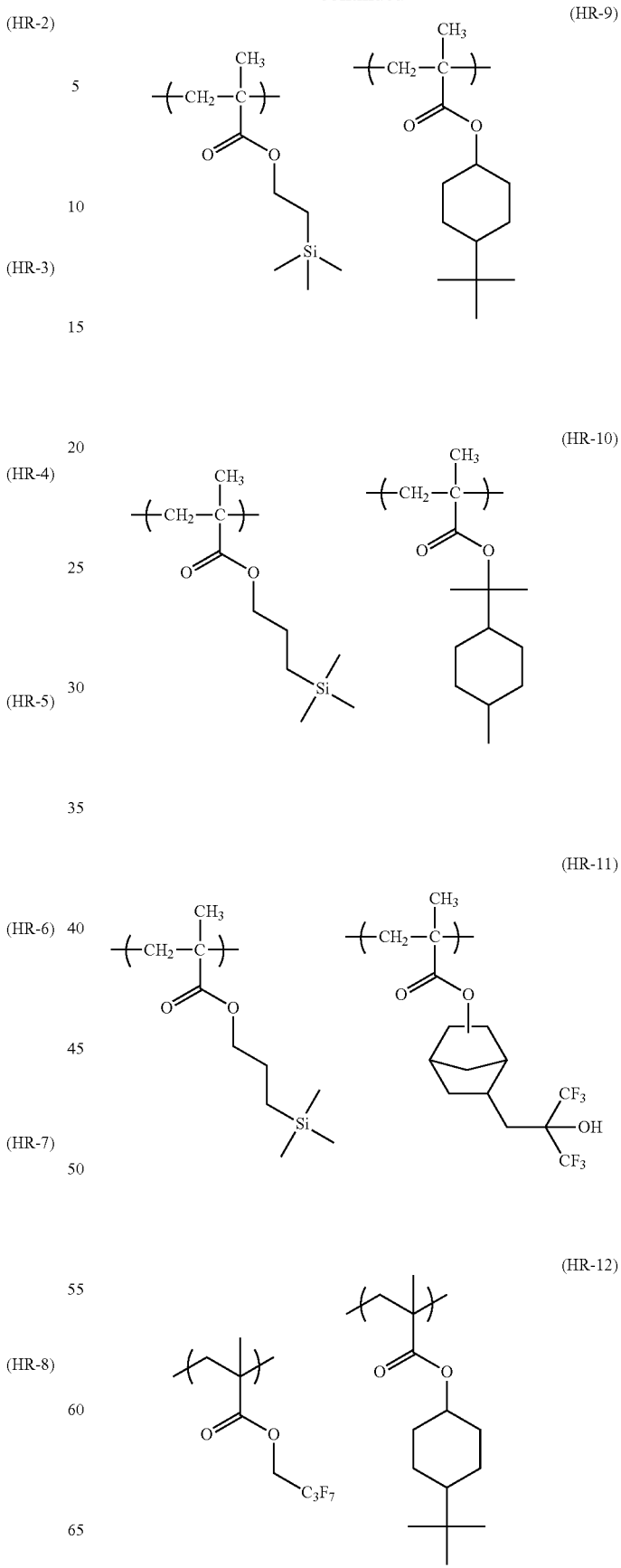

(HR-13) 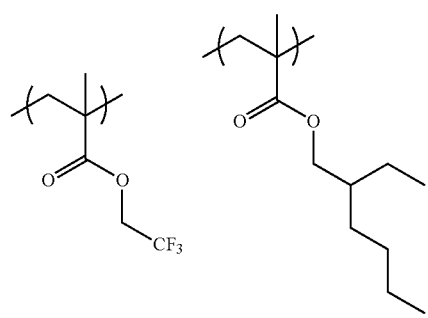
(HR-14) 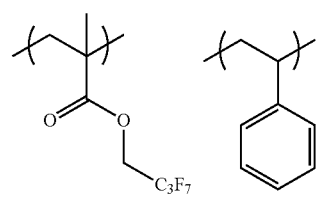
(HR-15) 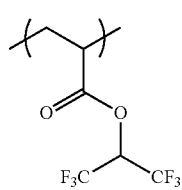
(HR-16) 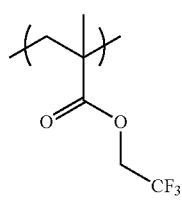
(HR-17) 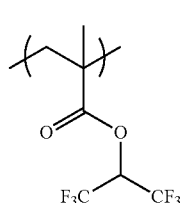
(HR-18) 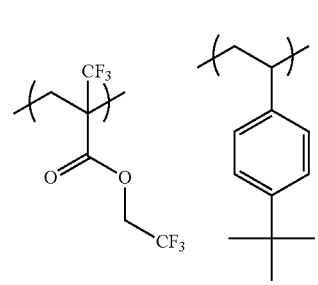
(HR-19) 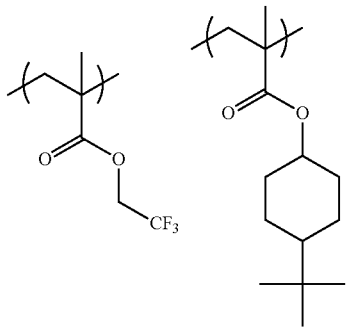
(HR-20) 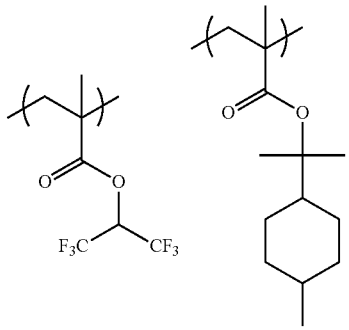
(HR-21) 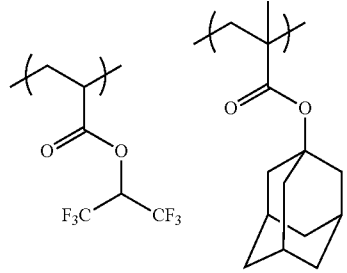
(HR-22) 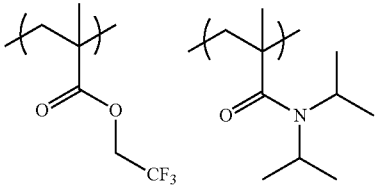
(HR-23) 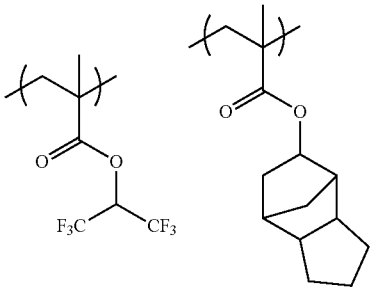

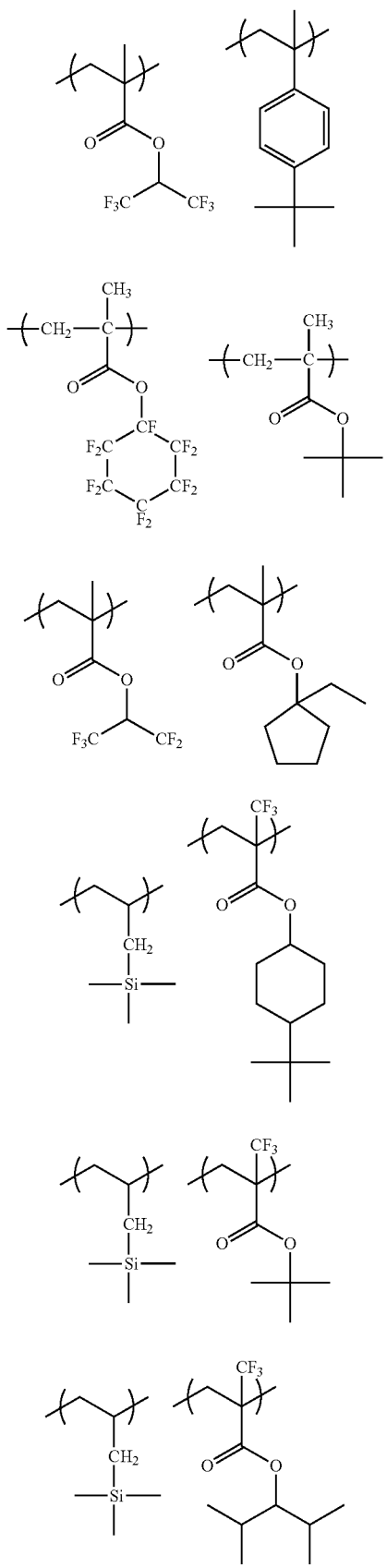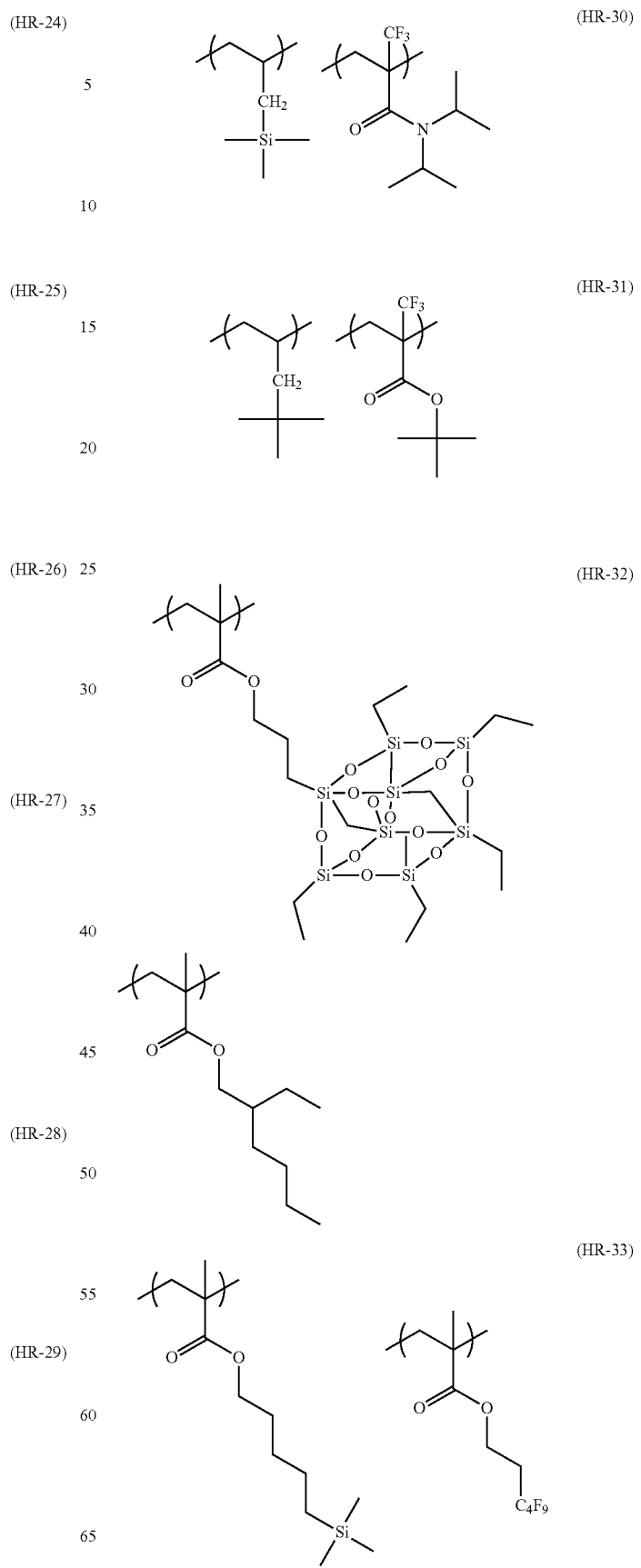

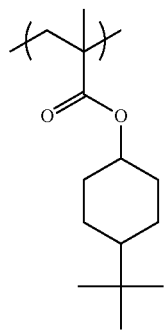
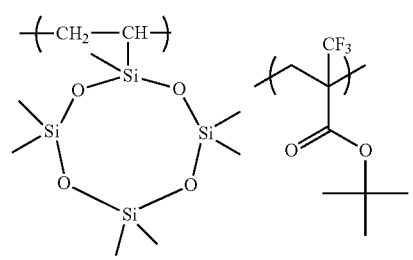
(HR-34)
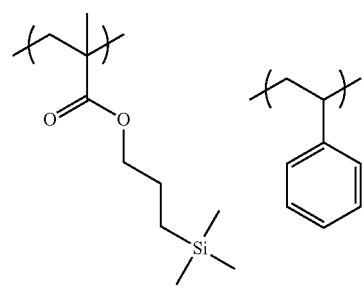
(HR-35)
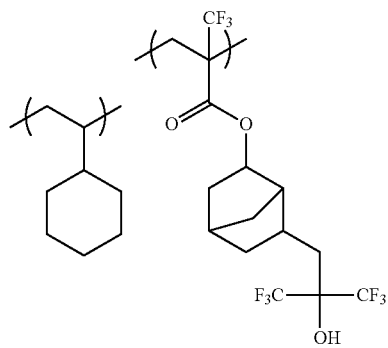
(HR-36)
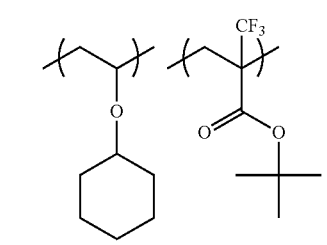
(HR-37)
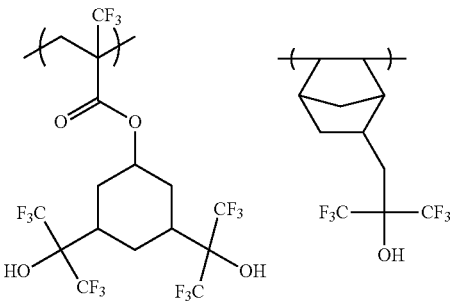
(HR-38)
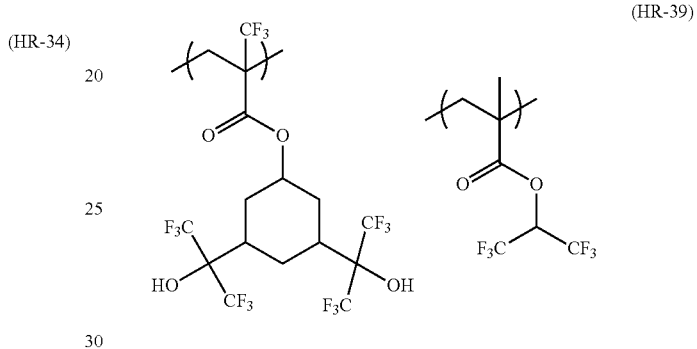
(HR-39)
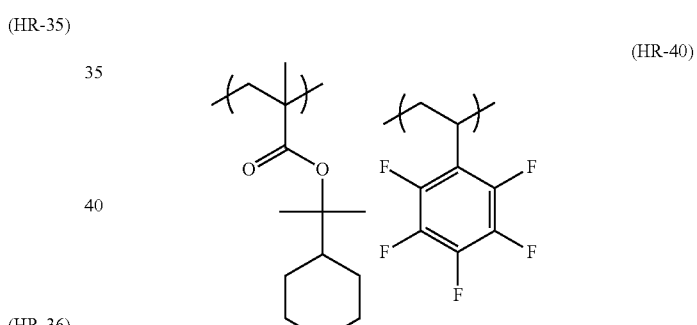
(HR-40)
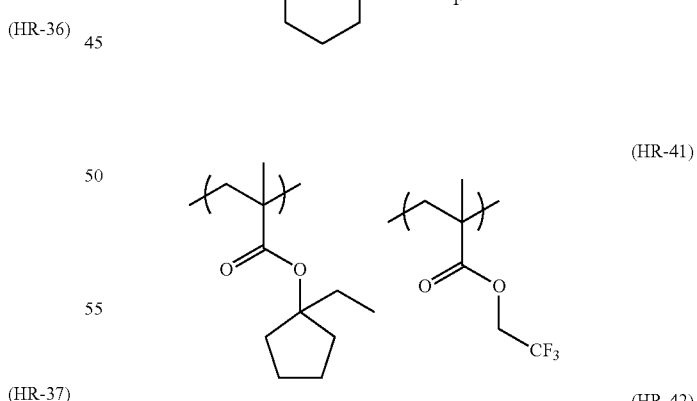
(HR-41)
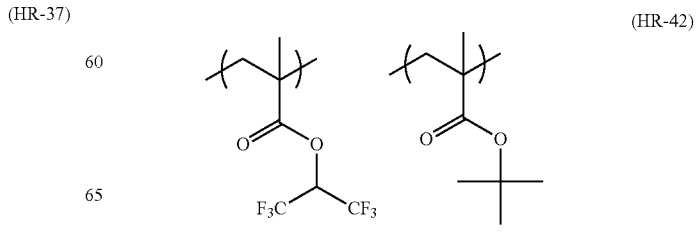
(HR-42)

-continued
(HR-43)
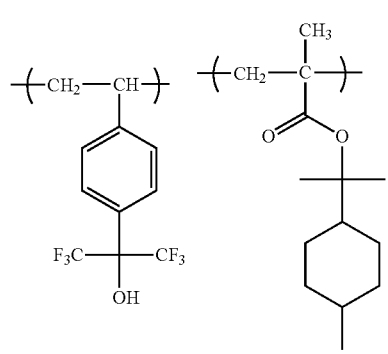
(HR-44)
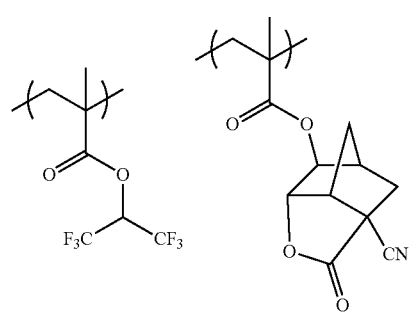
(HR-45)
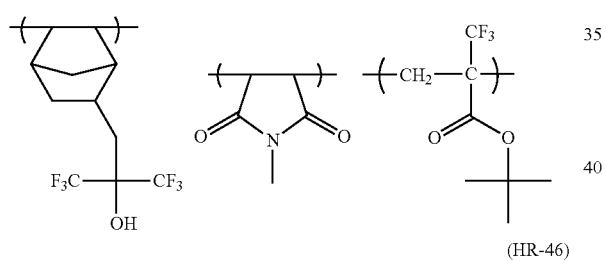
(HR-46)
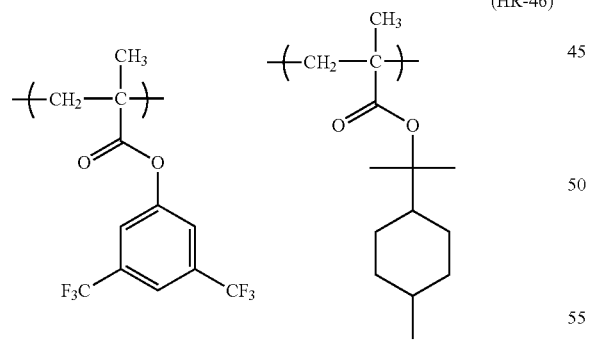
(HR-47)
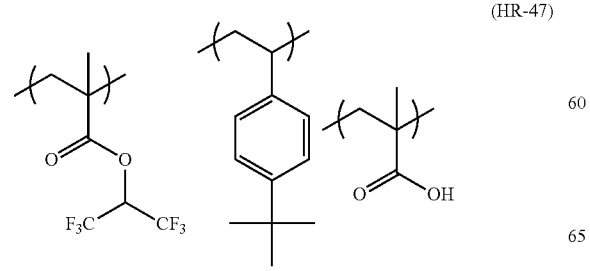
-continued
(HR-48)
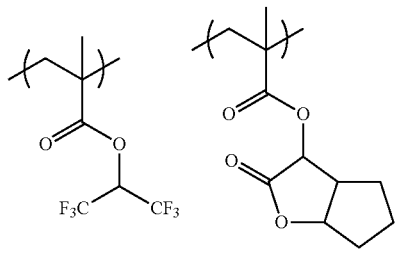
(HR-49)
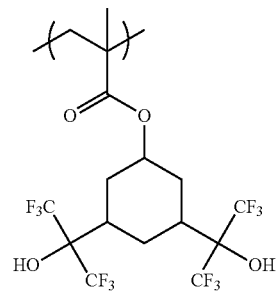
(HR-50)
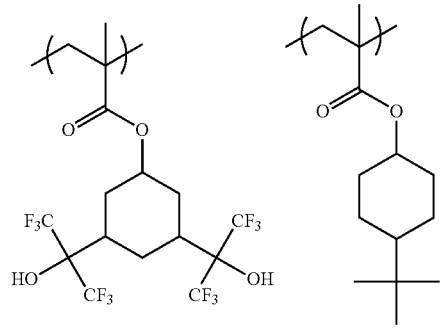
(HR-51)
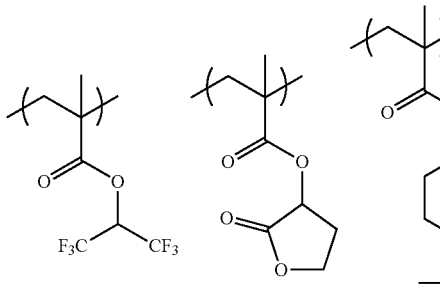
(HR-52)
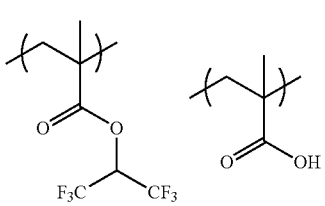

(HR-53)
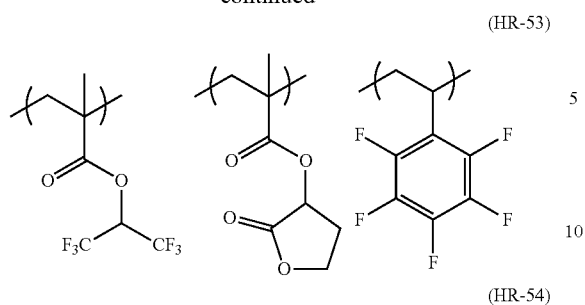
(HR-54)
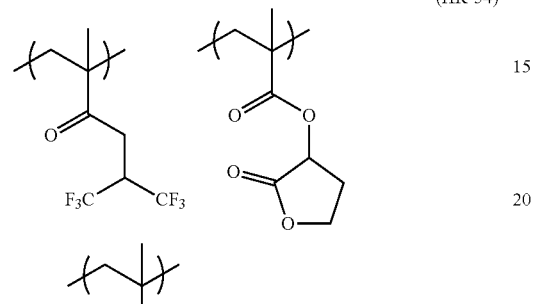
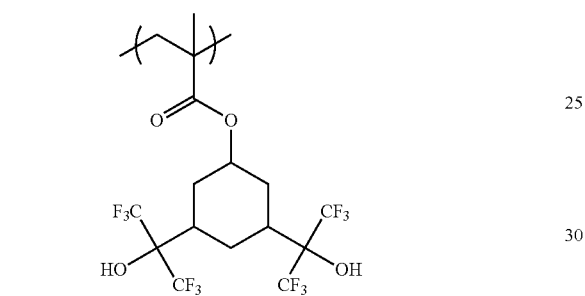
(HR-55)
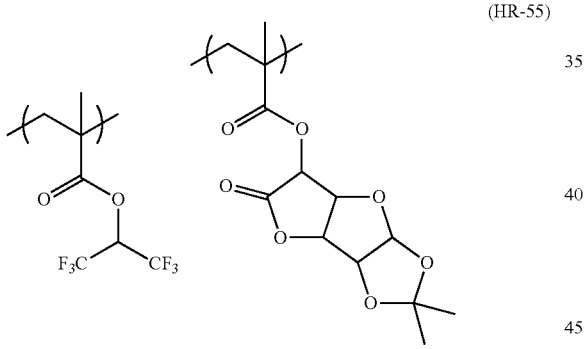
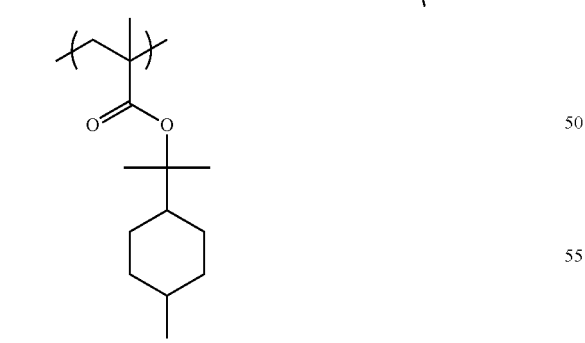
(HR-56)
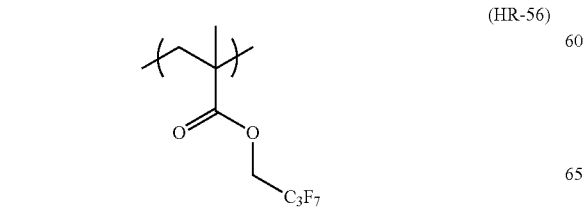
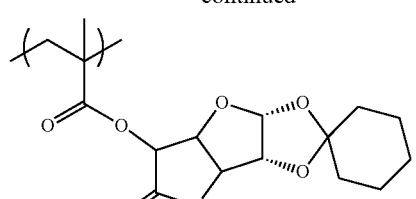
(HR-57)
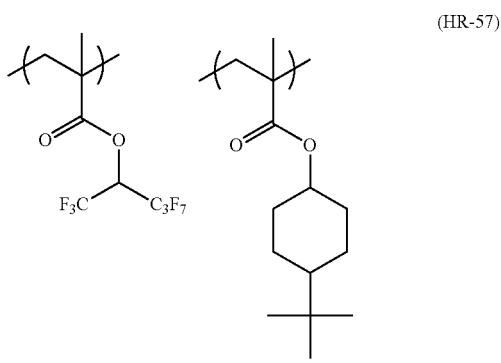
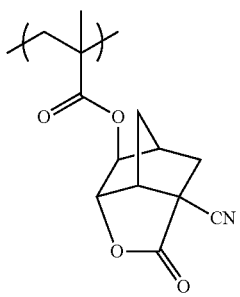
(HR-58)
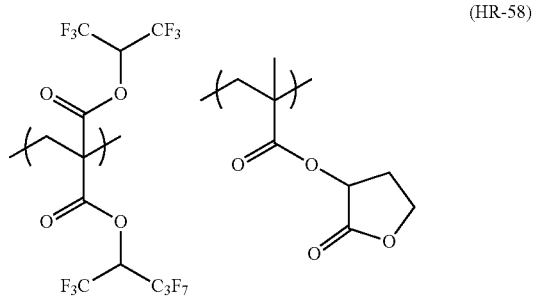
(HR-59)
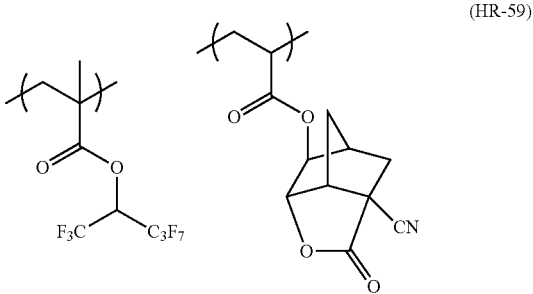

-continued
(HR-60)
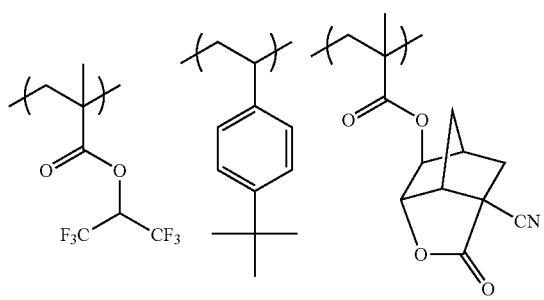
(HR-61)
(HR-62)
(HR-63)
(HR-64)
-continued
(HR-65)
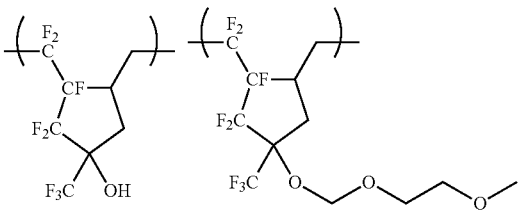
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |

-continued
| Resin | Composition | Mw | Mw/Mn |
|---|---|---|---|
| HR-64 | 100 | 5500 | 1.8 |
| HR-65 | 50/50 | 9500 | 1.9 |
(C-1)
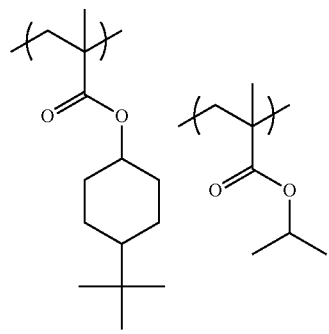
(C-2)
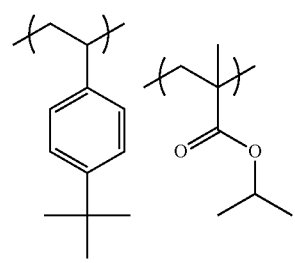
(C-3)
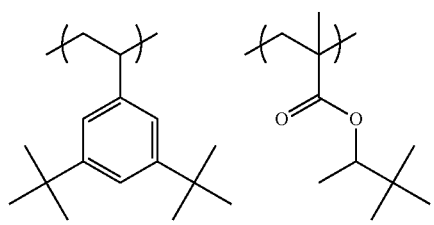
(C-4)
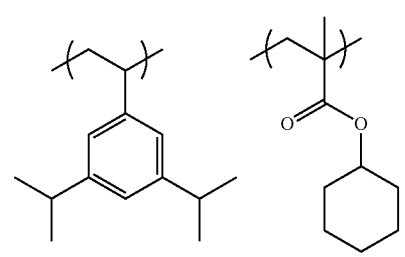
(C-5)
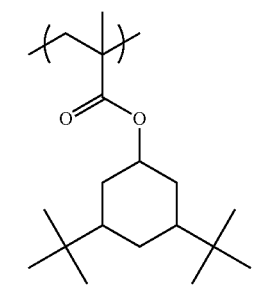
-continued
(C-6)
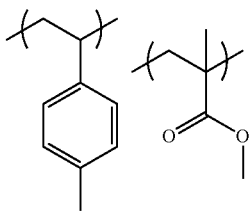
(C-7)
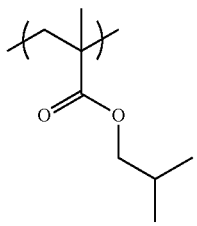
(C-8)
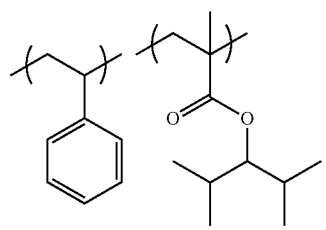
(C-9)
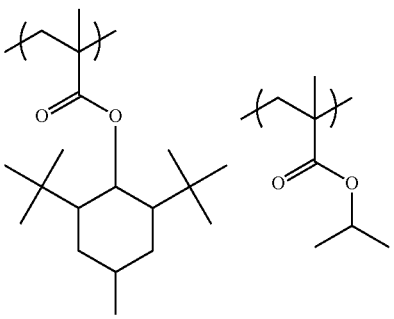
(C-10)
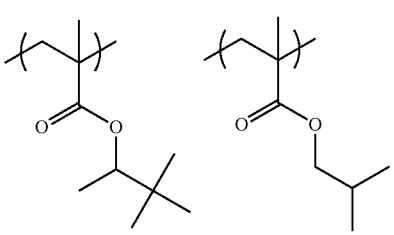
(C-11)
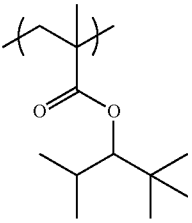

(C-12)
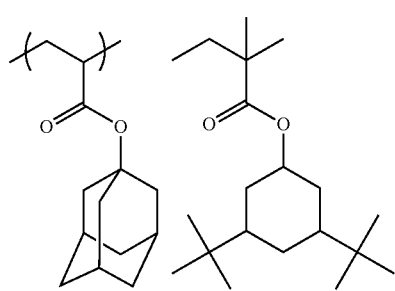
(C-13)
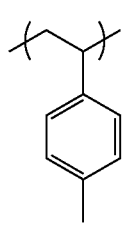
(C-14)
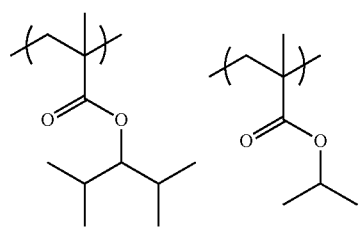
(C-15)
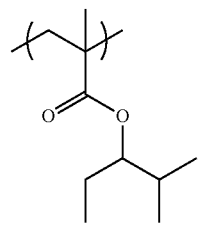
(C-16)
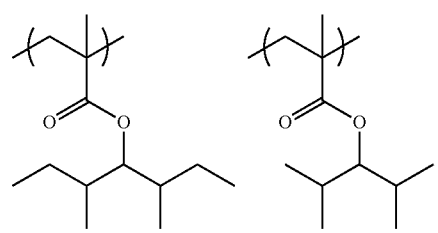
(C-17)
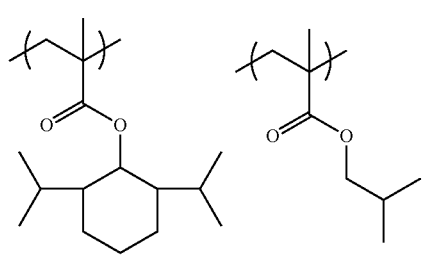
(C-18)
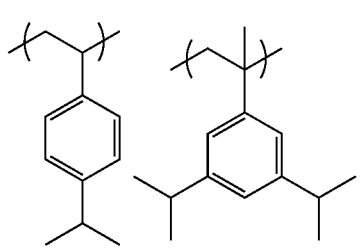
(C-19)
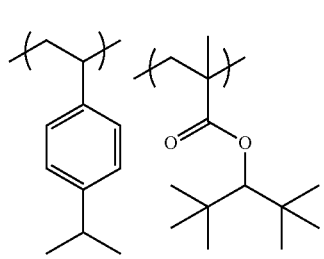
(C-20)
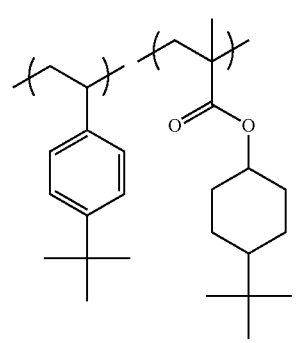
(C-21)
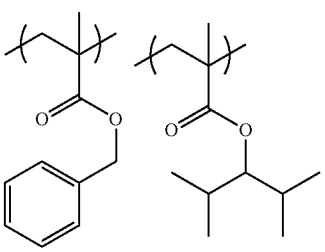
(C-22)
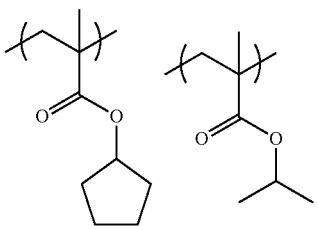
(C-23)
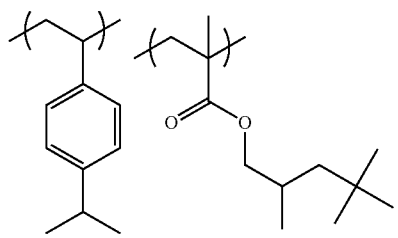

-continued

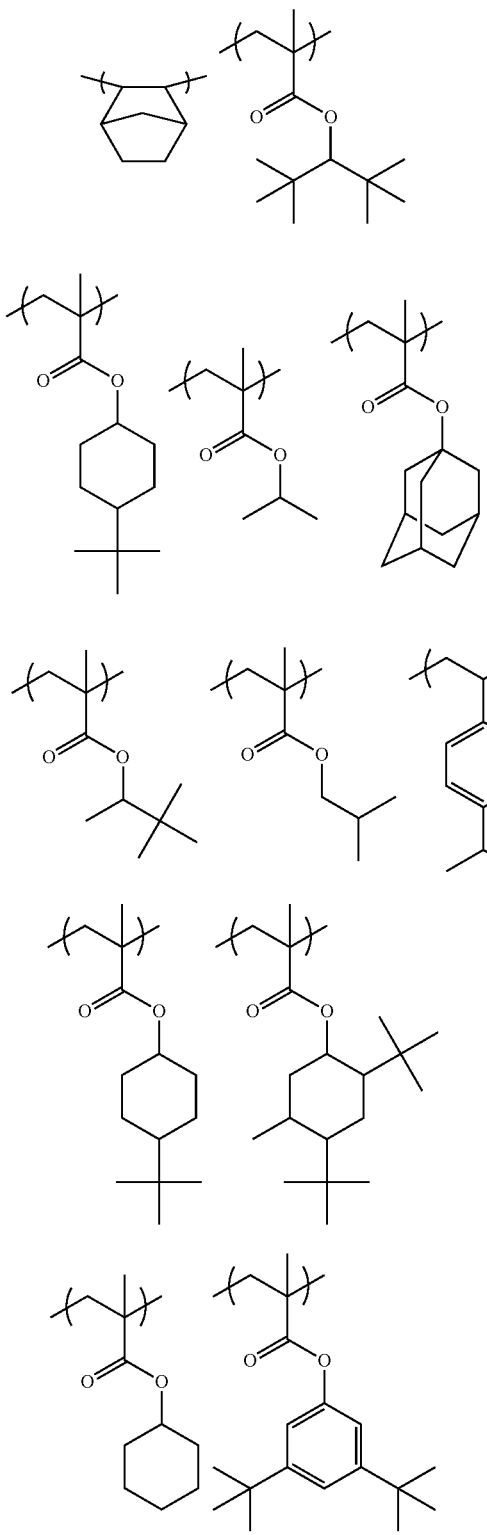

(C-24)
(C-25)
(C-26)
(C-27)
(C-28)

| Resin | Composition | Mw | Mw/Mn |
|---|---|---|---|
| C-1 | 50/50 | 9600 | 1.74 |
| C-2 | 60/40 | 34500 | 1.43 |

-continued

| Resin | Composition | Mw | Mw/Mn |
|---|---|---|---|
| C-3 | 30/70 | 19300 | 1.69 |
| C-4 | 90/10 | 26400 | 1.41 |
| C-5 | 100 | 27600 | 1.87 |
| C-6 | 80/20 | 4400 | 1.96 |
| C-7 | 100 | 16300 | 1.83 |
| C-8 | 5/95 | 24500 | 1.79 |
| C-9 | 20/80 | 15400 | 1.68 |
| C-10 | 50/50 | 23800 | 1.46 |
| C-11 | 100 | 22400 | 1.57 |
| C-12 | 10/90 | 21600 | 1.52 |
| C-13 | 100 | 28400 | 1.58 |
| C-14 | 50/50 | 16700 | 1.82 |
| C-15 | 100 | 23400 | 1.73 |
| C-16 | 60/40 | 18600 | 1.44 |
| C-17 | 80/20 | 12300 | 1.78 |
| C-18 | 40/60 | 18400 | 1.58 |
| C-19 | 70/30 | 12400 | 1.49 |
| C-20 | 50/50 | 23500 | 1.94 |
| C-21 | 10/90 | 7600 | 1.75 |
| C-22 | 5/95 | 14100 | 1.39 |
| C-23 | 50/50 | 17900 | 1.61 |
| C-24 | 10/90 | 24600 | 1.72 |
| C-25 | 50/40/10 | 23500 | 1.65 |
| C-26 | 60/30/10 | 13100 | 1.51 |
| C-27 | 50/50 | 21200 | 1.84 |
| C-28 | 10/90 | 19500 | 1.66 |

[5-1] (N) Basic Compound

The actinic ray-sensitive or radiation-sensitive resin composition of the present invention preferably contains a basic compound so as to reduce the change in performance over time from exposure to heating.

Preferred basic compounds include compounds having a structure represented by the following formulae (A) to (E):

(A)

(B)

(C)

(D)

(E)

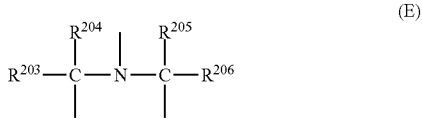

In formulae (A) and (E), each of $R^{200}$, $R^{201}$ and $R^{202}$, which may be the same as or different from one another, represents a hydrogen atom, an alkyl group (preferably having a carbon number of 1 to 20), a cycloalkyl group (preferably having a carbon number of 3 to 20) or an aryl group (having a carbon number of 6 to 20), and $R^{201}$ and $R^{202}$ may combine with each other to form a ring.

Each of $R^{203}$, $R^{204}$, $R^{205}$ and $R^{206}$, which may be the same as or different from one another, represents an alkyl group having a carbon number of 1 to 20.

As for the alkyl group above, the alkyl group having a substituent is preferably an aminoalkyl group having a carbon number of 1 to 20, a hydroxyalkyl group having a carbon number of 1 to 20, or a cyanoalkyl group having a carbon number of 1 to 20.

The alkyl group in formulae (A) and (E) is more preferably unsubstituted.

Preferred compounds include guanidine, aminopyrrolidine, pyrazole, pyrazoline, piperazine, aminomorpholine, aminoalkylmorpholine, piperidine, and the like. More preferred compounds include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; an aniline derivative having a hydroxyl group and/or an ether bond; and the like.

The compound having an imidazole structure includes imidazole, 2,4,5-triphenylimidazole, benzimidazole, 2-phenylbenzimidazole, and the like. The compound having a diazabicyclo structure includes 1,4-diazabicyclo[2,2,2]octane, 1,5-diazabicyclo[4,3,0]non-5-ene, 1,8-diazabicyclo[5,4,0]undec-7-ene, and the like. The compound having an onium hydroxide structure includes a tetrabutylammonium hydroxide, a triarylsulfonium hydroxide, a phenacylsulfonium hydroxide, a sulfonium hydroxide having a 2-oxoalkyl group, and the like, specifically, triphenylsulfonium hydroxide, tris(tert-butylphenyl)sulfonium hydroxide, bis(tert-butylphenyl)iodonium hydroxide, phenacylthiophenium hydroxide, 2-oxopropylthiophenium hydroxide, and the like. The compound having an onium carboxylate structure is a compound where the anion moiety of the compound having an onium hydroxide structure is changed to a carboxylate, and includes, for example, acetate, adamantane-1-carboxylate, and perfluoroalkyl carboxylate. The compound having a trialkylamine structure includes tri(n-butyl)amine, tri(n-octyl)amine, and the like. The aniline compound includes 2,6-diisopropylaniline, N,N-dimethylaniline, N,N-dibutylaniline, N,N-dihexylaniline, and the like. The alkylamine derivative having a hydroxyl group and/or an ether bond includes ethanolamine, diethanolamine, triethanolamine, N-phenyldiethanolamine, tris(methoxyethoxyethyl)amine, and the like. The aniline derivative having a hydroxyl group and/or an ether bond includes N,N-bis(hydroxyethyl)aniline and the like.

Other preferred basic compounds include a phenoxy group-containing amine compound, a phenoxy group-containing ammonium salt compound, a sulfonic acid ester group-containing amine compound, and a sulfonic acid ester group-containing ammonium salt compound. Examples of these compounds include Compounds (C1-1) to (C3-3) illustrated in paragraph [0066] of U.S. Patent Application Publication No. 2007/0224539A1.

The following compounds are also preferred as the basic compound.

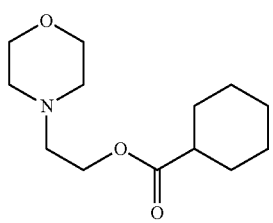

(MO-1)

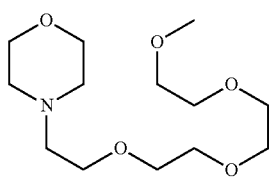

(MO-2)

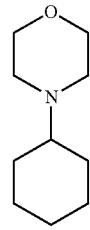

(MO-3)

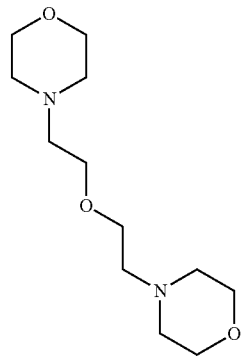

(MO-4)

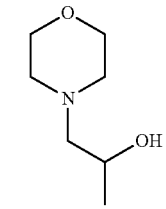

(MO-5)

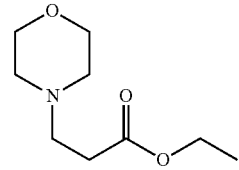

(MO-6)

In addition to the compounds described above, for example, compounds described in [0180] to [0225] of JP-A-2011-22560, [0218] to [0219] of JP-A-2012-137735, and [0416] to [0438] of International Publication WO2011/158687A1, pamphlet, may also be used as the basic compound. The basic compound may also be a basic compound or an ammonium salt compound, whose basicity decreases upon irradiation with an actinic ray or radiation.

Furthermore, a compound capable of decomposing upon irradiation with an actinic ray or radiation to generate an acid anion having a basic structure in the molecule, such as compounds (A-1) to (A-44) of US2010/0233629A and compounds (A-1) to (A-23) of US2012/0156617A, may also be used as the basic compound.

As for these basic compounds, one kind may be used alone, or two or more kinds may be used in combination.

The composition of the present invention may or may not contain a basic compound, but in the case of containing a basic compound, the content percentage thereof is usually from 0.001 to 10 mass %, preferably from 0.01 to 5 mass %, based on the solid content of the actinic ray-sensitive or radiation-sensitive resin composition.

The ratio between the acid generator and the basic compound used in the composition is preferably acid generator/basic compound (molar ratio)=from 2.5 to 300. That is, the molar ratio is preferably 2.5 or more in view of sensitivity and resolution and is preferably 300 or less from the standpoint of suppressing the reduction in resolution due to thickening of the resist pattern over time after exposure until heat treatment. The acid generator/basic compound (molar ratio) is more preferably from 5.0 to 200, still more preferably from 7.0 to 150.

The basic resin is preferably used, in terms of the molar ratio to the low molecular compound (N') described in item [5-2] below, in a ratio of low molecular compound (N')/basic compound=from 100/0 to 10/90, more preferably from 100/0 to 30/70, still more preferably from 100/0 to 50/50.

Incidentally, the basic compound as used herein excludes the below-described (N') low molecular compound containing a nitrogen atom and having a group capable of leaving by the action of an acid.

[5-2] Low Molecular Compound Containing a Nitrogen Atom and Having a Group Capable of Leaving by the Action of an Acid The composition of the present invention may contain a compound containing a nitrogen atom and having a group capable of leaving by the action of an acid (hereinafter, sometimes referred to as "compound (N')").

The group capable of leaving by the action of an acid is not particularly limited but is preferably an acetal group, a carbonate group, a carbamate group, a tertiary ester group, a tertiary hydroxyl group or a hemiaminal ether group, more preferably a carbamate group or a hemiaminal ether group.

The molecular weight of the (N') compound having a group capable of leaving by the action of an acid is preferably from 100 to 1,000, more preferably from 100 to 700, still more preferably from 100 to 500.

The compound (N') is preferably an amine derivative having on the nitrogen atom a group capable of leaving by the action of an acid.

The compound (N') may have a protective group-containing carbamate group on the nitrogen atom. The protective group constituting the carbamate group can be represented by the following formula (d-1):

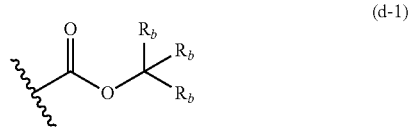

(d-1)

In formula (d-1), each Rb independently represents a hydrogen atom, an alkyl group (preferably having a carbon number of 1 to 10), a cycloalkyl group (preferably having a carbon number of 3 to 30), an aryl group (preferably having a carbon number of 3 to 30), an aralkyl group (preferably having a carbon number of 1 to 10) or an alkoxyalkyl group (preferably having a carbon number of 1 to 10). Respective Rb may combine with each other to form a ring.

Each of the alkyl group, cycloalkyl group, aryl group and aralkyl group represented by Rb may be substituted with a functional group such as hydroxyl group, cyano group, amino group, pyrrolidino group, piperidino group, morpholino group and oxo group, an alkoxy group or a halogen atom. The same applies to the alkoxyalkyl group represented by Rb.

Rb is preferably a linear or branched alkyl group, a cycloalkyl group or an aryl group, more preferably a linear or branched alkyl group or a cycloalkyl group.

The ring formed by combining two Rb with each other includes an alicyclic hydrocarbon group, an aromatic hydrocarbon group, a heterocyclic hydrocarbon group, derivatives thereof, and the like.

Specific structures of the group represented by formula (d-1) include, but are not limited to, structures disclosed in paragraph [0466] of U.S. Patent Application Publication No. 2012/0135348A1.

Among others, the compound (N') is preferably a compound having a structure represented by the following formula (6):

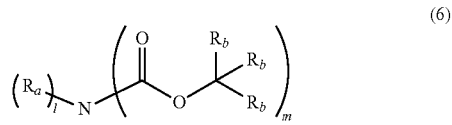

(6)

In formula (6), Ra represents a hydrogen atom, an alkyl group, a cycloalkyl group, an aryl group or an aralkyl group. Also, when l is 2, two Ra may be the same as or different from one another, and two Ra may combine with each other to form a heterocyclic ring together with the nitrogen atom in the formula. The heterocyclic ring may contain a heteroatom other than the nitrogen atom in the formula.

Rb has the same meaning as Rb in formula (d-1), and preferred examples are also the same.

l represents an integer of 0 to 2, m represents an integer of 1 to 3, and these satisfy l+m=3.

In formula (6), the alkyl group, cycloalkyl group, aryl group and aralkyl group of Ra may be substituted with the same group as the group recited above as a group which may be substituted on the alkyl group, cycloalkyl group, aryl group and aralkyl group of Rb.

Preferred examples of the alkyl group, cycloalkyl group, aryl group and aralkyl group of Ra (these alkyl group, cycloalkyl group, aryl group and aralkyl group may be substituted with the above-described group) are the same as preferred examples recited above for the groups of Rb.

The heterocyclic ring formed by combining Ra with each other preferably has a carbon number of 20 or less, and examples thereof include a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, and a group where the group derived from a heterocyclic compound is substituted with one or more kinds of or one or more groups of linear or branched alkane-derived groups, cycloalkane-derived groups, aromatic compound-derived groups, heterocyclic compound-derived groups, and functional groups such as hydroxyl group, cyano group, amino group, pyrrolidino group, piperidino group, morpholino group and oxo group.

Specific examples of the compound (N') particularly preferred in the present invention include, but are not limited to, compounds disclosed in paragraph [0475] of U.S. Patent Application Publication No. 2012/0135348A1.

The compound represented by formula (6) can be synthesized by referring to, for example, JP-A-2007-298569 and JP-A-2009-199021.

In the present invention, as for the low molecular weight compound (N'), one compound may be used alone, or two or more compounds may be mixed and used.

The content of the compound (N') in the actinic ray-sensitive or radiation-sensitive resin composition of the present invention is preferably from 0.001 to 20 mass %, more preferably from 0.001 to 10 mass %, still more preferably from 0.01 to 5 mass %, based on the total solid content of the composition.

[6] (E) Solvent

The solvent which can be used at the preparation of the actinic ray-sensitive or radiation-sensitive resin composition of the present invention includes, for example, an organic solvent such as alkylene glycol monoalkyl ether carboxylate, alkylene glycol monoalkyl ether, alkyl lactate, alkyl alkoxypropionate, cyclic lactone (preferably having a carbon number of 4 to 10), monoketone compound (preferably having a carbon number of 4 to 10) which may contain a ring, alkylene carbonate (propylene carbonate and the like), alkyl alkoxyacetate and alkyl pyruvate.

Specific examples of these solvents include those described in paragraphs [0441] to [0455] of U.S. Patent Application Publication No. 2008/0187860.

In the present invention, a mixed solvent prepared by mixing a solvent containing a hydroxyl group in the structure and a solvent not containing a hydroxyl group may be used as the organic solvent.

The solvent containing a hydroxyl group and the solvent not containing a hydroxyl group may be appropriately selected from the compounds exemplified above, but the solvent containing a hydroxyl group is preferably an alkylene glycol monoalkyl ether, an alkyl lactate or the like, more preferably propylene glycol monomethyl ether (PGME, another name: 1-methoxy-2-propanol) or ethyl lactate. The solvent not containing a hydroxyl group is preferably an alkylene glycol monoalkyl ether acetate, an alkyl alkoxypropionate, a monoketone compound which may contain a ring, a cyclic lactone, an alkyl acetate or the like and among these, more preferably propylene glycol monomethyl ether acetate (PGMEA, another name: 1-methoxy-2-acetoxypropane), propylene glycol monomethyl ether propionate, ethyl ethoxypropionate, 2-heptanone, γ-butyrolactone, cyclohexanone or butyl acetate, most preferably propylene glycol monomethyl ether acetate, ethyl ethoxypropionate or 2-heptanone.

The mixing ratio (by mass) of the solvent containing a hydroxyl group to the solvent not containing a hydroxyl group is from 1/99 to 99/1, preferably from 10/90 to 90/10, more preferably from 20/80 to 60/40. A mixed solvent in which the solvent not containing a hydroxyl group accounts for 50 mass % or more is particularly preferred in view of coating uniformity.

The solvent preferably contains propylene glycol monomethyl ether acetate and is preferably a solvent containing propylene glycol monomethyl ether acetate (PGMEA) alone or a mixed solvent of two or more kinds of solvents containing propylene glycol monomethyl ether acetate (PGMEA). Specific preferred examples of the mixed solvent include, but are not limited to, a mixed solvent containing PGMEA and a ketone-based solvent (such as cyclohexanone and 2-heptanone), a mixed solvent containing PGMEA and a lactone-based solvent (such as γ-butyrolactone), a mixed solvent containing PGMEA and PGME, a mixed solvent containing three kinds of solvents of PGMEA, a ketone-based solvent and a lactone-based solvent, a mixed solvent containing three kinds of solvents of PGMEA, PGME and a lactone-based solvent, and a mixed solvent containing three kinds of solvents of PGMEA, PGME and a ketone-based solvent.

[7] (F) Surfactant

The actinic ray-sensitive or radiation-sensitive resin composition of the present invention may or may not further contain a surfactant, but in the case of containing a surfactant, it is preferred to contain any one of fluorine-containing and/or silicon-containing surfactants (a fluorine-containing surfactant, a silicon-containing surfactant and a surfactant containing both a fluorine atom and a silicon atom), or two or more thereof.

By containing a surfactant, the actinic ray-sensitive or radiation-sensitive resin composition of the present invention can give a resist pattern improved in the sensitivity, resolution and adherence and reduced in the development defect when using an exposure light source of 250 nm or less, particularly 220 nm or less.

The fluorine-containing and/or silicon-containing surfactants include surfactants described in paragraph [0276] of U.S. Patent Application Publication No. 2008/0248425, for example, Ftop EF301 and EF303 (produced by Shin-Akita Kasei K.K.); Florad FC430, 431 and 4430 (produced by Sumitomo 3M Inc.); Megaface F171, F173, F176, F189, F113, F110, F177, F120 and R08 (produced by DIC Corporation); Surflon S-382, SC101, 102, 103, 104, 105 and 106, and KH-20 (produced by Asahi Glass Co., Ltd.); Troysol S-366 (produced by Troy Chemical); GF-300 and GF-150 (produced by Toagosei Chemical Industry Co., Ltd.); Surflon S-393 (produced by Seimi Chemical Co., Ltd.); EFtop EF121, EF122A, EF122B, RF122C, EF125M, EF135M, EF351, EF352, EF801, EF802 and EF601 (produced by JEMCO Inc.); PF636, PF656, PF6320 and PF6520 (produced by OMNOVA); and FTX-204G, 208G, 218G, 230G, 204D, 208D, 212D, 218D and 222D (produced by NEOS Co., Ltd.). In addition, Polysiloxane Polymer KP-341 (produced by Shin-Etsu Chemical Co., Ltd.) may also be used as the silicon-containing surfactant.

Other than those known surfactants, a surfactant using a polymer having a fluoro-aliphatic group derived from a fluoro-aliphatic compound which is produced by a telomerization process (also called a telomer process) or an oligomerization process (also called an oligomer process), may be used. The fluoro-aliphatic compound can be synthesized by the method described in JP-A-2002-90991.

The surfactant coming under the surfactant above includes Megaface F178, F-470, F-473, F-475, F-476 and F-472 (produced by DIC Corporation); a copolymer of a $C_6F_{13}$ group-containing acrylate (or methacrylate) with a (poly(oxyalkylene)) acrylate (or methacrylate); a copolymer of a $C_3F_7$ group-containing acrylate (or methacrylate) with a (poly(oxyethylene)) acrylate (or methacrylate) and a (poly(oxypropylene)) acrylate (or methacrylate); and the like.

In the present invention, surfactants other than the fluorine-containing and/or silicon-containing surfactants, described in paragraph [0280] of U.S. Patent Application Publication No. 2008/0248425, may also be used.

One of these surfactants may be used alone, or some of them may be used in combination.

In the case where the actinic ray-sensitive or radiation-sensitive resin composition contains a surfactant, the amount of the surfactant used is preferably from 0.0001 to 2 mass %, more preferably from 0.0005 to 1 mass %, based on the total amount of the actinic ray-sensitive or radiation-sensitive resin composition (excluding the solvent).

On the other hand, when the amount of the surfactant added is set to be 10 ppm or less based on the total amount of the actinic ray-sensitive or radiation-sensitive resin composition (excluding the solvent), the hydrophobic resin can be more unevenly distributed to the surface, whereby the resist film surface can be made more hydrophobic and the followability of water at the immersion exposure can be enhanced.

From the standpoint of enhancing the resolution, the actinic ray-sensitive or radiation-sensitive resin composition of the present invention is preferably used in a film thickness of 30 to 250 nm, more preferably from 30 to 200 nm. Such a film thickness can be achieved by setting the solid content concentration in the composition to an appropriate range, thereby imparting an appropriate viscosity and enhancing the coatability and film-forming property.

The solid content concentration of the actinic ray-sensitive or radiation-sensitive resin composition of the present invention is usually from 1.0 to 10 mass %, preferably from 2.0 to 5.7 mass %, more preferably from 2.0 to 5.3 mass %. By setting the solid content concentration to the range above, the resist solution can be uniformly coated on a substrate and furthermore, a resist pattern improved in the line width roughness can be formed. The reason therefor is not clearly known, but it is considered that by virtue of setting the solid content concentration to be 10 mass % or less, preferably 5.7 mass % or less, the materials, particularly the photoacid generator, in the resist solution can be prevented from aggregation, as a result, a uniform resist film can be formed.

The solid content concentration is a weight percentage of the weight of resist components excluding the solvent, based on the total weight of the actinic ray-sensitive or radiation-sensitive resin composition.

The actinic ray-sensitive or radiation-sensitive resin composition of the present invention is used by dissolving the components above in a predetermined organic solvent, preferably in the above-described mixed solvent, filtering the solution through a filter, and coating the filtrate on a predetermined support (substrate). The filter used for filtration is preferably a polytetrafluoroethylene-, polyethylene- or nylon-made filter having a pore size of 0.1 μm or less, more preferably 0.05 μm or less, still more preferably 0.03 μm or less. In the filtration through a filter, as described, for example, in JP-A-2002-62667, circulating filtration may be performed, or the filtration may be performed by connecting a plurality of kinds of filters in series or in parallel. Also, the composition may be filtered a plurality of times. Furthermore, a deaeration treatment or the like may be applied to the composition before and after filtration through a filter.

The pattern forming method according to the present invention is described below.

The pattern forming method of the present invention comprises:
(i) a step of forming a film (resist film) containing the actinic ray-sensitive or radiation-sensitive resin composition of the present invention,
(ii) a step of irradiating (exposing) the film with an actinic ray or radiation, and
(iii) a step of developing the exposed film by using a developer.

The exposure in the step (ii) may be immersion exposure.

The pattern forming method of the present invention preferably includes (iv) a heating step after the exposure step (ii).

In the pattern forming method of the present invention, the exposure step (ii) may be performed a plurality of times.

In the pattern forming method of the present invention, the heating step (iv) may be performed a plurality of times.

The resist film of the present invention is formed from the above-described actinic ray-sensitive or radiation-sensitive resin composition of the present invention and, more specifically, is preferably a film formed by coating the actinic ray-sensitive or radiation-sensitive resin composition on a base material. In the pattern forming method of the present invention, the step of forming a film on a substrate by using the actinic ray-sensitive or radiation-sensitive resin composition, the step of exposing the film, and the development step can be performed by generally known methods.

It is also preferred to include, after film formation, a preheating step (PB; Prebake) before entering the exposure step.

Furthermore, it is also preferred to include a post-exposure heating step (PEB; Post Exposure Bake) after the exposure step but before the development step.

As for the heating temperature, both PB and PEB are preferably performed at 70 to 130° C., more preferably at 80 to 120° C.

The heating time is preferably from 30 to 300 seconds, more preferably from 30 to 180 seconds, still more preferably from 30 to 90 seconds.

The heating can be performed using a device attached to an ordinary exposure/developing machine or may be performed using a hot plate or the like.

Thanks to baking, the reaction in the exposed area is accelerated, and the sensitivity and pattern profile are improved.

The light source used for the exposure apparatus in the present invention is not limited in its wavelength but includes, for example, near infrared light, visible light, ultraviolet light, far ultraviolet light, extreme-ultraviolet light, X-ray, electron beam and is preferably far ultraviolet light at a wavelength of 250 nm or less, more preferably 220 nm or less, still more preferably from 1 to 200 nm. Specifically, the light source includes KrF excimer laser (248 nm), ArF excimer laser (193 nm), $F_2$ excimer laser (157 nm), X-ray, EUV (13 nm), electron beam and the like, and is preferably KrF excimer laser, ArF excimer laser, EUV or electron beam, more preferably ArF excimer laser.

In the step of performing exposure of the present invention, an immersion exposure method can be applied. The immersion exposure method can be combined with a super-resolution technology such as phase-shift method and modified illumination method.

In the case of performing immersion exposure, a step of washing the film surface with an aqueous chemical solution may be performed (1) after forming a film on a substrate but before the step of exposing the film and/or (2) after the step of exposing the film through an immersion liquid but before the step of heating the film.

The immersion liquid is preferably a liquid being transparent to light at the exposure wavelength and having as small a temperature coefficient of refractive index as possible in order to minimize the distortion of an optical image projected on the film. Particularly, when the exposure light source is ArF excimer laser (wavelength: 193 nm), water is preferably used in view of availability and ease of handling, in addition to the above-described aspects.

In the case of using water, an additive (liquid) capable of decreasing the surface tension of water and increasing the interface activity may be added in a small ratio. This additive is preferably an additive that does not dissolve the resist layer on the wafer and at the same time, gives only a negligible effect on the optical coat at the undersurface of the lens element.

Such an additive is preferably, for example, an aliphatic alcohol having a refractive index substantially equal to that of water, and specific examples thereof include methyl alcohol, ethyl alcohol and isopropyl alcohol. By virtue of adding an alcohol having a refractive index substantially equal to that of water, even when the alcohol component in water is evaporated and its content concentration is changed, the change in the refractive index of the liquid as a whole can be advantageously made very small.

On the other hand, if a substance opaque to light at 193 nm or an impurity greatly differing in the refractive index from water is mingled, this incurs distortion of the optical image projected on the resist. Therefore, the water used is preferably distilled water. Furthermore, pure water after filtration through an ion exchange filter or the like may also be used.

The electrical resistance of water used as the immersion liquid is preferably 18.3 MΩcm or more, and TOC (total organic carbon) is preferably 20 ppb or less. The water is preferably subjected to a deaeration treatment.

Also, the lithography performance can be enhanced by raising the refractive index of the immersion liquid. From such a standpoint, an additive for raising the refractive index may be added to water, or heavy water ($D_2O$) may be used in place of water.

The receding contact angle of the resist film formed using the actinic ray-sensitive or radiation-sensitive resin composition of the present invention is 70° or more at a temperature of 23±3° C. and a humidity of 45±5%, and when exposing the film through an immersion medium, the receding contact angle is preferably 75° or more, more preferably from 75 to 85°.

If the receding contact angle is too small, the composition cannot be suitably used when exposing the film through an immersion medium and at the same time, the effect of reducing the watermark defect cannot be satisfactorily brought out. In order to realize the preferred receding contact angle, it is preferred to incorporate the above-described hydrophobic resin (D) into the actinic ray-sensitive or radiation-sensitive composition. Alternatively, the receding contact angle may be enhanced by forming a coating layer (so-called "topcoat") from a hydrophobic resin composition on the resist film.

In the immersion exposure step, the immersion liquid must move on a wafer by conforming to the movement of an exposure head that is scanning the wafer at a high speed to form an exposure pattern. Therefore, the contact angle of the immersion liquid for the resist film in a dynamic state is important, and the resist is required to have a performance allowing the immersion liquid to follow the high-speed scanning of an exposure head with no remaining of a liquid droplet.

In the present invention, the substrate on which the film is formed is not particularly limited, and an inorganic substrate such as silicon, SiN, $SiO_2$ and SiN, a coating-type inorganic substrate such as SOG, or a substrate generally used in the process of producing a semiconductor such as IC or producing a liquid crystal device or a circuit board such as thermal head or in the lithography of other photofabrication processes, can be used. If desired, an antireflection film may be formed between the resist film and the substrate. As the antireflection film, a known organic or inorganic antireflection film can be appropriately used.

The development step (iii) in the pattern forming method of the present invention may be (iii-1) a step of developing the resist film by using an organic solvent-containing developer or (iii-2) a step of developing the resist film by using an alkali developer. The pattern forming method may includes both the steps (iii-1) and (iii-2) and in this case, the order of the steps (iii-1) and (iii-2) is not particularly limited.

In the present invention, generally, a negative pattern is formed when the step (iii-1) of developing the resist film by using an organic solvent-containing developer is performed, and a positive pattern is formed when the step (iii-2) of developing the resist film by using an alkali developer is performed. Also, when both the steps (iii-1) and (iii-2) are performed, as described in FIG. 1 to FIG. 11 of U.S. Pat. No. 8,227,183B, a pattern with a resolution as high as two times the frequency of an optical spatial image can be obtained.

In the pattern forming method of the present invention, as for the developer usable in the step (iii-1) of developing the resist film by using an organic solvent-containing developer (hereinafter, sometimes referred to as an "organic developer"), a polar solvent such as ketone-based solvent, ester-based solvent, alcohol-based solvent, amide-based solvent and ether-based solvent, or a hydrocarbon-based solvent can be used. Specific examples of these solvents include developers described in paragraphs 0633 to 0641 of US2008/0187860A.

The ketone-based solvent includes, for example, 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

The ester-based solvent includes, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

The alcohol-based solvent includes, for example, an alcohol such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol.

The ether-based solvent includes, for example, dioxane and tetrahydrofuran, in addition to the glycol ether-based solvents above.

The amide-based solvent which can be used includes, for example, N-methyl-2-pyrrolidone, N,N-dimethylacetamide, N,N-dimethylformamide, hexamethylphosphoric triamide, and 1,3-dimethyl-2-imidazolidinone.

The hydrocarbon-based solvent includes, for example, an aromatic hydrocarbon-based solvent such as toluene and xylene, and an aliphatic hydrocarbon-based solvent such as pentane, hexane, octane and decane.

In particular, the organic developer is preferably a developer containing at least one kind of an organic solvent selected from the group consisting of a ketone-based solvent and an ester-based solvent, more preferably a developer containing butyl acetate as the ester-based solvent or containing methyl amyl ketone (2-heptanone) as the ketone-based solvent.

A plurality of these solvents may be mixed, or the solvent may be used by mixing it with a solvent other than those described above or with water. However, in order to sufficiently bring out the effects of the present invention, the water content percentage in the entire developer is preferably less than 10 mass %, and it is more preferred to contain substantially no water.

That is, the amount of the organic solvent used in the organic developer is preferably from 90 to 100 mass %, more preferably from 95 to 100 mass %, based on the total amount of the developer.

The vapor pressure at 20° C. of the organic developer is preferably 5 kPa or less, more preferably 3 kPa or less, still more preferably 2 kPa or less. By setting the vapor pressure of the organic developer to 5 kPa or less, evaporation of the developer on a substrate or in a development cup is suppressed and the temperature uniformity in the wafer plane is enhanced, as a result, the dimensional uniformity in the wafer plane is improved.

In the organic developer, an appropriate amount of a surfactant can be added, if desired.

The surfactant is not particularly limited but, for example, ionic or nonionic fluorine-containing and/or silicon-containing surfactants can be used. These fluorine-containing and/or silicon-containing surfactants include, for example, surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988 and U.S. Pat. Nos. 5,405,720, 5,360,692, 5,529,881, 5,296,330, 5,436,098, 5,576,143, 5,294,511 and 5,824,451. A nonionic surfactant is preferred. The nonionic surfactant is not particularly limited, but use of a fluorine-containing surfactant or a silicon-containing surfactant is more preferred.

The amount of the surfactant used is usually from 0.001 to 5 mass %, preferably from 0.005 to 2 mass %, more preferably from 0.01 to 0.5 mass %, based on the total amount of the developer.

In addition, the organic developer may also contain a nitrogen-containing compound such as those recited in paragraphs 0041 to 0063 of Japanese Patent No. 5,056,974.

As regards the developing method, for example, a method of dipping the substrate in a bath filled with the developer for a fixed time (dipping method), a method of raising the developer on the substrate surface by the effect of a surface tension and keeping it still for a fixed time, thereby performing development (puddling method), a method of spraying the developer on the substrate surface (spraying method), and a method of continuously ejecting the developer on the substrate spinning at a constant speed while scanning with a developer ejecting nozzle at a constant rate (dynamic dispense method) may be applied.

In the case where the above-described various developing methods include a step of ejecting the developer toward the resist film from a development nozzle of a developing apparatus, the ejection pressure of the developer ejected (the flow velocity per unit area of the developer ejected) is, for example, preferably 2 mL/sec/mm$^2$ or less, more preferably 1.5 mL/sec/mm$^2$ or less, still more preferably 1 mL/sec/mm$^2$ or less. The lower limit of the flow velocity is not particularly limited but in view of throughput, is preferably 0.2 mL/sec/mm$^2$ or more. This is described in detail particularly in paragraphs 0022 to 0029 of JP-A-2010-232550, and the like.

After the step of developing the resist film by using an organic solvent-containing developer, a step of stopping the development while replacing the solvent with another solvent may be practiced.

In the case where the pattern forming method of the present invention includes (iii-2) a step of developing the resist film by using an alkali developer, the alkali developer that can be used is not particularly limited, and an aqueous solution of tetramethylammonium hydroxide at 2.38 mass % is generally used, but a developer at other concentrations (for example, at a lower concentration) can also be used. Furthermore, the alkaline aqueous solution may also be used after adding thereto alcohols and a surfactant each in an appropriate amount.

The alkali concentration of the alkali developer is usually from 0.1 to 20 mass %.

The pH of the alkali developer is usually from 10.0 to 15.0.

As the rinsing solution in the rinsing treatment performed after the alkali development, pure water is used and may be used after adding thereto an appropriate amount of a surfactant.

Also, after the development or rinsing treatment, a treatment of removing the developer or rinsing solution adhering on the pattern by a supercritical fluid may be performed.

The pattern forming method preferably includes a step of rinsing the film by using a rinsing solution, after the step (iii-1) of developing the resist film by using an organic solvent-containing developer. The rinsing solution here is not particularly limited, and a solution containing a general organic solvent can be used. As this rinsing solution, a rinsing solution containing at least one kind of an organic solvent selected from the group consisting of a hydrocarbon-based solvent, a ketone-based solvent, an ester-based solvent, an alcohol-based solvent, an amide-based solvent and an ether-based solvent is preferably used.

Specific examples of the hydrocarbon-based solvent, ketone-based solvent, ester-based solvent, alcohol-based solvent, amide-based solvent and ether-based solvent are the same as those described in the organic solvent-containing developer.

After the step (iii-1) of developing the resist film by using an organic solvent-containing developer, more preferably, a step of rinsing the film by using a rinsing solution containing at least one kind of an organic solvent selected from the group consisting of a ketone-based solvent, an ester-based solvent, an alcohol-based solvent and an amide-based solvent is preformed; still more preferably, a step of rinsing the film by using a rinsing solution containing an alcohol-based solvent or an ester-based solvent is performed; yet still more preferably, a step of rinsing the film by using a rinsing solution containing a monohydric alcohol is performed; and most preferably, a step of rinsing the film by using a rinsing solution containing a monohydric alcohol having a carbon number of 5 or more is performed.

The monohydric alcohol used in the rinsing step includes a linear, branched or cyclic monohydric alcohol, and specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol and the like can be used. As the particularly preferred monohydric alcohol having a carbon number of 5 or more, 1-hexanol, 2-hexanol, 4-methyl-2-pentanol, 1-pentanol, 3-methyl-1-butanol and the like can be used.

A plurality of these components may be mixed, or the solvent may be used by mixing it with an organic solvent other than those described above.

The water content percentage in the rinsing solution is preferably 10 mass % or less, more preferably 5 mass % or less, still more preferably 3 mass % or less. By setting the water content percentage to 10 mass % or less, good development characteristics can be obtained.

The vapor pressure at 20° C. of the rinsing solution used after the step of developing the resist film by using an organic solvent-containing developer is preferably from 0.05 to 5 kPa, more preferably from 0.1 to 5 kPa, and most preferably from 0.12 to 3 kPa. By setting the vapor pressure of the rinsing solution to be from 0.05 to 5 kPa, the temperature uniformity in the wafer plane is enhanced and moreover, swelling due to permeation of the rinsing solution is suppressed, as a result, the dimensional uniformity in the wafer plane is improved.

The rinsing solution may also be used after adding thereto an appropriate amount of a surfactant.

In the rinsing step, the wafer subjected to development using an organic solvent-containing developer is rinsed by using a rinsing solution containing the above-described organic solvent. The method for rinsing treatment is not particularly limited but, for example, a method of continuously ejecting the rinsing solution on the substrate spinning at a constant speed (spin coating method), a method of dipping the substrate in a bath filled with the rinsing solution for a fixed time (dipping method), and a method of spraying the rinsing solution on the substrate surface (spraying method) can be applied. Above all, it is preferred to perform the rinsing treatment by the spin coating method and after the rinsing, remove the rinsing solution from the substrate surface by spinning the substrate at a rotational speed of 2,000 to 4,000 rpm. It is also preferred to include a heating step (Post Bake) after the rinsing step. The developer and rinsing solution remaining between patterns and in the inside of the pattern are removed by the baking. The heating step after the rinsing step is performed at usually from 40 to 160° C., preferably from 70 to 95° C., for usually from 10 seconds to 3 minutes, preferably from 30 to 90 seconds.

In the organic developer, alkali developer and/or rinsing solution for use in the present invention, the content of various fine particles or impurities such as metal element is preferably small. For obtaining such a chemical solution with few impurities, it is preferred to reduce the impurities, for example, by producing the chemical solution in a clean room or performing filtration through various filters such as Teflon filer, polyolefin-based filter and ion exchange filter. As for the metal element, any of metal element concentrations of Na, K, Ca, Fe, Cu, Mg, Mn, Li, Al, Cr, Ni and Zn is preferably 10 ppm or less, more preferably 5 ppm or less.

Also, the container for storing the developer or rinsing solution is not particularly limited, and a container made of a polyethylene resin, a polypropylene resin, a polyethylene-polypropylene resin or the like, which is used in the application of electronic materials, may be used, but in order to reduce impurities dissolved out from the container, it is also preferred to select a container that is less likely to cause elution of a component from the inner wall of the container to the chemical solution. Such a container includes a container where the inner wall of the container is formed of a perfluororesin (for example, a FluoroPure PFA composite drum (inner surface coming into contact with liquid: PFA resin lining) manufactured by Entegris, and a steel-made drum (inner surface coming into contact with liquid: zinc phosphate coat) manufactured by JFE), and the like.

The pattern obtained by the method of the present invention is typically used, for example, as a mask in the etching step for semiconductor production and may also be used as a core material (core) in the spacer process disclosed in JP-A-3-270227 and JPA-2013-164509. Furthermore, the pattern can also be suitably used for guide pattern formation in DSA (Directed Self-Assembly) (see, for example, *ACS Nano*, Vol. 4, No. 8, pp. 4815-4823). In addition, the pattern can be applied to various uses.

The present invention also relates to a method for manufacturing an electronic device, comprising the pattern forming method of the present invention, and an electronic device manufactured by this manufacturing method.

The electronic device of the present invention is suitably mounted on electric electronic equipment (such as home electronics, OA•media equipment, optics and communication equipment).

EXAMPLES

The present invention is described in greater detail below, but the contents of the present invention are not limited thereto.

Compound (A)

As the compound (A), a compound was appropriately selected from Compounds (A-1) to (A-55) and used.

Synthesis Example (1) of Compound (A)

Synthesis of Compound (A-1)

A mixture of 9.94 g (70 mmol) of propanesulfonyl chloride and 70 ml of acetonitrile was ice-cooled and 10.5 ml of an aqueous 28 wt % ammonia solution was added dropwise thereto over 30 minutes. The resulting reaction solution was stirred at room temperature for 1 hour and after adding 200 ml of ethyl acetate thereto, the organic layer was washed in sequence with aqueous 1 N hydrochloric acid, water and sodium bicarbonate water to remove the solvent, whereby 5.0 g of propanesulfonamide was obtained (yield: 58%).

A mixture of 5.0 g (40.6 mmol) of propanesulfonamide, 10.38 g (44.6 mmol) of heptafluoropropanoic acid chloride and 60 ml of acetonitrile was ice-cooled and thereto, a mixture of 13.6 g (89.3 mmol) of diazabicycloundecene and 20 ml of acetonitrile was added dropwise to reach the internal temperature of 15° C. or less. The resulting reaction solution was stirred at room temperature for 1 hour and after adding 150 ml of aqueous 1 N hydrochloric acid and 150 ml of ethyl acetate, a separation operation was performed to obtain an organic layer. The obtained organic layer was washed with water and saturated brine to remove the solvent, and the obtained solid was washed with hexane to obtain 10.6 g of Compound (A-1a) shown below (yield: 82%).

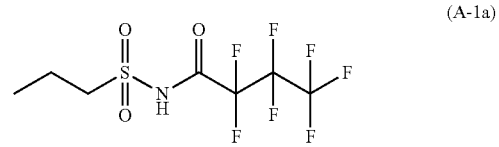 [SMILES: CCCS(=O)(=O)NC(=O)C(F)(F)C(F)(F)C(F)(F)F]
(A-1a)

10 g (31.4 mmol) of Compound (A-1a), 10.8 g (31.4 mmol) of triphenylsulfonium bromide and 5.25 g (63 mmol)

of sodium bicarbonate were added to 100 ml of chloroform and 100 ml of water and dissolved, and the resulting solution was stirred at room temperature for 1 hour. Thereafter, the organic layer was washed with water four times to remove the solvent and then subjected to purification by column chromatography (SiO$_2$, ethyl acetate/methanol=20/1 by volume) to obtain 15.0 g of the target Compound (A-1) as a colorless oil (yield: 82%).

$^1$H-NMR (400 MHz in (CD$_3$)$_2$CO): δ (ppm)=0.993 (t, J=7.4 Hz, 3H), 1.8-1.9 (m, 2H), 3.23 (tt, 2H), 7.6-7.8 (m, 15H).

$^{19}$F-NMR (400 MHz in (CD$_3$)$_2$CO): δ (ppm)=−126.1 (2F), −117.2 (2F), −80.7 (3F).

Synthesis Example (2) of Compound (A)

Synthesis of Compound (A-42)

A mixture of 1.70 g (15 mmol) of trifluoroacetamide, 3.49 g (15 mmol) of heptafluoropropanoic acid chloride and 30 ml of methylene chloride was ice-cooled, and 3.04 g (30 mmol) of triethylamine was added dropwise to reach the internal temperature of 10° C. or less. The resulting reaction solution was stirred at room temperature for 2 hours and after adding 5.15 g (15 mmol) of triphenylsulfonium bromide and 30 ml of water, further stirred at room temperature for 1 hour. Subsequently, the organic layer was washed with water three times to remove the solvent and then subjected to purification by column chromatography (SiO$_2$, chloroform/methanol=9/1 by volume) to obtain 3.1 g of the target Compound (A-42) as a white solid (yield: 36%).

$^1$H-NMR (400 MHz in (CD$_3$)$_2$CO): δ (ppm)=7.6-7.8 (m, 15H).

$^{19}$F-NMR (400 MHz in (CD$_3$)$_2$CO): δ (ppm)=−126.5 (2F), −116.7 (2F), −80.7 (3F), −74.6 (3F).

Other compounds A were synthesized in the same manner as above.

Examples 1 to 70 and Comparative Examples 1 and 2 (ArF Exposure)

Acid-Decomposable Resin (P)

As the acid-decomposable resin (P), Resins (P-1) to (P-9) shown below were used.

(P-1)

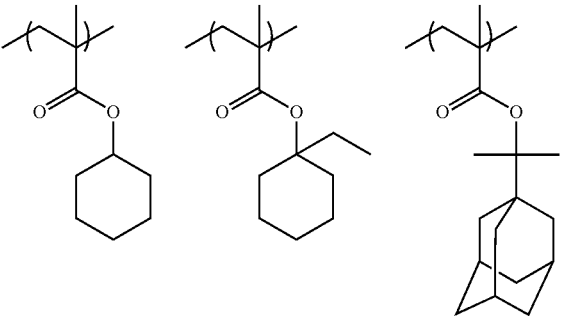

(P-2)

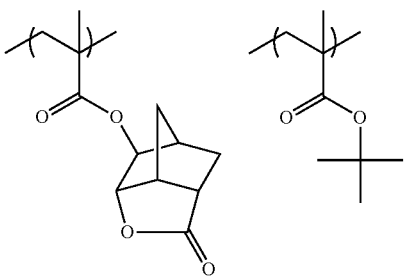

(P-3)

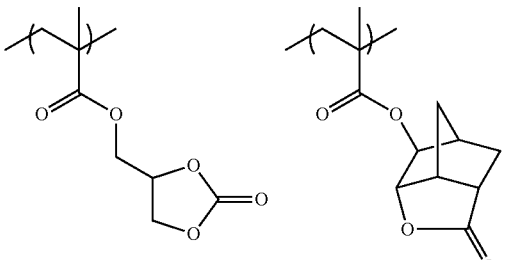

(P-4)

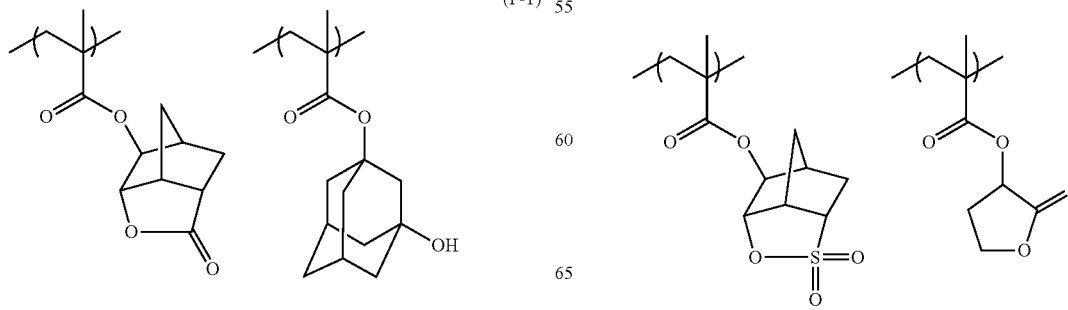

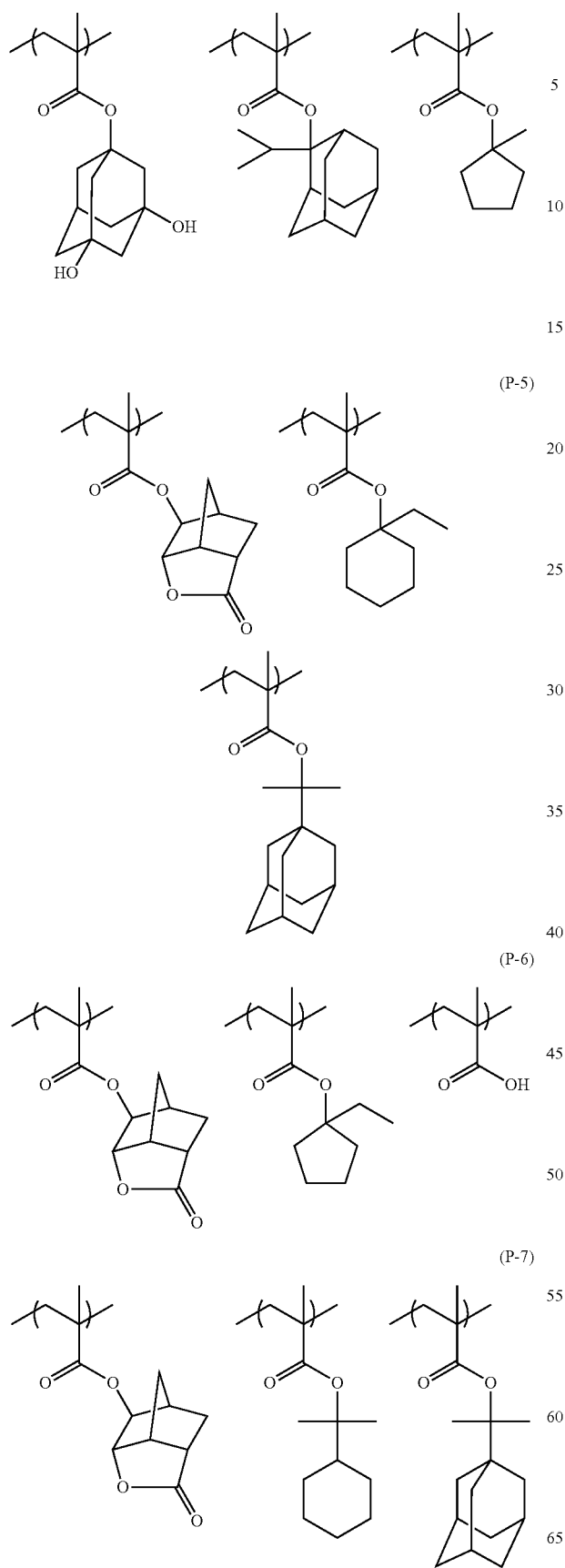
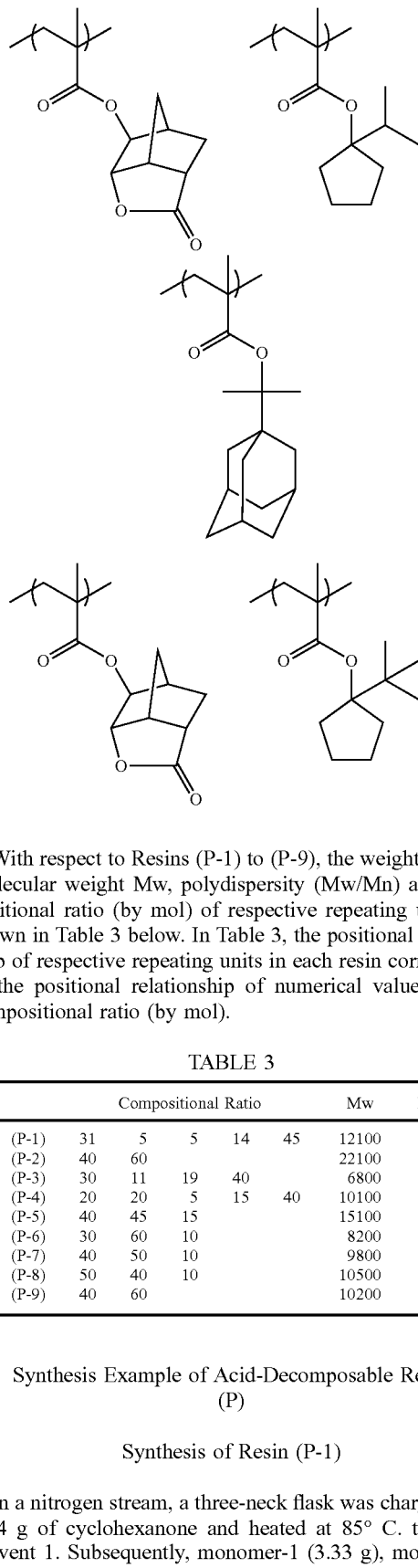

With respect to Resins (P-1) to (P-9), the weight average molecular weight Mw, polydispersity (Mw/Mn) and compositional ratio (by mol) of respective repeating units are shown in Table 3 below. In Table 3, the positional relationship of respective repeating units in each resin corresponds to the positional relationship of numerical values in the compositional ratio (by mol).

TABLE 3

| | Compositional Ratio | | | | | Mw | Mw/Mn |
|---|---|---|---|---|---|---|---|
| (P-1) | 31 | 5 | 5 | 14 | 45 | 12100 | 1.62 |
| (P-2) | 40 | 60 | | | | 22100 | 1.93 |
| (P-3) | 30 | 11 | 19 | 40 | | 6800 | 1.48 |
| (P-4) | 20 | 20 | 5 | 15 | 40 | 10100 | 1.55 |
| (P-5) | 40 | 45 | 15 | | | 15100 | 1.72 |
| (P-6) | 30 | 60 | 10 | | | 8200 | 1.53 |
| (P-7) | 40 | 50 | 10 | | | 9800 | 1.68 |
| (P-8) | 50 | 40 | 10 | | | 10500 | 1.58 |
| (P-9) | 40 | 60 | | | | 10200 | 1.63 |

Synthesis Example of Acid-Decomposable Resin (P)

Synthesis of Resin (P-1)

In a nitrogen stream, a three-neck flask was charged with 6.44 g of cyclohexanone and heated at 85° C. to obtain Solvent 1. Subsequently, monomer-1 (3.33 g), monomer-2 (0.59 g), monomer-3 (0.42 g), monomer-4 (4.42 g) and monomer-5 (1.97 g), which are shown below, were dissolved in cyclohexanone (25.75 g) to prepare a monomer solution. Furthermore, polymerization initiator V-601 (produced by Wako Pure Chemical Industries, Ltd.) was added in a ratio of 4.2 mol % based on the total amount of monomers and dissolved, and the resulting solution was added dropwise to Solvent 1 over 6 hours. After the completion of dropwise addition, the reaction was further allowed to proceed at 85° C. for 2 hours. The reaction solution was left to cool and added dropwise to a mixed solvent of 270 g of methanol/30 g of water, and the precipitated powder was dolled ted by filtration and dried to obtain 8.6 g of Resin (P-1). The weight average molecular weight of Resin (P-1) obtained was 12,100, the polydispersity (Mw/Mn) was 1.62, and the compositional ratio (by mol) measured by $^{13}$C-NMR was 31/5/5/45/14.

monomer-1

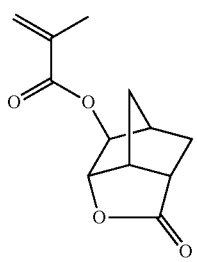

monomer-2

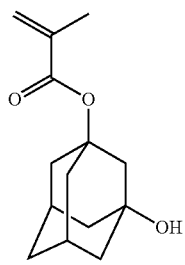

monomer-3

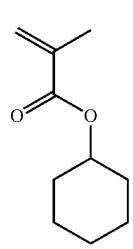

monomer-4

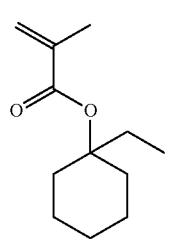

-continued monomer-5

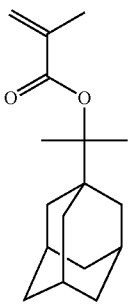

Resins (P-2) to (P-9) were synthesized in the same manner as Resin (P-1).

<Acid Generator>

As the acid generator, a compound was appropriately selected from Acid Generators z1 to z106 and used.

<Basis Compound>

As the basic compound, the following Compounds (N-1) to (N-9) were used.

(N-1)

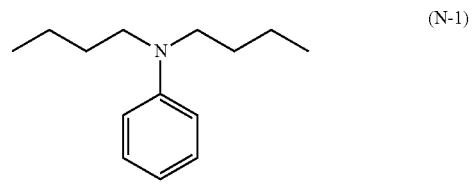

(N-2)

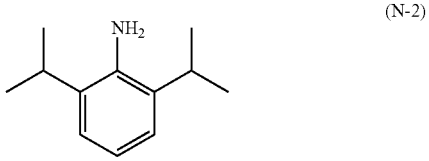

(N-3)

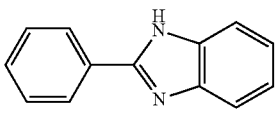

(N-4)

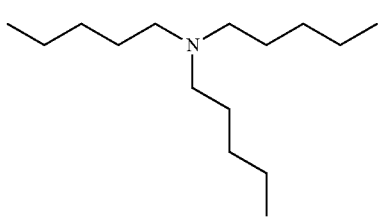

(N-5)

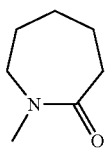

-continued

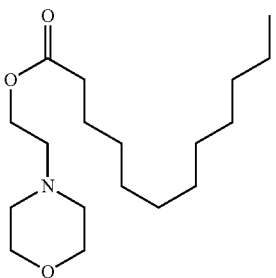
(N-6)

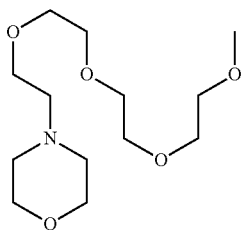
(N-7)

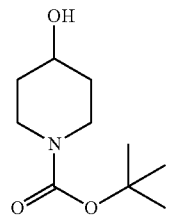
(N-8)

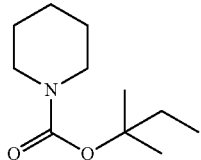
(N-9)

<Hydrophobic Resin (D)>

As the hydrophobic resin (D), a resin was appropriately selected from Resins (HR-1) to (HR-65) and Resins (C-1) to (C-28) and used.

<Surfactant>

As the surfactant, the followings were used.
W-1: Megaface F176 (produced by DIC Corporation; fluorine-containing)
W-2: Megaface R08 (produced by DIC Corporation; containing fluorine and silicon)
W-3: Polysiloxane Polymer KP-341 (produced by Shin-Etsu Chemical Co., Ltd.; silicon-containing)
W-4: Troysol S-366 (produced by Troy Chemical)
W-5: KH-20 (produced by Asahi Glass Co., Ltd.)
W-6: PolyFox PF-6320 (produced by OMNOVA Solutions Inc.; fluorine-containing)

<Solvent>

As the solvent, the followings were prepared.
(Group a)
SL-1: Propylene glycol monomethyl ether acetate (PGMEA)
SL-2: Propylene glycol monomethyl ether propionate
SL-3: 2-Heptanone
(Group b)
SL-4: Ethyl lactate
SL-5: Propylene glycol monomethyl ether (PGME)
SL-6: Cyclohexanone
(Group c)
SL-7: γ-Butyrolactone
SL-8: Propylene carbonate <Developer>

As the developer, the followings were prepared.
SG-1: Butyl acetate
SG-2: Methyl amyl ketone
SG-3: Ethyl-3-ethoxypropionate
SG-4: Pentyl acetate
SG-5: Isopentyl acetate
SG-6: Propylene glycol monomethyl ether acetate (PGMEA)
SG-7: Cyclohexanone <Rinsing Solution>

As the rinsing solution, the followings were used.
SR-1: 4-Methyl-2-pentanol
SR-2: 1-Hexanol
SR-3: Butyl acetate
SR-4: Methyl amyl ketone
SR-5: Ethyl-3-ethoxypropionate (Resist Preparation and Pattern Formation The components shown in Tables 4 and 5 below were dissolved in the solvent shown in the same Table to give a concentration of 3.4 mass % in terms of solid content, and each of the obtained solutions was filtered through a polyethylene filter having a pore size of 0.03 μm to prepare an actinic ray-sensitive or radiation-sensitive resin composition (resist composition). An organic antireflection film, ARC29SR (produced by Nissan Chemical Industries, Ltd.), was coated on a silicon wafer and baked at 205° C. for 60 seconds to form an antireflection film having a thickness of 95 nm, and the resist composition was coated thereon and baked (PB: Prebake) at the temperature shown in Table 6 for 60 seconds to form a resist film having a thickness of 90 nm.

The obtained wafer was patternwise exposed through a binary mask by using an ArF immersion exposure apparatus (XT1700i, manufactured by ASML, NA: 1.20, C-Quad, outer sigma: 0.900, inner sigma: 0.812, XY deflection). As the immersion liquid, ultrapure water was used. Thereafter, the resist film was baked at the temperature shown in Table 6 for 60 seconds (PEB: Post Exposure Bake), developed with a developer shown in Table 6 for 30 seconds, and then rinsed with a rising solution. Subsequently, the wafer was spun at a rotational speed of 4,000 rpm for 30 seconds, whereby a resist pattern of trenches with a pitch of 128 nm and a space of 40 nm was obtained.

<Evaluation Method>

(Line Width Roughness; LWR)

The obtained resist pattern of trenches with a pitch of 128 nm and a space of 40 nm was observed using a critical dimension scanning electron microscope (SEM; S-938011, manufactured by Hitachi, Ltd.). The line width was measured at 50 equally-spaced points in the longitudinal 2 μm region of the space pattern, and 3σ was computed from the standard deviation thereof. A smaller value indicates better performance.

(Exposure Latitude; EL)

The exposure dose for forming the obtained resist pattern of trenches with a pitch of 128 nm and a space of 40 nm was taken as the optimum exposure dose, and the exposure dose range allowing a variation of ±10% of the pattern size was determined by changing the exposure dose. The obtained value was divided by the optimum exposure dose and expressed in percentage. A larger value indicates that the performance change due to change in the exposure dose is smaller and the EL is better.

(Defocus Latitude; DOF)

The exposure dose and focus for forming the resist pattern of trenches with a pitch of 128 nm and a space of 40 nm were taken as the optimum exposure dose and optimum focus, respectively, and the focus range allowing a variation of ±10% of the pattern size was determined by changing the focus (defocusing) while keeping the exposure dose at the optimal exposure dose. A larger value indicates that the performance change due to change in the focus is smaller and the defocus latitude (DOF) is better.

The formulations of compositions used in Examples and Comparative Examples are shown in Tables 4 and 5 below, and the temperature conditions (° C.) of PE and PEB in pattern formation of and the developer and rinsing solution used in Examples and Comparative Examples are shown in Table 6 below.

(Evaluation Method of Acid Decomposability)

Using the Resin (P) and the compound (A) in each Example, the evaluation of acid decomposability was performed in accordance with the above-described <Evaluation Method of Acid Decomposability>, and in all cases, the film thickness was less than 30 nm, confirming that the resin (P) was not decomposed (that is, the resin (P) did not interact with the acid generated from the compound (A)). On the other hand, when the acid decomposability was evaluated in the same manner for Acid Generator (z95) and Resin (P-1) used in Comparative Examples, the film thickness was 75 nm and thus, the resin was acid-decomposed (that is, the resin (P) interacted with the acid generated from the compound (A)).

TABLE 4

|  | Compound (A) | (g) | Acid generator (B) | (g) | Basic Compound | (g) | Resin (P) | (g) | Hydrophobic Resin (D) |
|---|---|---|---|---|---|---|---|---|---|
| Resist 1 | A-1 | 0.3 | z93/z99 | 0.2/0.6 | N-3 | 0.008 | P-1 | 10 | HR-1 |
| Resist 2 | A-2 | 0.4 | z45 | 0.7 | N-8 | 0.006 | P-3 | 10 | HR-19 |
| Resist 3 | A-3 | 0.1 | z74 | 1.1 | N-9 | 0.009 | P-2 | 10 | HR-24 |
| Resist 4 | A-4 | 0.25 | z72 | 0.8 | N-4 | 0.008 | P-4 | 10 | HR-37 |
| Resist 5 | A-5 | 0.3 | z76 | 0.9 | N-1 | 0.007 | P-5 | 10 | HR-39 |
| Resist 6 | A-6 | 0.4 | z93 | 0.7 | N-6 | 0.006 | P-6 | 10 | C-14 |
| Resist 7 | A-7 | 0.15 | z99 | 0.8 | N-2 | 0.009 | P-1 | 10 | C-19 |
| Resist 8 | A-8 | 0.2 | z95 | 0.7 | N-7 | 0.008 | P-3 | 10 | C-1/C-10 |
| Resist 9 | A-9 | 0.3 | z74/z76 | 0.2/0.6 | N-9 | 0.008 | P-2 | 10 | HR-1 |
| Resist 10 | A-10 | 0.4 | z45 | 0.7 | N-8 | 0.006 | P-4 | 10 | HR-19 |
| Resist 11 | A-11 | 0.1 | z74 | 1.1 | N-3 | 0.009 | P-5 | 10 | HR-24 |
| Resist 12 | A-12 | 0.25 | z72 | 0.8 | N-6 | 0.008 | P-6 | 10 | HR-37 |
| Resist 13 | A-13 | 0.3 | z76 | 0.9 | N-2 | 0.007 | P-1 | 10 | HR-39 |
| Resist 14 | A-14 | 0.4 | z93 | 0.7 | N-5 | 0.006 | P-3 | 10 | C-14 |
| Resist 15 | A-15 | 0.15 | z99 | 0.8 | N-3 | 0.009 | P-2 | 10 | C-19 |
| Resist 16 | A-16 | 0.2 | z95 | 0.7 | N-8 | 0.008 | P-4 | 10 | C-1/C-10 |
| Resist 17 | A-17 | 0.3 | z76/z99 | 0.2/0.6 | N-3 | 0.008 | P-5 | 10 | HR-1 |
| Resist 18 | A-18 | 0.4 | z45 | 0.7 | N-6 | 0.006 | P-6 | 10 | HR-19 |
| Resist 19 | A-19 | 0.1 | z74 | 1.1 | N-2 | 0.009 | P-1 | 10 | HR-24 |
| Resist 20 | A-20 | 0.25 | z72 | 0.8 | N-6 | 0.008 | P-3 | 10 | HR-37 |
| Resist 21 | A-21 | 0.3 | z76 | 0.9 | N-7 | 0.007 | P-2 | 10 | HR-39 |
| Resist 22 | A-22 | 0.4 | z93 | 0.7 | N-5 | 0.006 | P-4 | 10 | C-14 |
| Resist 23 | A-23 | 0.15 | z99 | 0.8 | — | — | P-5 | 10 | C-19 |
| Resist 24 | A-24 | 0.2 | z95 | 0.7 | N-1 | 0.008 | P-6 | 10 | C-1/C-10 |
| Resist 25 | A-25 | 0.3 | z45/z72 | 0.2/0.6 | N-6 | 0.008 | P-1/P-2 | 5/5 | HR-1 |
| Resist 26 | A-26 | 0.4 | z45 | 0.7 | N-9 | 0.006 | P-1 | 10 | HR-19 |
| Resist 27 | A-27 | 0.1 | z74 | 1.1 | N-8 | 0.009 | P-3 | 10 | HR-24 |
| Resist 28 | A-28 | 0.25 | z72 | 0.8 | N-3 | 0.008 | P-2 | 10 | HR-37 |
| Resist 29 | A-29 | 0.3 | z76 | 0.9 | N-6 | 0.007 | P-4 | 10 | HR-39 |
| Resist 30 | A-30 | 0.4 | z93 | 0.7 | N-3 | 0.006 | P-5 | 10 | C-14 |
| Resist 31 | A-31 | 0.15 | z99 | 0.8 | — | — | P-6 | 10 | C-19 |
| Resist 32 | A-32 | 0.2 | z95 | 0.7 | N-1 | 0.008 | P-1 | 10 | C-1/C-10 |
| Resist 33 | A-33 | 0.3 | z93/z95 | 0.2/0.6 | N-9 | 0.008 | P-3 | 10 | HR-1 |
| Resist 34 | A-34 | 0.2 | z45 | 0.7 | N-7 | 0.006 | P-2 | 10 | HR-19 |
| Resist 35 | A-35 | 0.1 | z74 | 1.1 | N-8 | 0.009 | P-4 | 10 | HR-24 |

|  | (g) | Surfactant | (g) | Solvent | (mass ratio) | Evaluation of Acid Decomposability, Residual Film After Heating (nm) |
|---|---|---|---|---|---|---|
| Resist 1 | 0.4 | W-1 | 0.001 | SL-1/SL-6 | 70/30 | 2 |
| Resist 2 | 0.1 | W-2 | 0.002 | SL-1/SL-7 | 90/10 | 1 |
| Resist 3 | 0.03 | W-3 | 0.001 | SL-1/SL-4 | 90/10 | 1 |
| Resist 4 | 0.2 | W-4 | 0.001 | SL-1/SL-5 | 70/30 | 3 |
| Resist 5 | 0.1 | W-5 | 0.002 | SL-1/SL-6/SL-7 | 80/15/5 | 11 |
| Resist 6 | 0.08 | W-6 | 0.001 | SL-3/SL-8 | 95/5 | 13 |
| Resist 7 | 0.06 | W-2 | 0.001 | SL-2 | 100 | 15 |
| Resist 8 | 0.1/0.03 | W-3 | 0.002 | SL-3/SL-4 | 80/20 | 10 |
| Resist 9 | 0.4 | W-4 | 0.001 | SL-2/SL-6 | 80/20 | 0 |
| Resist 10 | 0.1 | W-5 | 0.001 | SL-1/SL-6 | 70/30 | 2 |
| Resist 11 | 0.03 | W-6 | 0.002 | SL-1/SL-7 | 90/10 | 3 |

TABLE 4-continued

|  |  |  |  |  |  |  |
|---|---|---|---|---|---|---|
| Resist 12 | 0.2 | W-1 | 0.001 | SL-1/SL-4 | 90/10 | 0 |
| Resist 13 | 0.1 | W-3 | 0.001 | SL-1/SL-5 | 70/30 | 1 |
| Resist 14 | 0.08 | — | — | SL-1/SL-6/SL-8 | 80/15/5 | 2 |
| Resist 15 | 0.06 | W-5 | 0.001 | SL-3/SL-7 | 95/5 | 1 |
| Resist 16 | 0.1/0.03 | W-6 | 0.001 | SL-3 | 100 | 3 |
| Resist 17 | 0.4 | W-1 | 0.002 | SL-3/SL-5 | 80/20 | 1 |
| Resist 18 | 0.1 | W-2 | 0.001 | SL-2/SL-7 | 80/20 | 2 |
| Resist 19 | 0.03 | W-4 | 0.001 | SL-1/SL-6 | 70/30 | 0 |
| Resist 20 | 0.2 | W-5/W-6 | 0.001/0.001 | SL-1/SL-7 | 90/10 | 2 |
| Resist 21 | 0.1 | W-6 | 0.001 | SL-1/SL-4 | 90/10 | 2 |
| Resist 22 | 0.08 | W-3 | 0.001 | SL-1/SL-5 | 70/30 | 3 |
| Resist 23 | 0.06 | W-1 | 0.002 | SL-1/SL-6/SL-7 | 80/15/5 | 0 |
| Resist 24 | 0.1/0.03 | W-2 | 0.001 | SL-3/SL-7 | 95/5 | 15 |
| Resist 25 | 0.4 | W-3 | 0.001 | SL-4 | 100 | 10 |
| Resist 26 | 0.1 | — | — | SL-3/SL-6 | 80/20 | 13 |
| Resist 27 | 0.03 | W-5 | 0.001 | SL-2/SL-8 | 80/20 | 10 |
| Resist 28 | 0.2 | W-6 | 0.001 | SL-1/SL-6 | 70/30 | 0 |
| Resist 29 | 0.1 | W-2 | 0.002 | SL-1/SL-7 | 90/10 | 2 |
| Resist 30 | 0.08 | W-3 | 0.001 | SL-1/SL-4 | 90/10 | 3 |
| Resist 31 | 0.06 | W-4 | 0.001 | SL-1/SL-5 | 70/30 | 0 |
| Resist 32 | 0.1/0.03 | W-5 | 0.002 | SL-1/SL-6/SL-7 | 80/15/5 | 1 |
| Resist 33 | 0.4 | W-6 | 0.001 | SL-3/SL-7 | 95/5 | 2 |
| Resist 34 | 0.1 | W-1 | 0.001 | SL-5 | 100 | 1 |
| Resist 35 | 0.03 | W-3 | 0.002 | SL-3/SL-7 | 80/20 | 3 |

TABLE 5

|  | Compound (A) | (g) | Acid generator (B) | (g) | Basic Compound | (g) | Resin (P) | (g) | Hydrophobic Resin (D) |
|---|---|---|---|---|---|---|---|---|---|---|
| Resist 36 | A-36 | 0.25 | z72 | 0.8 | N-3 | 0.008 | P-5 | 10 | HR-37 |
| Resist 37 | A-37 | 0.3 | z76 | 0.9 | N-6 | 0.007 | P-6 | 10 | HR-39 |
| Resist 38 | A-38 | 0.3 | z76/z99 | 0.2/0.6 | N-3 | 0.008 | P-1 | 10 | HR-1 |
| Resist 39 | A-39 | 0.4 | z45 | 0.7 | N-6 | 0.006 | P-3 | 10 | HR-19 |
| Resist 40 | A-40 | 0.1 | z74 | 1.1 | N-2 | 0.009 | P-2 | 10 | HR-24 |
| Resist 41 | A-41 | 0.25 | z72 | 0.8 | N-6 | 0.008 | P-4 | 10 | HR-37 |
| Resist 42 | A-42 | 0.3 | z76 | 0.9 | N-7 | 0.007 | P-5 | 10 | HR-39 |
| Resist 43 | A-43 | 0.4 | z93 | 0.7 | N-5 | 0.006 | P-6 | 10 | C-14 |
| Resist 44 | A-44 | 0.15 | z99 | 0.8 | — | — | P-2 | 10 | C-19 |
| Resist 45 | A-45 | 0.2 | z95 | 0.7 | N-1 | 0.008 | P-4 | 10 | C-1/C-10 |
| Resist 46 | A-46 | 0.3 | z45/z72 | 0.2/0.6 | N-6 | 0.008 | P-1/P-2 | 5/5 | HR-1 |
| Resist 47 | A-47 | 0.2 | z45 | 0.7 | N-9 | 0.006 | P-1 | 10 | HR-19 |
| Resist 48 | A-48 | 0.1 | z74 | 1.1 | N-8 | 0.009 | P-3 | 10 | HR-24 |
| Resist 49 | A-49 | 0.25 | z72 | 0.8 | N-3 | 0.008 | P-2 | 10 | HR-37 |
| Resist 50 | A-50 | 0.15 | z76 | 0.9 | N-6 | 0.007 | P-4 | 10 | HR-39 |
| Resist 51 | A-51 | 0.2 | z93 | 0.7 | N-3 | 0.006 | P-5 | 10 | C-14 |
| Resist 52 | A-52 | 0.3 | z99 | 0.8 | — | — | P-6 | 10 | C-19 |
| Resist 53 | A-53 | 0.4 | z95 | 0.7 | N-1 | 0.008 | P-4 | 10 | C-1/C-10 |
| Resist 54 | A-54 | 0.1 | z93/z95 | 0.2/0.6 | N-9 | 0.008 | P-1 | 10 | HR-1 |
| Resist 55 | A-55 | 0.25 | z45 | 0.7 | N-7 | 0.006 | P-5 | 10 | HR-19 |
| Resist 56 | A-1/A-10 | 0.2/0.1 | z93 | 0.7 | N-2 | 0.006 | P-6 | 10 | C-14 |
| Resist 57 | A-1 | 0.1 | z100/z104 | 0.5/0.5 | N-3 | 0.008 | P-1 | 10 | HR-1 |
| Resist 58 | A-34 | 0.3 | z101/z105 | 0.2/1.0 | N-8 | 0.006 | P-2 | 10 | HR-19 |
| Resist 59 | A-6 | 0.3 | z102/z106 | 0.3/0.5 | N-9 | 0.009 | P-3 | 10 | HR-24 |
| Resist 60 | A-13 | 0.2 | z103 | 0.8 | N-4 | 0.008 | P-4 | 10 | HR-37 |
| Resist 61 | A-5 | 0.1 | z100/z104 | 0.5/0.5 | N-1 | 0.007 | P-5 | 10 | HR-39 |
| Resist 62 | A-45 | 0.3 | z101/z105 | 0.2/1.0 | N-6 | 0.006 | P-6 | 10 | C-14 |
| Resist 63 | A-22 | 0.3 | z102/z106 | 0.3/0.5 | N-2 | 0.009 | P-7 | 10 | C-19 |
| Resist 64 | A-39 | 0.2 | z103 | 0.8 | N-7 | 0.008 | P-8 | 10 | C-1/C-10 |
| Resist 65 | A-39 | 0.2 | z103 | 0.9 | N-9 | 0.008 | P-9 | 10 | HR-1 |
| Resist 66 | A-25 | 0.3 | z93/z99 | 0.2/0.6 | N-8 | 0.006 | P-7 | 10 | HR-19 |

TABLE 5-continued

| | | | | | | | | | |
|---|---|---|---|---|---|---|---|---|---|
| Resist 67 | A-3 | | 0.2 | z45 | 0.7 | N-3 | 0.009 | P-8 | 10 HR-24 |
| Resist 68 | A-15 | | 0.3 | z74 | 1.1 | N-8 | 0.006 | P-9 | 10 HR-37 |

Comparative Example

| | | | | | | | | | |
|---|---|---|---|---|---|---|---|---|---|
| Resist 69 | — | | — | z95 | 1 | N-3 | 0.012 | P-1 | 10 HR-1 |
| Resist 70 | — | | — | z69/z95 | 0.5/0.5 | N-8 | 0.012 | P-1 | 10 HR-1 |

| | (g) | Surfactant | (g) | Solvent | (mass ratio) | Evaluation of Acid Decomposability, Residual Film After Heating (nm) |
|---|---|---|---|---|---|---|
| Resist 36 | 0.2 | W-4 | 0.001 | SL-2/SL-8 | 80/20 | 1 |
| Resist 37 | 0.1 | — | — | SL-1/SL-6 | 70/30 | 2 |
| Resist 38 | 0.4 | W-1 | 0.002 | SL-3/SL-5 | 80/20 | 0 |
| Resist 39 | 0.1 | W-2 | 0.001 | SL-2/SL-7 | 80/20 | 2 |
| Resist 40 | 0.03 | W-4 | 0.001 | SL-1/SL-6 | 70/30 | 2 |
| Resist 41 | 0.2 | W-5/W-6 | 0.001/0.001 | SL-1/SL-7 | 90/10 | 3 |
| Resist 42 | 0.1 | W-6 | 0.001 | SL-1/SL-4 | 90/10 | 0 |
| Resist 43 | 0.08 | W-3 | 0.001 | SL-1/SL-5 | 70/30 | 3 |
| Resist 44 | 0.06 | W-1 | 0.002 | SL-1/SL-6/SL-7 | 80/15/5 | 0 |
| Resist 45 | 0.1/0.03 | W-2 | 0.001 | SL-3/SL-7 | 95/5 | 1 |
| Resist 46 | 0.4 | W-3 | 0.001 | SL-4 | 100 | 2 |
| Resist 47 | 0.1 | — | — | SL-3/SL-6 | 80/20 | 1 |
| Resist 48 | 0.03 | W-5 | 0.001 | SL-2/SL-8 | 80/20 | 3 |
| Resist 49 | 0.2 | W-6 | 0.001 | SL-1/SL-6 | 70/30 | 1 |
| Resist 50 | 0.1 | W-2 | 0.002 | SL-1/SL-7 | 90/10 | 2 |
| Resist 51 | 0.08 | W-3 | 0.001 | SL-1/SL-4 | 90/10 | 0 |
| Resist 52 | 0.06 | W-4 | 0.001 | SL-1/SL-5 | 70/30 | 2 |
| Resist 53 | 0.1/0.03 | W-5 | 0.002 | SL-1/SL-6/SL-7 | 80/15/5 | 2 |
| Resist 54 | 0.4 | W-6 | 0.001 | SL-3/SL-7 | 95/5 | 3 |
| Resist 55 | 0.1 | W-1 | 0.001 | SL-5 | 100 | 0 |
| Resist 56 | 0.08 | W-6 | 0.002 | SL-1/SL-7 | 90/10 | 3 |
| Resist 57 | 0.4 | W-1 | 0.001 | SL-1/SL-6 | 70/30 | 1 |
| Resist 58 | 0.1 | W-2 | 0.002 | SL-1/SL-7 | 90/10 | 1 |
| Resist 59 | 0.03 | W-3 | 0.001 | SL-1/SL-4 | 90/10 | 3 |
| Resist 60 | 0.2 | W-4 | 0.001 | SL-1/SL-5 | 70/30 | 0 |
| Resist 61 | 0.1 | W-5 | 0.002 | SL-1/SL-6/SL-7 | 80/15/5 | 10 |
| Resist 62 | 0.08 | W-6 | 0.001 | SL-3/SL-8 | 95/5 | 3 |
| Resist 63 | 0.06 | W-2 | 0.001 | SL-2 | 100 | 1 |
| Resist 64 | 0.1/0.03 | W-3 | 0.002 | SL-3/SL-4 | 80/20 | 2 |
| Resist 65 | 0.4 | W-1 | 0.001 | SL-1/SL-6 | 70/30 | 1 |
| Resist 66 | 0.1 | W-2 | 0.002 | SL-1/SL-7 | 90/10 | 13 |
| Resist 67 | 0.03 | W-3 | 0.001 | SL-1/SL-4 | 90/10 | 2 |
| Resist 68 | 0.2 | W-4 | 0.001 | SL-1/SL-5 | 70/30 | 1 |

Comparative Example

| | | | | | | |
|---|---|---|---|---|---|---|
| Resist 69 | 0.2 | W-1 | 0.001 | SL-1/SL-6 | 70/30 | — |
| Resist 70 | 0.1 | W-1 | 0.001 | SL-1/SL-7 | 90/10 | — |

TABLE 6

| | Resist Composition | PB (° C.) | PEB (° C.) | Developer | Rinsing Solution | LWR (nm) | EL (%) | DOF (μm) |
|---|---|---|---|---|---|---|---|---|
| Example 1 | Resist 1 | 110 | 100 | SG-1 | SR-1 | 3.5 | 12 | 0.14 |
| Example 2 | Resist 2 | 105 | 95 | SG-1 | SR-2 | 3.8 | 13 | 0.16 |
| Example 3 | Resist 3 | 110 | 100 | SG-1 | SR-1 | 3.6 | 12 | 0.14 |
| Example 4 | Resist 4 | 105 | 95 | SG-2 | — | 3.5 | 13 | 0.14 |
| Example 5 | Resist 5 | 100 | 105 | SG-2 | SR-3 | 3.7 | 12 | 0.16 |
| Example 6 | Resist 6 | 105 | 90 | SG-3 | SR-1 | 3.9 | 13 | 0.14 |
| Example 7 | Resist 7 | 95 | 100 | SG-1 | — | 3.8 | 12 | 0.12 |
| Example 8 | Resist 8 | 90 | 95 | SG-4 | SR-1 | 4.2 | 10 | 0.16 |
| Example 9 | Resist 9 | 100 | 100 | SG-5 | SR-5 | 4.4 | 9 | 0.14 |
| Example 10 | Resist 10 | 110 | 95 | SG-1 | — | 4.3 | 9 | 0.14 |
| Example 11 | Resist 11 | 105 | 105 | SG-1 | SR-1 | 4.4 | 10 | 0.14 |
| Example 12 | Resist 12 | 110 | 90 | SG-6 | SR-1 | 3.5 | 12 | 0.16 |
| Example 13 | Resist 13 | 105 | 100 | SG-2 | — | 3.8 | 12 | 0.14 |
| Example 14 | Resist 14 | 100 | 95 | SG-1 | SR-1 | 3.7 | 13 | 0.14 |
| Example 15 | Resist 15 | 105 | 100 | SG-7 | SR-1 | 3.6 | 12 | 0.16 |
| Example 16 | Resist 16 | 95 | 95 | SG-1 | SR-3 | 3.8 | 13 | 0.14 |
| Example 17 | Resist 17 | 90 | 100 | SG-2 | — | 3.6 | 12 | 0.12 |
| Example 18 | Resist 18 | 100 | 90 | SG-1 | SR-4 | 3.5 | 12 | 0.16 |
| Example 19 | Resist 19 | 110 | 100 | SG-1 | SR-1 | 3.8 | 12 | 0.14 |
| Example 20 | Resist 20 | 105 | 90 | SG-1 | SR-5 | 3.6 | 13 | 0.14 |

TABLE 6-continued

|  | Resist Composition | PB (° C.) | PEB (° C.) | Developer | Rinsing Solution | LWR (nm) | EL (%) | DOF (μm) |
|---|---|---|---|---|---|---|---|---|
| Example 21 | Resist 21 | 110 | 100 | SG-1 | — | 3.7 | 12 | 0.14 |
| Example 22 | Resist 22 | 105 | 85 | SG-2 | SR-1 | 3.6 | 13 | 0.12 |
| Example 23 | Resist 23 | 100 | 105 | SG-2 | SR-1 | 3.8 | 12 | 0.16 |
| Example 24 | Resist 24 | 105 | 90 | SG-3 | — | 3.5 | 12 | 0.14 |
| Example 25 | Resist 25 | 95 | 100 | SG-1 | SR-1 | 3.6 | 13 | 0.14 |
| Example 26 | Resist 26 | 90 | 95 | SG-4 | SR-1 | 3.7 | 12 | 0.14 |
| Example 27 | Resist 27 | 100 | 100 | SG-5 | SR-3 | 4.3 | 10 | 0.16 |
| Example 28 | Resist 28 | 110 | 95 | SG-1 | SR-1 | 4.4 | 9 | 0.14 |
| Example 29 | Resist 29 | 105 | 105 | SG-1 | — | 4.2 | 10 | 0.14 |
| Example 30 | Resist 30 | 110 | 90 | SG-6 | SR-1 | 4.4 | 9 | 0.12 |
| Example 31 | Resist 31 | 105 | 100 | SG-2 | SR-5 | 3.7 | 12 | 0.16 |
| Example 32 | Resist 32 | 100 | 95 | SG-1 | SR-1 | 3.6 | 13 | 0.14 |
| Example 33 | Resist 33 | 105 | 100 | SG-7 | — | 3.8 | 12 | 0.14 |
| Example 34 | Resist 34 | 95 | 95 | SG-1 | SR-1 | 3.6 | 12 | 0.14 |
| Example 35 | Resist 35 | 90 | 105 | SG-2 | SR-2 | 3.5 | 12 | 0.12 |
| Example 36 | Resist 36 | 100 | 90 | SG-1 | — | 3.8 | 13 | 0.16 |
| Example 37 | Resist 37 | 110 | 100 | SG-1 | SR-1 | 3.6 | 12 | 0.14 |
| Example 38 | Resist 38 | 105 | 95 | SG-1 | SR-3 | 3.7 | 13 | 0.14 |
| Example 39 | Resist 39 | 105 | 95 | SG-2 | — | 3.6 | 12 | 0.14 |
| Example 40 | Resist 40 | 100 | 85 | SG-2 | SR-3 | 3.5 | 12 | 0.16 |
| Example 41 | Resist 41 | 105 | 90 | SG-3 | SR-1 | 3.8 | 13 | 0.14 |
| Example 42 | Resist 42 | 95 | 100 | SG-1 | — | 3.6 | 12 | 0.12 |
| Example 43 | Resist 43 | 90 | 95 | SG-4 | SR-1 | 3.7 | 13 | 0.16 |
| Example 44 | Resist 44 | 100 | 100 | SG-5 | SR-5 | 3.6 | 12 | 0.14 |
| Example 45 | Resist 45 | 110 | 95 | SG-1 | — | 3.8 | 12 | 0.14 |
| Example 46 | Resist 46 | 105 | 105 | SG-1 | SR-1 | 3.5 | 12 | 0.14 |
| Example 47 | Resist 47 | 110 | 90 | SG-6 | SR-1 | 3.6 | 13 | 0.14 |
| Example 48 | Resist 48 | 105 | 100 | SG-2 | — | 3.5 | 12 | 0.12 |
| Example 49 | Resist 49 | 100 | 85 | SG-1 | SR-1 | 3.8 | 12 | 0.16 |
| Example 50 | Resist 50 | 105 | 100 | SG-7 | SR-1 | 3.6 | 13 | 0.14 |
| Example 51 | Resist 51 | 95 | 95 | SG-1 | SR-3 | 3.7 | 12 | 0.14 |
| Example 52 | Resist 52 | 90 | 105 | SG-2 | — | 3.6 | 13 | 0.14 |
| Example 53 | Resist 53 | 100 | 90 | SG-1 | SR-1 | 3.8 | 12 | 0.14 |
| Example 54 | Resist 54 | 105 | 100 | SG-7 | SR-1 | 3.5 | 12 | 0.12 |
| Example 55 | Resist 55 | 95 | 95 | SG-1 | SR-3 | 3.6 | 12 | 0.16 |
| Example 56 | Resist 56 | 90 | 105 | SG-2 | — | 3.8 | 13 | 0.14 |
| Example 57 | Resist 55 | 105 | 95 | SG-1 | — | 3.6 | 12 | 0.14 |
| Example 58 | Resist 56 | 110 | 100 | SG-4 | SR-1 | 3.8 | 12 | 0.16 |
| Example 59 | Resist 57 | 105 | 90 | SG-1 | SR-1 | 3.6 | 12 | 0.16 |
| Example 60 | Resist 58 | 95 | 100 | SG-6 | SR-1 | 3.5 | 13 | 0.12 |
| Example 61 | Resist 59 | 90 | 95 | SG-2 | — | 3.7 | 12 | 0.14 |
| Example 62 | Resist 60 | 100 | 100 | SG-1 | SR-1 | 3.9 | 13 | 0.16 |
| Example 63 | Resist 61 | 110 | 95 | SG-7 | SR-1 | 3.8 | 12 | 0.14 |
| Example 64 | Resist 62 | 105 | 105 | SG-1 | SR-3 | 3.5 | 12 | 0.16 |
| Example 65 | Resist 63 | 110 | 90 | SG-2 | — | 3.8 | 12 | 0.12 |
| Example 66 | Resist 64 | 105 | 100 | SG-1 | SR-4 | 3.5 | 13 | 0.16 |
| Example 67 | Resist 65 | 100 | 95 | SG-1 | SR-1 | 3.7 | 13 | 0.14 |
| Example 68 | Resist 66 | 105 | 100 | SG-1 | SR-5 | 3.6 | 12 | 0.16 |
| Example 69 | Resist 67 | 95 | 95 | SG-1 | — | 3.5 | 12 | 0.14 |
| Example 70 | Resist 68 | 90 | 100 | SG-2 | SR-1 | 3.8 | 13 | 0.16 |
| Comparative Example 1 | Resist 69 | 90 | 100 | SG-4 | SR-1 | 5.5 | 7 | 0.04 |
| Comparative Example 2 | Resist 70 | 100 | 95 | SG-5 | SR-1 | 5.8 | 7 | 0.06 |

As apparent from the results in Tables, in Examples 1 to 70, the performances in terms of LWR, EL and DOF were very excellent as compared with Comparative Examples 1 and 2 not containing the compound (A).

Also, in Examples 1 to 7, 12 to 26, 31 to 41, 56, 58 to 63, 65 and 66 using, as the compound (A), a compound which is a compound represented by formula (I-2a) and satisfies "$R_2$ represents a hydrogen atom, an unsubstituted alkyl group, an unsubstituted cycloalkyl group or an unsubstituted alkoxy group", the results of LWR and EL were more excellent.

Each of Resists 1, 7, 41, 42 and 51 prepared above was exposed through a 6% halftone mask having a 1:1 line-and-space pattern with a line width of 75 nm, developed with an aqueous tetramethylammonium hydroxide solution (2.38 mass %) for 30 seconds, rinsed with pure water and then spin-dried, as a result, a positive pattern was obtained.

Examples 71 to 75 and Comparative Example 3
(EUV Exposure)

Acid-Decomposable Resin (P)

As the acid-decomposable resin (P), Resins (P-2-1) to (P-2-5) shown below were used. A compositional ratio of each of the repeating units in the following resins is represented by molar ratio.

P-2-1

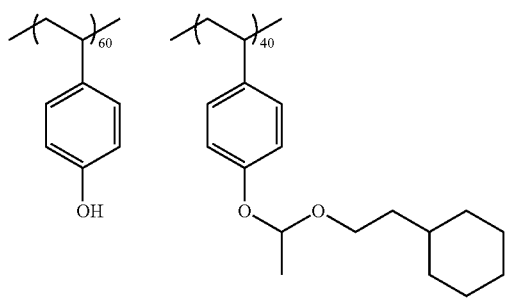

Mw: 5000
Mw/Mn: 1.20

P-2-2

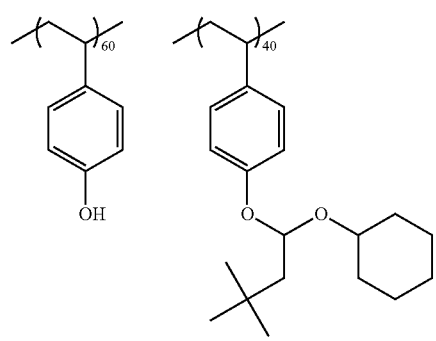

Mw: 4800
Mw/Mn: 1.18

P-2-3

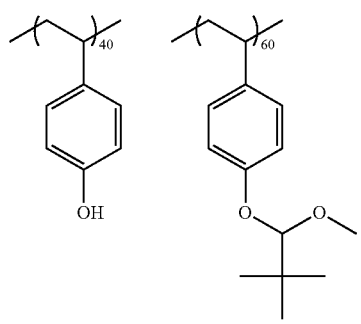

Mw: 4500
Mw/Mn: 1.23

P-2-4

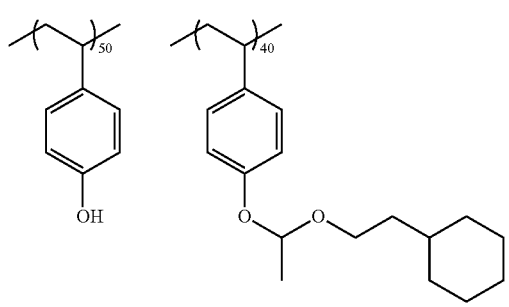

-continued

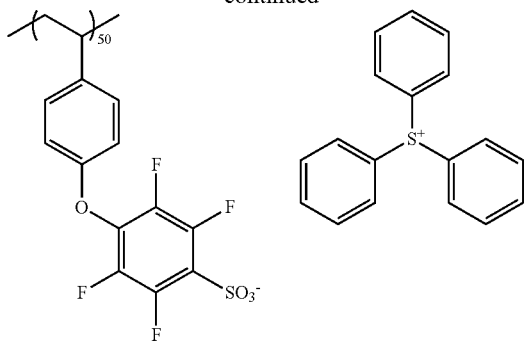

Mw: 12200
Mw/Mn: 1.79

P-2-5

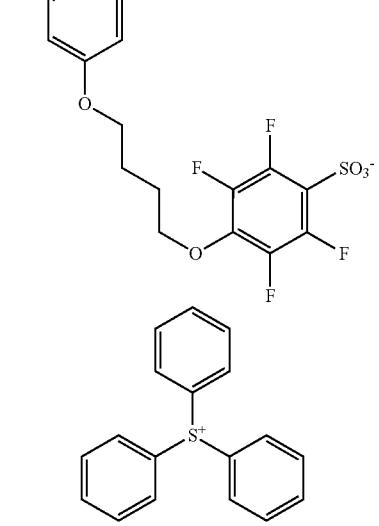

Mw: 5800
Mw/Mn: 1.21

Synthesis Example 3

Synthesis of Resin (P-2-1)

20.0 g of poly(p-hydroxystyrene) (VP-2500, produced by Nippon Soda Co., Ltd.) was dissolved in 80.0 g of propylene glycol monomethyl ether acetate (PGMEA). To this solution, 10.3 g of 2-cyclohexylethyl vinyl ether and 20 mg of comphorsulfonic acid were added, and the mixture was stirred at room temperature for 2 hours. Furthermore, 84 mg of triethylamine was added and after stirring for a while, the reaction solution was transferred to a separating funnel containing 100 mL of ethyl acetate. The organic layer was washed with 50 mL of distilled water three times and thereafter, this organic layer was concentrated in an evaporator. The obtained polymer was dissolved in 300 mL of acetone and reprecipitated by dropwise addition to 3,000 g of hexane, and the precipitate was filtered to obtain 18.3 g of (P-2-1).

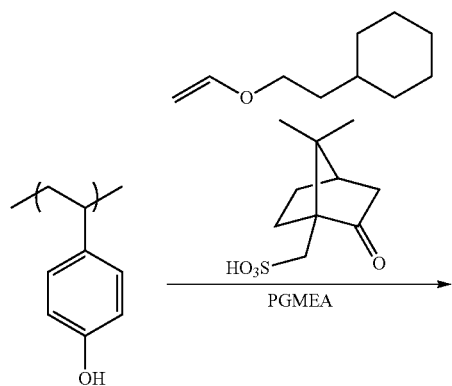

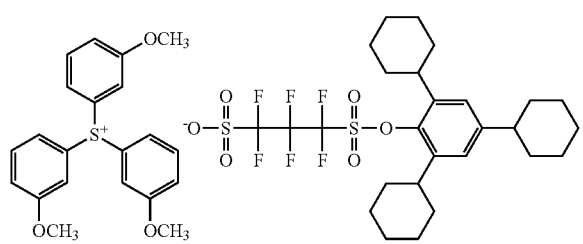

(P-2-1)

Resins (P-2-2) to (P-2-5) were synthesized in the same manner as Resin (P-2-1).

<Acid Generator>

As the acid generator, Compounds (z2-1) and (z2-2) shown below were used.

(z2-1)

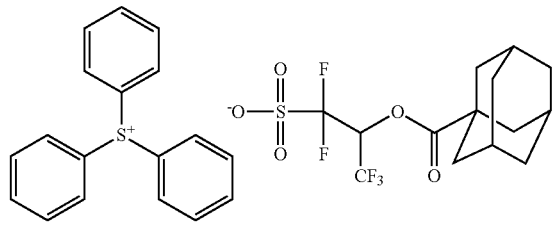

(z2-2)

As for other components, developer and rinsing solution, those described in [Examples 1 to 70 and Comparative Examples 1 and 2 (ArF exposure)] were used.

(1) Preparation and Coating of Coating Solution of Actinic Ray-Sensitive or Radiation-Sensitive Resin Composition The components shown in Table 7 below were dissolved in the solvent shown in the same Table to give a concentration of 3.4 mass % in terms of solid content, and each of the obtained solutions was filtered through a polyethylene filter having a pore size of 0.05 µm to prepare an actinic ray-sensitive or radiation-sensitive resin composition (resist composition) solution.

This actinic ray-sensitive or radiation-sensitive resin composition solution was coated on a 6-inch Si wafer previously subjected to a hexamethyldisilazane (HMDS) treatment, by using a spin coater, Mark 8, manufactured by Tokyo Electron Ltd. and dried on a hot plate at 100° C. for 60 seconds to obtain a resist film having a thickness of 50 nm.

(2) EUV Exposure and Development

The resist film-coated wafer obtained in (1) above was patternwise exposed through an exposure mask (line/space=1/1) by using an EUV exposure apparatus (Micro Exposure Tool, manufactured by Exitech, NA: 0.3, Quadrupole, outer sigma: 0.68, inner sigma: 0.36). After the irradiation, the wafer was heated on a hot plate at 110° C. for 60 seconds, then developed by puddling the organic developer shown in the Table below for 30 seconds, rinsed by using the rinsing solution shown in Table 7 below, spun at a rotational speed of 4,000 rpm for 30 seconds and baked at 90° C. for 60 seconds to obtain a resist pattern having a 1:1 line-and-space pattern with a line width of 50 nm.

(3) Evaluation of Resist Pattern

Using a scanning electron microscope (S-9380II, manufacture by Hitachi Ltd.), the obtained resist pattern was evaluated for sensitivity and resolution by the following methods. The results obtained are shown in Table 7 below.

(3-1) Sensitivity

The irradiation energy below which the 1:1 line-and-space pattern with a line width of 50 nm cannot be resolved was taken as the sensitivity (Eop). A smaller value indicates better performance.

(3-2) Resolution

The minimum line width below which the 1:1 line-and-space pattern cannot be separated at the Eop above was taken as the resolution. A smaller value indicates better performance.

(Evaluation Method of Acid Decomposability)

Using the Resin (P) and the compound (A) in each Example, the evaluation of acid decomposability was performed in accordance with the above-described <Evaluation Method of Acid Decomposability>, and in all cases, the film thickness was less than 30 nm, confirming that the resin (P) was not decomposed (that is, the resin (P) did not interact with the acid generated from the compound (A)).

TABLE 7

| | Resin (P) | Concentration | Compound (A) | Concentration | Acid Generator | Concentration | Basic Compound | Concentration | Solvent | Mass Ratio |
|---|---|---|---|---|---|---|---|---|---|---|
| Example 71 | P-2-1 | 86.6 | A-2 | 3 | z2-1 | 10 | N-7 | 0.3 | SL-1/SL-5 | 40/60 |
| Example 72 | P-2-2 | 86.9 | A-43 | 3 | z2-2 | 10 | — | 0 | SL-1/SL-5 | 40/60 |
| Example 73 | P-2-3 | 86.7 | A-39 | 3 | z2-1 | 10 | N-4 | 0.2 | SL-1/SL-5 | 40/60 |
| Example 74 | P-2-4 | 96.6 | A-5 | 3 | none | 0 | N-6 | 0.3 | SL-1/SL-6 | 40/60 |
| Example 75 | P-2-5 | 96.9 | A-21 | 3 | none | 0 | — | 0 | SL-1/SL-5 | 40/60 |
| Comparative Example 3 | P-2-1 | 88.9 | — | 0 | z2-1 | 10 | N-3 | 1 | SL-1/SL-6 | 40/60 |

| | Surfactant | Concentration | Developer | Rinsing Solution | Sensitivity (mJ/cm$^2$) | Resolution (nm) | Evaluation of Acid Decomposability, Residual Film After Heating (nm) |
|---|---|---|---|---|---|---|---|
| Example 71 | W-1 | 0.1 | SG-1 | none | 25.0 | 30 | 5 |
| Example 72 | W-2 | 0.1 | SG-1 | SR-1 | 26.0 | 28 | 8 |
| Example 73 | W-1 | 0.1 | SG-1 | SR-1 | 24.0 | 30 | 10 |
| Example 74 | W-1 | 0.1 | SG-1 | none | 25.0 | 28 | 8 |
| Example 75 | W-2 | 0.1 | SG-1 | SR-1 | 27.0 | 30 | 5 |
| Comparative Example 3 | W-1 | 0.1 | SG-1 | none | 29.0 | 40 | — |

The concentration of each component indicates the concentration (mass %) based on the total solid content concentration.

As apparent from the results shown in the Table, in Examples 71 to 75, the resolution was very excellent as compared with Comparative Example 3 not containing the compound (A).

In addition, using Resists 1 to 3 and referring to, for example, Example 7 of U.S. Pat. No. 8,227,183B, both butyl acetate development and alkali development were performed after the exposure of line-and-space mask pattern, as a result, a pattern with a pitch of ½ of the mask pattern could be formed.

Furthermore, evaluations were performed in the same manner as in Examples 1 to 3 except for adding a small amount of tri-n-octylamine to the developer (butyl acetate), as a result, good pattern formation could be performed also in these cases.

In the foregoing pages, Examples are described, but the present invention is not limited only to these Examples, but, for example, also in the following embodiments, pattern formation is possible.

- An embodiment where negative development is performed by adding about 1 mass % of a nitrogen-containing basic compound such as trioctylamine to the organic solvent-containing developer in each of Examples.
- An embodiment where exposure to an ArF excimer laser is replaced by EUV exposure in each of Examples, or furthermore, an embodiment where a resin (resin containing an aromatic ring-containing unit) presented as the above-described "resin that can be suitably used particularly when performing EUV exposure or electron beam exposure" is used as the resin in the resist composition.

In addition, as for the pattern formed in the Examples, after evaluation and measurement, the pattern was stripped off from the substrate by a dissociation solution. Specifically, a dissociation solution having a composition of 70% by mass of dimethylsulfoxide and 15% by mass of monoethanolamine and 15% by mass of diglycolamine was supplied on the substrate by using a single wafer processing apparatus, and the resist pattern was stripped off.

INDUSTRIAL APPLICABILITY

According to the present invention, a pattern forming method, an actinic ray-sensitive or radiation-sensitive resin composition, a resist film and a compound, ensuring that in forming an ultrafine pattern (among others, a trench pattern having a trench width of 50 nm or less or a hole pattern having a hole size of 50 nm or less), the roughness performance such as line width roughness and the defocus performance are high and the resolution and the exposure latitude are excellent, as well as a manufacturing method of an electronic device, using the method, composition, film or compound, and an electronic device, can be provided.

This application is based on a Japanese patent application filed on Mar. 1, 2013 (Japanese Patent Application No. 2013-041153), US provisional application filed on Mar. 1, 2013 (U.S. Provisional Application No. 61/771,245), Japanese patent application filed on Feb. 20, 2014 (Japanese Patent Application No. 2014-030830) and the contents thereof are incorporated herein by reference.

The invention claimed is:

1. A pattern forming method comprising:
   (i) a step of forming a film containing an actinic ray-sensitive or radiation-sensitive resin composition containing (A) a compound represented by the following formula (I-1), (B) a compound different from the compound (A) and capable of generating an acid upon irradiation with an actinic ray or radiation, and (P) a resin that does not react with the acid generated from the compound (A) and is capable of decreasing the solubility for an organic solvent-containing developer by the action of the acid generated from the compound (B),
   (ii) a step of exposing the film, and
   (iii) a step of developing the exposed film by using an organic solvent-containing developer to form a negative pattern:

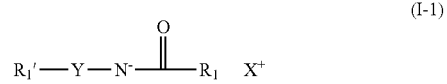
(I-1)

wherein
each of $R_1$ and $R_1'$ independently represents a monovalent organic group, Y represents —SO$_2$— or —CO—, and X$^+$ represents a counter cation.

2. The pattern forming method as claimed in claim 1, wherein the compound (A) is represented by the following formula (I-2a) or (I-2b):

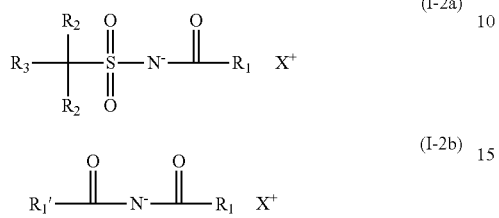

wherein each R$_2$ independently represents a hydrogen atom, an alkyl group, a cycloalkyl group or an alkoxy group, R$_3$ represents a hydrogen atom or a monovalent organic group, two or more members out of two R$_2$ and R$_3$ may combine with each other to form a ring, and R$_1$, R$_1$' and X$^+$ have the same meanings as R$_1$, R$_1$' and X$^+$ in formula (I-1).

3. The pattern forming method as claimed in claim 2, wherein the compound (A) is represented by the following formula (I-3a) or (I-3b):

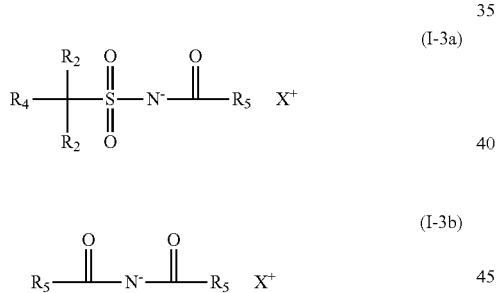

wherein each of R$_4$ and R$_5$ independently represents a fluorine atom, a hydroxyl group, an alkyl group or a cycloalkyl group, CH$_2$ contained in the alkyl group or cycloalkyl group represented by R$_4$ and R$_5$ may be replaced by —O—, —C(O)—, —S(O)$_n$—, —S(O)$_2$—NR$_6$—, —C(O)—NR$_6$—, —OC(O)—NR$_6$— or a combination thereof, R$_6$ represents a hydrogen atom or a monovalent organic group, n represents an integer of 0 to 2, two or more members out of two R$_2$ and R$_4$ may combine with each other to form a ring, and R$_2$ and X$^+$ have the same meanings as R$_2$ and X$^+$ in formula (I-2a).

4. The pattern forming method as claimed in claim 1, wherein the resin (P) contains a repeating unit represented by the following formula (II):

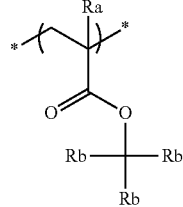

wherein

Ra represents a hydrogen atom or an alkyl group, each Rb independently represents an alkyl group or a cycloalkyl group, and two Rb may combine with each other to form a ring.

5. The pattern forming method as claimed in claim 1, wherein the resin (P) does not contain a repeating unit capable of decomposing by the action of an acid to produce an alcoholic hydroxyl group.

6. An actinic ray-sensitive or radiation-sensitive resin composition containing:

(A) a compound represented by formula (I-1), (B) a compound different from the compound (A) and capable of generating an acid upon irradiation with an actinic ray or radiation, and (P) a resin that does not react with the acid generated from the compound (A) and is capable of decomposing by the action of the acid generated from the compound (B) to produce a polar group:

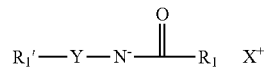

wherein each of R$_1$ and R$_1$' independently represents an alkyl group, a cycloalkyl group, an aryl group, an aralkyl group, or an alkenyl group, wherein each group may have, as a substituent, a halogen atom, a hydroxyl group, a nitro group, a cyano group, a carboxy group, a carbonyl group, a cycloalkyl group, an aryl group, an alkoxy group, an acyl group, an acyloxy group, an alkoxycarbonyl group, a silicon atom-containing group, or a group formed by combining two or more thereof, and when each of R$_1$ and R$_1$' independently represents an aryl group, a cycloalkyl group, or an aralkyl group, the group may have, as a substituent, an alkyl group, Y represents —SO$_2$— or —CO—, and X$^+$ represents a counter cation.

7. The actinic ray-sensitive or radiation-sensitive resin composition as claimed in claim 6, wherein the compound (A) is represented by the following formula (I-2a) or (I-2b):

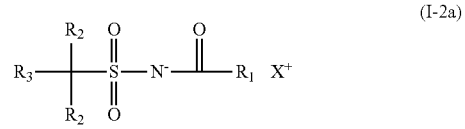

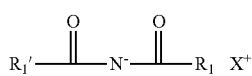
(I-2b)

wherein each $R_2$ independently represents a hydrogen atom, an alkyl group, a cycloalkyl group or an alkoxy group, $R_3$ represents a hydrogen atom, a halogen atom, a hydroxyl group, a nitro group, a cyano group, a carboxy group, a carbonyl group, a cycloalkyl group, an aryl group, an alkoxy group, an acyl group, an acyloxy group, or an alkoxycarbonyl group, two or more members out of two $R_2$ and $R_3$ may combine with each other to form a ring, and $R_1$, $R_1'$ and $X^+$ have the same meanings as $R_1$, $R_1'$ and $X^+$ in formula (I-1).

8. The actinic ray-sensitive or radiation-sensitive resin composition as claimed in claim 7, wherein the compound (A) is represented by the following formula (I-3a) or (I-3b):

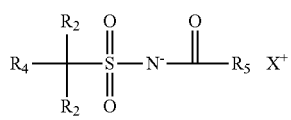
(I-3a)

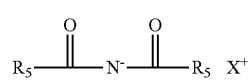
(I-3b)

wherein $R_4$ represents a fluorine atom, a hydroxyl group, an alkyl group or a cycloalkyl group, $R_5$ represents an alkyl group or a cycloalkyl group, wherein each group may have, as a substituent, a halogen atom, a hydroxyl group, a nitro group, a cyano group, a carboxy group, a carbonyl group, a cycloalkyl group, an aryl group, an alkoxy group, an acyl group, an acyloxy group, an alkoxycarbonyl group, or a silicon atom-containing group, and when $R_5$ represents a cycloalkyl group, it may have, as a substituent, an alkyl group, $CH_2$ contained in the alkyl group or cycloalkyl group represented by $R_4$ and $R_5$ may be replaced by —O—, —C(O)—, —S(O)$_n$—, or a combination thereof, $R_6$ represents a hydrogen atom or a monovalent organic group, n represents an integer of 0 to 2, and $R_2$ and $X^+$ have the same meanings as $R_2$ and $X^+$ in formula (I-2a).

9. The actinic ray-sensitive or radiation-sensitive resin composition as claimed in claim 6, wherein the resin (P) contains a repeating unit represented by the following formula (II):

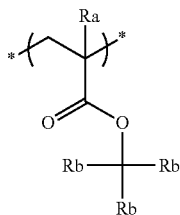
(II)

wherein

Ra represents a hydrogen atom or an alkyl group, each Rb independently represents an alkyl group or a cycloalkyl group, and two Rb may combine with each other to form a ring.

10. The actinic ray-sensitive or radiation-sensitive resin composition as claimed in claim 6, wherein the resin (P) does not contain a repeating unit capable of decomposing by the action of an acid to produce an alcoholic hydroxyl group.

11. A resist film formed of the actinic ray-sensitive or radiation-sensitive resin composition claimed in claim 6.

12. A method for manufacturing an electronic device, comprising performing a pattern forming method on a substrate, wherein the pattern forming method comprises:

(i) a step of coating the substrate with an actinic ray-sensitive or radiation-sensitive resin composition containing (A) a compound represented by the following formula (I-1), (B) a compound different from the compound (A) and capable of generating an acid upon irradiation with an actinic ray or radiation, and (P) a resin that does not react with the acid generated from the compound (A) and is capable of decreasing the solubility for an organic solvent-containing developer by the action of the acid generated from the compound (B), (ii) a step of exposing the film, and (iii) a step of developing the exposed film by using an organic solvent-containing developer to form a negative pattern:

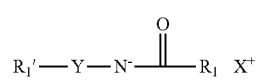
(I-1)

wherein each of $R_1$ and $R_1'$ independently represents a monovalent organic group, Y represents —SO$_2$— or —CO—, and $X^+$ represents a counter cation.

13. An electronic device manufactured by the manufacturing method of an electronic device claimed in claim 12.

14. A compound represented by the following formula (I-3a):

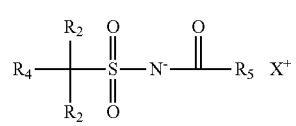
(I-3a)

wherein each $R_2$ independently represents a hydrogen atom, an alkyl group, a cycloalkyl group or an alkoxy group, $R_4$ represents a fluorine atom, a hydroxyl group, an alkyl group or a cycloalkyl group, $R_5$ represents an alkyl group or a cycloalkyl group, wherein each group may have, as a substituent, a halogen atom, a hydroxyl group, a nitro group, a cyano group, a carboxy group, a carbonyl group, a cycloalkyl group, an aryl group, an alkoxy group, an acyl group, an acyloxy group, an alkoxycarbonyl group, or a silicon atom-containing group, and when $R_5$ represents a cycloalkyl group, it may have, as a substituent, an alkyl group, $CH_2$ contained in the alkyl group or cycloalkyl group represented by $R_4$ and $R_5$ may be replaced by —O—, —C(O)—, —S(O)$_n$—, or a combination thereof, $R_6$ represents a hydrogen atom or a monovalent organic group, n represents an integer of 0 to 2, and $X^+$ represents a counter cation.

* * * * *